(12) United States Patent
Bashour et al.

(10) Patent No.: US 11,248,238 B2
(45) Date of Patent: Feb. 15, 2022

(54) METHODS, KITS, AGENTS AND APPARATUSES FOR TRANSDUCTION

(71) Applicant: Juno Therapeutics GmbH, Munich (DE)

(72) Inventors: Keenan Bashour, Seattle, WA (US); Semih U. Tareen, Seattle, WA (US)

(73) Assignee: Juno Therapeutics GmbH, Munich (DE)

( * ) Notice: Subject to any disclaimer, the term of this patent is extended or adjusted under 35 U.S.C. 154(b) by 102 days.

(21) Appl. No.: 15/770,177

(22) PCT Filed: Oct. 20, 2016

(86) PCT No.: PCT/IB2016/001605
§ 371 (c)(1),
(2) Date: Apr. 20, 2018

(87) PCT Pub. No.: WO2017/068419
PCT Pub. Date: Apr. 27, 2017

(65) Prior Publication Data
US 2020/0017880 A1    Jan. 16, 2020

Related U.S. Application Data

(60) Provisional application No. 62/245,265, filed on Oct. 22, 2015, provisional application No. 62/305,989, filed on Mar. 9, 2016, provisional application No. 62/369,020, filed on Jul. 29, 2016.

(51) Int. Cl.
| | |
|---|---|
| C12N 5/0783 | (2010.01) |
| C12N 15/86 | (2006.01) |
| C07K 14/315 | (2006.01) |
| C07K 14/725 | (2006.01) |
| C07K 16/28 | (2006.01) |

(52) U.S. Cl.
CPC ............ *C12N 15/86* (2013.01); *C07K 14/315* (2013.01); *C07K 14/7051* (2013.01); *C07K 16/2809* (2013.01); *C07K 16/2818* (2013.01); *C12N 5/0636* (2013.01); *C07K 2317/55* (2013.01); *C07K 2319/00* (2013.01); *C12N 2500/32* (2013.01); *C12N 2501/515* (2013.01); *C12N 2740/10043* (2013.01)

(58) Field of Classification Search
CPC ...... A61K 2039/625; A61K 2039/5154; A61K 2039/55516; A61K 39/21; A61K 47/646; A61K 48/00; A61K 2039/53; A61K 31/137; A61K 39/12; A61K 2039/5158; A61P 31/18; C07K 14/315; C07K 14/7051; C07K 14/70539; C07K 16/2809; C07K 16/2818; C07K 2319/00; C07K 2319/22; C07K 16/28; C12N 15/86; C12N 2501/515; C12N 5/0636; C12N 15/8203; C12N 2730/10134; C07D 487/04; C07D 207/36; C07D 231/20; C07D 239/62; C07D 275/04; C07D 285/01; C07D 291/06; C07D 307/60; C07D 333/32; C07D 401/06; C07D 403/06; C07D 409/06; C07D 417/06; C07D 421/06; C07D 471/04; C07D 491/044; C07D 498/04; C07D 519/00

See application file for complete search history.

(56) References Cited

U.S. PATENT DOCUMENTS

| | | | |
|---|---|---|---|
| 3,539,794 A | 11/1970 | Rauhut et al. | |
| 4,235,871 A | 11/1980 | Papahadjopoulos et al. | |
| 4,361,549 A | 11/1982 | Kung | |
| 4,452,773 A | 6/1984 | Molday | |
| 4,501,728 A | 2/1985 | Geho et al. | |
| 4,690,915 A | 9/1987 | Rosenberg | |
| 4,795,698 A | 1/1989 | Owen et al. | |
| 4,837,028 A | 6/1989 | Allen | |
| 4,851,341 A | 7/1989 | Hopp | |
| 5,019,369 A | 5/1991 | Presant et al. | |
| 5,033,252 A | 7/1991 | Carter | |
| 5,052,558 A | 10/1991 | Carter | |
| 5,087,616 A | 2/1992 | Myers et al. | |

(Continued)

FOREIGN PATENT DOCUMENTS

| | | |
|---|---|---|
| CN | 101 226 118 | 7/2008 |
| CN | 101 446 576 | 6/2009 |

(Continued)

OTHER PUBLICATIONS

Tatsuya et al. Pharmaceutical research, 2015, vol. 32, issue 11, pp. 3699-3707.*

(Continued)

*Primary Examiner* — Bao Q Li
(74) *Attorney, Agent, or Firm* — Morrison & Foerster LLP

(57) ABSTRACT

Provided herein are methods for transducing a plurality of cells in a composition of cells, such as a population of lymphocytes, containing viral particles. In some aspects, provided methods and reagents for the transduction of cell populations involve binding of agents to a molecule on the surface of the cells. In some cases, the reagents are multimerization reagents and the one or more agents are multimerized by reversibly binding to the reagent. In some aspects, the multimerized agent can provide for transduction and/or expansion or proliferation or other stimulation of a population of cells, and then such agents can be removed by disruption of the reversible bond. Also provided are compositions, apparatus and methods of use thereof.

49 Claims, 33 Drawing Sheets
Specification includes a Sequence Listing.

(56) References Cited

U.S. PATENT DOCUMENTS

| | | |
|---|---|---|
| 5,168,049 A | 12/1992 | Meade et al. |
| 5,168,062 A | 12/1992 | Stinski |
| 5,171,081 A | 12/1992 | Pita et al. |
| 5,200,084 A | 4/1993 | Liberti et al. |
| 5,323,907 A | 6/1994 | Kalvelage |
| 5,385,839 A | 1/1995 | Stinski |
| 5,506,121 A | 4/1996 | Skerra |
| 5,510,474 A | 4/1996 | Quail et al. |
| 5,686,278 A | 11/1997 | Williams et al. |
| 5,985,658 A | 11/1999 | Colinas |
| 5,994,136 A | 11/1999 | Naldini et al. |
| 6,013,516 A | 1/2000 | Verma et al. |
| 6,022,951 A | 2/2000 | Sano |
| 6,033,907 A | 3/2000 | Williams |
| 6,040,177 A | 3/2000 | Riddell et al. |
| 6,103,493 A | 8/2000 | Skerra et al. |
| 6,352,694 B1 | 3/2002 | June |
| 6,410,319 B1 | 6/2002 | Raubitschek et al. |
| 6,451,995 B1 | 9/2002 | Cheung et al. |
| 6,670,177 B2 | 12/2003 | Williams |
| 7,033,834 B2 * | 4/2006 | Valerio .................. A61K 48/00 435/455 |
| 7,070,995 B2 | 7/2006 | Jensen |
| 7,083,979 B1 | 8/2006 | Williams et al. |
| 7,265,209 B2 | 9/2007 | Jensen |
| 7,354,762 B2 | 4/2008 | Jensen |
| 7,446,191 B2 | 4/2008 | Jensen |
| 7,446,179 B2 | 11/2008 | Jensen et al. |
| 7,446,190 B2 | 11/2008 | Sadelain et al. |
| 7,482,000 B2 | 1/2009 | DeVaux |
| 7,494,656 B2 * | 2/2009 | Bachmann ............. A61K 39/35 424/192.1 |
| 7,592,431 B2 | 9/2009 | Har-Noy |
| 7,704,708 B2 | 4/2010 | Wu et al. |
| 7,776,562 B2 | 8/2010 | Busch |
| 7,981,632 B2 | 7/2011 | Schmidt |
| 8,298,782 B2 | 10/2012 | Busch |
| 8,324,353 B2 | 12/2012 | Jensen |
| 8,339,645 B2 | 12/2012 | Nakawaki |
| 8,389,282 B2 | 3/2013 | Sadelain et al. |
| 8,449,874 B2 * | 5/2013 | Bachmann ............. A61P 19/06 424/85.2 |
| 8,479,118 B2 | 7/2013 | Lyndersay et al. |
| 8,735,330 B2 | 5/2014 | Geir |
| 8,735,540 B2 | 5/2014 | Schmidt |
| 9,023,604 B2 | 5/2015 | Schmidt et al. |
| 10,228,312 B2 | 3/2019 | Stadler |
| 2002/0131960 A1 | 9/2002 | Sadelain et al. |
| 2003/0175850 A1 | 9/2003 | Ross et al. |
| 2004/0082012 A1 | 4/2004 | Busch et al. |
| 2006/0019319 A1 | 1/2006 | Billadeau et al. |
| 2006/0106199 A1 | 5/2006 | Erdmann et al. |
| 2007/0241061 A1 | 10/2007 | Engstrom et al. |
| 2008/0085532 A1 | 4/2008 | Gorlach et al. |
| 2008/0131415 A1 | 6/2008 | Riddell |
| 2008/0255004 A1 | 10/2008 | Neurauter et al. |
| 2010/0068738 A1 | 3/2010 | Kawamura et al. |
| 2010/0267057 A1 | 10/2010 | Rakestraw et al. |
| 2011/0070581 A1 | 3/2011 | Gupta |
| 2012/0214187 A1 | 8/2012 | Lees et al. |
| 2012/0321665 A1 | 12/2012 | Bollyky et al. |
| 2013/0287748 A1 | 10/2013 | Hjune et al. |
| 2014/0295458 A1 | 10/2014 | Schmidt |
| 2014/0314795 A1 | 10/2014 | Riddell |
| 2015/0024411 A1 | 1/2015 | Stadler |
| 2015/0283178 A1 | 10/2015 | June et al. |
| 2015/0306141 A1 | 10/2015 | Jensen |
| 2016/0362472 A1 | 12/2016 | Bitter et al. |
| 2017/0037368 A1 | 2/2017 | Germeroth et al. |
| 2017/0037369 A1 | 2/2017 | Ramsborg et al. |
| 2017/0037370 A1 | 2/2017 | Kaiser et al. |
| 2017/0051252 A1 | 2/2017 | Morgan et al. |
| 2017/0052176 A1 | 2/2017 | Carl et al. |
| 2018/0296602 A1 | 10/2018 | Riddell et al. |
| 2019/0112576 A1 | 4/2019 | Germeroth et al. |
| 2019/0136186 A1 | 5/2019 | Germeroth et al. |
| 2019/0226951 A1 | 7/2019 | Stadler |
| 2019/0234844 A1 | 8/2019 | Stadler |
| 2020/0384025 A1 | 12/2020 | Mujacic et al. |

FOREIGN PATENT DOCUMENTS

| | | |
|---|---|---|
| CN | 101 535 466 | 9/2009 |
| CN | 101 622 340 | 1/2010 |
| CN | 101 978 269 | 2/2011 |
| CN | 103 305 464 | 9/2013 |
| CN | 103 502 438 | 1/2014 |
| EP | 452342 | 11/1994 |
| EP | 835934 A2 * | 10/1996 |
| EP | 0700430 | 4/2005 |
| EP | 2537416 | 12/2012 |
| EP | 2886645 | 6/2015 |
| JP | 2004-525354 | 8/2004 |
| JP | 2006-516197 | 6/2006 |
| JP | 2006-525013 | 11/2006 |
| JP | 2009-531062 | 9/2009 |
| JP | 2010-75191 | 4/2010 |
| RU | 2249039 | 3/2005 |
| RU | 2469044 | 12/2012 |
| WO | WO-1996/023879 | 8/1996 |
| WO | WO-2000/14257 | 3/2000 |
| WO | WO 2000/043551 | 7/2000 |
| WO | WO-2001/004144 | 1/2001 |
| WO | WO-2002/054065 | 7/2002 |
| WO | WO-2002/077018 | 10/2002 |
| WO | WO-2003/029462 | 4/2003 |
| WO | WO-2004/029221 | 4/2004 |
| WO | WO-2004/096975 | 11/2004 |
| WO | WO-2004/104185 | 12/2004 |
| WO | WO-2005/050209 | 6/2005 |
| WO | WO-2006/044650 | 4/2006 |
| WO | WO-2006/058226 | 6/2006 |
| WO | WO-2006/060878 | 6/2006 |
| WO | WO-2007/112012 | 10/2007 |
| WO | WO-2007/117602 | 10/2007 |
| WO | WO-2008/011486 | 1/2008 |
| WO | WO 2008/100122 | 8/2008 |
| WO | WO-2008/140573 | 11/2008 |
| WO | WO-2009/003493 | 1/2009 |
| WO | WO-2009/072003 | 6/2009 |
| WO | WO-2009/097119 | 6/2009 |
| WO | WO-2009/092068 | 7/2009 |
| WO | WO-2009/076524 | 9/2009 |
| WO | WO-2010/033140 | 3/2010 |
| WO | WO-2010/080032 | 7/2010 |
| WO | WO2010080032 A2 * | 7/2010 |
| WO | WO-2011/107489 | 9/2011 |
| WO | WO-2012/017081 | 2/2012 |
| WO | WO-2012/129514 | 9/2012 |
| WO | WO-2013/011011 | 1/2013 |
| WO | WO 2013/038272 | 3/2013 |
| WO | WO-2013/071154 | 5/2013 |
| WO | WO-2013/088148 | 6/2013 |
| WO | WO-2013/123061 | 8/2013 |
| WO | WO-2013/124474 | 8/2013 |
| WO | WO-2013/126726 | 8/2013 |
| WO | WO2013124474 A2 * | 8/2013 |
| WO | WO-2013/166321 | 11/2013 |
| WO | WO-2014/011489 | 1/2014 |
| WO | WO-2014/011996 | 1/2014 |
| WO | WO-2014/031687 | 2/2014 |
| WO | WO-2014/048920 | 4/2014 |
| WO | WO-2014/055668 | 4/2014 |
| WO | WO-2014/076277 | 5/2014 |
| WO | WO2014076277 A1 * | 5/2014 |
| WO | WO-2015/036713 | 3/2015 |
| WO | WO-2015/095895 | 7/2015 |
| WO | WO-2015/158868 | 10/2015 |
| WO | WO-2015/162211 | 10/2015 |
| WO | WO-2015/164675 | 10/2015 |
| WO | WO-2016/073602 | 5/2016 |
| WO | WO-2016/090190 | 6/2016 |
| WO | WO-2016/166568 | 10/2016 |
| WO | WO-2016/1645813 | 10/2016 |

(56) References Cited

FOREIGN PATENT DOCUMENTS

| WO | WO-2017/068421 | 4/2017 |
|---|---|---|
| WO | WO-2017/068425 | 4/2017 |
| WO | WO-2017/096329 | 6/2017 |
| WO | WO-2017/165245 | 9/2017 |
| WO | WO-2018/106732 | 6/2018 |
| WO | WO-2018/197949 | 11/2018 |
| WO | WO-2020/033927 | 2/2020 |
| WO | WO-2020/089343 | 5/2020 |

OTHER PUBLICATIONS

Chen et al. PLoS One, Aug. 2012, vol. 7, Issue 8, e42376, pp. 1-8.*
Sawai ey al. Molecular Genetics of Metabolim, 1998, vol. 64, pp. 44-51.*
Williams et al. Journal of Chromatography B, 2005, vol. 820, Issue 1, pp. 111-119.*
Sano et al. Nature, 1991, vol. 9, pp. 1378-1381.*
Morizona et al. Journal of Gene Medicine, published on May 19, 2009, vol. 11, Issue 8, pp. 655-663.*
Al-Aghbar et al., "High-Affinity Ligands Can Trigger T Cell Receptor Signaling Without CD45 Segregation." Front Immunol. (2018); 9: 713.
Arndt et al., "Analysis of TCR activation kinetics in primary human T cells upon focal or soluble stimulation," J Immunol Methods. (2013) 387(1-2): 276-283.
Berg et al., "Sustained TCRsignaling is required for mitogen-activated protein kinase activation anddegranulation by cytotoxic T lymphocytes." 1998. J. Immunol. 161(6); 2919-2924.
Berger et al., "Adoptive transfer of effector CD8 T cells derived from central memory cells establishes persistent T cell memory in primates." J Clin Invest (2008) 118(1): 294-305.
Birnbaum et al., "Molecular architecture of the αβ T cell receptor-CD3 complex." Proc Natl Acad Sci USA. (2014) 111 (49): 17576-17581.
Boerman et al., "Pretargeted radioimmunotherapy of cancer: progress step by step." J Nucl Med. (2003) 44(3); 400-411.
Buckle et al., "Integrating Experiment and Theory to Understand TCR-pMHC Dynamics," Front Immunol. (2018) 9:2898.
Busch et al., "Differing roles of inflammation and antigen in T cell proliferation and memory generation." J Immunol. (2000) 164(8); 4063-4070.
Carpentier et al., "T-cell artificial focal triggering tools: linking surface interactions with cell response." PLoS One (2009) 4(3), e4784.
Choudhuri et al., "Signaling microdomains in T cells." FEBS Lett. (2010) 584(24): 4823-4831.
Clement et al., "Analysis of the monocyte Fc receptors and antibody-mediated cellular interactions required for the induction of T cell proliferation by anti-T3 antibodies." J Immunol. (1985) 135(1): 165-171.
Davis et al., "The kinetic-segregation model: TCR triggering and beyond." Nat. Immunol. (2006) 7(8); 803-809.
Effenberger et al., "FLEXamers: A Double Tag for Universal Generation of Versatile Peptide-MHC Multimers." J Immunol. (2019) 202(7): 2164-2171.
Garlie et al., "T cells coactivated with immobilized anti-CD3 and anti-CD28 as potential immunotherapy for cancer." J. Immunother. (1999) 22(4); 336-345.
Ghassemi et al., "Reducing Ex Vivo Culture Improves the Antileukemic Activity of Chimeric Antigen Receptor (CAR) T Cells," Cancer Immunology Research (2018) 6(9):1100-1109.
Goyette et al., "How does T cell receptor clustering impact on signal transduction?" J Cell Sci. (2019) 132(4); jcs226423.
Lenschow, D.J. et al. (1996). "CD28/B7 System of T Cell Costimulation," Ann. Rev. Immunol. 14:233-258.
Levine et al., 1997. "Effects of CD28 costimulation on long-term proliferation of CD4+ T cells in the absence of exogenous feeder cells." J. Immunol. (1997) 159(12), 5921-5930.

Li et al.. "T cell receptor signalling in the control of regulatory T cell differentiation and function." Nat Rev Immunol. (2016) 16(4): 220-233.
Mehlhop-Williams et al., "Memory CD8+ T cells exhibit increased antigen threshold requirements for recall proliferation." J Exp Med. (2014) 211(2): 345-56.
Meyer et al., "Biodegradable nanoellipsoidal artificial antigen presenting ceils for antigen specific T-cell activation." Small. (2015) 11(13): 1519-1525.
Mohr et al., "Efficient immunoaffinity chromatography of lymphocytes directly from whole blood." Sci Rep. 2018 8 (1):16731.
Nauerth et al., "Flow cytometry-based TCR-ligand Koff-rate assay for fast avidity screening of even very small antigen-specific T cell populations ex vivo." Cytometry A. (2016) 89(9): 816-825.
Neuenhahn et al., "Transfer of minimally manipulated CMV-specific T cells from stem cell or third-party donors to treat CMV infection after alloHSCT." Leukemia (2017) 31(10): 2161-2171.
Pearce El. "Metabolism in T cell activation and differentiation," Curr. Opin. Immunol. (2010) 22(3), 314-320.
Poltorak et al., "TCR activation kinetics and feeDynaBeads™ack regulation in primary human T cells." Cell Commun Signal. (2013) 11:4.
Rapoport et al., "Restoration of immunity in lymphopenic individuals with cancer by vaccination and adoptive T-cell transfer." Nat Med. (2005) 11(11): 1230-1237.
Riddell et al., "The use of anti-CD3 and anti-CD28 monoclonal antibodies to clone and expand human antigen-specific T cells." J Immunol Methods. (1990) 128(2): 189-201.
Rudd et al.,"CD28 and CTLA-4 coreceptor expression and signal transduction." Immunol Rev. (2009) 229(1); 12-26.
Sanchez-Paulete et al., "Deciphering CD137 (4-1BB) signaling in T-cell costimulation for translation into successful cancer immunotherapy." Eur. J. Immunol. (2016) 46(3); 513-522.
Schmidt et al., "Development of the Twin-Strep-tag and its application for purification of recombinant proteins from cell culture supernatants." Protein Expression and Purification (2013) 92(1); 54-61.
Schmidt et al., "Molecular Interaction Between the Strep-tag Affinity Peptide and its Cognate Target, Streptavidin." Mol. Biol. (1996) 255(5); 753-766.
Schmidt et al., "The random peptide library-assisted engineering of a C-terminal affinity peptide, useful for the detection and purification of a functional Ig Fv fragment." Protein Eng. (1993) 6(1); 109-122.
Schober et al., "Orthotopic replacement of T-cell receptor α- and β-chains with preservation of near-physiological T-cell function." Nat Biomed Eng. (2019) 3(12): 974-984.
Turtle et al., "Genetically retargeting CD8+ lymphocyte subsets for cancer immunotherapy." Curr Opin Immunol. (2011) 23(2); 299-305.
Van Panhuys et al., "T-cell-receptor-dependent signal intensity dominantly controls CD4(+) T cell polarization In Vivo." Immunity. (2014) 41(1): 63-74.
Van Stipdonk et al., "Naïve CTLs require a single brief period of antigenic stimulation for clonal expansion and differentiation." Nat Immunol. (2001) 2(5): 423-429.
Wang et al., "A transgene-encoded cell surface polypeptide for selection, in vivo tracking, and ablation of engineered cells," Blood (2011) 118(5): 1255-1263.
Wang et al., "Dynamics of proximal signaling events after TCR/CD8-mediated induction of proliferation or apoptosis in mature CD8+ T cells." J. Immunol. (2008) 180(10); 6703-6712.
Yang et al., "In vitro generated anti-tumor T lymphocytes exhibit distinct subsets mimicking in vivo antigen-experienced cells." Cancer Immunol Immunother (2011)60(5): 739-749.
Aksoy et al., "Human primary T cells: A practical guide," Published on Jun. 19, 2018. Retrieved on Jan. 7, 2020. Retrieved from https://peerj.com/preprints/26993/.
Anonymous, "Optimization of Human T Cell Expansion Protocol: Effects of Early Cell Dilution," Published Oct. 2018. Retrieved on Jan. 7, 2020. Retrieved on https://cdn.stemcell.com/media/files/

(56) References Cited

OTHER PUBLICATIONS techbulletin/TB27143-Optimization_of_Human_T_Cell_Expansion_Protocol.pdf?_ga=2.128430788.931468903.1578439383-852611746.1578439383.
Chang et al., "Identification and selective expansion of functionally superior T cells expressing chimeric antigen receptors," J Transl Med (2015) 13(1): 161.
Gunning et al., "A human beta-actin expression vector system directs high-level accumulation of antisense transcripts," Proc Natl Acad Sci USA (1987) 84(14):4831-4835.
Kohanski, R.A., Lane, M.D. "Monovalent avidin affinity columns" Methods Enzymol. 1990;184:194-200.
Lada et al., "Quantitation of Integrated HIV Provirus by Pulsed-Field Gel Electrophoresis and Droplet Digital PCR," J Clin Microbiol (2018) 56(12): e01158-18.
Li, Y. et al., "Comparison of anti-CD3 and anti-CD28-coated Beads With Soluble anti-CD3 for Expanding Human T Cells: Differing Impact on CD8 T Cell Phenotype and Responsiveness to Restimulation," J Transl Med (2010) 8: 104.
Lim et al. "Engineered Streptavidin Monomer and Dimer with Improved Stability and Function," Biochemistry (2010), 50:8682-91.
Lu et al., "A rapid cell expansion process for production of engineered autologous CAR-T cell therapies," Human Gene Therapy Methods (2016) 27(6):209-218.
Miller, A.D. et al. (Oct. 1989). "Improved Retroviral Vectors for Gene Transfer and Expression", Biotechniques. 7(9):980-990.
Neeson et al., "Ex Vivo Culture of Chimeric Antigen Receptor T Cells Generates Functional CD8+ T Cells With Effector and Central Memory-Like Phenotype," Gene Ther (2010) 17(9): 1105-16.
Okamoto et al., "A Promising Vector for TCR Gene Therapy: Differential Effect of siRNA, 2A Peptide, and Disulfide Bond on the Introduced TCR Expression," Mol Ther Nucleic Acids. (2012) 1(12): e63. 11 pages.
Rybak, J.N., et al. "Purification of biotinylated proteins on streptavidin resin: a protocol for quantitative elution" Proteomics. Aug. 2004;4(8):2296-9.
Trickett et al., "T cell stimulation and expansion using anti-CD3/CD28 beads" J. Immunol Methods (2003) 275(102):251-255.
Vormittag et al., "A Guide to Manufacturing CAR T Cell Therapies," Curr Opin Biotechnol (2018) 53:164-181.
Xu et al., "Closely Related T-memory Stem Cells Correlate With in Vivo Expansion of CAR.CD19-T Cells and Are Preserved by IL-7 and IL-15," Blood (2014) 123 (24): 3750-3759.
Xu et al., "Multiparameter Comparative Analysis Reveals Differential Impacts of Various Cytokines on CART Cell Phenotype and Function Ex Vivo and in Vivo," Oncotarget (2016) 7(50): 82354-82368.
Yarilin, "Immunology principles," M. Medicine (1999) 184-195, 339-347 (English Translation included).
Zhao et al., "Development of the First World Health Organization Lentiviral Vector Standard: Toward the Production Control and Standardization of Lentivirus-Based Gene Therapy Products," Hum Gene Ther Methods (2017) 28 (4): 205-214.
U.S. Appl. No. 16/608,796, filed Apr. 27, 2018, by Schmidt et al. (Copy not provided). (Copy not submitted herewith pursuant to the waiver of 37 C.F.R. § 1.98(a)(2)(iii) issued by the Office on Sep. 21, 2004).
U.S. Appl. No. 16/769,971, filed Jun. 4, 2020, by Mujacic et al. (Copy not provided). (Copy not submitted herewith pursuant to the waiver of 37 C.F.R. § 1.98(a)(2)(iii) issued by the Office on Sep. 21, 2004).
Imadome, "The clinical condition and diagnosis of EBV-T/NK-LPD (CAEBV, EBV-HLH etc.)," [Rinsho Ketsueki] Japanese J Clin Hematol (2013) 54(10): 1992-98.
Kong et al., "Isolation of breast cancer stem cell and screening of specific polypeptide bonding to it," Chinese Journal of Cancer Prevention and Control (2013) 20(24):1892-1895.

Wigler, M. et al. (May 1977). "Transfer of Purified Herpes Virus Thymidine Kinase Gene to Cultured Mouse Cells", Cell 2(11):223-232.
Wu, S.C. et al. (Jun. 17, 2005). "Engineering soluble monomeric streptavidin with reversible biotin binding capability", *J. Biol. Chem*.280(24):23225-23231.
Xia et al., "Enrichment of haploid spermatids in mice by flow sorting," Natl Journal of Andrology (2014) 20(2):106-110.
Hobson et al., "In situ transduction of target cells on solid surfaces by immobilized viral vectors," BMC Biotechnol (2003) 3(4):1-10.
Schroeder, Nach Zellen Angeln. Faszination Forschung Jun. 30, 2010:28-37 Retrieved from the Internet: URL:http://portal.mytum.de/pressestelle/faszination-forschung/2010nr6/index.html [retrieved on Nov. 16, 2012] 15 pages (English translation provided).
Bambauer et al., "LDL-apheresis: technical and clinical aspects," The Scientific World Journal (2012).
Brosseron et al. "Isolating peripheral lymphocytes by density gradient centrifugation and magnetic cell sorting" Methods Mol Biol (2015) 1295:33-42.
Daniels et al., "Thymic Selection Threshold Defined by Compartmentalization of Ras/MAPK Signalling," Nature. Dec. 7, 2006; 444(7120): 724-729.
Depil et al., "'Off-the-shelf' allogeneic CAR T cells: development and challenges." Nat Rev Drug Discov (2020) 3: 185-199.
Gattinoni, L. et al. (2012, e-pub. Sep. 21, 2012)."Paths to stemness: building the ultimate antitumour T cell", Nature Reviews Cancer 12(671):1-14.
Godawat et al., "Period counter-current chromatography—design and operational considerations for integrated and continuous purification of proteins," Biotechnology journal (2012) 7(12):1496-1508.
Grutzkau et al. "Small but mighty: how the MACS-technology based on nanosized superparamagnetic particles has helped to analyze the immune system within the last 20 years." Cytometry A. (Jul. 2010) 77(7): 643-647.
Han et a., "Chimeric antigen receptor T-cell therapy for cancer: a basic research-oriented perspective," Mar. 2018;10(3):221-234.
Hobson et al., "In situ transfuction of target cells on solid surfaces by immobilized viral vectors," BMC Biotechnol (2003) 3(4):1-10.
Huppa et al., "T-cell-antigen recognition and the immunological synapse," Nat. Rev. Immunol. (2003) 3(12); 973-983.
Invitrogen, "Healthy cells in—good data out," Cell isolation and Activation (2010) p. 1-12.
Isozaki et al. "Intelligent image-activated cell sorting 2.0." Lab Chip. (Jun. 30, 2020) 20(13): 2263-2273.
Kacherovsky et al. "Traceless aptamer-mediated isolation of CD8+ T cells for chimeric antigen receptor T-cell therapy." Nat Biomed Eng. (Oct. 2019) 3(10):783-795.
Kim et al., "The ABCs of Artificial Antigen Presentation," Nat Biotechnol Apr. 2004;22(4): 403-10.
Kleymann et al. "Engineered Fv Fragments as a Tool for the One-Step Purification of Integral Multisubunit Membrane Protein Complexes." Nat Biotechnol (1995) 13: 155-160.
Korndorfer et al., "Improved affinity of engineered streptavidin for the Strep-tag 11 peptide is due to a fixed open conformation of the lid-like loop at the binding site," Protein Sci (2002) 11:883-893.
Kumar et al., "Integrated bioprocess for the production and isolation of urokinase from animal cell culture using supermacroporous cryogel matrices," Biotechnology and Bioengineering (2006) 93(4):636-646.
Kubben et al. "Identification of differential protein interactors of lamin A and progerin," Nucleus (2010) 1(6): 513-525.
Matic et al., "Ine Tuning and Efficient T Cell Activation with Stimulatory aCD3 Nanoarrays," Nano Letters (2013) 13:5090-5097.
Mittal et al. "Biotin-4-fluorescein based fluorescence quenching assay for determination of biotin binding capacity of streptavidin conjugated quantum dots." Bioconjug Chem. (2011) 22(3):362-368.
Mohr et al., "Minimally manipulated murine regulatory T cells purified by reversible Fab Multimers are potent suppressors for adoptive T-cell therapy." Eur. J. Immunol. (2017) 47: 2153-2162.

(56) References Cited

OTHER PUBLICATIONS

Murray et al. "Continuous and Quantitative Purification of T-Cell Subsets for Cell Therapy Manufacturing Using Magnetic Ratcheting Cytometry." SLAS Technol. (Aug. 2018) 23(4):326-337.
Poltorak et al., "Expamers: a new technology to control T cell activation." Sci. Rep. (2020) 10: 17832.
Pozarowski et al., "Analysis of Cell Cycle by Flow Cytometry," Methods Mol Biol. (2004) 281: 301-311.
Pritchard et al. "Cell sorting actuated by a microfluidic inertial vortex." Lab Chip. (Jul. 9, 2019) 19(14): 2456-2465.
Rossy et al., "How Does the Kinase Lck Phosphorylate the T Cell Receptor? Spatial Organization as a Regulatory Mechanism," Front Immunol. (2012) 3:167.
Singh et al. "CAR T cells: continuation in a revolution of immunotherapy." The Lancet Oncology (Mar. 2020) 21(3): e168-e178.
Tsiotis et al. "Isolation and structural characterization of trimeric cyanobacterial photosystem I complex with the help of recombinant antibody fragments." Eur J Biochem. (Aug. 1, 1995) 231(3): 823-30.
Turka et al., "CD28 is an Inducible T Cell Surface Antigen That Transduces a Proliferative Signal in CD3+ Mature Thymocytes," J Immunol (1990) 144:1646-1653.
Vadakekolathu et al. "T-Cell Manipulation Strategies to Prevent Graft-Versus-Host Disease in Haploidentical Stem Cell Transplantation." Biomedicines. (Jun. 21, 2017) 5(2): 33.
Valle et al., "Heterogeneous CD3 Expression Levels in Differing T Cell Subsets Correlate with the In Vivo Anti-CD3-Mediated T Cell Modulation." J Immunol. (2015) 5: 2117-2127.
Wang et al., "Open-tubular capillary cell affinity chromatography: single and tandem blood cell separation," Anal Chem (2008) 80(6):2118-2124.
Zeiser et al., "Acute Graft-versus-Host Disease—Biologic Process, Prevention, and Therapy," N Engl J Med (2017) 377: 2167-2179.
Zhang et al., "LAT: the ZAP-70 tyrosine kinase substrate that links T cell receptor to cellular activation," Cell (1998) 92(1):83-92.
Zhang, M. et al. (Aug. 7, 2015). "A novel approach to make homogeneous protease-stable monovalent streptavidin", Biochem Biophys Res Commun. 463(4):1059-1063.
U.S. Appl. No. 16/231,188, filed Dec. 21, 2018, by Stadler et al. (Copy not provided). (Copy not submitted herewith pursuant to the waiver of 37 C.F. R. § 1.98(a)(2)(iii) issued by the Office on Sep. 21, 2004).
U.S. Appl. No. 16/231,193, filed Dec. 21, 2018, by Stadler et al. (Copy not provided). (Copy not submitted herewith pursuant to the waiver of 37 C.F. R. § 1.98(a)(2)(iii) issued by the Office on Sep. 21, 2004).
U.S. Appl. No. 15/770,179, filed Oct. 20, 2016, by Germeroth et al. (Copy not provided). (Copy not submitted herewith pursuant to the waiver of 37 C.F. R. § 1.98(a)(2)(iii) issued by the Office on Sep. 21, 2004).
Adra et al., "Cloning and expression of the mouse pgk-1 gene and the nucleotide sequence of its promoter," Gene (1987) 60(1):65-74.
Alonso-Camino, V. et al. (May 2013, e-pub. May 21, 2013). "CARbodies: Human Antibodies Against Cell Surface Tumor Antigens Selected From Repertoires Displayed on T Cell Chimeric Antigen Receptors", 2(5):e93, 11 pages.
Ameres, S. et al. (2013). "Presentation of an Immunodominant Immediate-Early CD8+ T Cell Epitope Resists Human Cytomegalovirus Immunoevasion," PLoS Pathog. 9(5):e1003383, 15 pages.
Amstutz et al. (Aug. 2001). "In vitro Display Technologies: Novel Developments and Applications," Curr Opin Biotechnol. 12(4):400-5.
Anonymous, "Cross-linking reagents introduction to cross-linking single-step vs. multi-step reactions," Published on Jan. 1, 2005. Retrieved from http://www.korambiotech.com/upload/bbs/2/Cross-LinkingTechHB.pdf. Retrieved on Nov. 30, 2018.
Anonymous, "SMCC and Sulfo-SMCC," Published Jan. 1, 2018. Retrieved on https://assets.thermofisher.com/TFS-Assets/LSG/manuals/MAN0011295_SMCC_SulfoSMCC_UG.pdf. Retrieved on Dec. 3, 2018.
Anonymous, "Traut's reagent," Published on Jan. 1, 2012. Retrieved from https://assets.thermofisher.com/TFS-Assets/LSG/manuals/MAN0011238_Trauts_Reag_UG.pdf. Retrieved on Dec. 3, 2018.
Arakawa et al. (Sep. 1996). "Cloning and sequencing of the VH and V kappa genes of an anti-CD3 monoclonal antibody, and construction of a mouse/human chimeric antibody," J Biochem. 120(3):657-662.
Argarana et al. (Feb. 25, 1986). "Molecular cloning and nucleotide sequence of the streptavidin gene," Nucleic Acids Res. 14(4):1871-1882.
Barrett et al. "The length and mode of termination of individual muscle fibers in the human Sartorius and posterior femoral muscles," Cell Tissues Organs (1962) 48(3):242-257.
Bashour et al., "Functional Characterization of a T Cell Stimulation Reagent for the Production of Therapeutic Chimeric Antigen Receptor T Cells," Abstract of Poster, presented at American Society of Hematology Annual Meeting, Orlando, FL (Dec. 5, 2015) 1 page.
Bashour et al., "Functional Characterization of a T Cell Stimulation Reagent for the Production of Therapeutic Chimeric Antigen Receptor T Cells," Presentation of Poster, presented at American Society of Hematology Annual Meeting, Orlando, FL (Dec. 5, 2015).
Battaglia et al., "Interleukin-21 (IL-21) synergizes with IL-2 to enhance T-cell receptor-induced human T-cell proliferation and counteracts IL-2/transforming growth factor-β-induced regulatory T-cell development," Immunology. May 2013:139(1):109-120.
Bazdar et al. "Interleukin-7 enhances proliferation responses to T-cell receptor stimulation in naïve CD4+ T cells from human immunodeficiency virus-infected persons," J Virol. Nov. 2007; 81(22): 12670-12674.
Bes, C. et al. (2003). "Mapping the Paratope of Anti-CD4 Recombinant Fab 13B8.2 by Combining Parallel Peptide Synthesis and Site-directed Mutagenesis", The Journal of Biological Chemistry 278(16):14265-14273.
Beste et al., "Small antibody-like proteins with prescribed ligand specificities derived from the lipocalin fold," Proc Natl Acad Sci U S A. Mar. 2, 1999;96(5):1898-1903.
Boshart et al., "A very strong enhancer is located upstream of an immediate early gene of human cytomegalovirus," Cell (1985) 41(2):521-530.
Brown et al., "Structure-Based Mutagenesis of the Human Immunodeficiency Virus Type 1 DNA Attachment Site: Effects on Integration and cDNA Synthesis," J Virol (1999) 73(11):9011-9020.
Butler et al., "Ex Vivo Expansion of Human CD8+ T Cells Using Autologous CD4+ T Cell Help," PLoS ONE (2012) 7(1):e30229,11 pages.
Carlens, S. (Oct. 2000). "Ex vivo T lymphocyte expansion for retroviral transduction: influence of serum-free media on variations in cell expansion rates and lymphocyte subset distribution", Exp Hematool 28(10): 1137-1146.
Casalegno-Garduño et al. Multimer technologies for detection and adoptive transfer of antigen-specific T cells. Cancer Immunol Immunother. Feb. 2010;59(2): 195-202.
Casati et al., "Enrichment, stimulation, and viral transduction of naive and central memory CD8+ T cells under GMP conditions for translational research towards the development of adoptive cell therapy of cancer patients," MACS&more (2013) 15:20-24.
Cho, S. H. et al. (Jun. 21, 2010). "Human mammalian cell sorting using a highly integrated microfabricated fluorescence-activated cell sorter (μFACS)", Lab. Chip. 10(12): 1567-1573.
Church et al., "Tumor-specific CD4+ T cells maintain effector and memory tumor-specific CD8+ T cells," Eur J Immunol (2013) 44(1):69-79.
Cohen, C.J. (Nov. 1, 2005). "Recognition of Fresh Human Tumor by Human Peripheral Blood Lymphocytes Transduced with a Bicistronic Retroviral Vector Encoding a Murine Anti-p53 TCR", J. Immunol. 175(9):5799-5808.
Cornish et al., "Differential regulation of T-cell growth by IL-2 and IL-15," Blood. Jul. 15, 2006;108(2):600-608.

(56) References Cited

OTHER PUBLICATIONS

Costello, E. et al. "Gene transfer into stimulated and unstimulated T lymphocytes by HIV-1-derived lentiviral vectors," Gene Therapy, vol. 7, No. 7, Apr. 1, 2000 pp. 596-604.
Dainiak et al., Methods in Cell Separations. Adv Biochem Eng Biotechnol. 2007;106:1-18.
Davila, M. L. et al. (Apr. 9, 2013). "CD19 CAR-Targeted T Cells Induce Long-Term Remission and B Cell Aplasia in an Immunocompetent Mouse Model of B Cell Acute Lymphoblastic Leukemia", PLOS ONE 8(4):e61338, 14pgs.
Deglon et al., "Self-inactivating lentiviral vectors with enhanced transgene expression as potential gene transfer system in Parkinson's disease," Hum Gene Ther (2000) 11 (1):179-190.
Dienz et al., "The induction of antibody production by IL-6 is indirectly mediated by IL-21 produced by CD4+ T cells," J Exp Med. Jan. 16, 2009;206(1):69-78.
Dobson et al., "Conservation of high efficiency promoter sequences in *Sacchaomyces cerevisiae*," Nucleic Acids Research (1982) 10(8):2625-2637.
Dubel et al., "Bifunctional and multimeric complexes of streptavidin fused to single chain antibodies (scFv)," J Immunol Methods (1995) 178(2):201-209.
Dull et al., "A Third-Generation lentivirus vector with a conditional packaging system," J Virol (1998) 72(11):8463-8471.
Engelman et al., "Multiple effects of mutations in human immunodeficiency virus type 1 integrase on viral replication," J Virol (1995) 69(5):2729-2736.
Fedorov, V.D. et al. (Dec. 11, 2013). "PD-1- and CTLA-4-Based Inhibitory Chimeric Antigen Receptors (iCARs) Divert Off-Target Immunotherapy Responses", Sci. Transl. Med. 5(215):215ra172, 25 pgs.
Frecha et al., "Stable transduction of quiescent T cells without induction of cycle progression by a novel lentiviral vector pseudotyped with measles virus glycoproteins," Gene Therapy (2008) 12(13):4843-4852.
Gattinoni L et al., "Acquisition of full effector function in vitro paradoxically impairs the in vivo antitumor efficacy of adoptively transferred CD8+ T cells," Journal of Clinical Investigation, American Society for Clinical Investigation, US, vol. 115, No. 6, Jun. 1, 2005 pp. 1616-1626.
GenBank Accession No. AF451974.1, submitted Nov. 22, 2001, 2 pages.
Germeroth "IBA T-catch cell isolation in pipette tips" Apr. 23, 2014 Retrieved from the internet: URL:http://x.ymcdn.com/sites/www.celltherapysociety.org/resource/resmgr/2014_AnnualMtgPresentations/T2_L.Germeroth.pdf [Retrieved on Jan. 23, 2017].
Gill et al., "Biopharmaceutical drug discovery using novel protein scaffolds," Curr Opin Biotechnol. Dec. 2006;17(6):653-658.
Godin, J. et al. (Oct. 2008). "Microfluidics and photonics for Bio-System-on-a-Chip: A review of advancements in technology towards a microfluidic flow cytometry chip", J Biophotonics. 1(5):355-376.
Gossen et al., "Tight control of gene expression in mammalian cells by tetracycline-responsive promoters," Proc Natl Acad Sci USA (1992) 89(12):5547-5551.
Guibinga et al., "Ligand-Modified Vesicular Stomatitis Virus Glycoprotein Displays a Temperature-Sensitive Intracellular Trafficking and Virus Assembly Phenotype," Molecular Therapy (2004) 9, 76-84.
Hermans, I.F. et al. (2004). "The VITAL Assay: A Versatile Fluorometric Technique for Assessing CTL- and NKT-mediated Cytotoxicity Against Multiple Targets in Vitro and in Vivo", *J. Immunological Methods* 285(1):25-40.
Holl et al., "Nonneutralizing antibodies are able to inhibit human immunodeficiency virus type 1 replication in macrophages and immature dendritic cells," J Virol (2006) 80(12):6177-6181.
Holliger, P. et al., "Diabodies: small bivalent and bispecific antibody fragments," Proc Natl Acad Sci U S A. Jul. 15, 1993;90(14):6444-6448.
Holt et al., Domain antibodies: proteins for therapy. Trends Biotechnol. Nov. 2003;21(11):484-490.
Hoshino et al., "Activation via the CD3 and CD16 pathway mediates interleukin-2-dependent autocrine proliferation of granular lymphocytes in paiients with granular lymphocyte proliferative disorders," Blood. Dec. 15, 1991;78(12):3232-3240.
Hudecek et al., "Direct tumour recognition and helper function of CD4+ T cells modified to express a CD19-specific CAR in vitro and in a preclinical lymphoma model," Abstract for Presentation, 39th Annual Meeting of the European Group for Blood and Marrow Transplantation, London, UK (Apr. 10, 2013), 1 page.
Hudecek et al., "Receptor affinity and extracellular domain modifications affect tumor recognition by ROR1-specific chimeric antigen receptor T cells," Clin Cancer Res. Jun. 15, 2013;19(12):3153-3164.
Hudson et al., "Engineered Antibodies," Nature Medicine (2003) 9(1):129-133.
Hunziker et al., "Exhaustion of cytotoxic T cells during adoptive immunotherapy of virus carrier mice can be prevented by B cells or CD4+ T cells," Eur J Immunol (2002) 32(2):374-382.
Hutten et al., New magnetic nanoparticles for biotechnology. J Biotechnol. Aug. 26, 2004;112(1-2):47-63.
Iliades et al., "Triabodies: single chain Fv fragments without a linker form trivalent trimers," FEBS Lett. Jun. 16, 1997;409(3):437-441.
Ill et al., "Design and construction of a hybrid immunoglobulin domain with properties of both heavy and light chain variable regions," Protein Eng. Aug. 1997;10(8):949-957.
International Search Report and Written Opinion for PCT/EP2013/053650, dated Oct. 11, 2013.
Kameyama et al., "Antibody-dependent gene transduction using gammaretroviral and lentiviral vectors pseudotyped with chimeric vesicular stomatitis virus glycoprotein," J Virol (2008) 153(1):49-54.
Klebanoff, C.A et al. (Nov. 2012). "Sorting through subsets: Which T cell populations mediate highly effective adoptive immunotherapy? ", J Immunother 35(9):651-660.
Knabel et al., "Reversible MHC multimer staining for functional isolation of T-cell populations and effective adoptive transfer," Nat Med. Jun. 2002;8(6):631-637.
Kochenderfer, J.N. et al. (Sep. 2009). "Construction and Pre-clinical Evaluation of an Anti-CD19 Chimeric Antigen Receptor", J Immunother. 32(7):689-702.
Koste, L. et al. (May 2014, e-pub. Apr. 3, 2014). "T-cell receptor transfer into human T cells with ecotropic retroviral vectors", Gene Ther 21(5):533-538.
Kumar et al., "Cell separation using cryogel-based affinity chromatography",Nature Protocols, Nature Publishing Group, GB, vol. 5, No. 11, Nov. 1, 2010, pp. 1737-1747.
Kumar et al., Affinity binding of cells to cryogel adsorbents with immobilized specific ligands: effect of ligand coupling and matrix architecture. J Mol Recognit. Jan.-Feb. 2005;18(1):84-93.
Kung et al., "A Murine Leukemia Virus (MuLV) Long Terminal Repeat Derived from Rhesus Macaques in the Context of a Lentivirus Vector and MuLV gag Sequence Results in High-Level Gene Expression in Human T Lymphocytes," J Virol (2000) 74(8):3668-3681.
Kwon et al., "Quantitative evaluation of the relative cell permeability of peptoids and peptides," J Am Chem Soc. Feb. 14, 2007;129(6):1508-1509.
Larvor et al., Measurement of the dissociation rate constant of antigen/antibody complexes in solution by enzyme-linked immunosorbent assay. J Immunol Methods. Apr. 15, 1994;170(2):167-175.
Lefrancois, "Protection against lethal viral infection by neutralizing and nonneutralizing monoclonal antibodies: distinct mechanisms of action in vivo," J Virol (1984) 51(1):208-214.
Levin et al., "Optimizing the affinity and specificity of proteins with molecular display," Mol BioSyst (2006) 2:49-57.
Li et al., "Comparison of anti-CD3 and anti-CD28-coated beads with soluble anti-CD3 for expanding human T cells: Differing impact on CD8 T cell phenotype and responsiveness to restimulation," J Transl Med. 2010; 8:104, 15 pages.

(56) References Cited

OTHER PUBLICATIONS

Li et al., "Comparison of inlet geomery in microfluidic cell affinity chromatography," Analytical chemistry (2011) 83(3):774-781.
Li et al., "Negative enrichment of target cells by microfluidic affinity chromatography," Analytical Chemistry (2011) 83(20):7863-7869.
Li et al., "Multiparameter cell affinity chromatography: Separation and analysis in a single microfluidic channel," Anal Chem (2012) 84(19):8140-8148.
Li, Y. et al. (Mar. 2005, e-pub Feb. 20, 2005). "Directed evolution of human T-cell receptors with picomolar affinities by phage display", Nat Biotechnol. 23(3):349-354.
Lindemann et al., "Versatile retrovirus vector systems for regulated gene expression in vitro and in vivo," Mol Med (1997) 3(7):466-476.
Liu et al., "Characterization of TectoRNA Assembly with Cationic Conjugated Polymers," J Am Chem Soc (2004) 126(13):4076-4077.
Lowman, "Bacteriophage display and discovery of peptide leads for drug development," Annu Rev Biophys Biomol Struct. (1997);26:401-424.
Martin et al., "The affinity-selection of a minibody polypeptide inhibitor of human interleukin-6," EMBO J. Nov. 15, 1994;13(22):5303-5309.
McWilliams et al., "Mutations in the 5' end of the human immunodeficiency virus type 1 polypurine tract affect RNase H cleavage specificity and virus titer," J Virol (2003) 77(20): 11150-11157.
Miltenyi et al., High Gradient Magnetic Cell Separation With MACS. Cytometry. 1990;11(2):231-238.
Miyoshi et al. "Development of a self-inactivating lentivirus vector," J Virol (1998) 72(10):8150-8157.
Morizono et al., "A versatile targeting system with lentiviral vectors bearing the biotin-adaptor peptide," J Gene Med. Aug. 2009;11(8):655-63.
Mosavi et al., "The ankyrin repeat as molecular architecture for protein recognition," Protein Sci. Jun. 2004;13(6):1435-1448.
Mullen, C. A. et al. (Jan. 1992). "Transfer of the bacterial gene for cytosine deaminase to mammalian cells confers lethal sensitivity to 5-fluorocytosine: A negative selection system", Proc. Natl. Acad. Sci. USA 89:33-37.
Naldini et al., "Efficient transfer, integration, and sustained long-term expression of the transgene in adult rat brains injected with a lentiviral vector, " Proc Natl Acad Sci USA (1996) 93:11382-11388.
Naldini, "Lentiviruses as gene transfer agents for delivery to nondividing cells," Cum Opin Biotechnol (1998) 9(5):457-463.
Noguchi et al., "Preparation and properties of the immunoconjugate composed of anti-human colon cancer monoclonal antibody and mitomycin C-dextran conjugate," Bioconjug Chem. Mar.-Apr. 1992;3(2):132-7.
Padmanabhan et al., Purification of Transiently Transfected Cells by Magnetic Affinity Cell Sorting. J Immunogenet. Apr. 1989;16(2):91-102.
Park, T. S. et al. (Nov. 2011). "Treating Cancer with Genetically Engineered T Cells", Trends Biotechnol. 29(11):550-557.
Parkhurst, M.R. et al. (Jan. 1, 2009). "Characterization of Genetically Modified T-Cell Receptors that Recognize the CEA:691-699 Peptide in the Context of HLA-A2.1 on Human Colorectal Cancer Cells", Clin. Cancer Res. 15(1):169-180.
Pfeifer et al., "Gene therapy: promises and problems," Annu Rev Genomics Hum Genet (2001) 2:177-211 (Need to buy).
Philpott et al., "Use of Nonintegrating Lentiviral Vectors for Gene Therapy," Human Gene Therapy (2007) 18:483.
Plieva et al., "Characterization of supermacroporous monolithic polyacrylamide based matrices designed for chromatography of bioparticles," Journal of Chromatography (2004) 807(1):129-137.
Powell et al., "Sequence and structural determinants required for priming of plus-strand DNA synthesis by the human immunodeficiency virus type 1 polypurine tract," J Virol (1996) 70(8):5288-5296.
Pullagurla et al., "Parallel affinity-based isolation of leukocyte subsets using microfluidics application for stroke diagnosis," Analytical chemistry (2014) 86(8):4058-4065.
Qiagen: "Strep-tagged Protein Purification Handbook For expressing, purifying, and detecting proteins carrying a Strep-tag II or a 6xHis tag and a Strep-tag II Two-step protein purification system His.Strep pQE-TriSystem Vector Set pQE-TriSystem Strep Vector Strep-Tactin Superflow and Superflow Cartridge", Apr. 1, 2007.
Riddell et al., "Adoptive Therapy with Chimeric Antigen Receptor Modified T Cells of Defined Subset Composition," cancer J. (2014) 20(2): 141-144.
Rodi et al., "Phage-display technology—finding a needle in a vast molecular haystack," Curr Opin Biotechnol. Feb. 1999; 10(1):87-93.
Rosenberg, S.A. (Aug. 2011). "Cell transfer immunotherapy for metastatic solid cancer—what clinicians need to know", 8(10):577-585.
Sabatino et al., "Generation of clinical-grade CD19-specific CAR-modified CD8+ memory stem cells for the treatment of human B-cell malignancies," Blood. Jul. 28, 2016;128(4):519-28.
Sadelain, M. et al. (Apr. 2013, e-pub. Apr. 2, 2013). "The basic principles of chimeric antigen receptor (CAR) design", Cancer Disc. 3(4):388-398.
Schmidt and Skerra, The Strep-tag system for one-step purification and high-affinity detection or capturing of proteins. Nat Protoc. 2007;2(6): 1528-1535.
Schmitt et al., "Adoptive transfer and selective reconstitution of streptamer-selected cytomegalovirus-specific CD8+ T cells leads to virus clearance in patients after allogeneic peripheral blood stem cell transplantation," Transfusion. Mar. 2011;51(3):591-9.
Schroeder, Nach Zellen Angeln. Faszination Forschung Jun. 30, 2010:28-37 Retrieved from the Internet: URL:http://portal.mytum.de/pressestelle/faszination-forschung/2010nr6/index html [retrieved on Nov. 16, 2012]—p. 34-p. 37.
Shockett et al., "A modified tetracycline-regulated system provides autoregulatory, inducible gene expression in cultured cells and transgenic mice," PNAS (1995) 92(14):6522-6526.
Silverman et al., "Multivalent avimer proteins evolved by exon shuffling of a family of human receptor domains," Nat Biotechnol. Dec. 2005;23(12):1556-61.
Singer-Sam et al., "Sequence of the promoter region of the gene for human X-linked 3-phosphoglycerate kinase," Gene (1984) 32(3):409-417.
Skerra et al., "Applications of a Peptide Ligand for Streptavidin: The Strep-Tag," Biomolecular Engineer (1999) 16(1-4):79-86.
Skerra, "Engineered protein scaffolds for molecular recognition," J Mol Recognit. Jul.-Aug. 2000;13(4):167-87.
Smith et al., "Ex vivo expansion of human T cells for adoptive immunotherapy using the novel Xeno-free CTS Immune Cell Serum Replacement," Clinical & Translational Immunology (2015) 4:e31.
Stemberger et al., Novel Serial Positive Enrichment Technology Enables Clinical Multiparameter Cell Sorting. PLoS One. 2012;7(4):e35798 (11 pp).
Stone et al., "The assembly of single domain antibodies into bispecific decavalent molecules," J Immunol Methods. Jan. 10, 2007;318(1-2):88-94.
Szoka et al., "Comparative properties and methods of preparation of lipid vesicles (liposomes)," Annu Rev Biophy Bioeng (1980) 9:467-508.
Terakura, S. et al. (Jan. 5, 2012, e-pub. Oct. 26, 2011). "Generation of CD19-chimeric antigen receptor modified CD8+ T cells derived from virus-specific central memory T cells", Blood 119(1)72-82.
Themeli, M. et al. (Oct. 2013, e-pub. Aug. 11, 2013). "Generation of tumor-targeted human T Tymphocytes from induced pluripotent stem cells for cancer therapy", Nat Biotechnol. 31 (10):928-933.
ThermoFisher Scientific, Avidin-Biotein Interaction, retrieved from https://www.thermofisher.com/us/en/home/life-science/protein-biology/protein-biology-learning-center/protein-biology-resource-library/pierce-protein-methods/avidin-biotin-interaction.html on Apr. 9, 2019, pp. 1-7.

(56) References Cited

OTHER PUBLICATIONS

Thomsen et al., "Promoter-regulatory region of the major immediate early gene of human cytomegalovirus," Proc Natl Acad Sci USA (1984) 81(3):659-663.
Traunecker et al., "Janusin: new molecular design for bispecific reagents," Int J Cancer Suppl. (1992);7:51-2.
Tsukahara, T. et al. (Aug. 16, 2013, Jul. 17, 2013). "CD19 target-engineered T-cells accumulate at tumor lesions in human B-cell lymphoma xenograft mouse models", 438(1):84-89.
Tumaini et al., "Simplified process for the production of anti-CD19-CAR-engineered T cells," Cytotherapy. Nov. 2013;15(11):1406-15.
Turtle, C.J. et al., "CD19 CAR-T cells of defined CD4+:CD8+ composition in adult B cell ALL patients," The Journal of Clinical Investigation, vol. 126, No. 6, Jun. 2016 pp. 2123-2138.
Turtle, C.J et al. (Oct. 2012, e-pub. Jul. 18, 2012). "Engineered T cells For Anti-Cancer Therapy", Curr. Opin. Immunol. 24(5):633-639.
Vanhove et al., "Selective blockade of CD28 and not CTLA-4 with a single-chain Fv-alpha1-antitrypsin fusion antibody," Blood. Jul. 15, 2003;102(2):564-570.
Varela-Rohena, A. et al. (Dec. 2008). "Control of HIV-1 immune escape by CD8 T-cells expressing enhanced T-cell receptor", Nat. Med. 14(12): 1390-1395.
Verhoeyen et al., "IL-7 surface-engineered lentiviral vectors promote survival and efficient gene transfer in resting primary T lymphocytes," Blood (2003) 101(6):2167-2174.
Vitale et al., "NK-active cytokines IL-2, IL-12, and IL-15 selectively modulate specific protein kinase C (PKC) isoforms in primary human NK cells," Anat Rec. Feb. 1, 2002;266(2):87-92.
Voss, S. et al. (1997). "Mutagenesis of a flexible loop in Streptavidin Leads to Higher Affinity for the *Strep*-tag II Peptide and Improved Performance in Recombinant Protein Purification", Protein Engineering 10(8):975-982.
Wadhwa et al., "Receptor Mediated Glycotargeting," J. Drug Targeting (1995) 3:111.
Wang et al., "Clinical manufacturing of CAR T cells: foundation of a promising therapy," Mol Ther Oncolytics (2016) 3:16015.
Wang et al., "Phenotypic and functional attributes of lentivirus-modified CD19-specific human CD8+ central memory T cells manufactured at clinical scale," J Immunother. (2012) 35(9):689-701.
Wang et al.. Database Biosis. Database accession No. PREV200900325303.Abstract Only Mar. 2009: 1 page.
Wang et al., Generation of leukaemia antigen-specific donor lymphocyte infusions powered by streptamer-based selection. Bone Marrow Transplantation Mar. 2009;43(Suppl1):S73.
Wang et al., Open-Tubular Capillary Cell Affinity Chromatography: Single and Tandem Blood Cell Separation. Anal Chem. Mar. 15, 2008;80(6):2118-2124.
Wang et al., "Streptamer-based selection of WT1-specific CD8+ T cells for specific donor lymphocyte infusions",Experimental Hematology, vol. 38, No. 11, Nov. 1, 2010 (Nov. 1, 2010), pp. 1066-1073.
Wilson et al., "The use of mRNA display to select high-affinity protein-binding peptides," Proc Natl Acad Sci U S A. Mar. 27, 2001;98(7):3750-5.
Wu, R. et al. (Mar. 2012). "Adoptive T-cell Therapy Using Autologous Tumor-infiltrating Lymphocytes for Metastatic Melanoma: Current Status and Future Outlook", Cancer J. 18(2):160-175.
Xu et al., Aptamer-Based Microfluidic Device for Enrichment, Sorting, and Detection of Multiple Cancer Cells. Anal Chem. Sep. 1, 2009;81(17)7436-7442.
Yang et al., "Targeting lentiviral vectors to specific cell types in vivo," PNAS USA (2006) 103(31): 11479-11484.
Zhang et al., "CD137 promotes proliferation and survival of human B cells," J Immunol. Jan. 15, 2010; 184(2)787-95.
Zhou X et al., "Lentivirus-mediated gene transfer and expression in established human tumor antigen-specific cytotoxic T cells and primayr unstimulated T cels," Human Gene Therapy, vol. 14 No. 11, Jul. 20, 2003 pp. 1089-1105.
Zufferey et al. "Self-Inactivating Lentivirus Vector for Safe and Efficient In Vivo Gene Delivery," J. Virol (1998) 72(12):9873-9880.
Zufferey et al., "Woodchuck Hepatitis Virus Posttranscriptional Regulatory Element Enhances Expression of Transgenes Delivered by Retroviral Vectors," J Virol (1999) 73(4):2886-2892.
Qureshi et al., "Development and characterization of a series of soluble tetrameric and monomeric streptavidin muteins with differential biotin binding affinities," The Journal of Biological Chemistry (2001) 276(49):46422-46428.
Sun et al., "Plug-and-go strategy to manipulate streptavidin valencies," Bioconjugate Chem (2014) 25:1375-1380.

\* cited by examiner

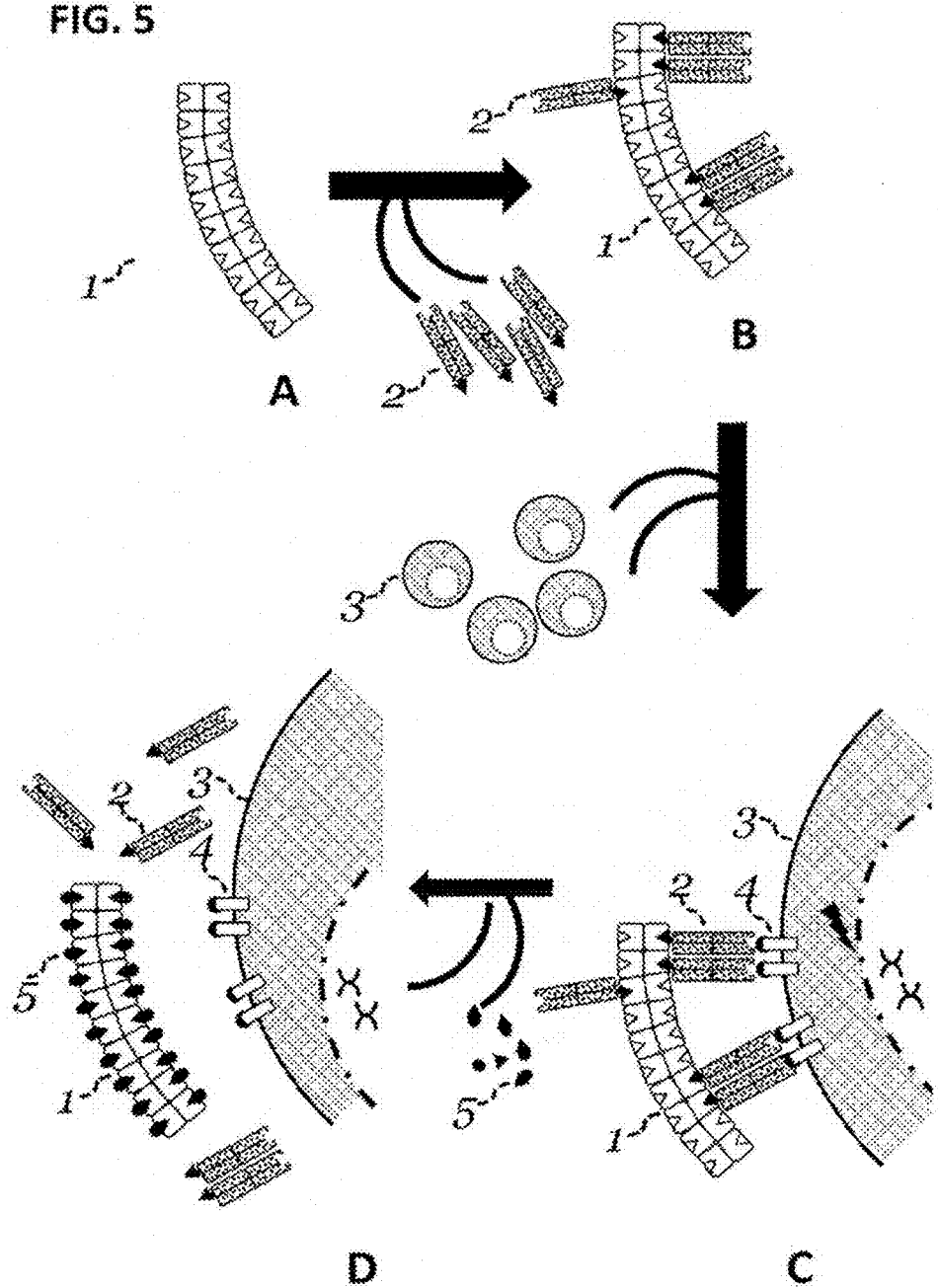

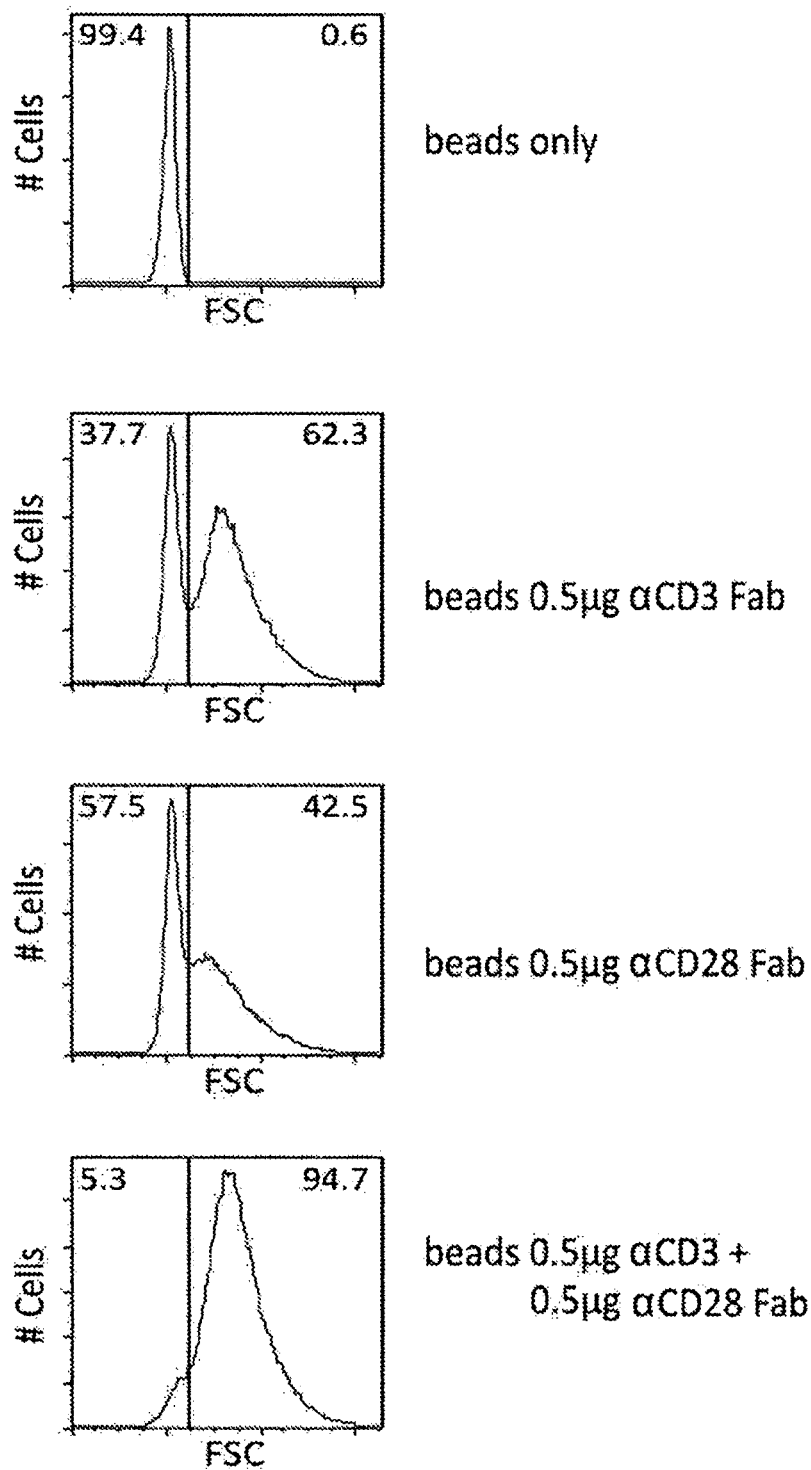

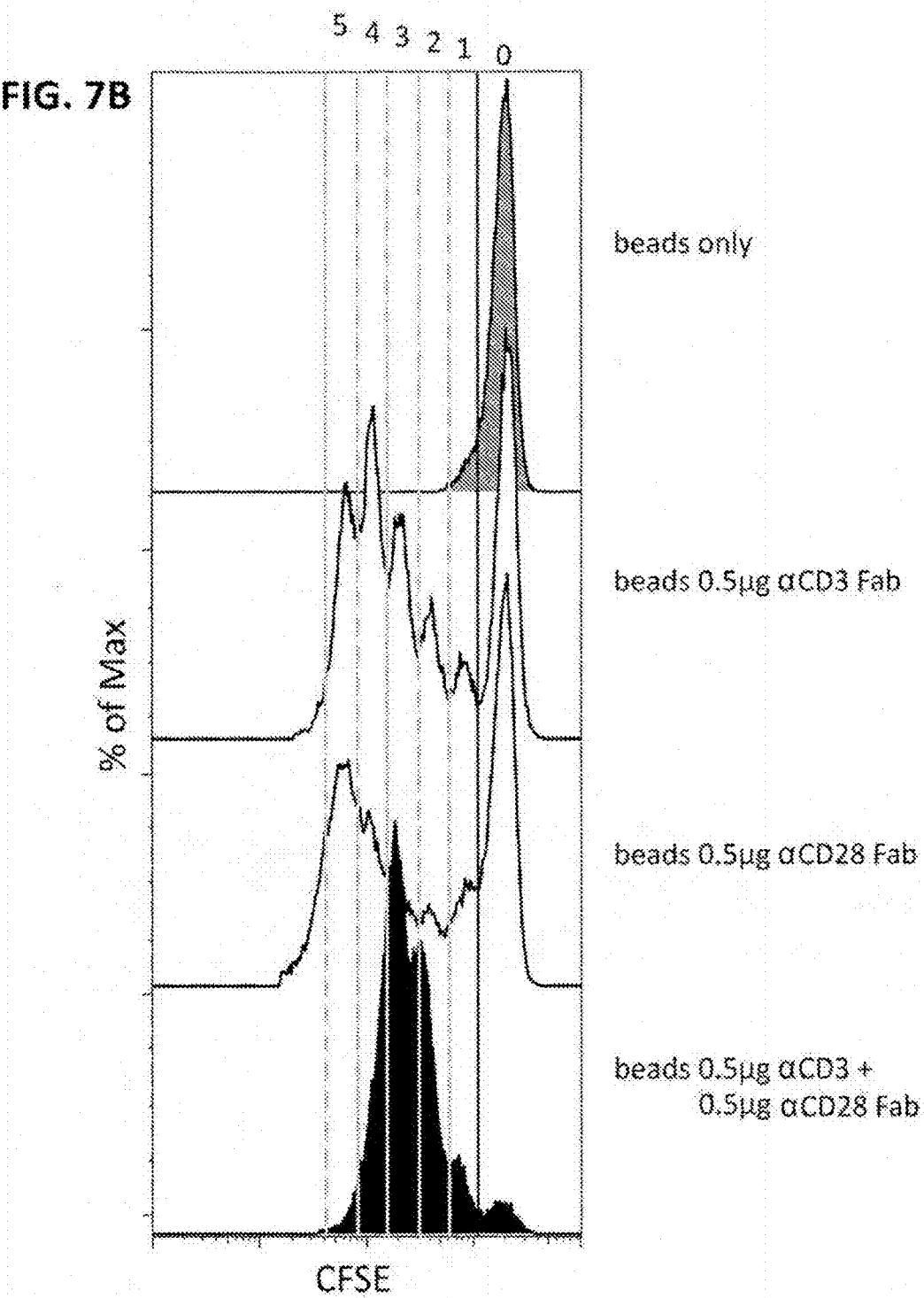

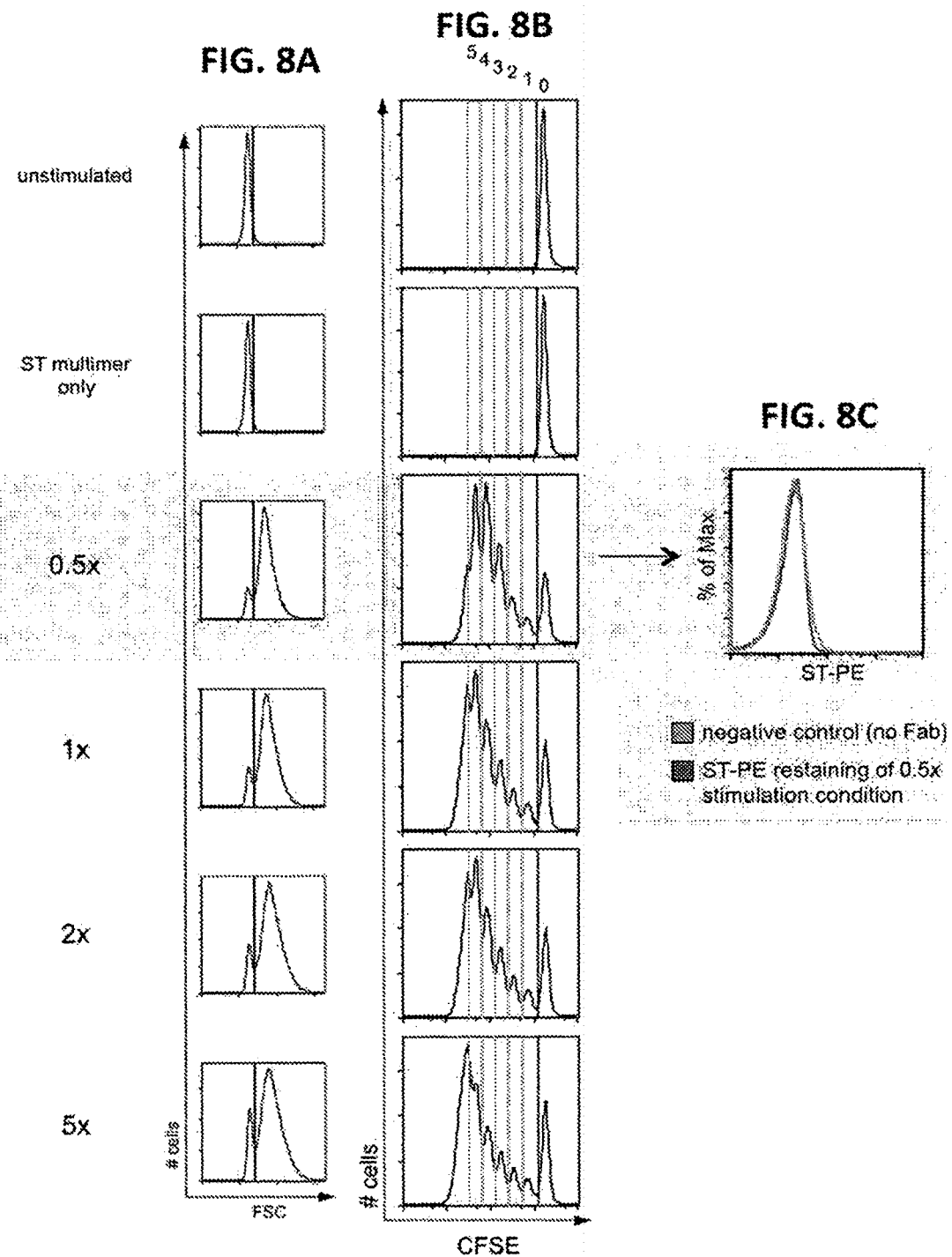

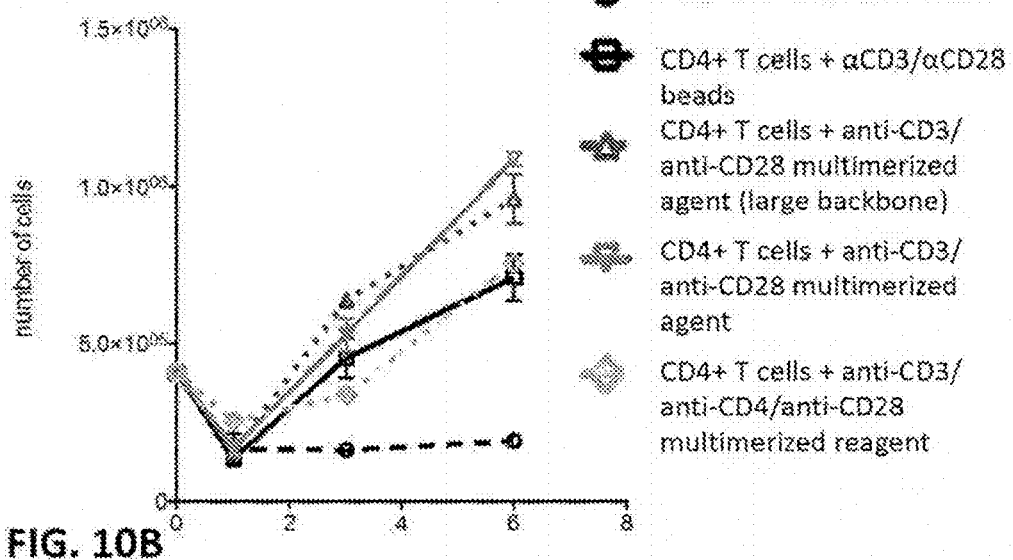
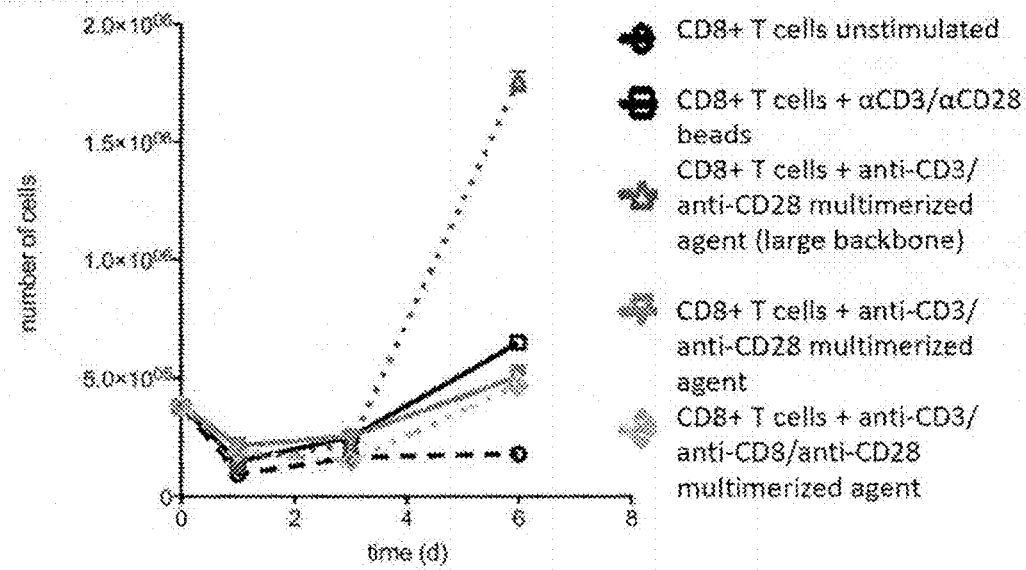

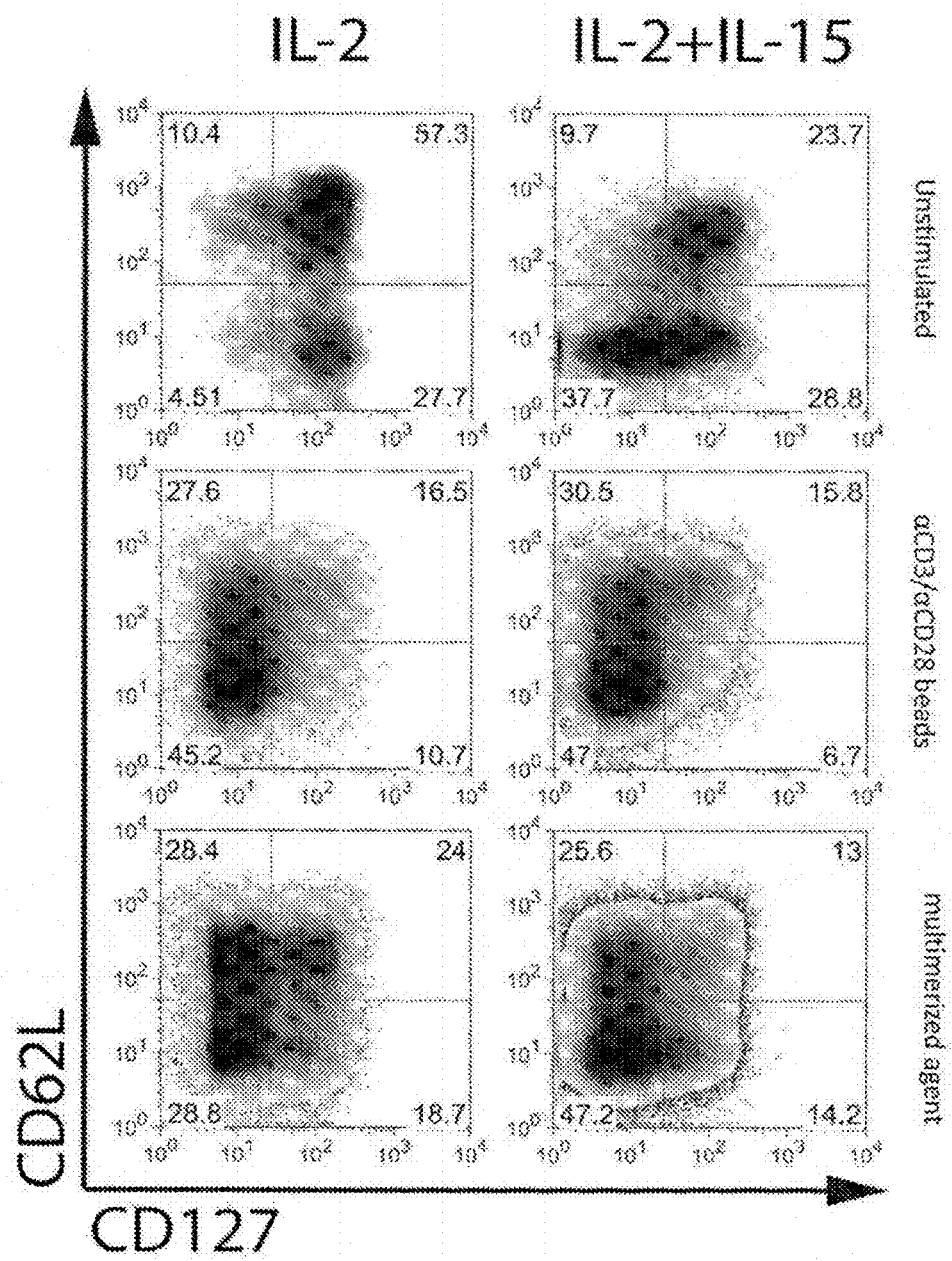

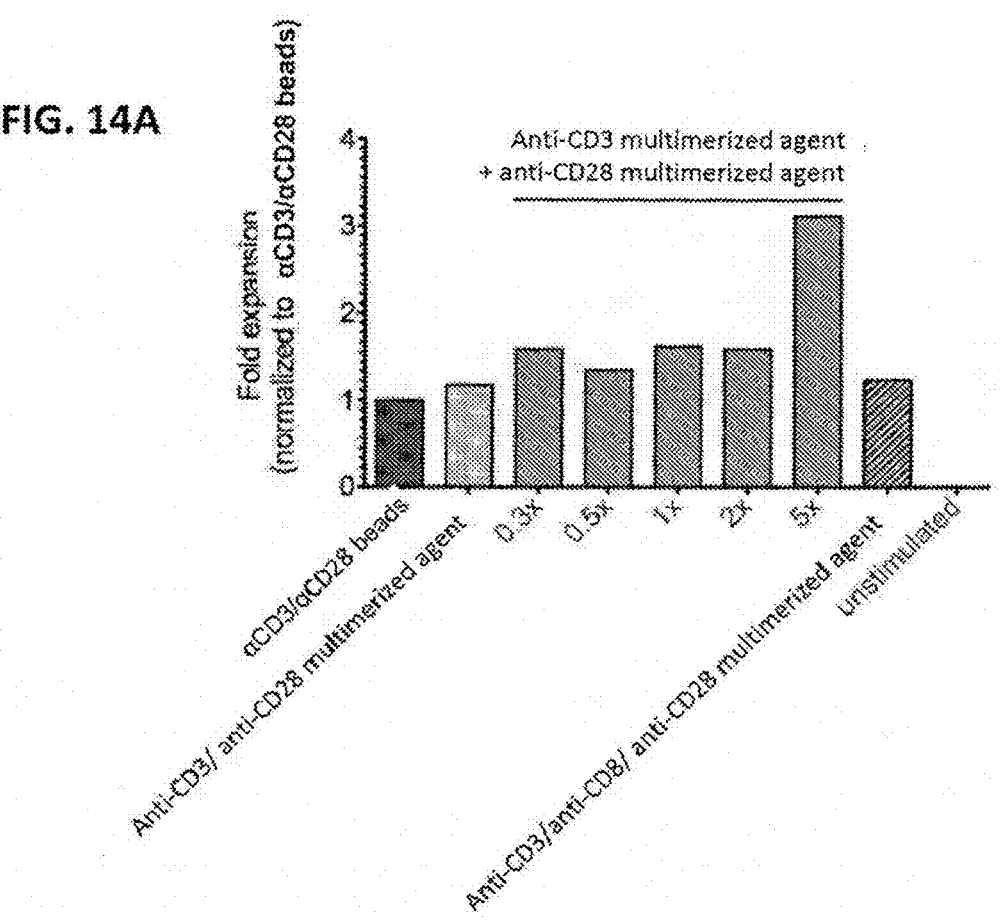

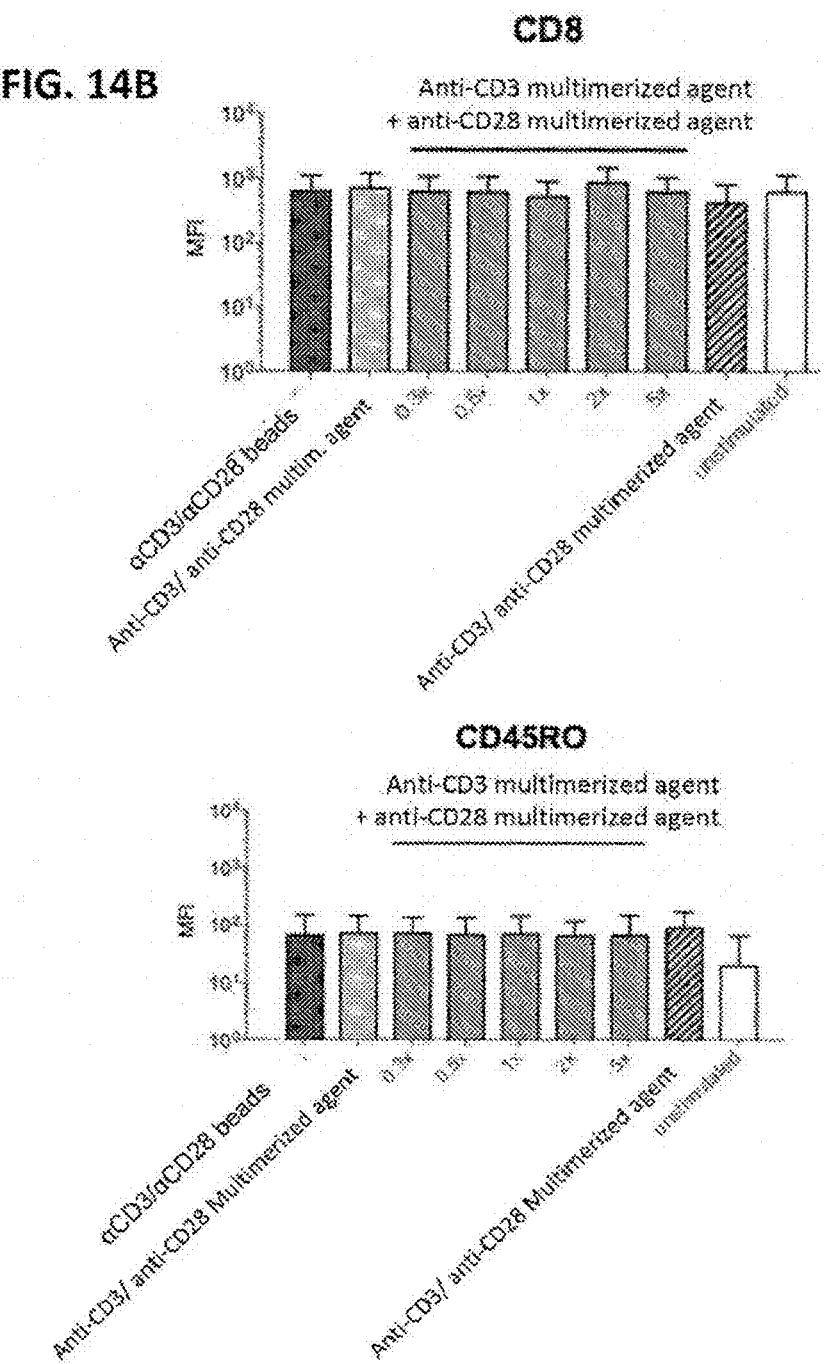

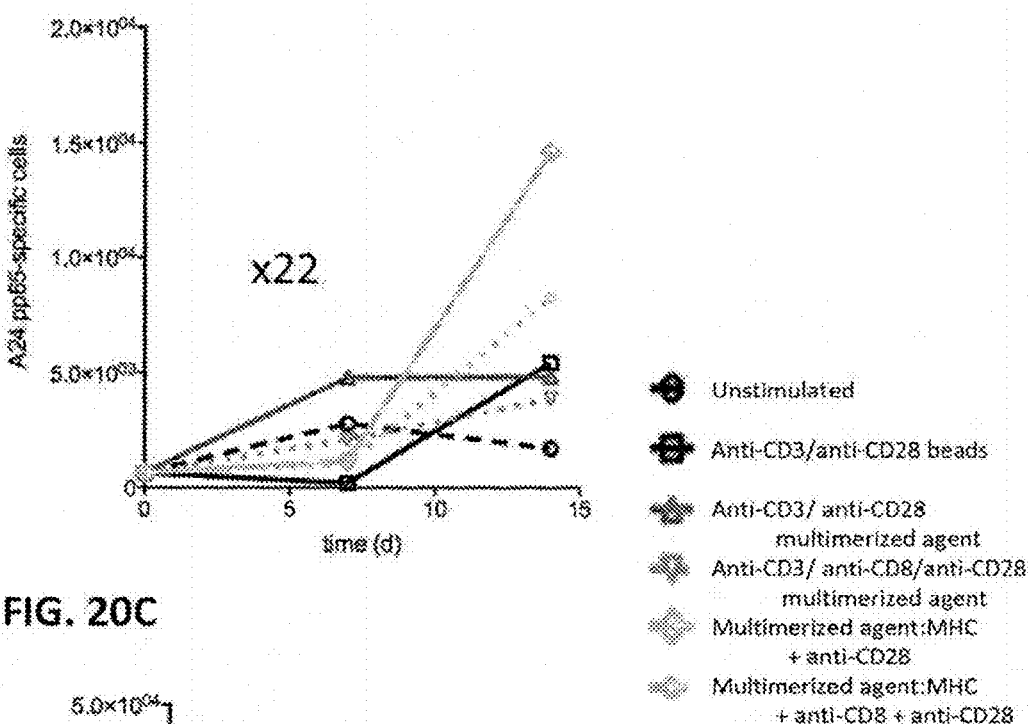
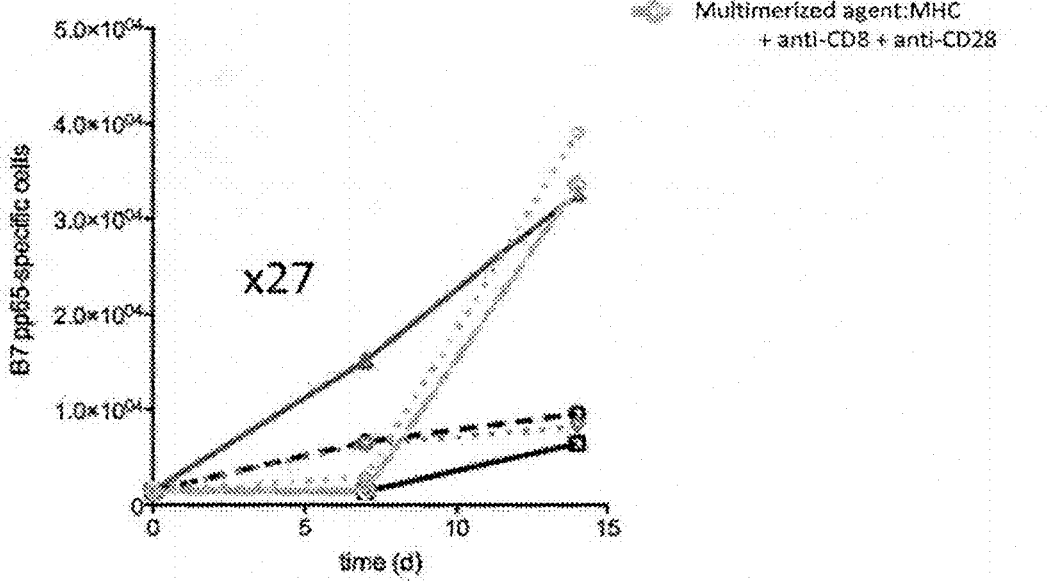

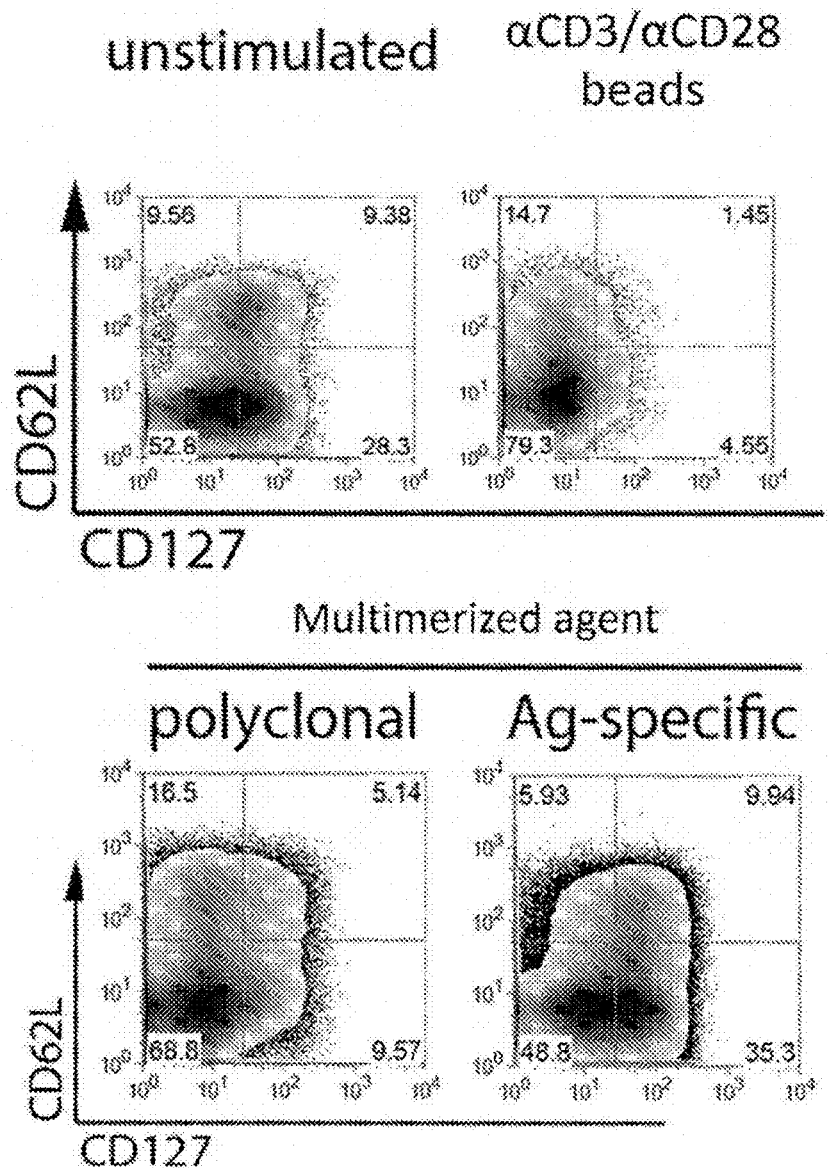

SEQUENCE LISTING

<160> NUMBER OF SEQ ID NOS: 49

<210> SEQ ID NO 1
<211> LENGTH: 159
<212> TYPE: PRT
<213> ORGANISM: Streptomyces avidinii
<220> FEATURE:
<223> OTHER INFORMATION: Streptavidin
<300> PUBLICATION INFORMATION:
<308> DATABASE ACCESSION NUMBER: UniProt No. P22629
<309> DATABASE ENTRY DATE: 1991-08-01

<400> SEQUENCE: 1

Asp Pro Ser Lys Asp Ser Lys Ala Gln Val Ser Ala Ala Glu Ala Gly
1               5                   10                  15

Ile Thr Gly Thr Trp Tyr Asn Gln Leu Gly Ser Thr Phe Ile Val Thr
            20                  25                  30

Ala Gly Ala Asp Gly Ala Leu Thr Gly Thr Tyr Glu Ser Ala Val Gly
        35                  40                  45

Asn Ala Glu Ser Arg Tyr Val Leu Thr Gly Arg Tyr Asp Ser Ala Pro
    50                  55                  60

Ala Thr Asp Gly Ser Gly Thr Ala Leu Gly Trp Thr Val Ala Trp Lys
65                  70                  75                  80

Asn Asn Tyr Arg Asn Ala His Ser Ala Thr Thr Trp Ser Gly Gln Tyr
                85                  90                  95

Val Gly Gly Ala Glu Ala Arg Ile Asn Thr Gln Trp Leu Leu Thr Ser
            100                 105                 110

Gly Thr Thr Glu Ala Asn Ala Trp Lys Ser Thr Leu Val Gly His Asp
        115                 120                 125

Thr Phe Thr Lys Val Lys Pro Ser Ala Ala Ser Ile Asp Ala Ala Lys
    130                 135                 140

Lys Ala Gly Val Asn Asn Gly Asn Pro Leu Asp Ala Val Gln Gln
145                 150                 155

<210> SEQ ID NO 2
<211> LENGTH: 126
<212> TYPE: PRT
<213> ORGANISM: Streptomyces avidinii
<220> FEATURE:
<223> OTHER INFORMATION: Minimal streptavidin

<400> SEQUENCE: 2

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Glu Ser
            20                  25                  30

Ala Val Gly Asn Ala Glu Ser Arg Tyr Val Leu Thr Gly Arg Tyr Asp
        35                  40                  45

Ser Ala Pro Ala Thr Asp Gly Ser Gly Thr Ala Leu Gly Trp Thr Val
    50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Ala Asn Ala Trp Lys Ser Thr Leu Val
            100                 105                 110

Gly His Asp Thr Phe Thr Lys Val Lys Pro Ser Ala Ala Ser
        115                 120                 125

<210> SEQ ID NO 3
<211> LENGTH: 159
<212> TYPE: PRT
<213> ORGANISM: Streptomyces avidinii
<220> FEATURE:
<223> OTHER INFORMATION: Mutein Streptavidin Val44-Thr45-Ala46-Arg47

<400> SEQUENCE: 3

```
Asp Pro Ser Lys Asp Ser Lys Ala Gln Val Ser Ala Ala Glu Ala Gly
1               5                   10                  15

Ile Thr Gly Thr Trp Tyr Asn Gln Leu Gly Ser Thr Phe Ile Val Thr
            20                  25                  30

Ala Gly Ala Asp Gly Ala Leu Thr Gly Thr Tyr Val Thr Ala Arg Gly
        35                  40                  45

Asn Ala Glu Ser Arg Tyr Val Leu Thr Gly Arg Tyr Asp Ser Ala Pro
    50                  55                  60

Ala Thr Asp Gly Ser Gly Thr Ala Leu Gly Trp Thr Val Ala Trp Lys
65                  70                  75                  80

Asn Asn Tyr Arg Asn Ala His Ser Ala Thr Thr Trp Ser Gly Gln Tyr
                85                  90                  95

Val Gly Gly Ala Glu Ala Arg Ile Asn Thr Gln Trp Leu Leu Thr Ser
            100                 105                 110

Gly Thr Thr Glu Ala Asn Ala Trp Lys Ser Thr Leu Val Gly His Asp
        115                 120                 125

Thr Phe Thr Lys Val Lys Pro Ser Ala Ala Ser Ile Asp Ala Ala Lys
    130                 135                 140

Lys Ala Gly Val Asn Asn Gly Asn Pro Leu Asp Ala Val Gln Gln
145                 150                 155
```

<210> SEQ ID NO 4
<211> LENGTH: 126
<212> TYPE: PRT
<213> ORGANISM: Streptomyces avidinii
<220> FEATURE:
<223> OTHER INFORMATION: Mutein Streptavidin Val44-Thr45-Ala46-Arg47

<400> SEQUENCE: 4

```
Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Val Thr
            20                  25                  30

Ala Arg Gly Asn Ala Glu Ser Arg Tyr Val Leu Thr Gly Arg Tyr Asp
        35                  40                  45

Ser Ala Pro Ala Thr Asp Gly Ser Gly Thr Ala Leu Gly Trp Thr Val
    50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Ala Asn Ala Trp Lys Ser Thr Leu Val
            100                 105                 110

Gly His Asp Thr Phe Thr Lys Val Lys Pro Ser Ala Ala Ser
        115                 120                 125
```

<210> SEQ ID NO 5
<211> LENGTH: 159
<212> TYPE: PRT
<213> ORGANISM: Streptomyces avidinii

```
<220> FEATURE:
<223> OTHER INFORMATION: Mutein Streptavidin Ile44-Gly45-Ala-46-Arg47

<400> SEQUENCE: 5

Asp Pro Ser Lys Asp Ser Lys Ala Gln Val Ser Ala Ala Glu Ala Gly
1               5                   10                  15

Ile Thr Gly Thr Trp Tyr Asn Gln Leu Gly Ser Thr Phe Ile Val Thr
            20                  25                  30

Ala Gly Ala Asp Gly Ala Leu Thr Gly Thr Tyr Ile Gly Ala Arg Gly
        35                  40                  45

Asn Ala Glu Ser Arg Tyr Val Leu Thr Gly Arg Tyr Asp Ser Ala Pro
50                  55                  60

Ala Thr Asp Gly Ser Gly Thr Ala Leu Gly Trp Thr Val Ala Trp Lys
65                  70                  75                  80

Asn Asn Tyr Arg Asn Ala His Ser Ala Thr Thr Trp Ser Gly Gln Tyr
                85                  90                  95

Val Gly Gly Ala Glu Ala Arg Ile Asn Thr Gln Trp Leu Leu Thr Ser
            100                 105                 110

Gly Thr Thr Glu Ala Asn Ala Trp Lys Ser Thr Leu Val Gly His Asp
        115                 120                 125

Thr Phe Thr Lys Val Lys Pro Ser Ala Ala Ser Ile Asp Ala Ala Lys
    130                 135                 140

Lys Ala Gly Val Asn Asn Gly Asn Pro Leu Asp Ala Val Gln Gln
145                 150                 155

<210> SEQ ID NO 6
<211> LENGTH: 126
<212> TYPE: PRT
<213> ORGANISM: Streptomyces avidinii
<220> FEATURE:
<223> OTHER INFORMATION: Mutein Streptavidin Ile44-Gly45-Ala-46-Arg47

<400> SEQUENCE: 6

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Ile Gly
            20                  25                  30

Ala Arg Gly Asn Ala Glu Ser Arg Tyr Val Leu Thr Gly Arg Tyr Asp
        35                  40                  45

Ser Ala Pro Ala Thr Asp Gly Ser Gly Thr Ala Leu Gly Trp Thr Val
    50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Ala Asn Ala Trp Lys Ser Thr Leu Val
            100                 105                 110

Gly His Asp Thr Phe Thr Lys Val Lys Pro Ser Ala Ala Ser
        115                 120                 125

<210> SEQ ID NO 7
<211> LENGTH: 8
<212> TYPE: PRT
<213> ORGANISM: Artificial Sequence
<220> FEATURE:
<223> OTHER INFORMATION: Streptavidin binding peptide, Strep-tag

<400> SEQUENCE: 7
```

```
Trp Arg His Pro Gln Phe Gly Gly
1               5

<210> SEQ ID NO 8
<211> LENGTH: 8
<212> TYPE: PRT
<213> ORGANISM: Artificial Sequence
<220> FEATURE:
<223> OTHER INFORMATION: Strep-tag II

<400> SEQUENCE: 8

Trp Ser His Pro Gln Phe Glu Lys
1               5

<210> SEQ ID NO 9
<211> LENGTH: 3
<212> TYPE: PRT
<213> ORGANISM: Artificial Sequence
<220> FEATURE:
<223> OTHER INFORMATION: Streptavidin Binding peptide
<220> FEATURE:
<221> NAME/KEY: VARIANT
<222> LOCATION: (3)...(3)
<223> OTHER INFORMATION: Xaa is Gln, Asp, or Met

<400> SEQUENCE: 9

His Pro Xaa
1

<210> SEQ ID NO 10
<211> LENGTH: 4
<212> TYPE: PRT
<213> ORGANISM: Artificial Sequence
<220> FEATURE:
<223> OTHER INFORMATION: Streptavidin Binding peptide

<400> SEQUENCE: 10

His Pro Gln Phe
1

<210> SEQ ID NO 11
<211> LENGTH: 8
<212> TYPE: PRT
<213> ORGANISM: Artificial Sequence
<220> FEATURE:
<223> OTHER INFORMATION: Streptavidin Binding peptide
<220> FEATURE:
<221> NAME/KEY: VARIANT
<222> LOCATION: (1)...(1)
<223> OTHER INFORMATION: Xaa is Trp, Lys or Arg
<220> FEATURE:
<221> NAME/KEY: VARIANT
<222> LOCATION: (2)...(2)
<223> OTHER INFORMATION: Xaa is any amino acid
<220> FEATURE:
<221> NAME/KEY: VARIANT
<222> LOCATION: (7)...(7)
<223> OTHER INFORMATION: Xaa is Gly or Glu
<220> FEATURE:
<221> NAME/KEY: VARIANT
<222> LOCATION: (8)...(8)
<223> OTHER INFORMATION: Xaa is Gly, Lys or Arg

<400> SEQUENCE: 11

Xaa Xaa His Pro Gln Phe Xaa Xaa
1               5

<210> SEQ ID NO 12
<211> LENGTH: 8
<212> TYPE: PRT
```

```
<213> ORGANISM: Artificial Sequence
<220> FEATURE:
<223> OTHER INFORMATION: Streptavidin Binding peptide
<220> FEATURE:
<221> NAME/KEY: VARIANT
<222> LOCATION: (2)...(2)
<223> OTHER INFORMATION: Xaa is any amino acid
<220> FEATURE:
<221> NAME/KEY: VARIANT
<222> LOCATION: (7)...(7)
<223> OTHER INFORMATION: Xaa is Gly or Glu
<220> FEATURE:
<221> NAME/KEY: VARIANT
<222> LOCATION: (8)...(8)
<223> OTHER INFORMATION: Xaa is Gly, Lys or Arg

<400> SEQUENCE: 12

Trp Xaa His Pro Gln Phe Xaa Xaa
1               5

<210> SEQ ID NO 13
<211> LENGTH: 28
<212> TYPE: PRT
<213> ORGANISM: Artificial Sequence
<220> FEATURE:
<223> OTHER INFORMATION: Sequential modules of streptavidin-binding
      peptide
<220> FEATURE:
<221> NAME/KEY: VARIANT
<222> LOCATION: (9)...(9)
<223> OTHER INFORMATION: Xaa is any amino acid
<220> FEATURE:
<221> NAME/KEY: VARIANT
<222> LOCATION: (10)...(10)
<223> OTHER INFORMATION: Xaa is any amino acid
<220> FEATURE:
<221> NAME/KEY: VARIANT
<222> LOCATION: (11)...(11)
<223> OTHER INFORMATION: Xaa is any amino acid
<220> FEATURE:
<221> NAME/KEY: VARIANT
<222> LOCATION: (12)...(12)
<223> OTHER INFORMATION: Xaa is any amino acid
<220> FEATURE:
<221> NAME/KEY: VARIANT
<222> LOCATION: (13)...(13)
<223> OTHER INFORMATION: Xaa is any amino acid
<220> FEATURE:
<221> NAME/KEY: VARIANT
<222> LOCATION: (14)...(14)
<223> OTHER INFORMATION: Xaa is any amino acid
<220> FEATURE:
<221> NAME/KEY: VARIANT
<222> LOCATION: (15)...(15)
<223> OTHER INFORMATION: Xaa is any amino acid
<220> FEATURE:
<221> NAME/KEY: VARIANT
<222> LOCATION: (16)...(16)
<223> OTHER INFORMATION: Xaa is any amino acid
<220> FEATURE:
<221> NAME/KEY: VARIANT
<222> LOCATION: (17)...(17)
<223> OTHER INFORMATION: Xaa is any amino acid or null
<220> FEATURE:
<221> NAME/KEY: VARIANT
<222> LOCATION: (18)...(18)
<223> OTHER INFORMATION: If Xaa at position 17 is any amino acid, then
      Xaa at position 18 is any amino acid. If Xaa at
      position 17 is null, then Xaa at position 18 is
      null
<220> FEATURE:
<221> NAME/KEY: VARIANT
<222> LOCATION: (19)...(19)
<223> OTHER INFORMATION: If Xaa at position 17 is any amino acid, then
      Xaa at position 19 is any amino acid. If Xaa at
      position 17 is null, then Xaa at position 19 is
      null
```

```
<220> FEATURE:
<221> NAME/KEY: VARIANT
<222> LOCATION: (20)...(20)
<223> OTHER INFORMATION: If Xaa at position 17 is any amino acid, then
      Xaa at position 20 is any amino acid. If Xaa at
      position 17 is null, then Xaa at position 20 is
      null

<400> SEQUENCE: 13

Trp Ser His Pro Gln Phe Glu Lys Xaa Xaa Xaa Xaa Xaa Xaa Xaa
1               5                   10                  15

Xaa Xaa Xaa Xaa Trp Ser His Pro Gln Phe Glu Lys
            20                  25

<210> SEQ ID NO 14
<211> LENGTH: 28
<212> TYPE: PRT
<213> ORGANISM: Artificial Sequence
<220> FEATURE:
<223> OTHER INFORMATION: Sequential modules of streptavidin-binding
      peptide
<220> FEATURE:
<221> NAME/KEY: VARIANT
<222> LOCATION: (17)...(17)
<223> OTHER INFORMATION: Xaa is Gly or null
<220> FEATURE:
<221> NAME/KEY: VARIANT
<222> LOCATION: (18)...(18)
<223> OTHER INFORMATION: If Xaa at position 17 is Gly, then Xaa at
      position 18 is Gly. If Xaa at position 17 is null, then Xaa
      at position 18 is null.
<220> FEATURE:
<221> NAME/KEY: VARIANT
<222> LOCATION: (19)...(19)
<223> OTHER INFORMATION: If Xaa at position 17 is Gly, then Xaa at
      position 19 is Gly. If Xaa at position 17 is null, then Xaa
      at position 19 is null.
<220> FEATURE:
<221> NAME/KEY: VARIANT
<222> LOCATION: (20)...(20)
<223> OTHER INFORMATION: If Xaa at position 17 is Gly, then Xaa at
      position 20 is Gly. If Xaa at position 17 is null, then Xaa
      at position 20 is null.

<400> SEQUENCE: 14

Trp Ser His Pro Gln Phe Glu Lys Gly Gly Gly Ser Gly Gly Gly Ser
1               5                   10                  15

Xaa Xaa Xaa Xaa Trp Ser His Pro Gln Phe Glu Lys
            20                  25

<210> SEQ ID NO 15
<211> LENGTH: 30
<212> TYPE: PRT
<213> ORGANISM: Artificial Sequence
<220> FEATURE:
<223> OTHER INFORMATION: Twin-Strep-tag

<400> SEQUENCE: 15

Ser Ala Trp Ser His Pro Gln Phe Glu Lys Gly Gly Gly Ser Gly Gly
1               5                   10                  15

Gly Ser Gly Gly Gly Ser Trp Ser His Pro Gln Phe Glu Lys
            20                  25                  30

<210> SEQ ID NO 16
<211> LENGTH: 30
<212> TYPE: PRT
<213> ORGANISM: Artificial Sequence
<220> FEATURE:
<223> OTHER INFORMATION: Twin-Strep-tag
```

```
<400> SEQUENCE: 16

Ser Ala Trp Ser His Pro Gln Phe Glu Lys Gly Gly Gly Ser Gly
1               5                   10                  15

Gly Ser Gly Gly Ser Ala Trp Ser His Pro Gln Phe Glu Lys
            20                  25                  30

<210> SEQ ID NO 17
<211> LENGTH: 28
<212> TYPE: PRT
<213> ORGANISM: Artificial Sequence
<220> FEATURE:
<223> OTHER INFORMATION: Twin-Strep-tag

<400> SEQUENCE: 17

Trp Ser His Pro Gln Phe Glu Lys Gly Gly Gly Ser Gly Gly Ser
1               5                   10                  15

Gly Gly Gly Ser Trp Ser His Pro Gln Phe Glu Lys
            20                  25

<210> SEQ ID NO 18
<211> LENGTH: 24
<212> TYPE: PRT
<213> ORGANISM: Artificial Sequence
<220> FEATURE:
<223> OTHER INFORMATION: Twin-Strep-tag

<400> SEQUENCE: 18

Trp Ser His Pro Gln Phe Glu Lys Gly Gly Gly Ser Gly Gly Ser
1               5                   10                  15

Trp Ser His Pro Gln Phe Glu Lys
            20

<210> SEQ ID NO 19
<211> LENGTH: 28
<212> TYPE: PRT
<213> ORGANISM: Artificial Sequence
<220> FEATURE:
<223> OTHER INFORMATION: Twin-Strep-tag

<400> SEQUENCE: 19

Trp Ser His Pro Gln Phe Glu Lys Gly Gly Gly Ser Gly Gly Ser
1               5                   10                  15

Gly Gly Ser Ala Trp Ser His Pro Gln Phe Glu Lys
            20                  25

<210> SEQ ID NO 20
<211> LENGTH: 9
<212> TYPE: PRT
<213> ORGANISM: Artificial Sequence
<220> FEATURE:
<223> OTHER INFORMATION: HA-tag

<400> SEQUENCE: 20

Tyr Pro Tyr Asp Val Pro Asp Tyr Ala
1               5

<210> SEQ ID NO 21
<211> LENGTH: 11
<212> TYPE: PRT
<213> ORGANISM: Artificial Sequence
<220> FEATURE:
<223> OTHER INFORMATION: VSV-G-tag

<400> SEQUENCE: 21
```

Tyr Thr Asp Ile Glu Met Asn Arg Leu Gly Lys
1               5                   10

<210> SEQ ID NO 22
<211> LENGTH: 11
<212> TYPE: PRT
<213> ORGANISM: Artificial Sequence
<220> FEATURE:
<223> OTHER INFORMATION: HSV-tag

<400> SEQUENCE: 22

Gln Pro Glu Leu Ala Pro Glu Asp Pro Glu Asp
1               5                   10

<210> SEQ ID NO 23
<211> LENGTH: 10
<212> TYPE: PRT
<213> ORGANISM: Artificial Sequence
<220> FEATURE:
<223> OTHER INFORMATION: T7 epitope

<400> SEQUENCE: 23

Ala Ser Met Thr Gly Gly Gln Gln Met Gly
1               5                   10

<210> SEQ ID NO 24
<211> LENGTH: 11
<212> TYPE: PRT
<213> ORGANISM: Artificial Sequence
<220> FEATURE:
<223> OTHER INFORMATION: HSV epitope

<400> SEQUENCE: 24

Gln Pro Glu Leu Ala Pro Glu Asp Pro Glu Asp
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Myc epitope

<400> SEQUENCE: 25

Glu Gln Lys Leu Ile Ser Glu Glu Asp Leu
1               5                   10

<210> SEQ ID NO 26
<211> LENGTH: 14
<212> TYPE: PRT
<213> ORGANISM: Artificial Sequence
<220> FEATURE:
<223> OTHER INFORMATION: V5-tag

<400> SEQUENCE: 26

Gly Lys Pro Ile Pro Asn Pro Leu Leu Gly Leu Asp Ser Thr
1               5                   10

<210> SEQ ID NO 27
<211> LENGTH: 126
<212> TYPE: PRT
<213> ORGANISM: Streptomyces avidinii
<220> FEATURE:
<223> OTHER INFORMATION: Mutein Streptavidin Val44-Thr45-Ala46-Arg47 and
      Glu117, Gly120, Try121 (mutein m1-9)

<400> SEQUENCE: 27

-continued

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Val Thr
            20                  25                  30

Ala Arg Gly Asn Ala Glu Ser Arg Tyr Val Leu Thr Gly Arg Tyr Asp
            35                  40                  45

Ser Ala Pro Ala Thr Asp Gly Ser Gly Thr Ala Leu Gly Trp Thr Val
    50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Glu Asn Ala Gly Tyr Ser Thr Leu Val
            100                 105                 110

Gly His Asp Thr Phe Thr Lys Val Lys Pro Ser Ala Ala Ser
            115                 120                 125

<210> SEQ ID NO 28
<211> LENGTH: 139
<212> TYPE: PRT
<213> ORGANISM: Streptomyces avidinii
<220> FEATURE:
<223> OTHER INFORMATION: Mutein Streptavidin Val44-Thr45-Ala46-Arg47 and
      Glu117, Gly120, Try121 (mutein m1-9)

<400> SEQUENCE: 28

Asp Pro Ser Lys Asp Ser Lys Ala Gln Val Ser Ala Ala Glu Ala Gly
1               5                   10                  15

Ile Thr Gly Thr Trp Tyr Asn Gln Leu Gly Ser Thr Phe Ile Val Thr
            20                  25                  30

Ala Gly Ala Asp Gly Ala Leu Thr Gly Thr Tyr Val Thr Ala Arg Gly
            35                  40                  45

Asn Ala Glu Ser Arg Tyr Val Leu Thr Gly Arg Tyr Asp Ser Ala Pro
    50                  55                  60

Ala Thr Asp Gly Ser Gly Thr Ala Leu Gly Trp Thr Val Ala Trp Lys
65                  70                  75                  80

Asn Asn Tyr Arg Asn Ala His Ser Ala Thr Thr Trp Ser Gly Gln Tyr
                85                  90                  95

Val Gly Gly Ala Glu Ala Arg Ile Asn Thr Gln Trp Leu Leu Thr Ser
            100                 105                 110

Gly Thr Thr Glu Glu Asn Ala Gly Tyr Ser Thr Leu Val Gly His Asp
            115                 120                 125

Thr Phe Thr Lys Val Lys Pro Ser Ala Ala Ser
            130                 135

<210> SEQ ID NO 29
<211> LENGTH: 253
<212> TYPE: PRT
<213> ORGANISM: Artificial Sequence
<220> FEATURE:
<223> OTHER INFORMATION: Variable Heavy chain of Fab fragment m13B8.2

<400> SEQUENCE: 29

Ala Met Gln Val Gln Leu Lys Gln Ser Gly Pro Gly Leu Val Gln Pro
1               5                   10                  15

Ser Gln Ser Leu Ser Ile Thr Cys Thr Val Ser Gly Phe Ser Leu Thr
            20                  25                  30

Thr Phe Gly Val His Trp Val Arg Gln Ser Pro Gly Lys Gly Leu Glu

```
                35                  40                  45
Trp Leu Gly Val Ile Trp Ala Ser Gly Ile Thr Asp Tyr Asn Val Pro
 50                      55                  60
Phe Met Ser Arg Leu Ser Ile Thr Lys Asp Asn Ser Lys Ser Gln Val
65                      70                  75                  80
Phe Phe Lys Leu Asn Ser Leu Gln Pro Asp Thr Ala Ile Tyr Tyr
                    85                  90                  95
Cys Ala Lys Asn Asp Pro Gly Thr Gly Phe Ala Tyr Trp Gly Gln Gly
                100                 105                 110
Thr Leu Val Thr Val Ser Ala Gly Ser Thr Lys Gly Pro Ser Val Phe
                115                 120                 125
Pro Leu Ala Pro Ser Ser Lys Ser Thr Ser Gly Gly Thr Ala Ala Leu
130                     135                 140
Gly Cys Leu Val Lys Asp Tyr Phe Pro Glu Pro Val Thr Val Ser Trp
145                     150                 155                 160
Asn Ser Gly Ala Leu Thr Ser Gly Val His Thr Phe Pro Ala Val Leu
                    165                 170                 175
Gln Ser Ser Gly Leu Tyr Ser Leu Ser Ser Val Val Thr Val Pro Ser
                180                 185                 190
Ser Ser Leu Gly Thr Gln Thr Tyr Ile Cys Asn Val Asn His Lys Pro
                195                 200                 205
Ser Asn Thr Lys Val Asp Lys Lys Val Glu Pro Lys Ser Cys Gly Ser
210                     215                 220
Ala Trp Ser His Pro Gln Phe Glu Lys Gly Gly Gly Ser Gly Gly Gly
225                     230                 235                 240
Ser Gly Gly Ser Ala Trp Ser His Pro Gln Phe Glu Lys
                    245                 250

<210> SEQ ID NO 30
<211> LENGTH: 218
<212> TYPE: PRT
<213> ORGANISM: Artificial Sequence
<220> FEATURE:
<223> OTHER INFORMATION: Variable Light chain of Fab Fragment m13B8.2

<400> SEQUENCE: 30

Ala Met Asp Ile Gln Met Thr Gln Ser Pro Ala Ser Leu Ser Ala Ser
1               5                   10                  15
Val Gly Glu Thr Val Thr Phe Thr Cys Arg Ala Ser Glu Met Ile Tyr
                    20                  25                  30
Ser Tyr Leu Ala Trp Tyr Gln Gln Lys Gln Gly Lys Ser Pro Gln Leu
                35                  40                  45
Leu Val His Asp Ala Lys Thr Leu Ala Glu Gly Val Pro Ser Arg Phe
 50                     55                  60
Ser Gly Gly Gly Ser Gly Thr Gln Phe Ser Leu Lys Ile Asn Thr Leu
65                      70                  75                  80
Gln Pro Glu Asp Phe Gly Thr Tyr Tyr Cys Gln Ala His Tyr Gly Asn
                    85                  90                  95
Pro Pro Thr Phe Gly Gly Gly Thr Lys Leu Glu Ile Lys Arg Gly Ile
                100                 105                 110
Ala Ala Pro Ser Val Phe Ile Phe Pro Pro Ser Asp Glu Gln Leu Lys
                115                 120                 125
Ser Gly Thr Ala Ser Val Val Cys Leu Leu Asn Asn Phe Tyr Pro Arg
                130                 135                 140
Glu Ala Lys Val Gln Trp Lys Val Asp Asn Ala Leu Gln Ser Gly Asn
```

145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
                180                 185                 190

Val Tyr Ala Cys Glu Val Thr His Gln Gly Leu Ser Ser Pro Val Thr
                195                 200                 205

Lys Ser Phe Asn Arg Gly Glu Cys Gly Ser
                210                 215

<210> SEQ ID NO 31
<211> LENGTH: 119
<212> TYPE: PRT
<213> ORGANISM: Artificial Sequence
<220> FEATURE:
<223> OTHER INFORMATION: Variable Heavy chain of anti-CD3 antibody OKT3

<400> SEQUENCE: 31

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
                20                  25                  30

Thr Met His Trp Val Lys Gln Arg Pro Gly Gln Gly Leu Glu Trp Ile
            35                  40                  45

Gly Tyr Ile Asn Pro Ser Arg Gly Tyr Thr Asn Tyr Asn Gln Lys Phe
        50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
                100                 105                 110

Thr Thr Leu Thr Val Ser Ser
            115

<210> SEQ ID NO 32
<211> LENGTH: 106
<212> TYPE: PRT
<213> ORGANISM: Artificial Sequence
<220> FEATURE:
<223> OTHER INFORMATION: Variable Light chain of anti-CD3 antibody OKT3

<400> SEQUENCE: 32

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
                20                  25                  30

Asn Trp Tyr Gln Gln Lys Ser Gly Thr Ser Pro Lys Arg Trp Ile Tyr
            35                  40                  45

Asp Thr Ser Lys Leu Ala Ser Gly Val Pro Ala His Phe Arg Gly Ser
        50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn
                100                 105

```
<210> SEQ ID NO 33
<211> LENGTH: 116
<212> TYPE: PRT
<213> ORGANISM: Artificial Sequence
<220> FEATURE:
<223> OTHER INFORMATION: Variable Heavy chain of anti-CD28 antibody
      CD28.3

<400> SEQUENCE: 33

Leu Gln Gln Ser Gly Ala Glu Leu Val Lys Pro Gly Ala Ser Val Arg
1               5                   10                  15

Leu Ser Cys Lys Ala Ser Gly Tyr Thr Phe Thr Glu Tyr Ile Ile His
            20                  25                  30

Trp Ile Lys Leu Arg Ser Gly Gln Gly Leu Glu Trp Ile Gly Trp Phe
        35                  40                  45

Tyr Pro Gly Ser Asn Asp Ile Gln Tyr Asn Ala Lys Phe Lys Gly Lys
    50                  55                  60

Ala Thr Leu Thr Ala Asp Lys Ser Ser Ser Thr Val Tyr Met Glu Leu
65                  70                  75                  80

Thr Gly Leu Thr Ser Glu Asp Ser Ala Val Tyr Phe Cys Ala Arg Arg
                85                  90                  95

Asp Asp Phe Ser Gly Tyr Asp Ala Leu Pro Tyr Trp Gly Gln Gly Thr
            100                 105                 110

Met Val Thr Val
        115

<210> SEQ ID NO 34
<211> LENGTH: 108
<212> TYPE: PRT
<213> ORGANISM: Artificial Sequence
<220> FEATURE:
<223> OTHER INFORMATION: Variable Light chain of anti-CD28 antibody
      CD28.3

<400> SEQUENCE: 34

Asp Ile Gln Met Thr Gln Ser Pro Ala Ser Leu Ser Val Ser Val Gly
1               5                   10                  15

Glu Thr Val Thr Ile Thr Cys Arg Thr Asn Glu Asn Ile Tyr Ser Asn
            20                  25                  30

Leu Ala Trp Tyr Gln Gln Lys Gln Gly Lys Ser Pro Gln Leu Leu Ile
        35                  40                  45

Tyr Ala Ala Thr His Leu Val Glu Gly Val Pro Ser Arg Phe Ser Gly
    50                  55                  60

Ser Gly Ser Gly Thr Gln Tyr Ser Leu Lys Ile Thr Ser Leu Gln Ser
65                  70                  75                  80

Glu Asp Phe Gly Asn Tyr Tyr Cys Gln His Phe Trp Gly Thr Pro Cys
                85                  90                  95

Thr Phe Gly Gly Gly Thr Lys Leu Glu Ile Lys Arg
            100                 105

<210> SEQ ID NO 35
<211> LENGTH: 11
<212> TYPE: PRT
<213> ORGANISM: Artificial Sequence
<220> FEATURE:
<223> OTHER INFORMATION: MAT tag

<400> SEQUENCE: 35

His Asn His Arg His Lys His Gly Gly Gly Cys
1               5                   10
```

<210> SEQ ID NO 36
<211> LENGTH: 118
<212> TYPE: PRT
<213> ORGANISM: Artificial Sequence
<220> FEATURE:
<223> OTHER INFORMATION: anti-CD16 antibody 3G8 VH

<400> SEQUENCE: 36

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Arg Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Asp Lys Arg Tyr Asn Pro Ala
    50                  55                  60

Leu Lys Ser Arg Leu Thr Ile Ser Lys Asp Thr Ser Ser Asn Gln Val
65                  70                  75                  80

Phe Leu Lys Ile Ala Ser Val Asp Thr Ala Asp Thr Ala Thr Tyr Tyr
                85                  90                  95

Cys Ala Gln Ile Asn Pro Ala Trp Phe Ala Tyr Trp Gly Gln Gly Thr
            100                 105                 110

Leu Val Thr Val Ser Ser
        115

<210> SEQ ID NO 37
<211> LENGTH: 111
<212> TYPE: PRT
<213> ORGANISM: Artificial Sequence
<220> FEATURE:
<223> OTHER INFORMATION: anti-CD16 antibody 3G8 VL

<400> SEQUENCE: 37

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Phe Asp
            20                  25                  30

Gly Asp Ser Phe Met Asn Trp Tyr Gln Gln Lys Pro Gly Gln Pro Pro
        35                  40                  45

Lys Leu Leu Ile Tyr Thr Thr Ser Asn Leu Glu Ser Gly Ile Pro Ala
    50                  55                  60

Arg Phe Ser Ala Ser Gly Ser Gly Thr Asp Phe Thr Leu Asn Ile His
65                  70                  75                  80

Pro Val Glu Glu Glu Asp Thr Ala Thr Tyr Tyr Cys Gln Gln Ser Asn
                85                  90                  95

Glu Asp Pro Tyr Thr Phe Gly Gly Gly Thr Lys Leu Glu Ile Lys
            100                 105                 110

<210> SEQ ID NO 38
<211> LENGTH: 9
<212> TYPE: PRT
<213> ORGANISM: Artificial Sequence
<220> FEATURE:
<223> OTHER INFORMATION: antigen-specific peptide

<400> SEQUENCE: 38

Cys Arg Val Leu Cys Cys Tyr Val Leu
1               5

<210> SEQ ID NO 39
<211> LENGTH: 9
<212> TYPE: PRT
<213> ORGANISM: Artificial Sequence
<220> FEATURE:
<223> OTHER INFORMATION: pp65 epitope of CMV (amino acids 341-350)

<400> SEQUENCE: 39

Gln Tyr Asp Pro Val Ala Ala Leu Phe
1               5

<210> SEQ ID NO 40
<211> LENGTH: 10
<212> TYPE: PRT
<213> ORGANISM: Artificial Sequence
<220> FEATURE:
<223> OTHER INFORMATION: pp65 epitope of CMV (amino acids 265-274)

<400> SEQUENCE: 40

Arg Pro His Glu Arg Asn Gly Phe Thr Val
1               5                   10

<210> SEQ ID NO 41
<211> LENGTH: 11
<212> TYPE: PRT
<213> ORGANISM: Artificial Sequence
<220> FEATURE:
<223> OTHER INFORMATION: hexon 5 epitope of adenovirus (amino acids
      114-124)

<400> SEQUENCE: 41

Cys Pro Tyr Ser Gly Thr Ala Tyr Asn Ser Leu
1               5                   10

<210> SEQ ID NO 42
<211> LENGTH: 314
<212> TYPE: PRT
<213> ORGANISM: Artificial Sequence
<220> FEATURE:
<223> OTHER INFORMATION: HLA-A*2402

<400> SEQUENCE: 42

Met Gly Ser His Ser Met Arg Tyr Phe Ser Thr Ser Val Ser Arg Pro
1               5                   10                  15

Gly Arg Gly Glu Pro Arg Phe Ile Ala Val Gly Tyr Val Asp Asp Thr
            20                  25                  30

Gln Phe Val Arg Phe Asp Ser Asp Ala Ala Ser Gln Arg Met Glu Pro
        35                  40                  45

Arg Ala Pro Trp Ile Glu Gln Glu Gly Pro Glu Tyr Trp Asp Glu Glu
    50                  55                  60

Thr Gly Lys Val Lys Ala His Ser Gln Thr Asp Arg Glu Asn Leu Arg
65                  70                  75                  80

Ile Ala Leu Arg Tyr Tyr Asn Gln Ser Glu Ala Gly Ser His Thr Leu
                85                  90                  95

Gln Met Met Phe Gly Cys Asp Val Gly Ser Asp Gly Arg Phe Leu Arg
            100                 105                 110

Gly Tyr His Gln Tyr Ala Tyr Asp Gly Lys Asp Tyr Ile Ala Leu Lys
        115                 120                 125

Glu Asp Leu Arg Ser Trp Thr Ala Ala Asp Met Ala Ala Gln Ile Thr
    130                 135                 140

Lys Arg Lys Trp Glu Ala Ala His Val Ala Glu Gln Gln Arg Ala Tyr
145                 150                 155                 160

-continued

Leu Glu Gly Thr Cys Val Asp Gly Leu Arg Arg Tyr Leu Glu Asn Gly
                165                 170                 175

Lys Glu Thr Leu Gln Arg Thr Asp Pro Lys Thr His Met Thr His
            180                 185                 190

His Pro Ile Ser Asp His Glu Ala Thr Leu Arg Cys Trp Ala Leu Gly
            195                 200                 205

Phe Tyr Pro Ala Glu Ile Thr Leu Thr Trp Gln Arg Asp Gly Glu Asp
            210                 215                 220

Gln Thr Gln Asp Thr Glu Leu Val Glu Thr Arg Pro Ala Gly Asp Gly
225                 230                 235                 240

Thr Phe Gln Lys Trp Ala Ala Val Val Pro Ser Gly Glu Glu Gln
                245                 250                 255

Arg Tyr Thr Cys His Val Gln His Glu Gly Leu Pro Lys Pro Leu Thr
                260                 265                 270

Leu Arg Trp Glu Pro Pro Ser Gly Ser Ser Ala Trp Ser His Pro
                275                 280                 285

Gln Phe Glu Lys Gly Gly Gly Ser Gly Gly Gly Ser Gly Gly Gly Ser
            290                 295                 300

Ser Ala Trp Ser His Pro Gln Phe Glu Lys
305                 310

<210> SEQ ID NO 43
<211> LENGTH: 314
<212> TYPE: PRT
<213> ORGANISM: Artificial Sequence
<220> FEATURE:
<223> OTHER INFORMATION: HLA-B*0702

<400> SEQUENCE: 43

Met Gly Ser His Ser Met Arg Tyr Phe Tyr Thr Ser Val Ser Arg Pro
1               5                   10                  15

Gly Arg Gly Glu Pro Arg Phe Ile Ser Val Gly Tyr Val Asp Asp Thr
            20                  25                  30

Gln Phe Val Arg Phe Asp Ser Asp Ala Ala Ser Pro Arg Glu Glu Pro
        35                  40                  45

Arg Ala Pro Trp Ile Glu Gln Glu Gly Pro Glu Tyr Trp Asp Arg Asn
    50                  55                  60

Thr Gln Ile Tyr Lys Ala Gln Ala Gln Thr Asp Arg Glu Ser Leu Arg
65                  70                  75                  80

Asn Leu Arg Gly Tyr Tyr Asn Gln Ser Glu Ala Gly Ser His Thr Leu
                85                  90                  95

Gln Ser Met Tyr Gly Cys Asp Val Gly Pro Asp Gly Arg Leu Leu Arg
            100                 105                 110

Gly His Asp Gln Tyr Ala Tyr Asp Gly Lys Asp Tyr Ile Ala Leu Asn
        115                 120                 125

Glu Asp Leu Arg Ser Trp Thr Ala Ala Asp Thr Ala Ala Gln Ile Thr
    130                 135                 140

Gln Arg Lys Trp Glu Ala Ala Arg Glu Ala Glu Gln Arg Arg Ala Tyr
145                 150                 155                 160

Leu Glu Gly Glu Cys Val Glu Trp Leu Arg Arg Tyr Leu Glu Asn Gly
                165                 170                 175

Lys Asp Lys Leu Glu Arg Ala Asp Pro Pro Lys Thr His Val Thr His
            180                 185                 190

His Pro Ile Ser Asp His Glu Ala Thr Leu Arg Cys Trp Ala Leu Gly
        195                 200                 205

Phe Tyr Pro Ala Glu Ile Thr Leu Thr Trp Gln Arg Asp Gly Glu Asp
            210                 215                 220

Gln Thr Gln Asp Thr Glu Leu Val Glu Thr Arg Pro Ala Gly Asp Arg
225                 230                 235                 240

Thr Phe Gln Lys Trp Ala Ala Val Val Pro Ser Gly Glu Glu Gln
                245                 250                 255

Arg Tyr Thr Cys His Val Gln His Glu Gly Leu Pro Lys Pro Leu Thr
            260                 265                 270

Leu Arg Trp Glu Pro Pro Ser Gly Ser Ala Trp Ser His Pro
            275                 280                 285

Gln Phe Glu Lys Gly Gly Ser Gly Gly Gly Ser Gly Gly Gly Ser
            290                 295                 300

Ser Ala Trp Ser His Pro Gln Phe Glu Lys
305                 310

<210> SEQ ID NO 44
<211> LENGTH: 321
<212> TYPE: PRT
<213> ORGANISM: Artificial Sequence
<220> FEATURE:
<223> OTHER INFORMATION: HLA-C*0702

<400> SEQUENCE: 44

Met Ala Leu Thr Glu Thr Trp Ala Cys Ser His Ser Met Arg Tyr Phe
1               5                   10                  15

Asp Thr Ala Val Ser Arg Pro Gly Arg Gly Glu Pro Arg Phe Ile Ser
            20                  25                  30

Val Gly Tyr Val Asp Asp Thr Gln Phe Val Arg Phe Asp Ser Asp Ala
        35                  40                  45

Ala Ser Pro Arg Gly Glu Pro Arg Ala Pro Trp Val Glu Gln Glu Gly
    50                  55                  60

Pro Glu Tyr Trp Asp Arg Glu Thr Gln Lys Tyr Lys Arg Gln Ala Gln
65                  70                  75                  80

Ala Asp Arg Val Ser Leu Arg Asn Leu Arg Gly Tyr Tyr Asn Gln Ser
                85                  90                  95

Glu Asp Gly Ser His Thr Leu Gln Arg Met Ser Gly Cys Asp Leu Gly
            100                 105                 110

Pro Asp Gly Arg Leu Leu Arg Gly Tyr Asp Gln Ser Ala Tyr Asp Gly
        115                 120                 125

Lys Asp Tyr Ile Ala Leu Asn Glu Asp Leu Arg Ser Trp Thr Ala Ala
    130                 135                 140

Asp Thr Ala Ala Gln Ile Thr Gln Arg Lys Leu Glu Ala Ala Arg Ala
145                 150                 155                 160

Ala Glu Gln Leu Arg Ala Tyr Leu Glu Gly Thr Cys Val Glu Trp Leu
                165                 170                 175

Arg Arg Tyr Leu Glu Asn Gly Lys Glu Thr Leu Gln Arg Ala Glu Pro
            180                 185                 190

Pro Lys Thr His Val Thr His His Pro Leu Ser Asp His Glu Ala Thr
        195                 200                 205

Leu Arg Cys Trp Ala Leu Gly Phe Tyr Pro Ala Glu Ile Thr Leu Thr
    210                 215                 220

Trp Gln Arg Asp Gly Glu Asp Gln Thr Gln Asp Thr Glu Leu Val Glu
225                 230                 235                 240

Thr Arg Pro Ala Gly Asp Gly Thr Phe Gln Lys Trp Ala Ala Val Val
                245                 250                 255

```
Val Pro Ser Gly Gln Glu Gln Arg Tyr Thr Cys His Met Gln His Glu
            260                 265                 270

Gly Leu Gln Glu Pro Leu Thr Leu Ser Trp Glu Pro Ser Ser Gln Pro
        275                 280                 285

Thr Ile Gly Ser Ala Trp Ser His Pro Gln Phe Glu Lys Gly Gly Gly
    290                 295                 300

Ser Gly Gly Gly Ser Gly Gly Ser Ala Trp Ser His Pro Gln Phe Glu
305                 310                 315                 320

Lys

<210> SEQ ID NO 45
<211> LENGTH: 100
<212> TYPE: PRT
<213> ORGANISM: Artificial Sequence
<220> FEATURE:
<223> OTHER INFORMATION: B2 microglobulin

<400> SEQUENCE: 45

Met Ile Gln Arg Thr Pro Lys Ile Gln Val Tyr Ser Arg His Pro Ala
1               5                   10                  15

Glu Asn Gly Lys Ser Asn Phe Leu Asn Cys Tyr Val Ser Gly Phe His
            20                  25                  30

Pro Ser Asp Ile Glu Val Asp Leu Leu Lys Asn Gly Glu Arg Ile Glu
        35                  40                  45

Lys Val Glu His Ser Asp Leu Ser Phe Ser Lys Asp Trp Ser Phe Tyr
    50                  55                  60

Leu Leu Tyr Tyr Thr Glu Phe Thr Pro Thr Glu Lys Asp Glu Tyr Ala
65                  70                  75                  80

Cys Arg Val Asn His Val Thr Leu Ser Gln Pro Lys Ile Val Lys Trp
                85                  90                  95

Asp Arg Asp Met
            100

<210> SEQ ID NO 46
<211> LENGTH: 11
<212> TYPE: PRT
<213> ORGANISM: Artificial Sequence
<220> FEATURE:
<223> OTHER INFORMATION: VSV-G tag

<400> SEQUENCE: 46

Tyr Thr Asp Ile Glu Met Asn Arg Leu Gly Lys
1               5                   10

<210> SEQ ID NO 47
<211> LENGTH: 10
<212> TYPE: PRT
<213> ORGANISM: Artificial Sequence
<220> FEATURE:
<223> OTHER INFORMATION: 10 amino acid tag from the collagen-binding
      domain of von Willebrand factor

<400> SEQUENCE: 47

Trp Arg Glu Pro Gly Arg Met Glu Leu Asn
1               5                   10

<210> SEQ ID NO 48
<211> LENGTH: 4
<212> TYPE: PRT
<213> ORGANISM: Artificial Sequence
<220> FEATURE:
```

```
<223> OTHER INFORMATION: Linker peptide

<400> SEQUENCE: 48

Gly Gly Gly Ser
1

<210> SEQ ID NO 49
<211> LENGTH: 283
<212> TYPE: PRT
<213> ORGANISM: Artificial Sequence
<220> FEATURE:
<223> OTHER INFORMATION: Human CD19 extracellular domain with His-Tag

<400> SEQUENCE: 49

Pro Glu Glu Pro Leu Val Val Lys Val Glu Glu Gly Asp Asn Ala Val
1               5                   10                  15

Leu Gln Cys Leu Lys Gly Thr Ser Asp Gly Pro Thr Gln Gln Leu Thr
            20                  25                  30

Trp Ser Arg Glu Ser Pro Leu Lys Pro Phe Leu Lys Leu Ser Leu Gly
        35                  40                  45

Leu Pro Gly Leu Gly Ile His Met Arg Pro Leu Ala Ile Trp Leu Phe
    50                  55                  60

Ile Phe Asn Val Ser Gln Gln Met Gly Gly Phe Tyr Leu Cys Gln Pro
65                  70                  75                  80

Gly Pro Pro Ser Glu Lys Ala Trp Gln Pro Gly Trp Thr Val Asn Val
                85                  90                  95

Glu Gly Ser Gly Glu Leu Phe Arg Trp Asn Val Ser Asp Leu Gly Gly
            100                 105                 110

Leu Gly Cys Gly Leu Lys Asn Arg Ser Ser Glu Gly Pro Ser Ser Pro
        115                 120                 125

Ser Gly Lys Leu Met Ser Pro Lys Leu Tyr Val Trp Ala Lys Asp Arg
    130                 135                 140

Pro Glu Ile Trp Glu Gly Glu Pro Pro Cys Leu Pro Pro Arg Asp Ser
145                 150                 155                 160

Leu Asn Gln Ser Leu Ser Gln Asp Leu Thr Met Ala Pro Gly Ser Thr
                165                 170                 175

Leu Trp Leu Ser Cys Gly Val Pro Pro Asp Ser Val Ser Arg Gly Pro
            180                 185                 190

Leu Ser Trp Thr His Val His Pro Lys Gly Pro Lys Ser Leu Leu Ser
        195                 200                 205

Leu Glu Leu Lys Asp Asp Arg Pro Ala Arg Asp Met Trp Val Met Glu
    210                 215                 220

Thr Gly Leu Leu Leu Pro Arg Ala Thr Ala Gln Asp Ala Gly Lys Tyr
225                 230                 235                 240

Tyr Cys His Arg Gly Asn Leu Thr Met Ser Phe His Leu Glu Ile Thr
                245                 250                 255

Ala Arg Pro Val Leu Trp His Trp Leu Leu Arg Thr Gly Gly Trp Lys
            260                 265                 270

Ala His His His His His His His His His
        275                 280
```

METHODS, KITS, AGENTS AND APPARATUSES FOR TRANSDUCTION

CROSS-REFERENCE TO RELATED APPLICATIONS

This application is a U.S. National Stage of International Application No. PCT/IB2016/001605 filed Oct. 20, 2016, which claims priority from U.S. provisional application No. 62/245,265 filed Oct. 22, 2015, entitled "Methods, Kits and Apparatus for Transducing a Population of Cells," U.S. provisional application No. 62/305,989 filed Mar. 9, 2016, entitled "Methods, Kits and Apparatus for Transducing a Population of Cells," and U.S. provisional application No. 62/369,020 filed Jul. 29, 2016, entitled "Methods and Agents for Promoting Transduction," the contents of which are incorporated by reference in their entirety.

INCORPORATION BY REFERENCE OF SEQUENCE LISTING

The present application is being filed with a Sequence Listing in electronic format. The Sequence Listing is provided as a file entitled 735042002800SeqList.txt, created on Mar. 11, 2019, which is 42,007 bytes in size. The information in electronic format of the Sequence Listing is incorporated by reference in its entirety.

FIELD

The present disclosure relates in some aspects to the transduction of a composition of cells, such as a population of lymphocytes. The methods involve the use of reagents, such as oligomeric protein reagents, that facilitate the transduction, and which also, in some cases can include binding agents reversibly bound thereto, where such binding is generally reversible by the addition of a substance. In some aspects, the disclosure provides methods and reagents for the transduction of cell populations that involve binding of agents to a molecule on the surface of the cells, thereby providing an incubated composition containing transduced cells. In some cases, the reagents are multimerization reagents and the one or more agents are multimerized by reversibly binding to the reagent. In some aspects, the multimerized agent can provide for transduction of a population of cells, and then such agents can be removed by disruption of the reversible bond. In some embodiments, the provided methods can be employing for transducing cells and further, in some cases, for enriching, activating, stimulating and/or expanding the transduced cells. Also provided are compositions, apparatus and methods of use thereof.

BACKGROUND

Various strategies are available for transducing T cell populations in vitro, including for transducing antigen-specific T cells in vitro for use in adoptive cellular immunotherapy or cancer therapy. In some aspects, infusions of T cell therapies, such as those engineered or transduced with a recombinant receptor, e.g. a chimeric antigen receptor, have been shown to have anti-tumor reactivity in a tumor-bearing host or for use to treat viral infections. Improved strategies are needed for transducing cell populations in vitro, including for research, diagnostic and therapeutic purposes. Provided are reagents, methods, articles of manufacture and kits that meet such needs.

SUMMARY

Provided herein in some embodiments is a method for transducing cells, including incubating a plurality of cells containing target cells with an oligomeric protein reagent; and a viral particle, wherein the method produces an output composition containing one or more cells transduced with the viral particle.

In some of any such embodiments, the oligomeric reagent contains a plurality of polypeptide monomeric units, wherein each unit contains at least at or about 10, 20, 30, or 40 amino acids in length and/or contains a molecular weight of at least at or about 20, 30, 40, or 50 kDA; and/or the oligomeric reagent contains a molecular weight of at least at or about 100, and/or between at or about 150 kDa to about 2000 kDa, about 150 kDa to about 1500 kDa, about 150 kDa to about 1250 kDa, about 150 kDa to 1000 kDa, about 150 kDa to about 500 kDa or about 150 kDa to about 300 kDa, about 300 kDa to about 2000 kDa, about 300 kDa to about 1500 kDa, about 300 kDa to about 1250 kDa, about 300 kDa to 1000 kDa, about 300 kDa to about 500 kDa, about 500 kDa to about 2000 kDa, about 500 kDa to about 1500 kDa, about 500 kDa to about 1250 kDa, about 500 kDa to 1000 kDa, about 1000 kDa to about 2000 kDa, about 1000 kDa to about 1500 kDa, about 1000 kDa to about 1250 kDa, about 1250 kDa to about 2000 kDa or about 1500 kDa to about 2000 kDa.

In some of any such embodiments, the reagent contains a plurality of multimeric subunits units that individually comprise the monomeric units. In some aspects, the multimeric subunits are tetrameric.

In some of any such embodiments, the oligomeric protein reagent contains a streptavidin, an avidin, a streptavidin analog or mutein or an avidin analog, a mutein or a biologically active fragment of any of the foregoing, and/or multiple subunits of any of the foregoing.

Also provided herein in some embodiments is a method for transducing cells, including incubating a plurality of cells comprising target cells with a protein reagent containing a streptavidin, an avidin, a streptavidin analog or mutein, an avidin analog, a mutein or a biologically active fragment of any of the foregoing, and/or multiple subunits of any of the foregoing; and a viral particle, wherein the method produces an output composition containing one or more cells transduced with the viral particle.

In some of any such embodiments, the incubating includes admixing the cell with the reagent and with the viral particle, simultaneously or sequentially, in either order. In some embodiments, during at least a portion of the incubating, the reagent and viral particle are in the presence of or contacted with the cell simultaneously.

Also provided herein in some embodiments is a method for transducing cells, the method including contacting a viral particle with an oligomeric protein reagent, thereby generating a mixture comprising viral particles associated with the reagent; and incubating the mixture with a plurality of cells comprising target cells, wherein the method produces an output composition containing one or more cells transduced with the viral particle.

In some embodiments, the method includes contacting a viral particle with a protein reagent containing a streptavidin, an avidin, a streptavidin analog or mutein, an avidin analog, a mutein or a biologically active fragment of any of the foregoing, and/or multiple subunits of any of the foregoing, thereby generating a mixture comprising viral particles associated with the reagent; and incubating the mixture with a plurality of cells, wherein the method produces an output composition containing one or more cells transduced with the viral particle.

In some of any such embodiments, the reagent has a net positive charge or an overall positive charge. In some cases, the reagent is naked.

In some of any such embodiments, the reagent does not contain and/or is not conjugated or reversibly bound to a binding agent; the reagent does not contain and or is not conjugated or bound to a molecule with a binding domain specific for a cell surface marker; the reagent does not contain and or is not conjugated or bound to an extracellular matrix component, adhesion molecule, an integrin, a lectin, an integrin-binding protein, a chemokines, a cytokine, a growth factor, an extracellular matrix-binding molecule, an ECM component, a viral protein, a viral entry-promoting cell surface receptor, heparin, heparan, glycans; and/or the reagent does not contain a heparin-binding domain and/or does not contain an integrin-binding domain and/or does not contain a VLA4-binding domain and/or does not contain a VLA5-binding domain; and/or the reagent does not contain and/or is not conjugated or coupled or bound to a viral binding agent or a cell selection agent.

In some of any such embodiments, the reagent further contains and/or is reversibly bound to a plurality of one or more binding agents that each is capable of specifically binding to a molecule on the surface of the viral particle and/or the surface of a target cell.

Provided herein in some embodiments are methods for transducing cells, which include incubating a plurality of target cells with an oligomeric protein reagent, and a viral particle, wherein: the oligomeric protein reagent includes a plurality of polypeptide monomeric units, wherein each unit includes at least at or about 10, 20, 30, or 40 amino acids in length and/or includes a molecular weight of at least at or about 20, 30, 40, or 50 kDa; and/or the oligomeric protein reagent includes a molecular weight, or includes on average a molecular weight, of at least at or about 100 kDa, wherein the method produces an output composition including one or more cells transduced with the viral particle.

In some embodiments of any of the methods provided herein, the oligomeric protein reagent includes a plurality of polypeptide units, individually including a streptavidin, an avidin, a biotin binding polypeptide, a strep tag-binding peptide, a streptavidin mutein, a streptaviidn analog, an avidin mutein, an avidin analog, and/or a biologically active fragment of any of the foregoing.

In some embodiments of any of the methods provided herein, the oligomeric protein reagent includes a, or a plurality of, multimeric subunits each individually including two or more of the polypeptide units.

Provided herein in some embodiments are methods for transducing cells, including incubating a plurality of target cells with (1) a protein reagent including a streptavidin, an avidin, a streptavidin analog or mutein, an avidin analog, a mutein or a biologically active fragment of any of the foregoing, and/or multiple subunits of any of the foregoing; and (2) a viral particle, wherein the method produces an output composition including one or more cells transduced with the viral particle.

In some embodiments of any of the methods provided herein, (i) the incubating includes admixing the target cells with the reagent, and/or admixing the target cells with the viral particle, sequentially, in either order, optionally wherein the admixing in (a) and the admixing in (b) are carried out within a period of no more than 1 hour, 2 hours, 3 hours, 4 hours, 5 hours, 6 hours, 7 hours, 8 hours, 9 hours, 10 hours, 11 hours, 12 hours, 18 hours, 24 hours, 36 hours, 48 hours, or 72 hours and/or the admixing in (a) is carried out no more than 1 hour, 2 hours, 3 hours, 4 hours, 5 hours, 6 hours, 7 hours, 8 hours, 9 hours, 10 hours, 11 hours, 12 hours, 18 hours, 24 hours, 36 hours, or 48 hours apart from the admixing in (b); (ii) the incubating includes admixing the target cells, the reagent, and the viral particle, said admixing carried out simultaneously or substantially simultaneously; (iii) the incubating includes admixing a composition that contains the target cells and the viral particles, and not including the reagent, optionally wherein: no more than 5%, 10%, 20%, 30%, or 40% of the target cells in the composition including the target cells and the reagent are activated cells, express a surface marker selected from the group consisting of HLA-DR, CD25, CD69, CD71, CD40L and 4-1BB; includes intracellular expression of a cytokine selected from the group consisting of IL-2, IFNgamma, TNF-alpha, and/or are capable of proliferating; and/or the admixing is carried out no more than 1 hour, 2 hours, 3 hours, 4 hours, 5 hours, 6 hours, 7 hours, 8 hours, 9 hours, 10 hours, 11 hours, 12 hours, 18 hours, 24 hours, 36 hours, or 48 hours following an admixing of the target cells and the viral particles in the composition; (iv) the incubation includes admixing a composition that contains the target cells and the reagent, and not including the viral particle, with the viral particle, optionally wherein: no more than 5%, 10%, 20%, 30%, or 40% of the target cells in the composition including the target cells and the reagent activated cells, express a surface marker selected from the group consisting of HLA-DR, CD25, CD69, CD71, CD40L and 4-1BB; including intracellular expression of a cytokine selected from the group consisting of IL-2, IFNgamma, TNF-alpha, and/or are capable of proliferating; and/or the admixing is carried out no more than 1 hour, 2 hours, 3 hours, 4 hours, 5 hours, 6 hours, 7 hours, 8 hours, 9 hours, 10 hours, 11 hours, 12 hours, 18 hours, 24 hours, 36 hours, or 48 hours following an admixing of the target cells and the viral particles in the composition; and/or (v) the incubation includes admixing a composition including the viral particles and the reagent with a composition that contains the target cells and not the viral particle and/or not the reagent, optionally wherein: no more than 5%, 10%, 20%, 30%, or 40% of the target cells in the composition including the target cells and the reagent are activated cells express a surface marker selected from the group consisting of HLA-DR, CD25, CD69, CD71, CD40L and 4-1BB; includes intracellular expression of a cytokine selected from the group consisting of IL-2, IFNgamma, TNF-alpha, and/or are capable of proliferating.

In some embodiments, the oligomeric protein reagent includes a plurality of one units including or more of the biotin binding polypeptide, the streptavidin, the avidin, the streptavidin analog, the streptavidin mutein, the avidin analog, the avidin mutein and the biologically active fragment.

In some embodiments, the reagent includes a plurality of multimeric subunits units that each individually includes two or more of the monomeric units. In some embodiments, the multimeric subunits are tetrameric and/or each individually includes four of the monomeric units.

In some embodiments, the incubating includes admixing the cell with the reagent and with the viral particle, simultaneously or sequentially, in either order. In some embodiments, during at least a portion of the incubating, the reagent and viral particle are in the presence of or contacted with the cell simultaneously.

Provided herein in some embodiments are methods for transducing cells, which include: (a) contacting a viral particle with an oligomeric protein reagent, thereby generating a composition including viral particles and the reagent, wherein the viral particles are optionally associated with the reagent; and (b) incubating the composition in (a) with a plurality of cells including target cells, wherein the method produces an output composition including one or more cells transduced with the viral particle.

Provided herein in some embodiments are methods for transducing cells, which include admixing a composition containing viral particles and an oligomeric protein reagent with a plurality of cells including target cells, wherein the method produces an output composition including one or more cells transduced with the viral particle.

Provided herein in some embodiments are methods for transducing cells, which include (a) contacting a viral particle with a protein reagent including a streptavidin, an avidin, a streptavidin analog or mutein, an avidin analog, a mutein or a biologically active fragment of any of the foregoing, and/or multiple subunits of any of the foregoing, thereby generating a composition including viral particles and the reagent, wherein the viral particles are optionally associated with the reagent; and (b) incubating the composition in (a) with a plurality of cells, wherein the method produces an output composition including one or more cells transduced with the viral particle.

Provided herein in some embodiments are methods for transducing cells, which include admixing a composition containing viral particles and a protein reagent with a plurality of cells including target cells, wherein: the protein reagent includes a streptavidin, an avidin, a streptavidin analog or mutein, an avidin analog, a mutein or a biologically active fragment of any of the foregoing, and/or multiple subunits of any of the foregoing; and the method produces an output composition including one or more cells transduced with the viral particle. In some embodiments, the reagent and/or each of the monomeric units and/or each of the multimeric units, has a net positive charge or an overall positive charge.

In some embodiments, the reagent does not include and/or is not conjugated or reversibly bound to a binding agent including an antibody or fragment thereof or does not include a binding agent including a human cell surface molecule or binding fragment thereof; the reagent does not include and or is not conjugated or bound to a molecule with a binding domain specific for a human cell surface marker, optionally a T cell marker; the reagent does not include and or is not conjugated or bound to an extracellular matrix component, adhesion molecule, an integrin, a lectin, an integrin-binding protein, a chemokines, a cytokine, a growth factor, extracellular matrix-binding molecule, an ECM component, a viral protein, a viral entry-promoting cell surface receptor, heparin, heparan, glycans; and/or the reagent does not include a heparin-binding domain and/or does not include an integrin-binding domain and/or does not include a VLA4-binding domain and/or does not include a VLA5-binding domain.

In some embodiments, the reagent also includes and/or is reversibly bound to a plurality of one or more binding agents that each is capable of specifically binding to a molecule on the surface of the viral particle and/or the surface of a target cell.

Provided herein in some embodiments in a method for transducing cells, including incubating a plurality of cells comprising target cells with 1) an oligomeric protein reagent containing a plurality of binding sites capable of reversibly binding to a binding agent, wherein one or more binding sites are reversibly bound to the binding agent; and 2) a viral particle, wherein at least a portion of the incubation in 1) occurs simultaneously with 2) and wherein the method produces an output composition containing one or more cells transduced with the viral particle. In some instances, the reagent comprises a plurality of binding sites capable of reversibly binding to each of the binding agents, the plurality of binding sites containing one or more binding site, Z, which is capable of binding to a binding partner, C; and the binding agent further contains one or more of the binding partner, C.

In some embodiments, the binding agent is or contains a receptor-binding agent. In some cases, the reagent further contains a further binding agent that is a selection agent that specifically binds to a molecule expressed on the surface of a target cell. In some aspects, the binding agent is a selection agent that specifically binding to a molecule expressed on the surface of one or more of the target cells. In some cases, the binding agent is a viral-binding agent that specifically binds to a molecule on the surface of the viral particle.

In some embodiments, provided is a method for transducing cells, the method including contacting a composition comprising a plurality of cells comprising target cells and a binding agent that is a selection agent that is capable of specifically binding to a molecule expressed by one or more of the target cells and is reversibly bound to a reagent comprising a plurality of binding sites capable of reversibly binding to the selection agent; an incubating at least a plurality of the cells in the presence of one or more viral particles, wherein the contacting and the incubating are carried out simultaneously or sequentially, in either order, wherein the method generates an output composition comprising cells transduced with the viral particle.

In some instances, the viral vector particles are reversibly bound to the reagent, said reagent containing a plurality of binding sites capable of reversibly binding, directly or indirectly, to a molecule on the surface of the viral particle. In some aspects, the viral particles are reversibly bound to the reagent via a viral particle-binding agent that specifically binds to a molecule on the surface of the viral particle, said reagent containing a plurality of binding sites capable of reversibly binding the viral particle-binding agent.

In some embodiments, the reagent comprises a plurality of binding sites, Z1, capable of reversibly binding to the selection agent and/or the reagent contains a plurality of binding sites, Z2, capable of reversibly binding to the one or more viral particles via the viral-binding agent.

In some embodiments, provided is a method for transducing cells, the method including contacting a composition comprising one or more viral particles and a binding agent that is a viral-binding agent that is capable of specifically binding to a molecule on the surface of the viral particle and is reversibly bound to a reagent comprising a plurality of binding sites capable of reversibly binding to the viral-binding agent; and incubating at least a plurality of cells containing target cells in the presence of the one or more viral particles, wherein the contacting and the incubating in are carried out simultaneously or sequentially, in either order, wherein the method generates an output composition comprising a plurality of cells transduced with the viral particle.

In some embodiments of any of the methods provided herein, the contacting in (1) and the incubating in (2) are carried out within a period of no more than 1 hour, 2 hours, 3 hours, 4 hours, 5 hours, 6 hours, 7 hours, 8 hours, 9 hours, 10 hours, 11 hours, 12 hours, 18 hours, 24 hours, 36 hours, 48 hours, or 72 hours and/or the admixing in (a) is carried out no more than 1 hour, 2 hours, 3 hours, 4 hours, 5 hours, 6 hours, 7 hours, 8 hours, 9 hours, 10 hours, 11 hours, 12 hours, 18 hours, 24 hours, 36 hours, or 48 hours apart from the incubating in (b).

In some of any such embodiments, the binding agent is or contains an antibody, an antibody fragment, a monovalent antibody fragment, a proteinaceous binding molecule with antibody-like binding properties, a molecule containing Ig domains, a cytokine, a chemokine, an aptamer, and MHC molecule or binding fragments thereof. In some cases, the antibody fragment contains a fragment selected from the group consisting of a Fab fragment, an Fv fragment, a (Fab')$_2$-fragment, and a divalent single-chain Fv (scFv) fragment.

In some of any such embodiments, the reagent is or contains an oligomeric protein reagent. In some cases, the oligomeric protein reagent contains a streptavidin, an avidin, a streptavidin analog or mutein or an avidin analog, a mutein or a biologically active fragment of any of the foregoing, and/or multiple subunits of any of the foregoing. In some of any such embodiments, the reagent is soluble.

In some of any such embodiments, the reagent is not, and is not bound to or associated with, a solid support, stationary phase, a bead, a microparticle, a magnetic particle, and/or a matrix during said incubation; and/or the reagent is flexible, does not contain a metal or magnetic core, is comprised entirely or primarily of organic multimer, is not spherical, is not substantially spherical or uniform in shape and/or is not rigid.

In some of any such embodiments, the reagent is immobilized, or is capable of being immobilized, on a support, directly or indirectly; and at least a portion of the incubation occurs on the support. In some aspects, the reagent is immobilized, or is capable of being immobilized, on a support, directly or indirectly, whereby the selection agent is immobilized or is capable of being immobilized on the support; and in further combining the support, whereby one or more target cells of the at least a plurality are immobilized on the support via the selection agent during at least a portion of the incubation.

Also provided herein in some embodiments is a method for transducing cells, the method including contacting a composition containing a plurality of cells comprising target cells, a selection agent that is capable of specifically binding to a selection marker expressed by one or more of the target cells and is immobilized, or is capable of being immobilized, on a support, directly or indirectly; and the support, whereby one or more target cells of the at least a plurality are immobilized on the support via the selection agent; and incubating at least a plurality of the cells in the presence of a composition comprising a plurality of viral particles, wherein one or more of the plurality of viral particles are capable of being immobilized on the support, directly or indirectly. In some cases, the contacting in and the incubating are carried out simultaneously or sequentially, in either order; the one or more target cells and the one or more viral particles are immobilized on the support during at least a portion of the incubation; and the method generates an output composition containing a plurality of the cells transduced with the viral particle.

In some of any such embodiments, the support is or comprises a stationary phase; and/or the support is or comprises a solid support. In some aspects wherein a reagent is immobilized or is capable of being immobilized on the support, said reagent contains a plurality of binding sites, Z1, capable of reversibly binding to the selection agent and a plurality of binding sites, Z2, capable of reversibly binding to the one or more viral particles via a viral-binding agent.

In some cases, the contacting step further includes combining the reagent, wherein the reagent is immobilized on the support. In some aspects, the reagent and the support are combined prior to combining thereto the selection agent and/or the composition containing a plurality of cells.

In some of any such embodiments, the selection agent is a first selection agent, the molecule is a first molecule and the incubation is further carried out in the presence of a second selection agent, which is capable of specifically binding to a second molecule expressed on the surface of one or more of the target cells. In some instances, the second selection agent is reversibly bound to the reagent or to a second reagent, the reagent or second reagent contains a plurality of binding sites capable of reversibly binding to the second selection agent, whereby the second selection agent is reversibly bound thereto.

In some of any such embodiments, the target cells contain blood cells; the target cells contain leukocytes; the target cells contain lymphocytes; the target cells contain B cells; the target cells contain a B cell population; the target cells contain T cells; the target cells contain a T cell population; and/or the target cells contain natural killer (NK) cells; the target cells contain dendritic cells; the target cells contain macrophages.

In some cases, the target cells contain antigen-specific T cells or a population thereof, a T helper cell or population thereof, a cytotoxic T cell or population thereof, a memory T cell or population thereof, a regulatory T cell or population thereof, or a NK cell or population thereof, antigen-specific B cells or a population thereof, a memory B cell or population thereof, or a regulatory B cell or population thereof.

In some of any such embodiments, the target cells contain T cells. In some instances, the T cells contain CD4+ and/or CD8+ T cells and/or a subpopulation or subset thereof and/or are enriched for a population of any of the foregoing.

In some of any such embodiments, the molecule is a B cell or T cell coreceptor; the molecule is or contains a member of a T cell or B cell antigen receptor complex; the molecule is or contains a CD3 chain; the molecule is or contains a CD3 zeta chain; the molecule is or contains a CD8; the molecule is or contains a CD4. In some embodiment, the molecule specifically bound by the selection agent is or contains CD25, CD28, CD62L, CCR7, CD27, CD127, CD3, CD4, CD8, CD45RA, and/or CD45RO.

In some of any such embodiments, the specific binding between the selection agent and the molecule does not induce a signal, or does not induce a stimulatory or activating or proliferative signal, to the target cells. In some embodiments, during at least a portion of the incubation, the selection agent binds to the molecule expressed on the surface of the target cell, thereby facilitating association between the reagent and the target cell. In some instances, the association between the reagent and the target cell enhancing the transduction of the target cell, compared to transduction of a non-target cell that does not express the molecule or is not specifically bound by the selection agent.

In some of any such embodiments, the plurality of cells comprises resting or naïve T cells. In some of any such embodiments, at least 40%, at least 50%, at least 60%, at least 70%, at least 80%, or at least 90% of the T cells in the plurality of cells are surface negative for a T cell activation marker selected from the group consisting of HLA-DR, CD25, CD69, CD71, CD40L and 4-1BB; and/or lack intracellular expression of a cytokine selected from the group consisting of IL-2, IFNgamma, TNF-alpha; and/or are capable of proliferating. In some embodiments, no more than 10% of the T cells in the plurality of cells comprise a T cell activation marker selected from the group consisting of HLA-DR, CD25, CD69, CD71, CD40L and 4-1BB; and/or lack intracellular expression of a cytokine selected from the group consisting of IL-2, IFNgamma, TNF-alpha; and/or are capable of proliferating.

In some of any such embodiments, prior to said incubating, the method does not include stimulating cells of the plurality of cells under conditions that promote T cell activation.

In some of any such embodiments, the plurality of cells have not, prior to said incubating, been subjected to an ex vivo stimulation including incubation at about 37° C. and/or incubation in the presence of an agent or agents selected from the group consisting of agents capable of activating, inducing a signal through a TCR complex in T cells, CD4+ T cells, and/or CD8+ T cells; agents capable of inducing proliferation of T cells, CD4+ T cells, and/or CD8+ T cells; CD3-binding molecules; CD28-binding molecules. In some embodiments, the plurality of cells comprises activated cells.

In some of any such embodiments, prior to or during the incubating with the reagent, the method includes activating the cells in the presence of a stimulatory agent under conditions whereby the one or more of the target cells are stimulated or activated by the stimulatory agent. In some instances, the target cells contain T cells and said stimulating conditions include the presence of an agent capable of activating one or more intracellular signaling domains of one or more components of a TCR complex. In some aspects, said agent contains a primary agent that specifically binds to a member of a TCR complex and a secondary agent that specifically binds to a T cell costimulatory molecule.

In some examples, the primary agent specifically binds to CD3; and/or the costimulatory molecule is selected from the group consisting of CD28, CD137 (4-1-BB), OX40, or ICOS. In some aspects, said primary and secondary agents comprise antibodies and/or are present on the surface of a solid support.

In some of any such embodiments, the method further includes culturing at least a plurality of cells in the presence of a receptor-binding agent that specifically binds a receptor expressed on the surface of one or more target cells to deliver a stimulatory signal and is reversibly bound to the reagent or a second reagent, the reagent or second reagent containing a plurality of binding sites each capable of reversibly binding to the receptor-binding agent, thereby inducing or modulating a signal in the cells. In some cases, said culturing is carried out and/or is initiated prior to said incubating.

In some embodiments, the reagent is a second reagent, wherein the second reagent is not bound to or associated with, a solid support, stationary phase, a bead, a microparticle, a magnetic particle, and/or a matrix during said incubation, and/or the second reagent is flexible, does not contain a metal or magnetic core, is comprised entirely or primarily of organic multimer, is not spherical, is not substantially spherical or uniform in shape, and/or is not rigid. In some instances, the reagent is a second reagent and the second reagent is immobilized on a support.

In some embodiments, the stimulatory agent comprises a contains an MHC I:peptide complex or functional portion thereof, an MHCII:peptide complex or functional portion thereof, and/or is capable of delivering a stimulatory signal through a TCR/CD3 complex in a T cell, a CD3-containing complex in a T cell, and/or an ITAM-containing molecule in a T cell.

In some of any such embodiments, the receptor-binding agent specifically binds to a member of a TCR/CD3 complex or specifically binds to CD3. In some cases, the receptor binding agent is a first receptor binding agent and the culturing is further carried out in the presence of a second receptor binding agent, said second receptor binding agent being an accessory binding agent capable of specifically binding to a second receptor on the surface of one or more of the t cells, thereby inducing a second signal in the cells to enhance, dampen or modify a signal delivered through the first receptor.

In some examples, the second receptor binding agent is reversibly bound to the reagent, the second reagent, or a third reagent; and the reagent, second reagent or third reagent comprises a plurality of binding sites capable of reversibly binding to the second receptor binding agent, whereby the second receptor binding agent is reversibly bound thereto. In some cases, the second receptor is a costimulatory molecule, accessory molecule, cytokine receptor, chemokine receptor, immune checkpoint molecule or is a member of the TNF family or the TNF receptor family.

In some of any such embodiments, the first and second receptor binding agents bind to a molecule expressed on the surface of the cell that is or comprises CD3 and/or CD28, respectively. In some aspects, the first and second receptor binding agent contains an anti-CD3 and/or anti-CD28 antibody or fragment, respectively.

In some of any such embodiments, the incubating and culturing are performed in separate vessels, which are operably connected, optionally by tubing. In some embodiments, the incubating and culturing are performed in a closed system.

In some embodiments, the method includes recovering cells reversibly bound to and stimulated by the receptor binding agent, which can be the first and/or the second receptor binding agent, thereby producing cultured cells, wherein the cultured cells are or contain the plurality of cells comprising target cells.

In some of any such embodiments, after said contacting, the method further includes separating and/or removing, from the immobilized target cells, other cells of the plurality of cells. In some cases, the separating and/or removing is carried out by performing a wash step. In some instances, said separating and/or said wash step is carried out prior to initiation of said incubation.

In some of any such embodiments, said incubating is carried out and/or is initiated prior to said contacting; or said incubating is carried out and/or is initiated subsequently to said contacting. In some of any such embodiments, said contacting is carried out during at least a portion of said incubation.

In some embodiments, the viral binding agent binds to a molecule on the surface of the viral particle that is selected from among an envelope glycoprotein, a variant of an envelope glycoprotein, a chimeric envelope glycoprotein, a viral capsid protein, a variant of a viral capsid protein, a viral matrix protein, a variant of a viral matrix protein, a synthetic moiety, a peptide, and a tag. In some cases, the envelope glycoprotein is selected from among a VSV glycoprotein (VSV-G), Sindbis glycoprotein, optionally SIN, a MMLV glycoprotein, an HSV glycoprotein, an MMTV glycoprotein, Measles virus glycoprotein, HTLV glycoprotein, SIV glycoprotein, an GALV glycoproteins, a HIV glycoprotein, optionally gp160, gp120 or gp41, and an RSV glycoprotein, optionally gp85 or gp37, or are variant, portion sufficient to be bound by the viral particle-binding agent or chimeric molecule thereof. In some aspects, the viral binding agent binds to a molecule on the surface of the viral particle that is a non-viral recombinant molecule heterologous to the virus.

In some embodiments, the molecule is a synthetic moiety, peptide or tag that is selected from among glutathione-S-transferase (GST), chitin binding protein (CBP), calmodulin binding peptide (CBP), FLAG-peptide, themagglutinin peptide, VSV-G-tag, HSV-tag, T7 epitope, maltose binding protein (MBP), HSV epitope, myc epitope, V5-tag, and a streptavidin-binding peptide. In some instances, the molecule is a streptavidin-binding peptide. In some aspects, the molecule is a synthetic moiety, peptide or tag and the viral particle is engineered to express the synthetic moiety, peptide or tag on its surface.

In some embodiments, the streptavidin-binding peptide contains the sequence of amino acids set forth in any of SEQ ID NO: 7, 8, 13, 14, and 15-19. In some cases, the molecule is or contains a ligand binding domain. In some examples, the molecule is or contains an antigen receptor. In some cases, the antigen receptor is a chimeric antigen receptor (CAR). In some aspects, the viral binding antigen is an antibody or antigen-binding fragment that specifically binds an extracellular region of the CAR. In some instances, the extracellular region is the antigen-binding domain or the hinge region.

In some of any such embodiments, the viral particle-binding agent is selected from among protamine, POLYBRENE® and RETRONECTIN®. In some embodiments, the viral particle contains a binding partner C1 or C2; and the reagent contains a plurality of binding sites, Z1 or Z2, capable of binding to the binding partner, C1 or C2, to form the reversible bond between the viral particle and the reagent. In some aspects, the viral particle is engineered to express a synthetic moiety, peptide or tag on its surface, wherein the synthetic moiety, peptide or tag is or contains the binding partner C1 or C2. In some cases, the peptide is a streptavidin-binding peptide. In some examples, the streptavidin-binding peptide contains the sequence of amino acids set forth in any of SEQ ID NO: 7, 8, 13, 14, and 15-19.

In some of any such embodiments, the viral particle associates with or binds the reagent. In some embodiments, the genome of the viral vector contains a heterologous nucleic acid molecule encoding a recombinant protein. In some cases, the recombinant protein is an antigen receptor. In some examples, the recombinant protein is a chimeric antigen receptor.

In some of any such embodiments, the viral particle is a retroviral vector particle. In some aspects, the viral particle is a lentiviral vector particle. In some cases, the lentiviral vector particle comprises a genome that is derived from HIV-1. In some of any such embodiments, the retroviral vector particle is a gammaretrovirus particle. In some examples, the gammaretrovirus particle is a murine leukemia virus (MLV) particle. In some embodiments, the viral vector particle is pseudotyped with a viral envelope glycoprotein. In some cases, the viral envelope glycoprotein is VSV-G.

In some of any such embodiments, the chimeric antigen receptor (CAR) contains an extracellular antigen-recognition domain that specifically binds to a target antigen and an intracellular signaling domain comprising an ITAM. In some cases, intracellular signaling domain contains an intracellular domain of a CD3-zeta (CD3ζ) chain. In some aspects, a transmembrane domain linking the extracellular domain and the intracellular signaling domain is included. In some cases, the transmembrane domain comprises a transmembrane portion of CD28. In some embodiments, the intracellular signaling domain further contains an intracellular signaling domain of a T cell costimulatory molecule. In some examples, the T cell costimulatory molecule is selected from the group consisting of CD28 and 41BB.

In some of any such embodiments, the nucleic acid further contains a promoter operably linked to the nucleic acid encoding the recombinant antigen receptor.

In some of any such embodiments, the plurality of cells contains peripheral blood mononuclear cells (PBMCs) or an enriched or isolated subset of cells thereof. In some embodiments, the plurality of cells comprise blood cells, leukocytes, lymphocytes, B cells, T cells or NK cells.

In some embodiments, the plurality of cells contains antigen-specific T cells or a population thereof, a T helper cell or population thereof, a cytotoxic T cell or population thereof, a memory T cell or population thereof, a regulatory T cell or population thereof, an NK cell or population thereof, antigen-specific B cells or a population thereof, a memory B cell or population thereof, or a regulatory B cell or population thereof. In some embodiments, the plurality of cells are primary cells. In some embodiments, plurality of cells contains T cells. In some aspects, the T cells are unfractionated T cells, are enriched or isolated CD3+ T cells, are enriched or isolated CD4+ T cells or are enriched or isolated CD8+ T cells.

In some of any such embodiments, the reagent is not toxic to the plurality of cells or at least or at least about 75%, 85%, 90%, 95% or more of the plurality of cells are viable after the contacting or incubating. In some of any such embodiments, the toxicity of the cells subsequent to the contacting and/or incubating is less than or less than about 1.2-fold, 1.5-fold, 2.0-fold, 3.0-fold, 4.0-fold, 5.0-fold or 10-fold of the toxicity of the cells when contacted or incubated with a polycation transduction adjuvant under the same conditions; and/or the viability of the cells subsequent to the contacting and/or incubating is greater than or greater than about 1.2-fold, 1.5-fold, 2.0-fold, 3.0-fold, 4.0-fold, 5.0-fold or 10-fold compared to the viability of the cells when contacted or incubated with a polycation transduction adjuvant under the same conditions. In some cases, the polycation transduction adjuvant is protamine sulfate, a fibronectin-derived transduction adjuvant or RetroNectin.

In some of any such embodiments, the reagent is or contains streptavidin, avidin, an analog or mutein of streptavidin that reversibly binds biotin, a biotin analog or a biologically active fragment thereof; an analog or mutein of avidin or streptavidin that reversibly binds a streptavidin-binding peptide; a reagent that comprises at least two chelating groups K, wherein the at least two chelating groups are capable of binding to a transition metal ion; an agent capable of binding to an oligohistidine affinity tag; an agent capable of binding to a glutathione-S-transferase; calmodulin or an analog thereof; an agent capable of binding to calmodulin binding peptide (CBP); an agent capable of binding to a FLAG-peptide; an agent capable of binding to an HA-tag; an agent capable of binding to maltose binding protein (MBP); an agent capable of binding to an HSV epitope; an agent capable of binding to a myc epitope; or an agent capable of binding to a biotinylated carrier protein In some of any such embodiments, the reagent is an oligomer or polymer of streptavidin, avidin, an analog or mutein of streptavidin that reversibly binds biotin or a biologically active fragment; a streptavidin or avidin analog or mutein that reversibly binds a streptavidin-binding peptide; a reagent that comprises at least two chelating groups K, wherein the at least two chelating groups are capable of binding to a transition metal ion; an agent capable of binding to an oligohistidine affinity tag; an agent capable of binding to a glutathione-S-transferase; calmodulin or an analog thereof; an agent capable of binding to calmodulin binding peptide (CBP); an agent capable of binding to a FLAG-peptide; an agent capable of binding to an HA-tag; an agent capable of binding to maltose binding protein (MBP); an agent capable of binding to an HSV epitope; an agent capable of binding to a myc epitope; or an agent capable of binding to a biotinylated carrier protein.

In some of any such embodiments, the reagent contains an oligomer or polymer of streptavidin, avidin, a streptavidin analog or mutein or and an avidin analog or mutein. In some aspects, the individual molecules of the oligomer or polymer are crosslinked by a polysaccharide or a bifunctional linker. In some of any such embodiments, the reagent is or contains a streptavidin analog or mutein or an avidin analog or mutein that reversibly binds to biotin or a biologically active fragment; the reagent is or contains a streptavidin analog or mutein or an avidin analog or mutein that reversibly binds to a biotin analog or a biologically active fragment; and/or the reagent is or contains a streptavidin analog or mutein or an avidin analog or mutein that reversibly binds to a streptavidin-binding peptide.

In some aspects, the streptavidin-binding peptide is selected from the group consisting of Trp-Ser-His-Pro-Gln-Phe-Glu-Lys (SEQ ID NO: 8), Trp-Ser-His-Pro-Gln-Phe-Glu-Lys-(GlyGlyGlySer)$_3$-Trp-Ser-His-Pro-Gln-Phe-Glu-Lys (SEQ ID NO: 17), Trp-Ser-His-Pro-Gln-Phe-Glu-Lys-(GlyGlyGlySer)$_2$-Trp-Ser-His-Pro-Gln-Phe-Glu-Lys (SEQ ID NO: 18) and Trp-Ser-His-Pro-Gln-Phe-Glu-Lys-(GlyGlyGlySer)$_2$Gly-Gly-Ser-Ala-Trp-Ser-His-Pro-Gln-Phe-Glu-Lys (SEQ ID NO: 19).

In some of any such embodiments, the reagent contains SEQ ID NO:1 or SEQ ID NO:2 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO:1 or SEQ ID NO:2. In some of any such embodiments, the reagent contains a streptavidin analog or mutein comprising the amino acid sequence Val$^{44}$-Thr$^{45}$-Ala$^{46}$-Arg$^{47}$ or Ile$^{44}$-Gly$^{45}$-Ala$^{46}$-Arg$^{47}$ at sequence positions corresponding to positions 44 to 47 with reference to positions in streptavidin in the sequence of amino acids set forth in SEQ ID NO:1; or the streptavidin analog or mutein contains the amino acid sequence Val$^{44}$-Thr$^{45}$-Ala$^{46}$-Arg$^{47}$ at sequence positions corresponding to positions 44 to 47 with reference to positions in streptavidin in the sequence of amino acids set forth in SEQ ID NO:1.

In some of any such embodiments, the streptavidin analog or mutein contains a) the sequence of amino acids set forth in any of SEQ ID NOS: 3-6, 27 and 28; b) a sequence of amino acids that exhibits at least 85%, 86%, 87%, 88%, 89%, 89%, 90%, 91%, 92%, 93%, 94%, 95%, 96%, 97%, 98%, 99% or more sequence identity to any of SEQ ID NOS:3-6, 27 and 28 and contains the amino acid sequence corresponding to Val$^{44}$-Thr$^{45}$-Ala$^{46}$-Arg$^{47}$ or Ile$^{44}$-Gly$^{45}$-Ala$^{46}$-Arg$^{47}$ and that reversibly binds to biotin or a biologically active form thereof, a biotin analog or mutein or a biologically active fragment thereof or a streptavidin-binding peptide; or c) a functional fragment of a) or b) that reversibly binds to biotin or a biologically active form thereof, a biotin analog or mutein or a biologically active fragment thereof or a streptavidin-binding peptide.

In some embodiments, the streptavidin analog or mutein further contains an amino acid replacement or replacements at a position corresponding to 117, 120 and/or 121 with reference to positions in streptavidin in the sequence of amino acids set forth in SEQ ID NO:1. In some examples, the amino acid replacement or replacements are selected from among Glu117, Asp117, Arg117, Ser120, Ala120, Gly120, Trp121, Tyr121 or Phe121; or the amino acid replacement or replacements are selected from one or more of Glu117, Gly120 or Tyr121; or the amino acid replacements are selected from Glu117, Gly120 or Tyr121.

In some of any such embodiments, the streptavidin analog or mutein contains a) the sequence of amino acids set forth in SEQ ID NO: 27 or 28; b) a sequence of amino acids that exhibits at least 85%, 86%, 87%, 88%, 89%, 89%, 90%, 91%, 92%, 93%, 94%, 95%, 96%, 97%, 98%, 99% or more sequence identity to SEQ ID NOS:28 and contains the amino acid sequence corresponding to Val$^{44}$, Thr$^{45}$, Ala$^{46}$, Arg$^{47}$, Glu$^{117}$, Gly$^{120}$ and Tyr$^{121}$ and reversibly binds to biotin or a biologically active fragment, a biotin analog or mutein or a biologically active fragment thereof or a streptavidin-binding peptide; or c) a functional fragment of a) or b) that reversibly binds to biotin or a biologically active fragment, a biotin analog or mutein or a biologically active fragment thereof or a streptavidin-binding peptide.

In some of any such embodiments, the binding agent contains a binding partner C that is a streptavidin-binding peptide. In some examples, the binding partner C contains a streptavidin-binding peptide selected from the group consisting of Trp-Ser-His-Pro-Gln-Phe-Glu-Lys (SEQ ID NO: 8), Trp-Ser-His-Pro-Gln-Phe-Glu-Lys-(GlyGlyGlySer)$_3$-Trp-Ser-His-Pro-Gln-Phe-Glu-Lys ((SEQ ID NO: 17), Trp-Ser-His-Pro-Gln-Phe-Glu-Lys-(GlyGlyGlySer)$_2$-Trp-Ser-His-Pro-Gln-Phe-Glu-Lys (SEQ ID NO: 18) and Trp-Ser-His-Pro-Gln-Phe-Glu-Lys-(GlyGlyGlySer)$_2$Gly-Gly-Ser-Ala-Trp-Ser-His-Pro-Gln-Phe-Glu-Lys (SEQ ID NO: 19).

In some of any such embodiments, the method includes disrupting the reversible binding between the one or more binding agent and the reagent. In some cases, said disruption comprises introducing to the cells a substance capable of reversing the bond between the one or more binding agent and the reagent. In some aspects, the substance is a free binding partner and/or is a competition agent. In some instances, the substance in the composition is not detrimental to the T cells or to the target cells and/or wherein the addition of said substance docs not reduce the percentage of surviving target cells to less than 90%, 80%, 70%, 60%, or 50%, as compared to incubation of the target cells, respectively, under comparable or the same conditions, without the substance.

In some of any such embodiments, the reagent is or contains a streptavidin, avidin, a streptavidin analog or mutein or and an avidin analog or mutein or biologically active fragments thereof; and the substance comprises a streptavidin-binding peptide, biotin or a biologically active fragment, optionally a D-biotin, or a biotin analog or biologically active fragment. In some examples, the substance is a streptavidin-binding peptide is selected from the group consisting of Trp-Ser-His-Pro-Gln-Phe-Glu-Lys (SEQ ID NO: 8), Trp-Ser-His-Pro-Gln-Phe-Glu-Lys-(GlyGlyGly Ser)$_3$-Trp-Ser-His-Pro-Gln-Phe-Glu-Lys ((SEQ ID NO: 17), Trp-Ser-His-Pro-Gln-Phe-Glu-Lys-(GlyGlyGlySer)$_2$-Trp-Ser-His-Pro-Gln-Phe-Glu-Lys (SEQ ID NO: 18) and Trp-Ser-His-Pro-Gln-Phe-Glu-Lys-(GlyGlyGlySer)$_2$Gly-Gly-Ser-Ala-Trp-Ser-His-Pro-Gln-Phe-Glu-Lys (SEQ ID NO: 19); and/or the substance is C1 or an analog thereof or is C2 or an analog thereof.

In some of any such embodiments, the method includes, after said disruption, recovering the cells. In some of any such embodiments, the method includes further incubating the cells. In some cases, the further incubation is performed under conditions to expand the cells. In some aspects, the incubation and further incubation are carried out in the same vessel; and/or the further incubation is carried out in the presence of the substance; and/or the method does not include removing the substance, selection agent, stimulatory agent, viral particle-binding agent and/or reagent from the incubated composition prior to the further incubation. In some embodiments, the reagent is not removed from the composition prior to the further incubation, is not removed from the composition during the further incubation, or is not removed from the composition during at least half of the further incubation.

In some embodiments, the further incubation is carried out at or about 37° C.±2° C.; and/or the further incubation is carried out in the presence of a further agent that is capable of delivering a signal to T cells during at least a portion of the incubation and/or further incubation. In some cases, the further agent is capable of enhancing or inducing proliferation of T cells, CD4+ T cells and/or CD8+ T cells. In some embodiments, the further agent is a cytokine selected from among IL-2, IL-15 and IL-7. In some aspects, the further incubation is carried out for a time that is no more than 14 days, no more than 12 days, no more than 10 days, no more than 8 days or no more than 6 days.

In some of any such embodiments, the support contains a resin or matrix; the support contains a gel filtration matrix; the support contains a chromatography matrix; and/or the support contains a cellulose-based or organic polymer-based membrane. In some of any such embodiments, the support comprises a microparticle, rigid particle, magnetic particle, or bead. In some cases, the chromatography matrix is present within a column and/or wherein the chromatography is column chromatography or planar chromatography. In some embodiments, the support is a stationary phase, present within a container during all or part of said incubation and/or said contacting.

In some of any such embodiments, the container contains a container selected from the group consisting of: columns, containers suitable for bidirectional flow, pipette tips, tubes, and columns suitable for flow-through of a liquid sample.

In some of any such embodiments, the one or more transduced cells in the output composition express a recombinant protein encoded by a heterologous nucleic acid contained by the viral particles. In some of any such embodiments, transduction of the cells is increased by greater than or greater than or about 1.2-fold, 1.5-fold, 2-fold, 3-fold, 4-fold, 5-fold, 10-fold or more compared to the transduction with the viral particle in the absence of the reagent.

In some of any such embodiments, the method results in selective transduction of target cells expressing the molecule bound by the selection agent. In some cases, transduction is at least 2-fold, 3-fold, 4-fold, 5-fold, 6-fold, 7-fold, 8-fold, 9-fold, 10-fold or greater in target cells that express the molecule than in non-target cells that do not express the molecule.

In some of any such embodiments, at least 2.5%, at least 5%, at least 6%, at least 8%, at least 10%, at least 20%, at least 25%, at least 30%, at least 40%, at least 50%, or at least 75% of said cells among the plurality of cells are transduced with said viral vector by the method; and/or at least 2.5%, at least 5%, at least 6%, at least 8%, at least 10%, at least 20%, at least 25%, at least 30%, at least 40%, at least 50%, or at least 75% of said cells in said further incubated composition are transduced with said viral vector; and/or at least 2.5%, at least 5%, at least 6%, at least 8%, at least 10%, at least 20%, at least 25%, at least 30%, at least 40%, at least 50%, or at least 75% of said cells in said incubated composition and/or further incubated composition express a product of a heterologous nucleic acid comprised within said viral vector.

In some of any such embodiments, the method is performed ex vivo. In some of any such embodiments, the method further includes recovering or isolating the transduced cells produced by the method.

Also provided is a transduced cell produced by any of the methods as described herein. In some cases, a composition comprising the transduced cell is also provided.

Also provided herein is a composition containing a viral vector particle-binding agent reversibly bound to a reagent, wherein the viral particle-binding agent is capable of specifically binding to a molecule on the surface of a viral particle; or a viral vector particle reversibly bound to the reagent. In some aspects, the reagent contains a plurality of binding sites, each capable of reversibly binding to the viral particle-binding agent. In some instances, the composition further contains a selection agent that is reversibly bound to the reagent and is capable of specifically binding to a molecule on the surface of a target cell. In some examples, the reagent is or comprises a streptavidin, an avidin, a streptavidin analog or mutein or an avidin analog or mutein, or a biologically active fragment of any of the foregoing, or is an oligomer comprising multiple units of any of the foregoing.

In some of any such embodiments, the viral binding agent binds to a molecule on the surface of the viral particle that is a non-viral recombinant molecule heterologous to the virus molecule; or binds to a molecule on the surface of the viral particle that is selected from among an envelope glycoprotein, a variant of an envelope glycoprotein, a chimeric envelope glycoprotein, a viral capsid protein, a variant of a viral capsid protein, a viral matrix protein, a variant of a viral matrix protein, a synthetic moiety, a peptide, and a tag.

In some cases, the envelope glycoprotein is selected from among a VSV glycoprotein (VSV-G), Sindbis glycoprotein, optionally SIN, a MMLV glycoprotein, an HSV glycoprotein, an MMTV glycoprotein, Measles virus glycoprotein, HTLV glycoprotein, SIV glycoprotein, an GALV glycoproteins, a HIV glycoprotein, optionally gp160, gp120 or gp41, and an RSV glycoprotein, optionally gp85 or gp37, or are variant, portion sufficient to be bound by the viral particle-binding agent or chimeric molecule thereof; or the molecule is a synthetic moiety, peptide or tag that is selected from among glutathione-S-transferase (GST), chitin binding protein (CBP), calmodulin binding peptide (CBP), FLAG-peptide, themagglutinin peptide, VSV-G-tag, HSV-tag, T7 epitope, maltose binding protein (MBP), HSV epitope, myc epitope, V5-tag, and a streptavidin-binding peptide In some examples, the non-viral recombinant molecule is or contains a ligand binding domain. In some cases, the molecule is or comprises an antigen receptor. In some aspects, the antigen receptor is a chimeric antigen receptor (CAR). In some cases, the viral binding antigen is an antibody or antigen-binding fragment that specifically binds an extracellular region of the CAR. In some embodiments, the extracellular region is the antigen-binding domain or the hinge region.

Also provided herein is an article of manufacture, containing the composition as described herein and a support, wherein the reagent is immobilized on the support. In some cases, the support is or contains a stationary phase and/or a solid support. In some examples, the support is a stationary phase which is or contains a chromatography matrix, wherein the article of manufacture further contains a container in which all or part of the chromatography matrix is contained. In some cases, the container is a column.

Also provided herein is an apparatus containing one or more containers containing one or more components selected from one or more oligomeric protein reagent, a plurality of cells comprising target cells and a viral particles and a support containing at least one stationary phase that is or contains a chromatography matrix. In some cases, the at least one oligomeric protein reagent is reversibly bound to a viral particle-binding agent, a selection agent and/or to a receptor-binding agent. In some aspects, the one or more containers are in fluid connection, whereby one or more of the components pass from one container to another within the apparatus.

In some of any such embodiments, the article of manufacture or apparatus described herein further contains a sample outlet fluidly connected to one of the at least one stationary phase for chromatography. In some embodiments, the article of manufacture or apparatus is a functionally closed or sterile system.

In some of any such embodiments, the article of manufacture or apparatus further contains one or more controls, capable of regulating or adjusting pH, $pO_2$, $pCO_2$, and/or thermostatic control of one or more containers or components thereof, or of at least one of the at least one stationary phase for chromatography. In some case, the article of manufacture or apparatus further contains a fluid connection to a container comprising medium and/or one or more nutrients and/or one or more carbon sources, whereby the connection is capable of delivering such medium, nutrients, and/or carbon sources to cells within the apparatus, optionally when said cells are immobilized on the stationary phase for chromatography. In some embodiments, at least one of the components and/or a container including the same is detachable from the apparatus in a sterile or aseptic fashion.

Also provided herein is a viral vector particle containing a streptavidin-binding peptide. In some cases, the streptavidin-binding peptide is a fusion protein with an envelope glycoprotein. In some examples, the envelope glycoprotein is VSV-G.

In some of any such embodiments, the viral vector is a retroviral vector, optionally a lentiviral vector. In some aspects, the streptavidin-binding peptide selected from the group consisting of Trp-Ser-His-Pro-Gln-Phe-Glu-Lys (SEQ ID NO: 8), Trp-Ser-His-Pro-Gln-Phe-Glu-Lys-(GlyGlyGly-Ser)$_3$-Trp-Ser-His-Pro-Gln-Phe-Glu-Lys (SEQ ID NO: 17), Trp-Ser-His-Pro-Gln-Phe-Glu-Lys-(GlyGlyGlySer)$_2$-Trp-Ser-His-Pro-Gln-Phe-Glu-Lys (SEQ ID NO: 18) and Trp-Ser-His-Pro-Gln-Phe-Glu-Lys-(GlyGlyGlySer)$_2$Gly-Gly-Ser-Ala-Trp-Ser-His-Pro-Gln-Phe-Glu-Lys (SEQ ID NO: 19). In some instances, the viral vector particle contains a genome encoding a recombinant antigen receptor, optionally a chimeric antigen receptor.

Also provided in some embodiments is a kit containing the viral vector particle described herein, a reagent comprising one or a plurality of binding sites capable or reversibly binding the viral vector particle; and optionally instructions for use. In some cases, the kit further contains a selection agent capable of binding a selection marker on the surface of a target cells, wherein the reagent contains one or a plurality of binding sites capable of reversibly binding the selection agent.

Also provided is a composition containing an oligomeric protein reagent associated with a viral particle. In some embodiments, the oligomeric reagent contains a plurality of polypeptide monomeric units, wherein each unit contains at least at or about 10, 20, 30, or 40 amino acids in length and/or comprises a weight of at least at or about 20, 30, 40, or 50 kDa; and/or the oligomeric reagents contains a molecular weight of at least at or about 100, and/or between at or about 150 kDa to about 2000 kDa, about 150 kDa to about 1500 kDa, about 150 kDa to about 1250 kDa, about 150 kDa to 1000 kDa, about 150 kDa to about 500 kDa or about 150 kDa to about 300 kDa, about 300 kDa to about 2000 kDa, about 300 kDa to about 1500 kDa, about 300 kDa to about 1250 kDa, about 300 kDa to 1000 kDa, about 300 kDa to about 500 kDa, about 500 kDa to about 2000 kDa, about 500 kDa to about 1500 kDa, about 500 kDa to about 1250 kDa, about 500 kDa to 1000 kDa, about 1000 kDa to about 2000 kDa, about 1000 kDa to about 1500 kDa, about 1000 kDa to about 1250 kDa, about 1250 kDa to about 2000 kDa or about 1500 kDa to about 2000 kDa.

In some embodiments, the oligomeric protein reagent contains an oligomer comprised of a plurality of multimeric subunits. In some examples, the multimeric subunits are tetrameric, units and individually contain the monomeric unit. In some aspects, the oligomeric protein reagent contains, and optionally contains multiple units of, a streptavidin, an avidin, a streptavidin analog or mutein or an avidin analog or mutein or a biologically active fragment of any of the foregoing, and/or a multimer of any of the foregoing.

In some embodiments, the viral particles contain a sequence of nucleotides encoding a heterologous nucleic acid.

In some of any such embodiments, the reagent is naked; the reagent does not contain and/or is not conjugated or reversibly bound to a binding agent; the reagent does not contain and/or is not conjugated or bound to a molecule with a binding domain specific for a cell surface marker, optionally selected from among adhesion molecules, integrins, chemokines, cytokines, growth factors, extracellular matrix-binding molecules, viral proteins, viral entry-promoting cell surface receptors, heparin, heparan, glycans a T-cell surface marker, a CD3, a CD28 a CD4 and/or a CD8; the reagent does not contain and or is not conjugated or bound to a mammalian cell surface marker, an extracellular matrix component, adhesion molecule, an integrin, a lectin, an integrin-binding protein, a chemokines, a cytokine, a growth factor, an extracellular matrix-binding molecule, an ECM component, a viral protein, a viral entry-promoting cell surface receptor, heparin, heparan, glycans; and/or the reagent does not contain a heparin-binding domain and/or does not contain an integrin-binding domain and/or does not contain a VLA4-binding domain and/or does not contain a VLA5-binding domain; and/or the reagent does not comprise and/or is not conjugated or coupled or bound to a viral binding agent or a cell selection agent.

In some embodiments, the reagent further contains and/or is reversibly bound to a plurality of one or more binding agents. In some examples, the binding agent is a viral particle-binding agent that specifically binds to a molecule on the surface of the viral particle, a selection agent that specifically binds to a molecule on the surface of a target cell, or a receptor binding agent that specifically binds to a receptor to deliver a stimulatory signal in a target cell.

In some embodiments, the binding agent is or contains an antibody, an antibody fragment, a monovalent antibody fragment, a proteinaceous binding molecule with antibody-like binding properties, a molecule containing Ig domains, a cytokine, a chemokine, an aptamer, and MHC molecule or binding fragments thereof. In some instances, the antibody fragment comprises a fragment selected from the group consisting of a Fab fragment, an Fv fragment, a (Fab')$_2$-fragment, and a divalent single-chain Fv (scFv) fragment.

In some of any such embodiments, the reagent includes SEQ ID NO:1 or SEQ ID NO:2 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO:1 or SEQ ID NO:2. In some embodiments, the reagent contains a streptavidin analog or mutein including the amino acid sequence Val$^{44}$-Thr$^{45}$-Ala$^{46}$-Arg$^{47}$ or Ile$^{44}$-Gly$^{45}$-Ala$^{46}$-Arg$^{47}$ at sequence positions corresponding to positions 44 to 47 with reference to positions in streptavidin in the sequence of amino acids set forth in SEQ ID NO:1; or the streptavidin analog or mutein including the amino acid sequence Val$^{44}$-Thr$^{45}$-Ala$^{46}$-Arg$^{47}$ at sequence positions corresponding to positions 44 to 47 with reference to positions in streptavidin in the sequence of amino acids set forth in SEQ ID NO:1.

In some of any such embodiments, the reagent contains a streptavidin analog or mutein, which includes a) the sequence of amino acids set forth in any of SEQ ID NOS: 3-6, 27 and 28; b) a sequence of amino acids that exhibits at least 85%, 86%, 87%, 88%, 89%, 89%, 90%, 91%, 92%, 93%, 94%, 95%, 96%, 97%, 98%, 99% or more sequence identity to any of SEQ ID NOS:3-6, 27 and 28 and contains the amino acid sequence corresponding to Val$^{44}$-Thr$^{45}$-Ala$^{46}$-Arg$^{47}$ or Ile$^{44}$-Gly$^{45}$-Ala$^{46}$-Arg$^{47}$ and that reversibly binds to biotin or a biologically active form thereof, a biotin analog or mutein or a biologically active fragment thereof or a streptavidin-binding peptide; or c) a functional fragment of a) or b) that reversibly binds to biotin or a biologically active form thereof, a biotin analog or mutein or a biologically active fragment thereof or a streptavidin-binding peptide.

In some embodiments, the streptavidin analog or mutein further contains an amino acid replacement or replacements at a position corresponding to 117, 120 and/or 121 with reference to positions in streptavidin in the sequence of amino acids set forth in SEQ ID NO:1. In some examples, the amino acid replacement or replacements are selected from among Glu117, Asp117, Arg117, Ser120, Ala120, Gly120, Trp121, Tyr121 or Phe121; or the amino acid replacement or replacements are selected from one or more of Glu117, Gly120 or Tyr121; or the amino acid replacements are selected from Glu117, Gly120 or Tyr121.

In some of any such embodiments, the reagent contains a streptavidin analog or mutein, which includes a) the sequence of amino acids set forth in SEQ ID NO: 27 or 28; b) a sequence of amino acids that exhibits at least 85%, 86%, 87%, 88%, 89%, 89%, 90%, 91%, 92%, 93%, 94%, 95%, 96%, 97%, 98%, 99% or more sequence identity to SEQ ID NOS:28 and contains the amino acid sequence corresponding to Val$^{44}$, Thr$^{45}$, Ala$^{46}$, Are, Glu$^{117}$, Gly$^{120}$ and Tyr$^{121}$ and reversibly binds to biotin or a biologically active fragment, a biotin analog or mutein or a biologically active fragment thereof or a streptavidin-binding peptide; or c) a functional fragment of a) or b) that reversibly binds to biotin or a biologically active fragment, a biotin analog or mutein or a biologically active fragment thereof or a streptavidin-binding peptide.

In some of any such embodiments, the genome of the viral vector contains a nucleic acid molecule encoding a recombinant protein. In some cases, the recombinant protein is an antigen receptor. In some embodiments, the viral particle is a retrovirus. In some instances, the retrovirus is a lentivirus. In some cases, the retrovirus is a gammaretrovirus. In some embodiments, the viral particle is replication defective.

In some of any such embodiments, the reagent is soluble.

Provided herein in some embodiments is a method for transducing cells. Provided herein is a method for transducing cells, comprising incubating, such as contacting, a plurality of cells comprising one or more target cells, such as present in an input composition comprising the plurality of cells, with (1) an oligomeric reagent; and (2) a viral particle, optionally wherein the method produces an output composition comprising one or more transduced cells.

Provided herein is a method for transducing cells, the method comprising: (a) contacting a viral particle with an oligomeric reagent, thereby generating a mixture comprising viral particles associated with the reagent; and (b) contacting the mixture with an input composition comprising a plurality of cells, optionally wherein the method produces an output composition comprising one or more transduced cells. In some embodiments the reagent is or comprises an oligomer. In some embodiments, the contacting comprises admixing the cell with the reagent and with the viral particle, simultaneously or sequentially, in either order. In some embodiments, during at least a portion of the contacting, the reagent and viral particle are in the presence of or contacted with the cell simultaneously.

In some of any of the embodiments, the oligomeric reagent is an oligomeric protein reagent; and/or the oligomeric reagent comprises a plurality of polypeptide monomeric units, wherein each unit optionally comprises at least at or about 10, 20, 30, or 40 amino acids in length, optionally at least at or about 50, 60, 65, 70, 80, 90, 100, 125, or 150 amino acids in length and/or comprises a weight of at least at or about 20, 30, 40, or 50 kDa, optionally wherein the reagent comprises an oligomer comprised of a plurality of multimeric subunits, which are optionally tetrameric, units and individually comprise the monomeric unit; and/or the oligomeric reagents comprises a molecular weight of at least at or about 100, and/or between at or about 150 kDa to about 2000 kDa, about 150 kDa to about 1500 kDa, about 150 kDa to about 1250 kDa, about 150 kDa to 1000 kDa, about 150 kDa to about 500 kDa or about 150 kDa to about 300 kDa, about 300 kDa to about 2000 kDa, about 300 kDa to about 1500 kDa, about 300 kDa to about 1250 kDa, about 300 kDa to 1000 kDa, about 300 kDa to about 500 kDa, about 500 kDa to about 2000 kDa, about 500 kDa to about 1500 kDa, about 500 kDa to about 1250 kDa, about 500 kDa to about 1000 kDa, about 1000 kDa to about 2000 kDa, about 1000 kDa to about 1500 kDa, about 1000 kDa to about 1250 kDa, about 1250 kDa to about 2000 kDa or about 1500 kDa to about 2000 kDa.

In some of any of the embodiments, the reagent, such as oligomeric protein reagent comprises, and optionally comprises multiple units of, a streptavidin, an avidin, a streptavidin analog or mutein or an avidin analog or mutein or a biologically active fragment of any of the foregoing, and/or a multimer of any of the foregoing.

In some embodiments, wherein the contacting comprises admixing the cell with the reagent and with the viral particle, simultaneously or sequentially, in either order. In some embodiments, during at least a portion of the contacting, the reagent and viral particle are in the presence of or contacted with the cell simultaneously.

In some embodiments, the one or more transduced cells in the output composition express a recombinant protein encoded by a heterologous nucleic acid comprised by the viral particles. In some embodiments, the viral particle is a retrovirus, such as a lentivirus or a gammaretrovirus.

In some embodiments, the provided methods increases transduction efficiency compared to have transduction was performed without the reagent or with an alternative adjuvant, such as with Retronectin or protamine sulfate. In some embodiments, transduction efficiency is increased greater than or greater than about 1.2-fold, 2-fold, 3-fold, 4-fold, 5-fold, 10-fold or more.

In some embodiments, the reagent is reversibly bound to a binding agent. In some embodiments, the binding agent on the cells can facilitate one of more of selection, isolation, activation, stimulation and or expansion of cells or a sub-population of cells. In some embodiments, the binding is any binding agent as described.

Also provided are compositions containing a reagent, such as any oligomeric protein reagent, such as any as described as a viral particle. In some embodiments, the viral particle is a retrovirus, such as a lentivirus or a gammaretrovirus.

Also provided is a kit comprising a reagent, such as any oligomeric protein reagent, such as any as described as a viral particle. In some embodiments, the viral particle is a retrovirus, such as a lentivirus or a gammaretrovirus.

BRIEF DESCRIPTION OF THE DRAWINGS

FIG. 2 provides a schematic representation of exemplary embodiments of viral transduction method employing reversible systems in accord with the provided methods.

FIG. 2B depicts a viral particle containing a binding partner in a viral envelope protein on the surface of the viral particle and an agent bound to a molecule on the surface of a cell.

FIG. 2D depicts a viral particle containing a binding partner in a viral envelope protein on the surface of the viral particle and an agent bound to a molecule on the surface of a cell.

FIG. 3 provides schematic representations of exemplary embodiments.

FIG. 5 provides a schematic representation of exemplary embodiments in which oligomeric reagents are used to multimerize stimulatory agents and the resulting complexes incubated with cells to deliver signals to the cells, followed by reversal of the binding. Panel A shows an oligomeric reagent 1, which is shown as not bound to any support and as being flexible. Stimulatory agents 2, which are shown here as Fab fragments and are capable of specifically binding to a molecule on the surface of a cell, are combined with the reagent. The agents comprise a binding partner (e.g. binding partner C) that is capable of reversibly binding to a binding site (e.g. binding site Z) on the reagent, multimerizing the agents. Panel B depicts the binding partner reversibly binding to a binding site on the reagent. Cells 3 are added to the system. Panel C depicts the multimerized agents (Fab fragments) specifically binding to the molecules 4 on the surface of a cell 3. In Panel C, the depicted agents are stimulatory receptor-binding agents, (e.g. a first receptor-binding agent and/or a second receptor-binding agent), which can induce or modulate a signal in a cell upon binding of the agent, to the molecule on the cell. As shown in panel D, a substance 5, such as a competitive reagent (e.g. biotin), is added to the composition, which can be a substance that exhibits a higher binding affinity for the binding site on the reagent than for the binding partner on the agent, thereby disrupting the reversible binding between the reagent 1 and the agent 2. In some cases, the agent, e.g., Fab fragment also can dissociate from its interaction with the molecule 4 on the cell 3. In some cases, this can disrupt, lessen and/or terminate the signaling in the cell.

FIGS. 7A-7C show the results of an experiment in which CD3+T responder cells were proliferated after being stimulated in vitro with αCD3 and αCD28 Fab fragments that were reversibly immobilized on beads coated with the streptavidin mutein Strep-tactin®. FIG. 7A is a histogram showing size-distribution (forward scatter) of stimulated cells, FIG. 7B depicts histograms representing the degree of proliferation according to the number of cells per cell division that are indicated on top of FIG. 7B (0 represents undivided cells; 5 represents cells that have gone through at least 5 divisions), and FIG. 7C shows a picture of the culture dish after 4 days of stimulation.

FIG. 8A-8E show the results of an experiment in which CD3+T responder cells were proliferated after being stimulated in vitro with reversible αCD3/αCD28 Fab fragments that were reversibly immobilized on soluble oligomeric streptavidin mutein acting a soluble reagent. For the experiments the results of which are shown in FIGS. 8A-8E, 300,000 CD3+ responder T cells (Tress) were labeled with 2 µM Carboxyfluorescein succinimidyl ester (CFSE) and stimulated with varying amounts of a preparation of soluble oligomeric streptavidin mutein on which a combination of αCD3 Fab fragment and αCD28 Fab both carrying a Strep-tag as streptavidin binding peptide at the heavy chain were immobilized. ("1×" corresponds to 3 µg oligomeric streptavidin mutein functionalized with 0.5 µs αCD3- and 0.5 µg αCD28 Fab; numbers indicate fold amount of "1×"). Tresp cells either left unstimulated or were stimulated with blank oligomeric streptavidin muteins (no Fab) served as negative control. Tresp cells were seeded in duplicates in 48-well plates along with 300,000 CD3 negative autologous feeder cells (irradiated with 30 Gy) in 1 ml cell culture medium supplemented with 20 U/ml interleukin 2 (IL-2). Cells were incubated at 37° C. without media exchange and proliferation was analyzed according to CFSE dilution after 5 days by FACS analysis (FIG. 8B). FIG. 8A shows size distribution of cells after 5 days in culture. Histograms show live CD3+ cells, while FIG. 8C shows cells after culture that were liberated by stimulation reagents after treated with 1 mM D-biotin and washed. The dissociation and removal of monomeric Fab fragments was analyzed by restaining with oligomeric streptavidin mutein labeled with phycoerythrine (ST-PE) as a fluorescent label and a representative histogram is shown. FIG. 8D shows the absolute number of live (trypan blue negative) cells after 5 days was counted using a Neubauer counting chamber and plotted against the respective stimulation condition. Median cell numbers are shown in FIG. 8D; error bars indicate standard deviation (SD). FIG. 8E shows a picture of the culture dish after 5 days of stimulation.

FIGS. 10A and 10B show the expansion kinetics of proliferation of purified CD4+ and CD8+T responder cells (Tresp) that were stimulated in vitro with αCD3/αCD28 Fab fragments that were reversibly immobilized fragments that were reversibly immobilized with two kinds of soluble oligomeric streptavidin mutein acting as soluble reagent. The first kind of oligomeric Strep-tactin® was the fraction of the oligomeric streptavidin mutein (n≥3) obtained in Example 3 (also referred herein as "conventional oligomeric streptavidin mutein backbone", illustrated by the triangle symbol with the tip down in FIGS. 10A and 10B), the second kind of this oligomeric streptavidin mutein used as soluble reagent was the HSA based soluble reagent, the abovementioned "large backbone"). In the experiments of FIGS. 10A and 10B the expansion was carried out with medium exchange. The results for the CD4+T responder cells are shown in FIG. 10A, the results for the CD8+T responder cells are shown in FIG. 10B.

FIGS. 12A-12C show the expansion kinetics and phenotype of CD3+ central memory T cells (Tcm) (CD3+CD62L+ CD45RA-Tcm) polyclonally stimulated in vitro with αCD3/αCD28 Fab fragments that were reversibly immobilized on the soluble oligomeric streptavidin mutein (with n≥3) described in Example 3. The graphs shown in FIGS. 12A and 12B represent the degree of proliferation according to the number of cells harvested per time point, with FIG. 12A showing the proliferation in only IL-2 supplemented media and in FIG. 12B showing the proliferation in IL-2 and IL-15 supplemented media. FIG. 12C shows a flow-cytometric analysis of CD62L and CD127 surface expression after 14 days of culture in these variable cytokine milieus.

FIG. 13A shows a graph of bars that represent the degree of proliferation according to the number of cells harvested at day 6 compared to the negative controls (unstimulated purified CD8+T responder cells) and normalized to the positive control (purified CD8+T responder stimulated with commercially available anti-CD3/anti-CD28 beads (beads on which αCD3 and αCD28 monoclonal antibodies are irreversible immobilized). FIG. 13B shows flow-cytometric analysis of the surface expression of CD8 and the T cell surface molecule CD45RO (that is indicative of T cell proliferation and activation) after cell culture. The various stimulating conditions were compared using one-way ANOVA and no significant difference (n.s.) was detected.

FIGS. 14A and 14B show the yield and phenotype for the expansion of purified CD8+T responder cells stimulated in vitro with αCD3/αCD28 Fab fragments that were reversibly immobilized on soluble oligomeric streptavidin mutein acting as a soluble reagent that were either functionalized with single Fab fragments or with a combination of Fab-fragments (as already described above). In these experiments, the CD8+T responder cells were stimulated with the soluble reagent (the soluble oligomeric streptavidin mutein (1 mg/ml) of Example 3) which was functionalized with varying amounts of αCD3 and αCD28 Fab fragments, optionally together with the αCD8 Fab fragment described above. The term "1×" corresponds to 1.5 µg oligomeric streptavidin mutein functionalized with 0.5 µg αCD3 Fab fragment alone and 1.5 µg oligomeric streptavidin mutein functionalized with 0.5 µg αCD28 Fab alone), or 3 µl of a preparation of oligomeric streptavidin mutein loaded with 0.5 µg αCD3 Fab fragment and 0.5 µg αCD28 Fab, or 4.5 µl of a preparation of oligomeric streptavidin mutein loaded with 0.5 µg strep-tagged αCD3, 0.5 µg strep-tagged αCD8 and 0.5 µg strep-tagged αCD28 Fab. Accordingly, the term "2×" corresponds to 3.0 µg oligomeric streptavidin mutein functionalized with 1 µg αCD3 Fab fragment alone and 3.0 µg oligomeric streptavidin mutein functionalized with 1 µg αCD28 Fab alone, meaning that twice the amount of immobilized αCD3 Fab fragment was used. Untreated Tresp cells served as negative control and purified CD8+T responder stimulated with commercially available anti-CD3/anti-CD28 beads (beads on which αCD3 and αCD28 monoclonal antibodies are irreversible immobilized) as positive control. FIG. 14A shows a graph in which the bars represent the degree of proliferation according to the number of cells harvested at day 5 compared to the negative controls and normalized to the positive control. FIG. 14B shows FACS analysis of CD8 and CD45RO surface expression after cell culture.

FIG. 15A shows that the reagent containing the αCD8 Fab fragment resulted in the highest number of expanded CD3+ cells. FIG. 15B shows that that amount of CD8+ T cells were the highest in the cell composition expanded with the reagent containing the αCD8 Fab fragment.

FIG. 16A: Jurkat cells were loaded with the calcium-sensitive dye Indo-1-AM and calcium release was triggered by injection of either αCD3 mAb (black squares) or αCD3 OKT3 Fab multimers (derived from the parental cell line OKT3) with or without prior D-biotin disruption (dark grey triangles and light grey circles respectively) compared to injection of PBS (inverted white triangles). Application of ionomycine served as positive control. Time-resolved changes in intracellular Ca2+ concentration were monitored by flow-cytometry based on the change in FL6/FL7 ratio. FIG. 16B: Indo-1-AM-labeled Jurkat cells were activated by different αCD3 stimuli as described in Example 11; OKT3: upper graph and αCD3 Fab-multimer: middle graph) followed by subsequent (t=140 s) D-biotin mediated disruption of αCD3 Fab-multimer signaling. Injection of PBS (lower graph) and ionomycine served as negative or positive control. Data are representative of three different experiments.

After selection, cells were treated with D-biotin and subsequently washed to remove magnetic beads and Fab-monomers. Liberated CD28+ cells were subsequently (re-)stained either with CD28 Fab-multimers (second right dot plot) or with the α-Ig kappa mAb (right dot plot) to detect potentially remaining Fab-monomers. Only live (PInegative) CD3+ cells are shown. Numbers in dot plots indicate the percentage of cells within gates.

Figure 19A:
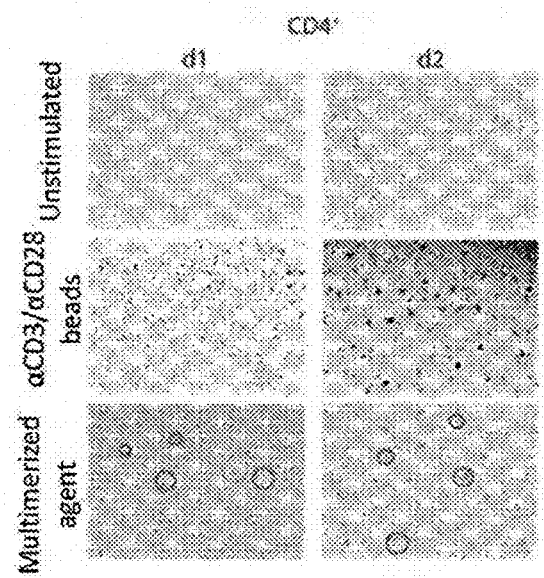
Figure 19B:
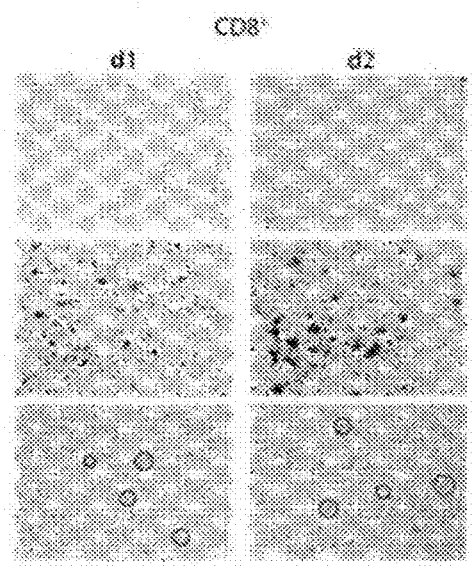

FIGS. 19A and 19B show early cluster formation of T cells after activation of purified CD4+ and CD8+T responder cells stimulated in vitro with αCD3/αCD28 Fab fragments that were reversibly immobilized on the soluble oligomeric streptavidin mutein (n≥3) described in Example 3. FIG. 19A depicts the results for CD4+ T cells and FIG. 19B depicts the results for the CD8+ T cells. Data for the Tresp stimulated with the soluble multimerization reagent (the oligomeric streptavidin mutein), the Tresp stimulated with the commercially available anti-CD3/anti-CD28 beads (positive control) and the unstimulated T cells (negative control) are shown.

Figure 20A:
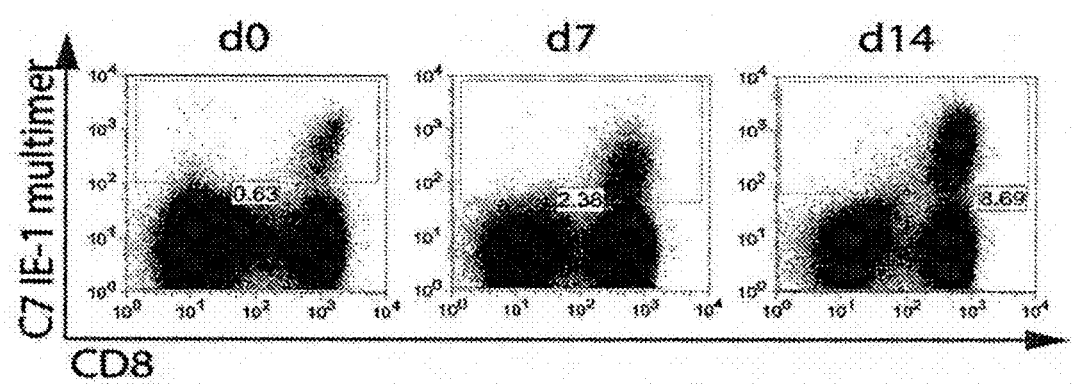
Figure 20D:
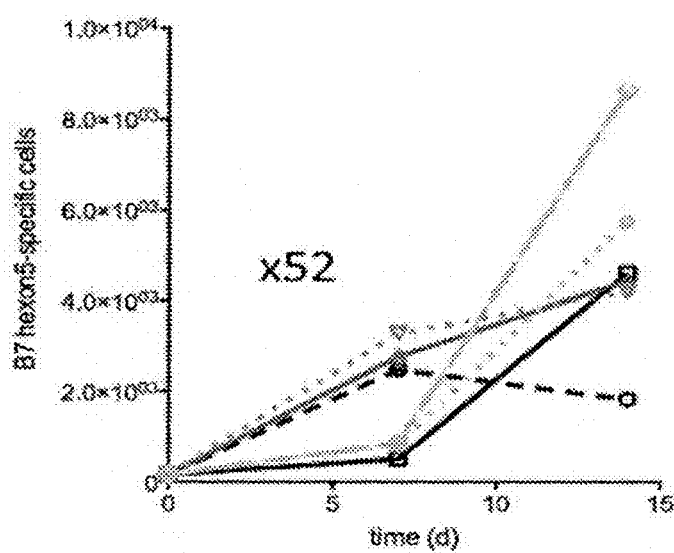
Figure 20E:
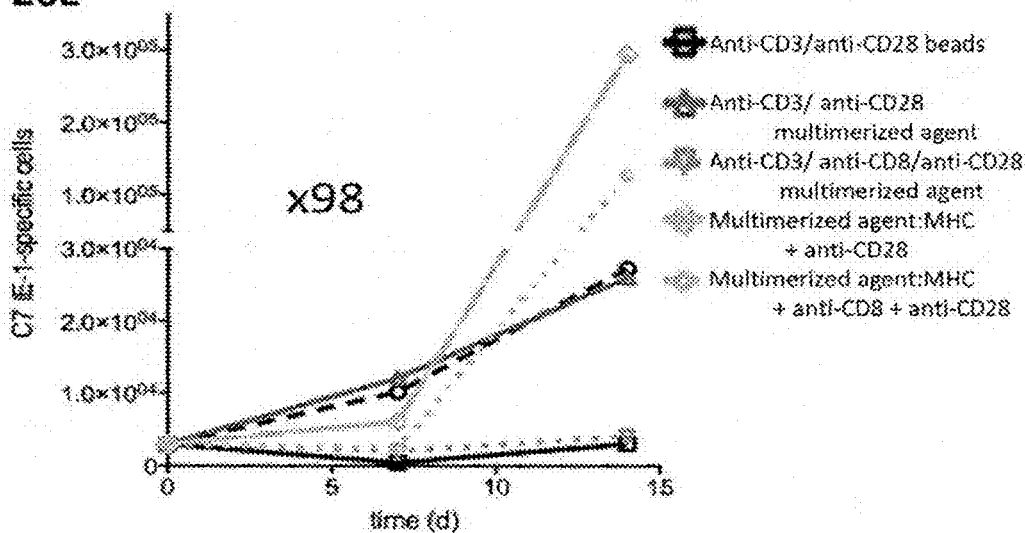

FIGS. 20A-F show the kinetics of selective antigen-specific (Ag-specific) expansion out of a bulk population of purified CD3+CD62L+CD45RA− Tcm responder cells that were stimulated in vitro with both a peptide:MHC molecule complex (that acts as first agent that provides a primary activation signal to the cells) and αCD28 Fab fragment (that acts as second agent that binds the accessory molecule on the surface of the cells) and unstimulated T cells (negative control) are shown. Both, the complex of antigen-specific peptide with the MHC molecule and the αCD28 Fab fragment were reversibly immobilized on the same soluble oligomeric streptavidin mutein (with n≥3) described in Example 3. The peptide used for the antigen-specific expansion in FIG. 20A was the peptide CRVLCCYVL (SEQ ID NO: 38), amino acids 309-317 of the immediate-early 1 protein restricted by the HLA-C702 MHC molecule (described in Ameres et al, PLOS Pathogens, May 2013, vol. 9, issue 5, e1003383) representing an HLA-C7/IE-1 epitope that is specific for cytomegalovirus (CMV). The MHC I molecule that presents the peptide carries at its C-terminus of the heavy chain the streptavidin binding peptide (SAWSHPQFEK(GGGS)2GGSAWSHPQFEK (SEQ ID NO: 16), that is commercially available as "Twin-Strep-tag®" from IBA GmbH, Göttingen, Germany). FIG. 20A shows exemplary flow-cytometric analysis for the fraction of the Ag-specific cells that were proliferated using the peptide:MHC-I complex specific for this HLA-C7/IE-1 epitope as first agent that provides a primary activation signal to the cells reversibly immobilized on the soluble oligomeric streptavidin mutein. The graphs in FIG. 20B to FIG. 20E illustrates the expansion kinetics of further Ag-specificities according to the number of specific peptide:MHCI multimer-positive cells harvested per time point in analogy to FIG. 20A using distinct complexes of an antigen-specific peptide with the MHC I molecule as first agent that provides a primary activation signal to the cells reversibly immobilized on the soluble oligomeric streptavidin mutein. In more detail, FIG. 20B shows the expansion of Ag-specific cells that were expanded using the peptide:MHC-I complex specific for the pp65 epitope of CMV (amino acids 341-350 (QYDPVAALF)(SEQ ID NO: 39) restricted by HLA-A2402), FIG. 20C shows the expansion of Ag-specific cells that were expanded using another peptide:MHC-I complex specific for the pp65 epitope of CMV (amino acids 265-274 (RPHERNGFTV)(SEQ ID NO: 40) restricted by HLA-B702), FIG. 20D shows the expansion of Ag-specific cells that were proliferated using the peptide:MHC-I complex specific for the hexon 5 epitope of adenovirus (amino acids 114-124 (CPYSGTAYNSL)(SEQ ID NO: 41) restricted by HLA-B702), FIG. 20E shows the expansion of Ag-specific cells that were proliferated using the peptide:MHC-I complex specific for the HLA-B7/IE-1309-317 epitope of CMV (exemplary FACS data see above FIG. 20A). All peptide:MHC molecules bearing the Twin Strep®-Tag are commercially available from IbaGmbH. In this context, the amino acid sequences of the HLA-A*2402, HLA-B*0702 and HLA-C*0702 molecules that carry the "Twin-Strep-tag®" as their C-terminus are shown as SEQ ID NO: 42, 43 and 44 in the accompanying Sequence Listings, while the amino acid sequence of the β2 microglobulin (which forms together with the α chain, that means the HLA encoded molecules the respective MHC I molecule) is shown as SEQ ID NO: 45 in the accompanying Sequence Listing. In addition, FIG. 20F shows exemplary flow-cytometric analysis of CD62L and CD127 surface expression after 14 days of culture for HLA-B7/Hexon5114-124 stimulated/expanded cells from FIG. 20D.

Figure 21:
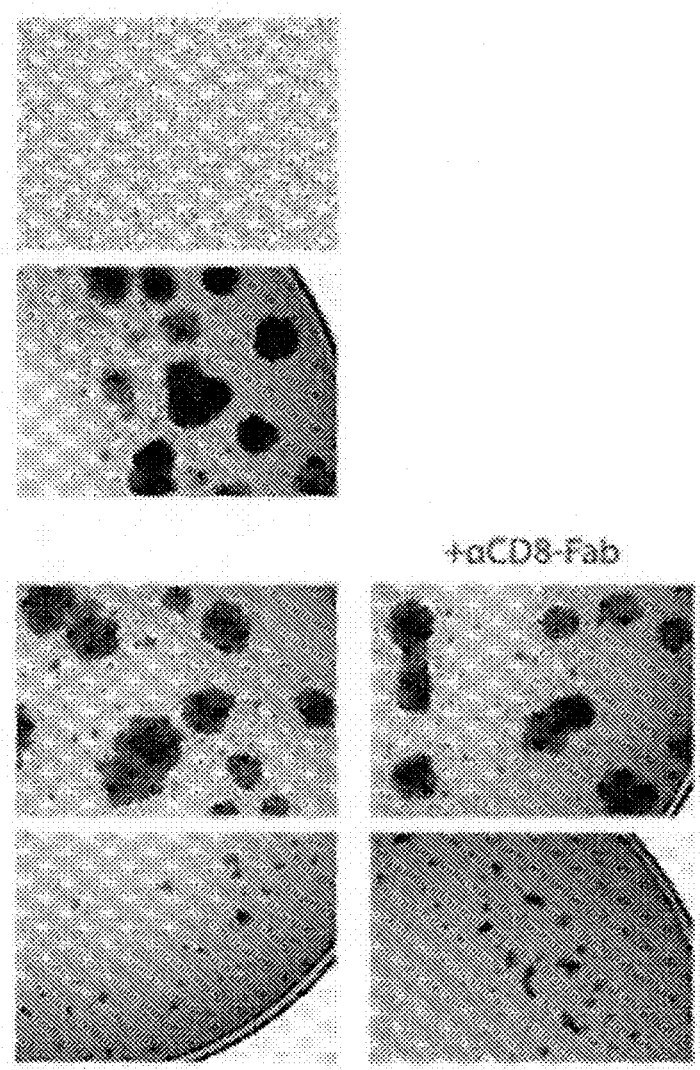

FIG. 21 shows the kinetics of selective Ag-specific expansion out of purified CD3+CD62L+CD45RA-Tcm responder cells that were stimulated in vitro with a) antigen specific peptide MHC I complexes and b) αCD28 Fab fragments that were reversibly immobilized as first and second agent on soluble oligomeric streptavidin muteins. For this purpose 500,000 CD3+CD62L+CD45RA− responder Tcm cells (Tresp) were stimulated Ag-specifically using 3 μl of a preparation of Streptactin multimerization reagent functionalized with peptide:MHC class I complexes equipped with a streptavidin binding peptide (the specific peptide represents amino acids 114-124 (CPYSGTAYNSL, SEQ ID NO: 41) of the Hexon 5 protein of the adenovirus restricted by HLA-B0702, see above) and 0.5 μg αCD28 Fab. As an alternative, 4.5 μl of a preparation of Streptactin multimerization reagent loaded with 0.5 μg this peptide:MHC class I complex, 0.5 μg αCD8 Fab and 0.5 μg αCD28 Fab. For comparison, polyclonal stimulation was performed, using 3 μl of a preparation of Streptactin multimerization reagent (1 mg/ml) either loaded with a combination of 0.5 μg αCD3 Fab and 0.5 μg αCD28 Fab. Again as the alternative stimulation condition described above, 4.5 μl of a preparation of Streptactin multimers loaded with 0.5 μg αCD3 Fab, 0.5 μg αCD8 Fab and 0.5 μg αCD28 Fab was used. Untreated (unstimulated) Tresp cells served as negative control and Tresp cells stimulated polyclonal with anti-CD3/anti-CD28 beads as positive control. Tresp cells were seeded in 48-well plates in 1 ml cell culture medium supplemented with 30 U/ml IL-2 and 5 ng/ml IL-15. Cells were incubated at 37° C. with media exchange every 3 days and cell count was analyzed after 7 and 14 days. The photographs shown in FIG. 21 represent the degree of cluster formation on day 5 for Ag-specific stimulation as exemplified for the HLA-B7/Hexon 5 epitope of adenovirus.

Figure 22A:
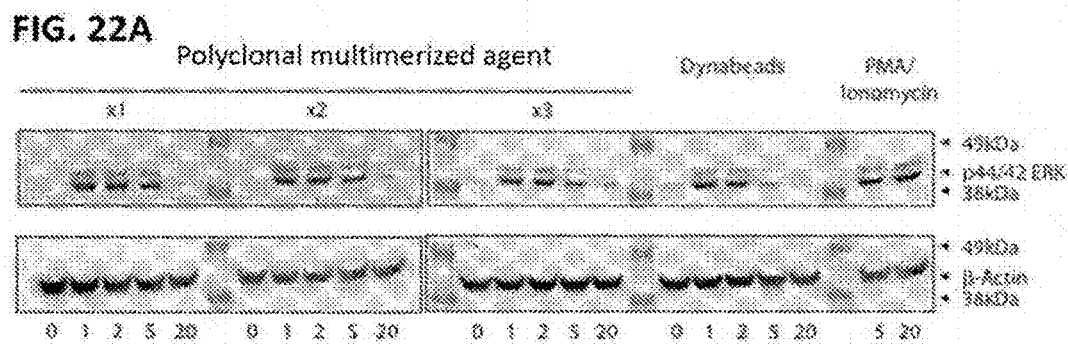
Figure 22B:
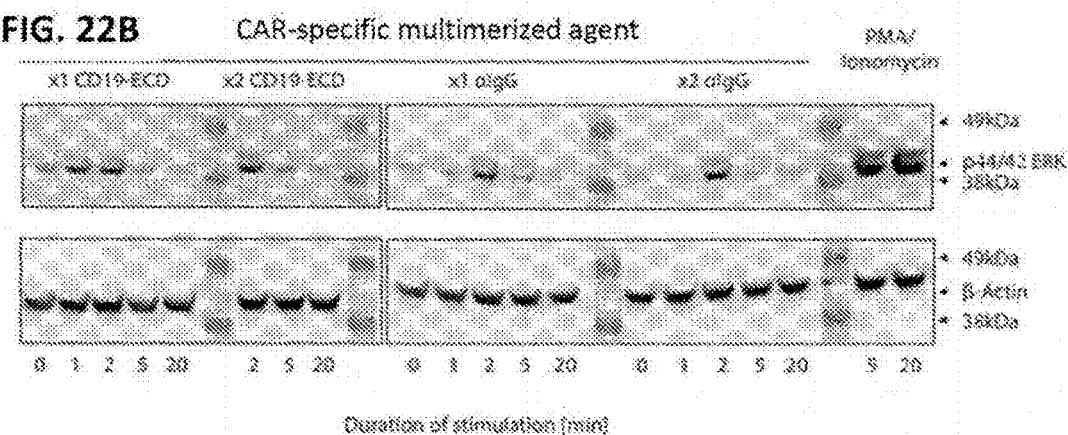

FIGS. 22A and 22B shows the activation of intracellular signaling cascades of transduced Jurkat cells that have been modified to express an αCD19 chimeric antigen receptor (CAR), and that were stimulated using the oligomeric Streptactin® of Example 3 as soluble multimerization reagent. The specificity of a CAR is typically derived from a scFv region assembled from the antigen-binding region of a monoclonal antibody (mAb) that specifically binds a target/tumor associated antigen such as CD19 and links it to T cell specific signaling (described in Hudecek et al, Clin Cancer Res. 2013 Jun. 15; 19(12): 3153-3164. In the experiments the extracellular domain (ECD) of CD19, which contains the natural ligand of the αCD19 CAR as well as the polyclonal αIgG F(ab)2 fragment that recognizes the IgG4 spacer (donkey-anti-human F(ab)2 is commercially available from Jackson Immuno Research) within the αCD19-CAR were also used in this experiment as first agent that provides a primary activation signal to the jurkat cells. The reversibly immobilization to the soluble oligomeric streptavidin mutein was provided by the streptavidin peptide SAWSHPQFEK(GGGS)2GGSAWSHPQFEK (SEQ ID NO: 16) that was fused to the C-terminus of the ECD of CD19 or by the biotinylated (Fab)2 fragment of the αIgG (since the streptavidin mutein "m2" binds biotin with reduced affinity, this binding is reversible and can for example be displaced by addition of an excess of free biotin). In the control experiment of FIG. 22A 300,000 CD3+ Jurkat responder cells (Jresp) were stimulated with varying amounts of a mixture of preparations of oligomeric Streptactin (1 mg/ml) that was functionalized with the αCD3 Fab and the αCD28 Fab ("×1" corresponds to 3 μg multimerized Streptactin functionalized with 0.5 μg αCD3- and 0.5 μg αCD28 Fab—polyclonal Streptamer multimer). In the experiment of FIG. 22B 3 μl of a preparation of the oligomeric Streptactin was functionalized with 0.5 μs (×1) or 1 μg (×2) of the extracellular domain (ECD) of CD19 or with 3 μl of a preparation of the oligomeric Streptactin loaded with 0.5 μg (×1) or 1 μg (×2) αIgG that recognizes the IgG4 spacer (which are both CAR-specific Streptamer® multimers). Jresp stimulated with anti-CD3/anti-CD28 beads (beads on which αCD3 and αCD28 monoclonal antibodies are irreversibly immobilized) or PMA and ionomycin served as positive controls. Jresp cells were seeded in 1.5 ml Eppendorf tubes in 200 μl cell culture medium supplemented with 30 U/ml IL-2. Cells were incubated at 37° C. and put on ice and lysed after 0 min to 20 min of stimulation.

Figure 23:
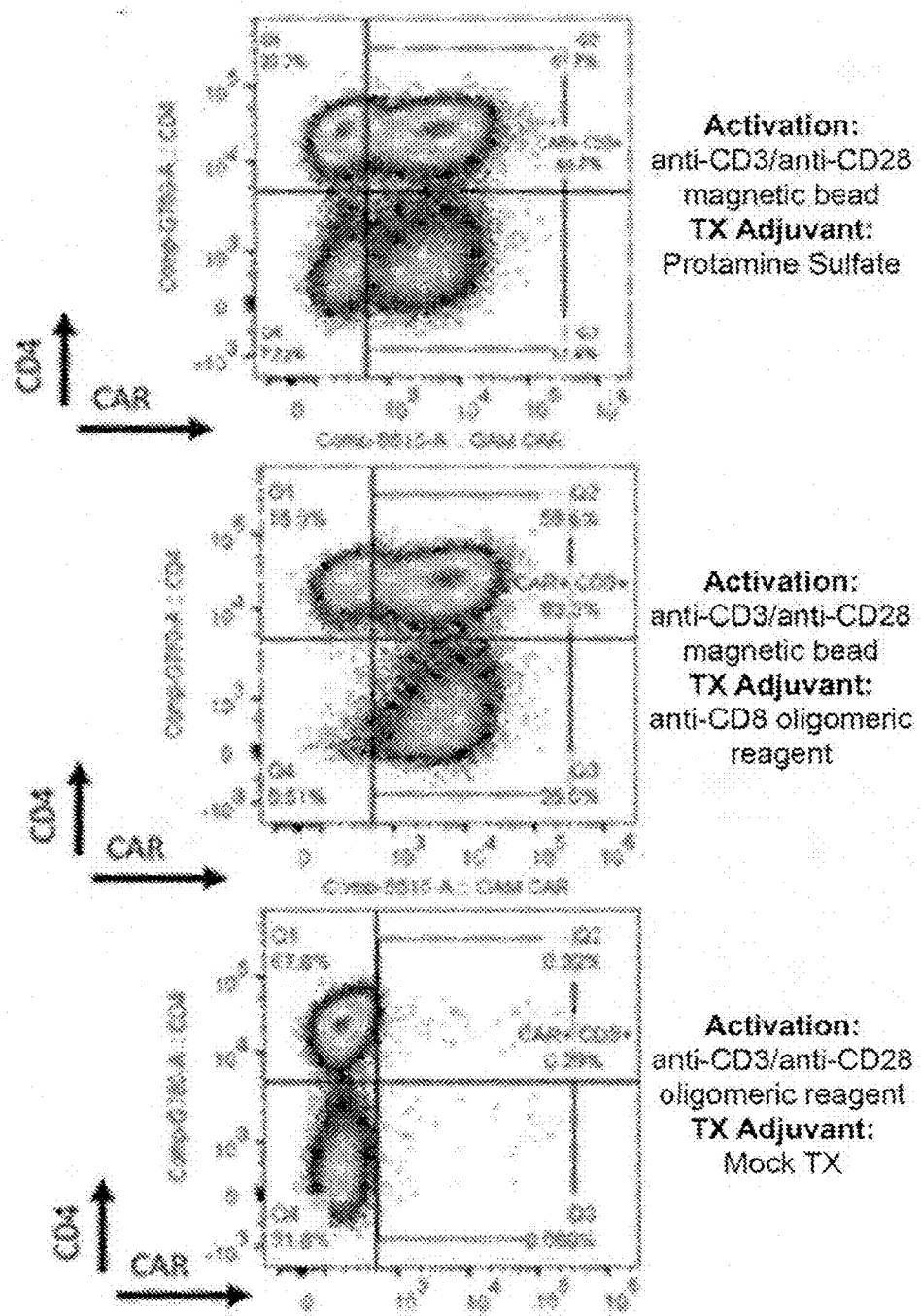

FIG. 23 shows dot plots for surface marker expression of CD4+(y axis) and CAR (x axis) on of live T (CD3+ gated) transduced with viral vectors in the presence of (1) anti-CD3/anti-CD28 magnetic beads and protamine sulfate adjuvant, (2) anti-CD3/anti-CD28 magnetic beads and an oligomeric protein reagent having reversibly bound anti-CD8 Fab, or (3) only an oligomeric protein reagent having reversibly bound anti-CD3/anti-CD28 Fabs.

DETAILED DESCRIPTION

Provided herein is a method of transducing cells by contacting, e.g. culturing or incubating, a target cell, such as a cell composition, with an oligomeric protein reagent and a viral vector particle. In some embodiments, the oligomeric protein reagent is a multimerization reagent having reversibly bound thereto a plurality of binding agents, such as a viral-binding agent or selection agent. In some embodiments, the method relates to reversible reagent systems in which the multimerization reagent is incubated in the presence of target cells and viral particles under conditions in which the multimerization reagent binds to one or more molecules on the surface of a target cell and/or viral particles, thereby generating a composition comprising a plurality of the target cells transduced with the viral vector. Also provided are compositions and articles of manufacture, such as kits, containing the viral vectors and oligomeric reagent, and devices and systems for use in connection with the provided method. In some embodiments, the compositions and kits can be used in methods and uses in accord with the provided disclosure.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference. For example, the contents of International PCT Application No. PCT/EP2015/058339 is incorporated by reference in its entirety.

The section headings used herein are for organizational purposes only and are not to be construed as limiting the subject matter described.

I. OVERVIEW OF METHODS OF CELL TRANSDUCTION

Provided herein is a method of transducing cells by contacting, e.g. culturing or incubating, a cell composition with an oligomeric protein reagent and a viral vector particle. In some embodiments, the cells are contacted or incubated with the oligomeric protein reagent and viral particles simultaneously or separately. In some embodiments, the viral particles and oligomeric reagents are mixed and the mixture is contacted or incubated with the cells. In some embodiments, the provided methods provide more efficient transduction of cells compared to methods using conventional transduction adjuvants (e.g. Retronectin® or polycations).

In some embodiments, the provided methods are based on the finding that muteins of streptavidin, such as an oligomeric form of a streptavidin mutein, facilitate viral transduction. In some aspects, the results have shown that the oligomeric streptavidin mutein reagent consistently results in higher transduction efficiency of cells compared to methods using other activation reagents or compared to transduction performed with other adjuvants. In some embodiments, the oligomeric protein (e.g. streptavidin) is capable of associating, e.g. binding or interacting, with the viral particles. In some embodiments, the oligomeric protein reagent (e.g. oligomeric streptavidin mutein) has a net positive charge.

In some aspects, the increased transduction efficiency is achieved with a naked oligomeric protein (e.g. streptavidin mutein) reagent that is not or need not be conjugated or associated to another binding moiety or agent for binding to a molecule on the cell or viral surface. In some embodiments, the oligomeric protein (e.g. streptavidin mutein) reagent does not comprise or is not conjugated to a viral binding agent. In some embodiments, the oligomeric protein (e.g. streptavidin mutein) reagent does not comprise or is not conjugated to a binding agent specific to a molecule on the surface of a cell, such as an immune cell, e.g. a selection agent or a stimulating agent. It is understood that while such binding agents may not be necessary to increase transduction efficiency, in some aspects, the oligomeric protein (e.g. streptavidin mutein) reagent can comprise, such as can be conjugated (e.g. reversibly conjugated), to a binding agent, such as a viral binding agent, selection agent or stimulation agent. In some embodiments, the addition of a binding agent, e.g. a viral-binding agent or selection agent, bound to the oligomeric protein reagent can enhance, modulate and/or selectively target the transduction of the cells.

In some embodiments, the methods employ reagents, which can be a multimerization reagent having bound thereon one or more agents, e.g. a first agent, second agent, etc. that is capable of specifically binding to a molecule on the surface of the viral particles and/or on the surface of one or more target cells. In some embodiments, the multimerization reagent has bound thereto a viral-binding agent that binds to a molecule on the surface of the viral particle, such as a molecule present on or as a part of the viral envelope. In some embodiments, the reagent, e.g., multimerization reagent, may thus have bound thereon one or more of the viral particles, which may be bound to the reagent via a viral particle-binding agent. In some embodiments, the multimerization reagent has bound thereto a selection agent that binds to a molecule on the surface of the cells, e.g., selection marker, expressed by one or more of the at least a plurality of the target cells. In some aspects, the agents, e.g. a first agent, second agent, etc., can either be bound reversibly or also irreversibly to the multimerization reagent.

Thus, the multimerization reagent provides typically more than one binding site, e.g. Z1, in which, in some cases, a plurality of agents can be reversibly bound to present the first agent, second agent and/or other agents in a sufficient density to the population of cells. In some embodiments, the multimerization reagent comprises at least one binding site Z, e.g. Z1, for the reversible binding of the first agent and the first agent also comprises at least one binding partner C, e.g. C1, wherein the binding partner C, e.g. C1, is able of reversibly binding to the binding site Z, e.g. Z1, of the multimerization reagent. In some aspects, it is noted that a multimerization agent can as such have multiple binding sites, e.g., Z1, for example, a streptavidin mutein (being a homo-tetramer) in its native state has four such binding sites, e.g. Z1, and can further be oligomerized. In some cases, a reagent may have only one binding site, e.g. Z1, for the reversible binding of a binding partner, e.g. C1. Such an example is multimeric calmodulin. Calmodulin as such has only one binding site for calmodulin binding peptides. However, calmodulin can be biotinylated and then reacted with streptavidin-oligomers (see also below), thereby providing a multimerization reagent in which multiple calmodulin molecules are presented in high density on a "scaffold", thereby providing multimeric calmodulin.

Thus, the first agent, when contacted or incubated with the multimerization reagent, can be reversibly bound to the multimerization reagent via the reversible bond formed between the binding partner C, e.g. C1, and the binding site Z, e.g. Z1. In addition, the second agent can comprises a binding partner C, e.g. C2, wherein the binding partner C2 is able of being reversibly bound to a binding site Z, e.g. Z2, respectively, of the multimerization reagent. In some embodiments, the second agent, when it is contacted or incubated with the multimerization agent, is reversibly bound to the multimerization reagent via the reversible bond formed between the binding partner C, e.g. C1 and the binding site Z, e.g. Z2. In some cases, C1 and C2 can be the same or substantially the same and/or comprise the same or substantially the same moiety. In some cases, Z1 and Z2 can be the same or substantially the same and/or comprise the same or substantially the same moiety.

In some embodiments, dissociation or disruption of binding between the multimerization reagent and the agent, e.g. viral-binding agent, selection agent or other agent as described, can be reversed or disrupted by incubation in the presence of a competition reagent or substance. In some embodiments, using as binding partners C1 and C2, moieties that bind to the same binding site of the multimerization agent has the advantage that the same competition reagent (of the first binding partner C1 and also of the second binding partner C2) or analog thereof can be used to disrupt, and in some cases terminate, the binding release the population of target cells (e.g. T cells) from the multimerization reagent, and hence, depending on the particular binding agent, terminate transduction, selection, stimulation or activation, and/or expansion of the population of target cells (e.g. T cells).

In some aspects, the binding agent, e.g. viral-binding agent, selection agent or other agent as described, is an antibody or antigen-binding fragment. In some embodiments, the binding affinity of antibody molecules towards their antigen, including for example, a cell surface receptor molecule is usually in the affinity range of the $K_D$ of $10^{-7}$ M to $10^{-13}$ M. Thus, conventional monoclonal antibodies can be used as an agent (first or second, receptor-binding, e.g. stimulatory agent, or selection agent). In some embodiments, in order to avoid any unwanted avidity effects that lead to a stronger binding, monoclonal antibodies can also be used in form of their monovalent antibody fragments such as Fab-fragments or single chain Fv fragments.

In some cases for producing the binding agents (e.g. first agent, second agent, etc., such as viral-binding agent, selection agent or receptor-binding agents, e.g. stimulatory agents) to comprise a binding partner C, the binding partner C, e.g. C1 or C2, can be provided by the respective expression vector used for the recombinant production of the agent (e.g. antibody fragment) so that the binding partner C, e.g. C1 or C2, is part of a fusion peptide with the agent at either the N-terminus or C-terminus. In some embodiments, in the context of an agent that is an antibody or antigen-binding fragment, the binding partner C, e.g. C1 or C2, can be present at the C-terminus of either the light or the heavy chain. Also this methodology of cloning a recombinant protein, such as the variable domains of an antibody molecule, and recombinantly producing a respective protein, e.g. antibody fragment, is well known to the person skilled in the art, see for example, Skerra, A. (1994). In some embodiments, an antibody molecule can be generated of artificial binding molecules with antibody like properties against a given target, such as CD3 or CD28 or other accessory or stimulatory agent molecules as described, such as by well-known evolutive methods such as phage display (reviewed, e.g., in Kay, B. K. et al. (1996) *Phage Display of Peptides and Proteins—A Laboratory Manual*, $1^{st}$ Ed., Academic Press, New York N.Y.; Lowman, H. B. (1997) *Annu. Rev. Biophys. Biornol. Struct.* 26, 401-424, or Rodi, D. J., and Makowski, L. (1999) *Curr. Opin. Biotechnol.* 10, 87-93), ribosome display (reviewed in Amstutz, P. et al. (2001) *Curr. Opin. Biotechnol.* 12, 400-405) or mRNA display as reported in Wilson, D. S. et al. (2001) *Proc. Natl. Acad. Sci. USA* 98, 3750-3755.

In some embodiments, the provided reagents and methods using such reagents include features that result in an increased transduction of immune cells and/or certain populations and/or subpopulations thereof, including those desirable for use in adoptive immunotherapy. In some embodiments, the methods provide the ability to transduce the cells at the same or a higher transduction efficiency compared with available methods, such as methods in which transduction is performed using a conventional adjuvant, e.g. Retronectin® or polycation adjuvant reagents (e.g. protamine sulfate). In some embodiments, although such other adjuvants can facilitate the engagement between the virus and the target cell to be infected, they also can result in toxic effects to the cells. For example, current protocols that make use of Retronectin® as a transduction adjuvant recommend a media exchange immediately following the transduction step. In some cases, this can limit the concentration of conventional adjuvants that can be employed, and hence the overall efficiency of transduction.

In contrast, the provided oligomeric reagents, such as reagents comprising streptavidin muteins, including multimerization reagents, can be maintained in cell culture for long periods of time without toxic effect. In some embodiments, the provided methods of transduction can be performed without removing the oligomeric reagent, such as multimerization reagent, from the cell prior to or during the contacting of the virus particles and cells. In some embodiments, it is not necessary to remove the oligomeric reagent, such as multimerization reagent, during at least a portion of a further incubation of the cells, such as a further incubation for expanding transduced cells.

In some embodiments, the cells include one or more nucleic acids introduced via genetic engineering in accord with the provided methods, and thereby express recombinant or genetically engineered products of such nucleic acids. In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature, including one comprising chimeric combinations of nucleic acids encoding various domains from multiple different cell types.

In some embodiments, the provided methods result in a transduction efficiency that is increased at least or about at least 1.2-fold, 1.5-fold, 2.0-fold, 3-fold, 4-fold, 5-fold or more compared to transduction performed in the presence of a conventional adjuvant, e.g. Retronectin® or polycation adjuvant reagent. In some embodiments, an increased transduction efficiency, such as enhancement or promotion or transduction in particular cells, is assessed by measuring the level of expression of a recombinant protein, such as a heterologous protein, encoded by a nucleic acid contained in the genome of the retroviral vector following transduction or other form of transfer of the vector into a cell, such as a T cell. The enhancement may be measured by determining a relative degree of such expression as compared to transduction that is performed by a method not including the oligomeric protein reagent or multimerization reagent, such as a method performed instead in the presence of a conventional adjuvant. A number of well-known methods for assessing expression level of recombinant molecules may be used, such as detection by affinity-based methods, e.g., immuno-affinity-based methods, e.g., in the context of cell surface proteins, such as by flow cytometry. In some examples, the expression is measured by detection of a transduction marker and/or reporter construct. In some embodiments, nucleic acid encoding a truncated surface protein is included within the vector and used as a marker of expression and/or enhancement thereof.

In some aspects, the reagent, such as oligomeric protein reagent, is a multimerizatio ragent that is reversibly bound or associated with a selection agent capable of specifically binding to a molecule on the surface of a cell in order to preferentially target transduction of cells expressing the marker. In some embodiments, a specific subpopulation of cells within a larger population can be selectively transduced compared to one or more other cells in the population. In some cases, transduction efficiency of a particular subpopulation of cells can be increased by greater than or greater than about 1.2-fold, 1.5-fold, 2.0-fold, 3.0-fold, 4.0-fold, 5.0-fold, 6.0-fold, 7.0-fold, 8.0-fold, 9.0-fold, 10-fold or more compared to other cells in a mixed population of cells. In some embodiments, targeting a subpopulation of a mixed culture may provide substantial benefit. In some embodiments, such processes can simply a manufacturing process, such that the resources required to preemptively purify a population of cells are reduced. In some embodiments, the provided methods for genetically engineered cells do not include a step of selecting cells prior to contacting the cells with an oligomeric protein (streptavidin mutein) reagent for transduction with a viral particle, where such oligomeric protein reagent is reversibly bound to a selection agent targeting transduction of a specific population of cells.

In some embodiments, the provided reagents and methods have additional advantages. In general, retroviral-based vectors can be used to stably integrate genes of interest into cells. In general, transduction of T cells using existing retroviral vectors requires activation of T cells by engagement of the T cell receptor (TCR) or by cytokine stimulation. In some instances, available procedures for preparing genetically engineered T cells for adoptive immunotherapy can require the sequential ex vivo steps of selection, activation, transduction and expansion. Such processing steps, however, may not always be desired for preparation of cells for certain adoptive immunotherapy methods, such as due to complexity in multiple processing steps, cost, and reproducibility. In some aspects, the provided methods permit one or more of these steps to be performed simultaneously as opposed to sequentially.

In some embodiments, the methods include other processing steps, including one or more of selecting, isolating, stimulating, activating and/or expanding cells. In some embodiments, the same oligomeric reagent, such as multimerization reagent, used to modulate transduction can be used in one or more of these other processing steps, such as can be used to select cells and/or to activate cells and/or to modulate transduction of cells. In some embodiments, the oligomeric reagent can be a multimerization reagent having bound thereto a binding agent specific to a molecule on the surface of the cells to facilitate one or more of selection, activation, stimulation and/or expansion of cells. In some embodiments, one or more of selecting cells, activating cells, modulating transduction of cells and/or expanding cells is performed in the presence of the same oligomeric reagent, such as same multimeric reagent, which, in some cases, can be performed as part of a continuous or semi-continuous process, optionally in a closed system. In some embodiments, the provided methods can be used in methods related to cell processing, including preparing cells for therapeutic uses, such as for adoptive cell therapy. In particular, the disclosure relates to methods providing advantages over available processing methods, such as available methods for large-scale processing. Such advantages include, for example, reduced cost, streamlining, increased efficacy, increased safety, and increased reproducibility among different subjects and conditions.

In general, retroviral-based vectors can be used to stably integrate genes of interest into cells. With existing retroviral vectors it may not always be possible to effectively stably genetically engineer quiescent and/or non-cycling cells, e.g., for use in cell therapy. For example, it may not be possible to effectively transduce non-cycling immune cells, such as non-cycling myeloid cells or resting T cells, with a retroviral vector using available methods. In some cases, for transduction to occur in T cells, activation of T cells by engagement of the T cell receptor (TCR) or by cytokine stimulation may be required. In some instances, available procedures for preparing genetically engineered T cells for adoptive immunotherapy can require the sequential ex vivo steps of selection, activation, transduction and expansion.

For example, the inclusion of activation and/or stimulation step(s), e.g., subsequent to cell selection can increase the time, cost, reagents, and/or user handling in preparing cells for adoptive cell therapy. Such outcomes can increase risk of variability among different processes and/or with cells from different subjects. Thus, in some embodiments, the provided methods are advantageous by way of simultaneously selecting or enriching a cell population, exposing the cell population to a retroviral vector particle as compared with other methods and/or activating or stimulating such cells.

In some aspects, the reagent, such as oligomeric protein reagent, can be reversibly bound or associated with a stimulatory agent (e.g. anti-CD3 and/or anti-CD28) to both modulate transduction and effect cell activation, which can be performed, in some cases, simultaneously during at least a portion of the contacting or incubating. In some embodiments of the provided transduction methods, cells, e.g., T cells, in the populations being transduced are not or need not be stimulated and/or activated prior to contacting or incubating the cells with a provided reagent and viral particle. In some embodiments, the provided methods employing an oligomeric reagent, such as an oligomeric protein (e.g. streptavidin mutein) reagent, that is a multimerization reagent reversibly bound or associated with a stimulating agent (e.g. anti-CD3 and/or anti-CD28) results in at least 1.2-fold, 1.5-fold, 2.0-fold, 3-fold, 4-fold, 5-fold or more increase in the transduction efficiency compared to methods performed by first activating cells with another activating reagent (e.g. anti-CD3/anti-CD28-coated magnetic particles) followed by transduction using a conventional adjuvant. In some aspects, this is an advantage over other systems or methods in which there is no transduction reagent that is capable of additionally delivering a specific activation signal. Likewise, there is no known activation reagent that is capable of additionally acting as a transduction adjuvant.

In some embodiments, the stimulatory agent, e.g., first or second stimulatory agent, is one that is capable of binding to molecules on the surface of a target cells, thereby providing a signal to the cells, which, in some cases, can be a primary activation signal and/or an accessory or costimulatory signal. In some embodiments, the primary activation signal may as such be sufficient to activate the cells to expand/proliferate. The multimerization reagent may have bound thereto also a second agent that stimulates an accessory molecule on the surface of the cells. The second agent, when binding to the accessory molecule on the surface on the surface of the cells, may thereby stimulate the activated cells to expand. Also this second agent can either be bound reversibly or also irreversibly to the multimerization reagent.

In some aspects, the method disclosed herein can involve a serial expansion of a population of cells in which a complete population of lymphocytes is stimulated/expanded, the reagents necessary for the expansion are then removed by chromatography on a suitable stationary phase. In some embodiments, the expanded/stimulated cells, which are the cultured cells, are optionally transfected with e.g. a T cell receptor or a chimeric antigen receptor (CAR) in accord with the provided methods and, in some aspects, can be subjected to a second stimulation expansion with a different stimulatory molecule that binds to the introduced T cell receptor or the chimeric antigen receptor.

In some embodiments, because dose of cells in adoptive cell therapy is determined by the number of cells that express the recombinant receptor, the higher transduction efficiency can reduce the culture time required to reach product dose. Thus, in some cases, the duration of the process or processes to expand the population of transduced cells, e.g. a further incubation of cells with a stimulating agent subsequent to the transduction, is reduced by the provided methods, such as is reduced by at least or about at least 20%, 30%, 40%, 50%, 60%, 70% or more. In some embodiments, the duration of the process or processes to expand the population to achieve a therapeutically effective dose of transduced cells is reduced by greater than or greater than about 2 hours, 6 hours, 12 hours, 24 hours, 48 hours, 72 hours or 96 hours. In some embodiments, the overall manufacture time of engineering a therapeutically effective dose of genetically engineered cells for adoptive cell therapy is reduced by at least or about at least 20%, 30%, 40%, 50%, 60%, 70% or more.

In some embodiments, the provided methods can be performed within a closed system, e.g. in an automated fashion. The oligomeric protein reagent, such as multimerization reagent, may either be immobilized on a solid support or soluble. In some embodiments, the contacting or incubation of cells and/or viral particles with the oligomeric protein (e.g. streptavidin mutein) reagent, such as multimerization reagent, is carried out in the presence of a support, such as a stationary phase or solid phase, which in some cases is a stationary phase or solid phase to which selection agents are bound. In some embodiments, the cells and/or viral particles used for transduction, and optionally the cells selected, stimulated and/or activated, are associated with the provided reagents in the stationary phase, such as, in some cases, immobilized, generally indirectly, such as, in some cases, immobilized, generally indirectly, thereon.

Also provided are compositions, kits and devices for performing the method in accord with the provided disclosure, such as for preparing genetically engineered cells for adoptive cell therapy. In some aspects, the cells are isolated from a subject, engineered in accord with the provided method, and administered to the same subject. In other aspects, they are isolated from one subject, engineered in accord with the provided method, and administered to another subject.

II. REAGENT SYSTEMS FOR TRANSDUCTION OF CELLS

Provided herein are methods that use reagents, such as oligomeric reagents, as a transduction adjuvant. In some embodiments, the same oligomeric reagent, or in some cases a different oligomeric reagent, also can be provided as a multimerization reagent having bound thereto one or more binding agent for use in methods to activate or stimulate cells prior to transduction, to select or preferentially target specific subsets of cells for transduction and/or to stimulate or expand cells.

In some embodiments, the reagent is an oligomeric protein reagent. In some embodiments, the reagent comprises one or more polypeptide sequences of at least or about at least 10, 20, 30, 40 amino acids in length, such as at least or about at least at or about 50, 60, 65, 70, 80, 90, 125, 150, 200, 250, 300 or more amino acids in length. In some embodiments, the oligomeric reagent contains a plurality of polypeptide monomeric units where each monomeric unit contains a polypeptide sequences of at least or about at least 10, 20, 30, 40 amino acids in length, such as at least or about at least at or about 50, 60, 65, 70, 80, 90, 125, 150, 200, 250, 300 or more amino acids in length. In some embodiments, the oligomeric protein is a dimer, trimer, tetramer or high-ordered oligomer. In some embodiments, the oligomeric protein reagent contains at least 2, 3, 4, 5, 6, 7, 8, 9, 10, 11, 12, 13, 14, 15, 16, 17, 18, 19, 20, 25, 30, 35, 40, 45, 50, 60 or more monomeric units. In some embodiments, each monomeric unit is the same. In some embodiments, the oligomeric reagent contains up to two, three, four, or more different monomeric units. In some embodiments, the reagent has a net positive charge or an overall positive charge.

In some embodiments, the methods provided herein involves incubating a plurality of target cells with an oligomeric protein reagent, and a viral particle, wherein the oligomeric protein reagent includes a plurality of polypeptide monomeric units, wherein each unit includes at least at or about 10, 20, 30, or 40 amino acids in length and/or includes a molecular weight of at least at or about 20, 30, 40, or 50 kDa; and/or the oligomeric protein reagent includes a molecular weight, or includes on average a molecular weight, of at least at or about 100 kDa, and the methods produce an output composition including one or more cells transduced with the viral particle.

In some embodiments, the oligomeric reagent comprises a molecular weight, or the reagents in a composition comprise on average a molecular weight, of at least or about at least 50 kDa, at least or about at least 100 kDa, at least or about at least 300 kDa, at least or about at least 500 kDa, at least or about at least 1000 kDa, at least or about at least 1250 kDa, at least or about at least 1500 kDa, at least or about at least 2000 kDa, In some embodiments, the oligomeric reagent comprises a molecular weight, or the reagents in a composition comprise on average a molecular weight, of between at or about 50 kDa to about 2000 kDa, about 50 kDa to about 1000 kDa, about 50 kDa to about 500 kDa, about 100 kDa to 2000 kDa, about 100 kDa to about 1000 kDa, about 100 kDa to about 500 kDa, about 150 kDa to about 2000 kDa, about 150 kDa to about 1500 kDa, about 150 kDa to about 1250 kDa, about 150 kDa to 1000 kDa, about 150 kDa to about 500 kDa or about 150 kDa to about 300 kDa, about 300 kDa to about 2000 kDa, about 300 kDa to about 1500 kDa, about 300 kDa to about 1250 kDa, about 300 kDa to 1000 kDa, about 300 kDa to about 500 kDa, about 500 kDa to about 2000 kDa, about 500 kDa to about 1500 kDa, about 500 kDa to about 1250 kDa, about 500 kDa to about 1000 kDa, about 1000 kDa to about 2000 kDa, about 1000 kDa to about 1500 kDa, about 1000 kDa to about 1250 kDa, about 1250 kDa to about 2000 kDa, about 1500 kDa to about 2000 kDa, about 50 kDa to 100 kDa, 50 kDa to 500 kDa, or 100 kDa to 500 kDa.

In some embodiments, the reagent is or comprises a streptavidin or avidin or muteins thereof. In some embodiments, the streptavidin can be wild-type streptavidin, streptavidin muteins or analogs, such as streptavidin-like polypeptides. Likewise, avidin, in some aspects, includes wild-type avidin or muteins or analogs of avidin such as neutravidin, a deglycosylated avidin with modified arginines that typically exhibits a more neutral pi and is available as an alternative to native avidin. Generally, deglycosylated, neutral forms of avidin include those commercially available forms such as "Extravidin", available through Sigma Aldrich, or "NeutrAvidin" available from Thermo Scientific or Invitrogen, for example.

In some embodiments, the reagent comprises the sequence of amino acids set forth in SEQ ID NO:1, 2, 3, 4, 5, 6, 27 or 28, or a sequence of amino acids that has at least 85%, 86%, 87%, 88%, 89%, 90%, 91%, 92%, 93%, 94%, 95%, 96%, 97%, 98%, 99% or more sequence identity to any of SEQ ID NOS: 1, 2, 3, 4, 5, 6, 27 or 28.

A. Reversible Reagent Systems

In some embodiments, the methods employ reversible systems in which at least one agent (e.g., a receptor-binding agent, selection agent or viral vector particle binding agent) capable of binding to a molecule on the surface of a biological particle, e.g. cell, microorganism or viral particle, is reversibly associated with the reagent. In some cases, the reagent contains a plurality of binding sites capable of reversibly binding to the agent. In some cases, the reagent is a multimerization reagent. In some embodiments, the at least one agent (e.g., receptor-binding agent, selection agent, viral particle binding agent) contains at least one binding site (either B or V) that can specifically bind an epitope or region of the molecule and also contains a binding partner C that specifically binds to at least one binding site Z of the reagent. In some cases, the binding interaction between the binding partner C and the at least one binding site Z is a non-covalent interaction. In some embodiments, the binding interaction, such as non-covalent interaction, between the binding partner C and the at least one binding site Z is reversible.

In some embodiments, the reversible association can be mediated in the presence of a substance, such as a competition reagent (also called an eluent reagent), that is or contains a binding site that also is able to bind to the at least one binding site Z. Generally, the substance (e.g. competition reagent) can act as a competitor due to a higher binding affinity for the binding site Z present in the reagent and/or due to being present at higher concentrations than the binding partner C, thereby detaching and/or dissociating the binding partner C from the reagent. In some embodiments, the affinity of the substance (e.g. competition reagent) for the at least one binding site Z is greater than the affinity of the binding partner C of the agent (e.g., receptor-binding agent, selection agent or viral particle binding agent) for the at least one binding site Z. Thus, in some cases, the bond between the binding site Z of the reagent and the binding partner C of the agent (e.g., receptor-binding agent, selection agent or viral particle binding agent) can be disrupted by addition of the substance (e.g. competition reagent), thereby rendering the association of the agent (e.g., receptor-binding agent, selection agent or viral particle binding agent) and reagent reversible.

Reagents that can be used in such reversible systems are described and known in the art, see e.g., U.S. Pat. Nos. 5,168,049; 5,506,121; 6,103,493; 7,776,562; 7,981,632; 8,298,782; 8,735,540; 9,023,604; and International published PCT Appl. Nos. WO2013/124474 and WO2014/076277. Non-limiting examples of reagents and binding partners capable of forming a reversible interaction, as well as substances (e.g. competition reagents) capable of reversing such binding, are described below.

I. Reagent

In some embodiments, the reagent contains one or a plurality of binding sites Z that are capable of reversibly binding to a binding partners C comprised by the agent (e.g., receptor-binding agent, selection agent or viral particle-binding agent). In some embodiments, the reagent contains a plurality of binding sites Z, which each are able to specifically bind to the binding partner C that is included in the agent, such that the reagent is capable of reversibly binding to a plurality of agents (e.g., a plurality of receptor-binding agents, selection agent and/or viral vector particle-binding agents), e.g., is a multimerization reagent. In some embodiments, the reagent is an oligomer or polymer of individual molecules (e.g. monomers) or is an oligomer or polymer of complexes of subunits that make up an individual molecule (e.g. tetramer), where such oligomer or polymer contains at least one binding site Z. In some embodiments, the reagent contains at least two binding sites Z, at least three binding sites Z, at least four binding sites Z, such as at least 5, 6, 7, 8, 9, 10, 11, 12, 13, 14, 15, 16, 17, 18, 19, 20, 24, 28, 32, 36, 40, 44, 48, 52, 56, 60, 64, 68, 72 or more binding sites Z. The binding sites can all be the same or the plurality of binding sites can contain one or more different binding sites (e.g., Z1, Z2, Z3, etc.).

In some embodiments, one or more agents, such as two or more agents, (e.g., receptor-binding agent, selection agent and/or viral vector particle-binding agent) associate with, such as are reversibly bound to, the reagent, such as via one or the plurality of binding sites Z present on the reagent. In some cases, this results in the agents (e.g., receptor-binding agent(s), selection agent(s) and/or viral vector particle-binding agent(s)) being closely arranged to each other such that an avidity effect can take place if a biological particle (e.g. target cell) having (at least two copies of) a molecule (e.g. cell surface molecule) is brought into contact with the agent that has one or more binding sites (B or V) able to bind the particular molecule.

In some embodiments, two or more different agents (e.g., receptor-binding agent, selection agent or viral vector particle-binding agent) that contain the same binding site (either B or V), can be reversibly bound to the reagent. In some embodiments, it is possible to use at least two different (kinds of) agents, and in some cases, three or four different (kinds of) agent, e.g., two or more different receptor-binding agents, selection agents and/or viral vector particle-binding agent. For example, in some embodiments, the reagent can be reversibly bound to a first agent (e.g., receptor-binding agent or selection agent) containing a binding site B1, B2, B3 or B4, etc., and a second agent (e.g., receptor-binding agent or selection agent) containing another binding site, e.g. another of a binding site B1, B2, B3, B4. In some cases, the binding site of the first agent and the second agent can be the same. For example, in some aspects, each of the at least two agents (e.g., receptor-binding agents or selection agents) can bind to the same molecule. In some cases, the binding site of the first agent and second agent can be different. In some aspects, each of the at least two agents (e.g., receptor-binding agents, selection agents) can bind to different molecule, such as a first molecule, second molecule and so on. In some cases, the different molecules, such as cell surface molecules, can be present on the same target cell. In other cases, the different molecules, such as cell surface molecules, can be present on different target cells that are present in the same population of cells. In some case, a third, fourth and so on agent (e.g., receptor-binding agent or selection agent) can be reversibly associated with the same reagent, each agent containing a further different binding site. In some embodiments, the reagent can be reversibly bound to at least a first agent (e.g. receptor-binding agent or selection agent) containing one or more binding site, B (e.g. B1, B2, B3), and also a viral vector particle-binding agent containing one or more binding site V (e.g. V1, V2, V3).

In some embodiments, the one or more agents, such as two or more different agents, (e.g., receptor-binding agents, selection agents and/or viral vector particle-binding agent) contain the same binding partner C. In some embodiments, the two or more different agents (e.g., receptor-binding agents or selection agents) contain different binding partners. In some aspects, a first agent (e.g., receptor-binding agent, selection agent or viral vector particle-binding agent) can have a binding partner C1 that can specifically bind to a binding site Z1 present on the reagent and a second agent (e.g., receptor-binding agents, selection agent or viral vector particle-binding agent) can have a binding partner C2 that can specifically bind to the binding site Z1 or to a binding site Z2 present on the reagent. Thus, in some instances, the plurality of binding sites Z comprised by the reagent comprises binding sites Z1 and Z2, which are capable of reversibly binding to binding partners C1 and C2, respectively, comprised by the agent (e.g., receptor-binding agent, selection agent or viral vector particle-binding agent). In some embodiments, C1 and C2 are the same, and/or Z1 and Z2 are the same. In other aspects, one or more of the plurality of binding sites Z can be different. In other instances, one or more of the plurality of binding partners C may be different. It is within a level of a skilled artisan to choose any combination of different binding partners C that are compatible with a reagent containing the binding sites Z, as long as each of the binding partners C are able to interact, such as specifically bind, with one of the binding sites Z.

In some embodiments of any of the methods provided herein, the oligomeric protein reagent includes a plurality of polypeptide units, individually including a streptavidin, an avidin, a biotin binding polypeptide, a strep tag-binding peptide, a streptavidin mutein, a streptaviidn analog, an avidin mutein, an avidin analog, and/or a biologically active fragment of any of the foregoing. For example, in some embodiments, the methods provided herein involves incubating a plurality of target cells with (1) a protein reagent including a streptavidin, an avidin, a streptavidin analog or mutein, an avidin analog, a mutein or a biologically active fragment of any of the foregoing, and/or multiple subunits of any of the foregoing; and (2) a viral particle, wherein the method produces an output composition including one or more cells transduced with the viral particle.

In some embodiments, the reagent is a streptavidin, a streptavidin mutein or analog, avidin, an avidin mutein or analog (such as neutravidin) or a mixture thereof, in which such reagent contains one or more binding sites Z for reversible association with a binding partner C. In some embodiments, the binding partner C can be a biotin, a biotin derivative or analog, or a streptavidin-binding peptide or other molecule that is able to specifically bind to streptavidin, a streptavidin mutein or analog, avidin or an avidin mutein or analog. In some embodiments, the reagent is or comprises streptavidin, avidin, an analog or mutein of streptavidin, or an analog or mutein or avidin that reversibly binds biotin, a biotin analog or a biologically active fragment thereof. In some embodiments, the reagent is or comprises an analog or mutein of streptavidin or an analog or mutein of avidin that reversibly binds a streptavidin-binding peptide. In some embodiments, the substance (e.g. competitive reagent) can be a biotin, a biotin derivative or analog or a streptavidin-binding peptide capable of competing for binding with the binding partner C for the one or more binding sites Z. In some embodiments, the binding partner C and the substance (e.g. competitive reagent) are different, and the substance (e.g. competitive reagent) exhibits a higher binding affinity for the one or more binding sites Z compared to the affinity of the binding partner.

In some embodiments, the streptavidin can be wild-type streptavidin, streptavidin muteins or analogs, such as streptavidin-like polypeptides. Likewise, avidin, in some aspects, includes wild-type avidin or muteins or analogs of avidin such as neutravidin, a deglycosylated avidin with modified arginines that typically exhibits a more neutral pi and is available as an alternative to native avidin. Generally, deglycosylated, neutral forms of avidin include those commercially available forms such as "Extravidin", available through Sigma Aldrich, or "NeutrAvidin" available from Thermo Scientific or Invitrogen, for example.

In some embodiments, the reagent is a streptavidin or a streptavidin mutein or analog. In some embodiments, wild-type streptavidin (wt-streptavidin) has the amino acid sequence disclosed by Argarana et al, Nucleic Acids Res. 14 (1986) 1871-1882 (SEQ ID NO: 1). In general, streptavidin naturally occurs as a tetramer of four identical subunits, i.e. it is a homo-tetramer, where each subunit contains a single binding site for biotin, a biotin derivative or analog or a biotin mimic. An exemplary sequence of a streptavidin subunit is the sequence of amino acids set forth in SEQ ID NO: 1, but sucla sequence also can include a sequence present in homologs thereof from other *Streptomyces* species. In particular, each subunit of streptavidin may exhibit a strong binding affinity for biotin with an equilibrium dissociation constant ($K_D$) on the order of about $10^{-14}$ M. In some cases, streptavidin can exist as a monovalent tetramer in which only one of the four binding sites is functional (Howarth et al. (2006) *Nat. Methods*, 3:267-73; Zhang et al. (2015) *Biochem. Biophys. Res. Commun.*, 463:1059-63)), a divalent tetramer in which two of the four binding sites are functional (Fairhead et al. (2013) *J. Mol. Biol.*, 426:199-214), or can be present in monomeric or dimeric form (Wu et al. (2005) *J. Biol. Chem.*, 280:23225-31; Lim et al. (2010) *Biochemistry*, 50:8682-91).

In some embodiments, streptavidin may be in any form, such as wild-type or unmodified streptavidin, such as a streptavidin from a *Streptomyces* species or a functionally active fragment thereof that includes at least one functional subunit containing a binding site for biotin, a biotin derivative or analog or a biotin mimic, such as generally contains at least one functional subunit of a wild-type streptavidin from *Streptomyces avidinii* set forth in SEQ ID NO: 1 or a functionally active fragment thereof. For example, in some embodiments, streptavidin can include a fragment of wild-type streptavidin, which is shortened at the N- and/or C-terminus. Such minimal streptavidins include any that begin N-terminally in the region of amino acid positions 10 to 16 of SEQ ID NO: 1 and terminate C-terminally in the region of amino acid positions 133 to 142 of SEQ ID NO: 1. In some embodiments, a functionally active fragment of streptavidin contains the sequence of amino acids set forth in SEQ ID NO: 2. In some embodiments, streptavidin, such as set forth in SEQ ID NO: 2, can further contain an N-terminal methionine at a position corresponding to Ala13 with numbering set forth in SEQ ID NO: 1. Reference to the position of residues in streptavidin or streptavidin muteins is with reference to numbering of residues in SEQ ID NO: 1.

In some aspects, streptavidin muteins include polypeptides that are distinguished from the sequence of an unmodified or wild-type streptavidin by one or more amino acid substitutions, deletions, or additions, but that include at least one functional subunit containing a binding site for biotin, a biotin derivative or analog or a streptavidin-binding peptide. In some aspects, streptavidin-like polypeptides and streptavidin muteins can be polypeptides which essentially are immunologically equivalent to wild-type streptavidin and are in particular capable of binding biotin, biotin derivatives or biotin analogues with the same or different affinity as wt-streptavidin. In some cases, streptavidin-like polypeptides or streptavidin muteins may contain amino acids which are not part of wild-type streptavidin or they may include only a part of wild-type streptavidin. In some embodiments, streptavidin-like polypeptides are polypeptides which are not identical to wild-type streptavidin, since the host does not have the enzymes which are required in order to transform the host-produced polypeptide into the structure of wild-type streptavidin. In some embodiments, streptavidin also may be present as streptavidin tetramers and streptavidin dimers, in particular streptavidin homotetramers, streptavidin homodimers, streptavidin heterotetramers and streptavidin heterodimers. Generally, each subunit normally has a binding site for biotin or biotin analogues or for streptavidin-binding peptides. Examples of streptavidins or streptavidin muteins are mentioned, for example, in WO 86/02077, DE 19641876 A1, U.S. Pat. No. 6,022,951, WO 98/40396 or WO 96/24606.

In some embodiments, a streptavidin mutein can contain amino acids that are not part of an unmodified or wild-type streptavidin or can include only a part of a wild-type or unmodified streptavidin. In some embodiments, a streptavidin mutein contains at least one subunit that can have one more amino acid substitutions (replacements) compared to a subunit of an unmodified or wild-type streptavidin, such as compared to the wild-type streptavidin subunit set forth in SEQ ID NO: 1 or a functionally active fragment thereof, e.g. set forth in SEQ ID NO: 2. In some embodiments, at least one subunit of a streptavidin mutein can have at least 1, 2, 3, 4, 5, 6, 7, 8, 9, 10, 11, 12, 13, 14, 15, 16, 17, 18, 19 or 20 amino acid differences compared to a wild-type or unmodified streptavidin and/or contains at least one subunit that comprising an amino acid sequence that exhibits at least 85%, 86%, 87%, 88%, 89%, 90%, 91%, 92%, 93%, 94%, 95%, 96%, 97%, 98%, 99% or more sequence identity to the sequence of amino acids set forth in SEQ ID NO: 1 or 2, where such streptavidin mutein exhibits functional activity to bind biotin, a biotin derivative or analog or biotin mimic. In some embodiments, the amino acid replacements (substitutions) are conservative or non-conservative mutations. Examples of streptavidin muteins are known in the art, see e.g., U.S. Pat. No. 5,168,049; 5,506,121; 6,022,951; 6,156, 493; 6,165,750; 6,103,493; or 6,368,813; or International published PCT App. No. WO2014/076277.

In some embodiments, streptavidin or a streptavidin mutein includes proteins containing one or more than one functional subunit containing one or more binding sites Z for biotin, a biotin derivative or analog or a streptavidin-binding peptide, such as two or more, three or more, four or more, and, in some cases, 5, 6, 7, 8, 9, 10, 11, 12 or more functional subunits. In some embodiments, streptavidin or streptavidin mutein can include a monomer; a dimer, including a heterodimer or a homodimer; a tetramer, including a homotetramer, a heterotetramer, a monovalent tetramer or a divalent tetramer; or can include higher ordered multimers or oligomers thereof.

In some embodiments, the binding affinity of streptavidin or a streptavidin mutein for a peptide ligand binding partner is less than $1\times10^{-4}$ M, $5\times10^{-4}$ M, $1\times10^{-5}$ M, $5\times10^{-5}$ M, $1\times10^{-6}$ M, $5\times10^{-6}$ M or $1\times10^{-7}$ M, but generally greater than $1\times10^{-13}$ M, $1\times10^{-12}$ M or $1\times10^{-11}$ M. For example, peptide sequences (Strep-tags), such as disclosed in U.S. Pat. No. 5,506,121, can act as biotin mimics and demonstrate a binding affinity for streptavidin, e.g., with a $K_D$ of approximately between $10^{-4}$ M and $10^{-5}$ M. In some cases, the binding affinity can be further improved by making a mutation within the streptavidin molecule, see e.g. U.S. Pat. No. 6,103,493 or International published PCT App. No. WO2014/076277. In some embodiments, binding affinity can be determined by methods known in the art, such as any described below.

In some embodiments, the reagent, such as a streptavidin or streptavidin mutein, exhibits binding affinity for a peptide ligand binding partner, which peptide ligand binding partner can be the binding partner C present in the agent (e.g., receptor-binding agent or selection agent). In some embodiments, the peptide sequence contains a sequence with the general formula set forth in SEQ ID NO: 9, such as contains the sequence set forth in SEQ ID NO: 10. In some embodiments, the peptide sequence has the general formula set forth in SEQ ID NO: 11, such as set forth in SEQ ID NO: 12. In one example, the peptide sequence is Trp-Arg-His-Pro-Gln-Phe-Gly-Gly (also called Strep-tag®, set forth in SEQ ID NO: 7). In one example, the peptide sequence is Trp-Ser-His-Pro-Gln-Phe-Glu-Lys (also called Strep-tag® II, set forth in SEQ ID NO: 8). In some embodiments, the peptide ligand contains a sequential arrangement of at least two streptavidin-binding modules, wherein the distance between the two modules is at least 0 and not greater than 50 amino acids, wherein one binding module has 3 to 8 amino acids and contains at least the sequence His-Pro-Xaa (SEQ ID NO: 9), where Xaa is glutamine, asparagine, or methionine, and wherein the other binding module has the same or different streptavidin peptide ligand, such as set forth in SEQ ID NO: 11 (see e.g. International Published PCT Appl. No. WO02/077018; U.S. Pat. No. 7,981,632). In some embodiments, the peptide ligand contains a sequence having the formula set forth in any of SEQ ID NO: 13 or 14. In some embodiments, the peptide ligand has the sequence of amino acids set forth in any of SEQ ID NOS: 15-19.

In some embodiments, the reagent is or comprises a streptavidin mutein. In some embodiments, the streptavidin muteins contain one or more mutations (e.g. amino acid replacements) compared to wild-type streptavidin set forth in SEQ ID NO: 1 or a biologically active portion thereof. For example, biologically active portions of streptavidin can include streptavidin variants that are shortened at the N- and/or the C-terminus, which in some cases is called a minimal streptavidin. In some embodiments, an N-terminally shortened minimal streptavidin, to which any of the mutations can be made, begins N-terminally in the region of the amino acid positions 10 to 16 and terminates C-terminally in the region of the amino acid positions 133 to 142 compared to the sequence set forth in SEQ ID NO: 1. In some embodiments, an N-terminally shortened streptavidin, to which any of the mutations can be made, comprises the amino acid sequence set forth in SEQ ID NO: 2. In some embodiments, the minimal streptavidin comprises an amino acid sequence from position Ala13 to Ser139 and optionally has an N-terminal methionine residue instead of Ala13. For purposes herein, the numbering of amino acid positions refers throughout to the numbering of wt-streptavidin set forth in SEQ ID NO: 1 (e.g. Argarana et al., Nucleic Acids Res. 14 (1986), 1871-1882, cf. also FIG. 3).

In some embodiments, the streptavidin mutein is a mutant as described in U.S. Pat. No. 6,103,493. In some embodiments, the streptavidin mutein contains at least one mutation within the region of amino acid positions 44 to 53, based on the amino acid sequence of wild-type streptavidin, such as set forth in SEQ ID NO: 1. In some embodiments, the streptavidin mutein contains a mutation at one or more residues 44, 45, 46, and/or 47. In some embodiments, the streptavidin mutein contains a replacement of Glu at position 44 of wild-type streptavidin with a hydrophobic aliphatic amino acid, e.g. Val, Ala, Ile or Leu, any amino acid at position 45, an aliphatic amino acid, such as a hydrophobic aliphatic amino acid at position 46 and/or a replacement of Val at position 47 with a basic amino acid, e.g. Arg or Lys, such as generally Arg. In some embodiments, Ala is at position 46 and/or Arg is at position 47 and/or Val or Ile is at position 44. In some embodiments, the streptavidin mutant contains residues $Val^{44}$-$Thr^{45}$-$Ala^{46}$-$Arg^{47}$, such as set forth in exemplary streptavidin muteins containing the sequence of amino acids set forth in SEQ ID NO: 3 or SEQ ID NO: 4 (also known as streptavidin mutant 1, SAM1). In some embodiments, the streptavidin mutein contains residues $Ile^{44}$-$Gly^{45}$-$Ala^{46}$-$Arg^{47}$, such as set forth in exemplary streptavidin muteins containing the sequence of amino acids set forth in SEQ ID NO: 5 or 6 (also known as SAM2). In some cases, such streptavidin mutein are described, for example, in U.S. Pat. No. 6,103,493, and are commercially available under the trademark Strep-Tactin®.

In some embodiment, the streptavidin mutein is a mutant as described in International Published PCT Appl. Nos. WO 2014/076277. In some embodiments, the streptavidin mutein contains at least two cysteine residues in the region of amino acid positions 44 to 53 with reference to amino acid positions set forth in SEQ ID NO: 1. In some embodiments, the cysteine residues are present at positions 45 and 52 to create a disulfide bridge connecting these amino acids. In such an embodiment, amino acid 44 is typically glycine or alanine and amino acid 46 is typically alanine or glycine and amino acid 47 is typically arginine. In some embodiments, the streptavidin mutein contains at least one mutation or amino acid difference in the region of amino acids residues 115 to 121 with reference to amino acid positions set forth in SEQ ID NO: 1. In some embodiments, the streptavidin mutein contains at least one mutation at amino acid position 117, 120 and 121 and/or a deletion of amino acids 118 and 119 and substitution of at least amino acid position 121.

In some embodiments, the streptavidin mutein contains a mutation at a position corresponding to position 117, which mutation can be to a large hydrophobic residue like Trp, Tyr or Phe or a charged residue like Glu, Asp or Arg or a hydrophilic residue like Asn or Gln, or, in some cases, the hydrophobic residues Leu, Met or Ala, or the polar residues Thr, Ser or His. In some embodiments, the mutation at position 117 is combined with a mutation at a position corresponding to position 120, which mutation can be to a small residue like Ser or Ala or Gly, and a mutation at a position corresponding to position 121, which mutation can be to a hydrophobic residue, such as a bulky hydrophobic residue like Trp, Tyr or Phe. In some embodiments, the mutation at position 117 is combined with a mutation at a position corresponding to position 120 of wildtype streptavidin set forth in SEQ ID NO:1 or a biologically active fragment thereof, which mutation can be a hydrophobic residue such as Leu, Ile, Met, or Val or, generally, Tyr or Phe, and a mutation at a position corresponding to position 121 compared to positions of wildtype streptavidin set forth in SEQ ID NO:1 or a biologically active fragment thereof, which mutation can be to a small residue like Gly, Ala, or Ser, or with Gln, or with a hydrophobic residue like Leu, Val, Ile, Trp, Tyr, Phe, or Met. In some embodiments, such muteins also can contain residues Val44-Thr45-Ala46-Arg47 or residues Ile44-Gly45-Ala46-Arg47. In some embodiments, the streptavidin mutein contains the residues Val44, Thr45, Ala46, Arg47, Glu117, Gly120 and Tyr121. In some embodiments, the mutein streptavidin comprises the sequence of amino acids set forth in SEQ ID NO:27 or SEQ ID NO:28, or a sequence of amino acids that exhibits at least 85%, 86%, 87%, 88%, 89%, 90%, 91%, 92%, 93%, 94%, 95%, 96%, 97%, 98%, 99% or more sequence identity to the sequence of amino acids set forth in SEQ ID NO: 27 or SEQ ID NO: 28, contains the residues Val44, Thr45, Ala46, Arg47, Glu117, Gly120 and Tyr121 and exhibits functional activity to bind to biotin, a biotin analog or a streptavidin-binding peptide.

In some embodiments, a streptavidin mutein can contain any of the above mutations in any combination, and the resulting streptavidin mutein may exhibit a binding affinity that is less than $2.7 \times 10^{-4}$ M for the peptide ligand (Trp Arg His Pro Gln Phe Gly Gly; also called Strep-tag®, set forth in SEQ ID NO: 7) and/or less than $1.4 \times 10^{-4}$ M for the peptide ligand (Trp Ser His Pro Gln Phe Glu Lys; also called Strep-tag® II, set forth in SEQ ID NO: 8) and/or is less than $1 \times 10^{-4}$M, $5 \times 10^{-4}$ M, $1 \times 10^{-5}$ M, $5 \times 10^{-5}$ M, $1 \times 10^{-6}$ M, $5 \times 10^{-6}$ M or $1 \times 10^{-7}$ M, but generally greater than $1 \times 10^{-13}$ M, $1 \times 10^{-12}$ M or $1 \times 10^{-11}$ M for any of the peptide ligands set forth in any of SEQ ID NOS:7-19.

In some embodiments, the streptavidin mutein exhibits the sequence of amino acids set forth in any of SEQ ID NOs: 3-6, 27 or 28, or a sequence of amino acids that exhibits at least 90%, 91%, 92%, 93%, 94%, 95%, 96%, 97%, 98%, 99% or more sequence identity to the sequence of amino acids set forth in any of SEQ ID NO: 3-6, 27 or 28, and exhibits a binding affinity that is less than $2.7 \times 10^{-4}$ M for the peptide ligand (Trp Arg His Pro Gln Phe Gly Gly; also called Strep-tag®, set forth in SEQ ID NO: 7) and/or less than $1.4 \times 10^{-4}$ M for the peptide ligand (Trp Ser His Pro Gln Phe Glu Lys; also called Strep-tag® II, set forth in SEQ ID NO: 8) and/or is less than $1 \times 10^{-4}$ M, $5 \times 10^{-4}$ M, $1 \times 10^{-5}$ M, $5 \times 10^{-5}$M, $1 \times 10^{-6}$M, $5 \times 10^{-6}$M or $1 \times 10^{-7}$ M, but generally greater than $1 \times 10^{-13}$ M, $1 \times 10^{-12}$ M or $1 \times 10^{-11}$ M for any of the peptide ligands set forth in any of SEQ ID NOS:7-19.

In some embodiments, the streptavidin mutein also exhibits binding to other streptavidin ligands, such as but not limited to, biotin, iminobiotin, lipoic acid, desthiobiotin, diaminobiotin, HABA (hydroxyazobenzene-benzoic acid) and/or dimethyl-HABA. In some embodiments, the streptavidin mutein exhibits a binding affinity for another streptavidin ligand, such as biotin or desthiobiotin, that is greater than the binding affinity of the streptavidin mutein for a biotin mimic peptide ligand, such as set forth in any of SEQ ID NOS: 7-19. Thus, in some embodiments, biotin or a biotin analog or derivative (e.g. desthiobiotin) can be employed as a competition reagent in the provided methods. For example, as an example, the interaction of a mutein streptavidin designated Strep-tactin® (e.g. containing the sequence set forth in SEQ ID NO: 4) with the peptide ligand designated Strep-tag II (e.g. set forth in SEQ ID NO: 8) is characterized by a binding affinity with a $K_D$ of approximately $10^{-6}$ M compared to approximately $10^{-13}$ M for the bitoin-streptavidin interaction. In some cases, biotin, which can bind with high affinity to the Strep-tactin® with a $K_D$ of between or between about $10^{-10}$ and $10^{-13}$ M, can compete with Strep-tag II for the binding site.

In some cases, the reagent comprises at least two chelating groups K that may be capable of binding to a transition metal ion. In some embodiments, the reagent may be capable of binding to an oligohistidine affinity tag, a glutathione-S-transferase, calmodulin or an analog thereof, calmodulin binding peptide (CBP), a FLAG-peptide, an HA-tag, maltose binding protein (MBP), an HSV epitope, a myc epitope, and/or a biotinylated carrier protein.

In some embodiments, the protein reagent is an oligomeric protein reagent, which can include one or a plurality of multimeric subunits each individually including two or more of the polypeptide units. In some embodiments, the oligomeric protein reagent includes a plurality of one units including or more of the biotin binding polypeptide, the streptavidin, the avidin, the streptavidin analog, the streptavidin mutein, the avidin analog, the avidin mutein and the biologically active fragment.

In some embodiments, the reagent is an oligomer or polymer. In some embodiments, the oligomer or polymer can be generated by linking directly or indirectly individual molecules of the protein as it exists naturally, either by linking directly or indirectly individual molecules of a monomer or a complex of subunits that make up an individual molecule (e.g. linking directly or indirectly dimers, trimers, tetramers, etc. of a protein as it exists naturally). For example, a tetrameric homodimer or heterodimer of streptavidin or avidin may be referred to as an individual molecule or smallest building block of a respective oligomer or polymer. In some embodiments, the oligomer or polymer can contain linkage of at least 2 individual molecules of the protein (e.g. is a 2-mer), or can be at least a 3-mer, 4-mer, 5-mer, 6-mer, 7-mer, 8-mer, 9-mer, 10-mer, 11-mer, 12-mer, 13-mer, 14-mer, 15-mer, 16-mer, 17-mer, 18-mer, 19-mer, 20-mer, 25-mer, 30-mer, 35-mer, 40-mer, 45-mer or 50-mer of individual molecules of the protein (e.g., monomers, tetramers).

Oligomers can be generated using any methods known in the art, such as any described in published U.S. Patent Application No. US2004/0082012. In some embodiments, the oligomer or polymer comprises two or more individual molecules that may be crosslinked, such as by a polysaccharide or a bifunctional linker.

In some embodiments, the oligomer or polymer is obtained by crosslinking individual molecules or a complex of subunits that make up an individual molecule in the presence of a polysaccharide. In some embodiments, oligomers or polymers can be prepared by the introduction of carboxyl residues into a polysaccharide, e.g. dextran. In some aspects, individual molecules of the reagent (e.g., monomers, tetramers) can be coupled via primary amino groups of internal lysine residues and/or the free N-terminus to the carboxyl groups in the dextran backbone using conventional carbodiimide chemistry. In some embodiments, the coupling reaction is performed at a molar ratio of about 60 moles of individual molecules of the reagent (e.g., monomers, tetramers) per mole of dextran.

In some embodiments the reagent is an oligomer or a polymer of one or more streptavidin or avidin or of any analog or mutein of streptavidin (e.g. Strep-Tactin® or Strep-Tactin® XT) or analog or mutein of avidin (e.g. neutravidin). In some embodiments, the binding site Z is a natural biotin binding site of avidin or streptavidin for which there can be up to four binding sites in an individual molecule (e.g. a tetramer contains four binding sites Z), whereby a homo-tetramer can contain up to 4 binding sites that are the same, i.e. Z1, whereas a hetero-tetramer can contain up to 4 binding sites that may be different, e.g. containing Z1 and Z2. In some embodiments, the oligomer is generated or produced from a plurality of individual molecules (e.g. a plurality of homo-tetramers) of the same streptavidin, streptavidin mutein, avidin or avidin mutein, in which case each binding site Z, e.g. Z1, of the oligomer is the same. For example, in some cases, an oligomer can contain a plurality of binding sites Z1, such as at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 40, 45, 50 or more binding sites Z1. In some embodiments, the oligomer is generated or produced from a plurality of individual molecules that can be heterotetramers of a streptavidin, streptavidin mutein, avidin or avidin mutein and/or from a plurality of two or more different individual molecules (e.g. different homo-tetramers) of streptavidin, streptavidin mutein, avidin or avidin mutein that differ in their binding sites Z, e.g. Z1 and Z2, in which case a plurality of different binding sites Z, e.g. Z1 and Z2, may be present in the oligomer. For example, in some cases, an oligomer can contain a plurality of binding sites Z1 and a plurality of binding sites Z, which, in combination, can include at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 40, 45, 50 or more combined binding sites Z1 and Z2.

In some embodiments, the oligomer or polymer is obtained by crosslinking individual molecules or a complex of subunits that make up an individual molecule using a bifunctional linker or other chemical linker, such as glutardialdehyde or by other methods known in the art. In some aspects, cross-linked oligomers or polymers of streptavidin or avidin or of any mutein or analog of streptavidin or avidin may be obtained by crosslinking individual streptavidin or avidin molecules via bifunctional molecules, serving as a linker, such as glutardialdehyde or by other methods described in the art. It is, for example, possible to generate oligomers of streptavidin muteins by introducing thiol groups into the streptavidin mutein (this can, for example, be done by reacting the streptavidin mutein with 2-iminothiolan (Trauts reagent) and by activating, for example in a separate reaction, amino groups available in the streptavidin mutein. In some embodiments, this activation of amino groups can be achieved by reaction of the streptavidin mutein with a commercially available heterobifunctional crosslinker such as sulfosuccinimidyl 4-(N-maleimidomethyl)cyclohexane-1-carboxylate (sulfo SMCC) or Succinimidyl-6-[(β-maleimidopropionamido)hexanoate (SMPH). In some such embodiments, the two reaction products so obtained are mixed together, typically leading to the reaction of the thiol groups contained in the one batch of modified streptavidin mutein with the activated (such as by maleimide functions) amino acids of the other batch of modified streptavidin mutein. In some cases, by this reaction, multimers/oligomers of the streptavidin mutein are formed. These oligomers can have any suitable number of individual molecules, such as at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 40, 45, 50 or more, and the oligomerization degree can be varied according to the reaction condition.

In some embodiments, the oligomeric or polymeric reagent can be isolated via size exclusion chromatography and any desired fraction can be used as the reagent. For example, in some embodiments, after reacting the modified streptavidin mutein, in the presence of 2-iminothiolan and a heterobifunctional crosslinker such as sulfo SMCC, the oligomeric or polymeric reagent can be isolated via size exclusion chromatography and any desired fraction can be used as the reagent. In some embodiments, the oligomers do not have (and do not need to have) a single molecular weight but they may observe a statistical weight distribution such as Gaussian distribution. In some cases, any oligomer with more than three streptavidin or mutein tetramers, e.g., homotetramers or heterotetramers, can be used as a soluble reagent, such as generally 3 to 50 tetramers, e.g., homotetramers or heterotetramers, 10 to 40 tetramers, e.g., homotetramers or heterotetramers, or 25 to 35 tetramers, e.g., homotetramers or heterotetramers. The oligomers might have, for example, from 3 to 25 streptavidin mutein tetramers, e.g., homotetramers or heterotetramers. In some aspects, with a molecular weight of about 50 kDa for streptavidin muteins, the soluble oligomers can have a molecular weight from about 150 kDa to about 2000 kDa, about 150 kDa to about 1500 kDa, about 150 kDa to about 1250 kDa, about 150 kDa to about 1000 kDa, about 150 kDa to about 500 kDa or about 150 kDa to about 300 kDa, about 300 kDa to about 2000 kDa, about 300 kDa to about 1500 kDa, about 300 kDa to about 1250 kDa, about 300 kDa to 1000 kDa, about 300 kDa to about 500 kDa, about 500 kDa to about 2000 kDa, about 500 kDa to about 1500 kDa, about 500 kDa to about 1250 kDa, about 500 kDa to about 1000 kDa, about 1000 kDa to about 2000 kDa, about 1000 kDa to about 1500 kDa, about 1000 kDa to about 1250 kDa, about 1250 kDa to about 2000 kDa or about 1500 kDa to about 2000 kDa. Generally, because each streptavidin molecule/mutein has four biotin binding sites, such a reagent can provide 12 to 160 binding sites Z, such as 12 to 100 binding sites Z.

In some embodiments, the reagent does not include and/or is not conjugated or reversibly bound to a binding agent including an antibody or fragment thereof or does not include a binding agent including a human cell surface molecule or binding fragment thereof; the reagent does not include and or is not conjugated or bound to a molecule with a binding domain specific for a human cell surface marker, optionally a T cell marker; the reagent does not include and or is not conjugated or bound to an extracellular matrix component, adhesion molecule, an integrin, a lectin, an integrin-binding protein, a chemokines, a cytokine, a growth factor, extracellular matrix-binding molecule, an ECM component, a viral protein, a viral entry-promoting cell surface receptor, heparin, heparan, glycans; and/or the reagent does not include a heparin-binding domain and/or does not include an integrin-binding domain and/or does not include a VLA4-binding domain and/or does not include a VLA5-binding domain.

In some embodiments, the reagent also includes and/or is reversibly bound to a plurality of one or more binding agents that each is capable of specifically binding to a molecule on the surface of the viral particle and/or the surface of a target cell.

2. Formal of Reagent a. Support

In some embodiments, the transduction and/or one or more of the other processing steps (e.g. selection, activation or expansion) can be carried out on a solid support, such as by using matrices, such as magnetic beads, agarose particles, cell culture dishes or other solid surface matrix, to which the oligomeric protein reagent or multimerization reagent has been immobilized, conjugated or bound. In some embodiments, the reagent is comprised on a support, such as a solid support or surface, e.g., bead, or a stationary phase (chromatography matrix). In some such embodiments, the reagent is reversibly immobilized on the support. In some cases, the reagent is immobilized to the support via covalent bonds. In some aspects, the reagent is reversibly immobilized to the support non-covalently. In some aspects, the target cells and/or viral particles, sequentially or simultaneously, are exposed or contacted with the reagent on the solid support, such as present as a stationary phase (e.g. chromatography matrix).

In some embodiments, the support is a solid support. Any solid support (surface) can be used for the reversible immobilization of the reagent. Illustrative examples of solid supports on which the reagent can be immobilized include a magnetic bead, a polymeric bead, a cell culture plate, a microliter plate, a membrane, or a hollow fiber. In some aspects, hollow fibers can be used as a bioreactor in the Quantum® Cell Expansion System, available from TerumoBCT Inc. (Lakewood, Colo., USA). In some embodiments, the reagent is covalently attached to the solid support. In other embodiments, non-covalent interactions can also be used for immobilization, for example on plastic substrates.

In some embodiments, the reagent can, for example, be a streptavidin or avidin mutein that reversibly binds a streptavidin binding peptide. Such streptavidin muteins can be covalently attached to any surface, for example, resin (beads) used for chromatography purification and are commercially available in such form from IBA GmbH, Göttingen, for example, as Strep-Tactin® Sepharose, Strep-Tactin® Superflow®, Strep-Tactin® Superflow® high capacity or Strep-Tactin® MacroPrep®.

Other illustrative examples that are readily commercially available are immobilized metal affinity chromatography (IMAC) resins such as the TALON® resins (Westburg, Leusden, The Netherlands) that can be used for the reversible immobilization of oligo-histidine tagged (his-tagged) proteins, such as for the reversible binding of an agent (e.g., receptor-binding agent or selection agent) that comprises as a binding partner C an oligohistidine tag such as an penta- or hexa-histidine tag. Other examples include calmodulin sepharose available from GE Life Sciences which can be used together with an agent (e.g., receptor-binding agent or selection agent) that comprises a calmodulin binding peptide as a binding partner C or sepharose, to which glutathion is coupled. In some such cases, the binding partner C is glutathion-S-transferase.

In some embodiments, a solid support employed in the present methods may include magnetically attractable matter such as one or more magnetically attractable particles or a ferrofluid. A respective magnetically attractable particle may comprise a reagent with a binding site that is capable of binding a target cell or a viral particle. In some cases, magnetically attractable particles may contain diamagnetic, ferromagnetic, paramagnetic or superparamagnetic material. In general, superparamagnetic material responds to a magnetic field with an induced magnetic field without a resulting permanent magnetization. Magnetic particles based on iron oxide are for example commercially available as Dynabeads® from Dynal Biotech, as magnetic MicroBeads from Miltenyi Biotec, as magnetic porous glass beads from CPG Inc., as well as from various other sources, such as Roche Applied Science, BIOCLON, BioSource International Inc., micromod, AMBION, Merck, Bangs Laboratories, Polysciences, or Novagen Inc., to name only a few. Magnetic nanoparticles based on superparamagnetic Co and FeCo, as well as ferromagnetic Co nanocrystals have been described, for example by Hutten, A. et al. (J. Biotech. (2004), 112, 47-63). In some embodiments, the cells and cell populations are separated or isolated using immunomagnetic (or affinity magnetic) separation techniques (reviewed in Methods in Molecular Medicine, vol. 58: Metastasis Research Protocols, Vol. 2: Cell Behavior In Vitro and In Vivo, p 17-25 Edited by: S. A. Brooks and U. Schumacher © Humana Press Inc., Totowa, N.J.).

In some embodiments, the support comprises a stationary phase. Thus, in some embodiments, the reagent is comprised on a stationary phase (also called chromatography matrix). In some such embodiments, the reagent is reversibly immobilized on the stationary phase. In some cases, the reagent is reversibly immobilized to the stationary phase via covalent bonds. In some aspects, the reagent is reversibly immobilized to the stationary phase non-covalently.

Any material may be employed as a chromatography matrix. In general, a suitable chromatography material is essentially innocuous, i.e. not detrimental to cell viability, such as when used in a packed chromatography column under desired conditions. In some embodiments, the stationary phase remains in a predefined location, such as a predefined position, whereas the location of the sample is being altered. Thus, in some embodiments the stationary phase is the part of a chromatographic system through which the mobile phase flows (either by flow through or in a batch mode) and where distribution of the components contained in the liquid phase (either dissolved or dispersed) between the phases occurs.

In some embodiments, the chromatography matrix has the form of a solid or semisolid phase, whereas the sample that contains the target cell to be isolated/separated is a fluid phase. The chromatography matrix can be a particulate material (of any suitable size and shape) or a monolithic chromatography material, including a paper substrate or membrane. Thus, in some aspects, the chromatography can be both column chromatography as well as planar chromatography. In some embodiments, in addition to standard chromatography columns, columns allowing a bidirectional flow such as PhyTip® columns available from PhyNexus, Inc. San Jose, Calif., U.S.A. or pipette tips can be used for column based/flow through mode based methods. Thus, in some cases, pipette tips or columns allowing a bidirectional flow are also comprised by chromatography columns useful in the present methods. In some cases, such as where a particulate matrix material is used, the particulate matrix material may, for example, have a mean particle size of about 5 µm to about 200 µm, or from about 5 µm to about 400 µm, or from about 5 µm to about 600 µm. In some aspects, the chromatography matrix may, for example, be or include a polymeric resin or a metal oxide or a metalloid oxide. In some aspects, such as where planar chromatography is used, the matrix material may be any material suitable for planar chromatography, such as conventional cellulose-based or organic polymer based membranes (for example, a paper membrane, a nitrocellulose membrane or a polyvinylidene difluoride (PVDF) membrane) or silica coated glass plates. In one embodiment, the chromatography matrix/stationary phase is a non-magnetic material or non-magnetizable material.

In some embodiments, non-magnetic or non-magnetizable chromatography stationary phases that are suitable in the present methods include derivatized silica or a crosslinked gel. In some aspects, a crosslinked gel may be based on a natural polymer, such as on a polymer class that occurs in nature. For example, a natural polymer on which a chromatography stationary phase may be based is a polysaccharide. In some cases, a respective polysaccharide is generally crosslinked. An example of a polysaccharide matrix includes, but is not limited to, an agarose gel (for example, Superflow™ agarose or a Sepharose® material such as Superflow™ Sepharose® that are commercially available in different bead and pore sizes) or a gel of crosslinked dextran(s). A further illustrative example is a particulate cross-linked agarose matrix, to which dextran is covalently bonded, that is commercially available (in various bead sizes and with various pore sizes) as Sephadex® or Superdex®, both available from GE Healthcare. Another illustrative example of such a chromatography material is Sephacryl® which is also available in different bead and pore sizes from GE Healthcare.

In some embodiments, a crosslinked gel may also be based on a synthetic polymer, such as on a polymer class that does not occur in nature. In some aspects, such a synthetic polymer on which a chromatography stationary phase is based is a polymer that has polar monomer units, and which is therefore in itself polar. Thus, in some cases, such a polar polymer is hydrophilic. Hydrophilic molecules, also termed lipophobic, in some aspects contain moieties that can form dipole-dipole interactions with water molecules. In general, hydrophobic molecules, also termed lipophilic, have a tendency to separate from water.

Illustrative examples of suitable synthetic polymers are polyacrylamide(s), a styrene-divinylbenzene gel and a copolymer of an acrylate and a diol or of an acrylamide and a diol. An illustrative example is a polymethacrylate gel, commercially available as a Fractogel®. A further example is a copolymer of ethylene glycol and methacrylate, commercially available as a Toyopearl®. In some embodiments, a chromatography stationary phase may also include natural and synthetic polymer components, such as a composite matrix or a composite or a copolymer of a polysaccharide and agarose, e.g. a polyacrylamide/agarose composite, or of a polysaccharide and N,N'-methylenebisacrylamide. An illustrative example of a copolymer of a dextran and N,N'-methylenebisacrylamide is the above-mentioned Sephacryl® series of material. In some embodiments, a derivatized silica may include silica particles that are coupled to a synthetic or to a natural polymer. Examples of such embodiments include, but are not limited to, polysaccharide grafted silica, polyvinylpyrrolidone grafted silica, polyethylene oxide grafted silica, poly(2-hydroxyethylaspartamide) silica and poly(N-isopropylacrylamide) grafted silica.

In some embodiments, a chromatography matrix employed in the present methods may also include magnetically attractable matter such as one or more magnetically attractable particles or a ferrofluid. A respective magnetically attractable particle may comprise a reagent with a binding site that is capable of binding a target cell. In some cases, magnetically attractable particles may contain diamagnetic, ferromagnetic, paramagnetic or superparamagnetic material. In general, superparamagnetic material responds to a magnetic field with an induced magnetic field without a resulting permanent magnetization. Magnetic particles based on iron oxide are for example commercially available as Dynabeads® from Dynal Biotech, as magnetic MicroBeads from Miltenyi Biotec, as magnetic porous glass beads from CPG Inc., as well as from various other sources, such as Roche Applied Science, BIOCLON, BioSource International Inc., micromod, AMBION, Merck, Bangs Laboratories, Polysciences, or Novagen Inc., to name only a few. Magnetic nanoparticles based on superparamagnetic Co and FeCo, as well as ferromagnetic Co nanocrystals have been described, for example by Hutten, A. et al. (J. Biotech. (2004), 112, 47-63). In other embodiments, a chromatography matrix employed in the present methods is void of any magnetically attractable matter.

b. Soluble

In some embodiments, the reagent is not bound to a solid support, i.e. it is present in soluble form or is soluble. In principle, the same reagent can be used as in the case of a reagent that is immobilized on a support, such as a solid support or stationary phase. For example, any of the exemplary of reagents described above can be used without immobilizing or attaching such reagent to a support, e.g. solid support or stationary phase. In some embodiments, the reagent contains a plurality of binding sites, Z, for reversibly binding to a binding agent via interaction with a binding partner, C. In some cases, the reagent is an oligomer or polymer of individual molecules or an oligomer or polymer of a complex of subunits that make up the individual molecule (e.g. oligomers or polymers of a dimeric, trimeric or tetrameric protein). In some embodiments, the reagent can, for example, be a streptavidin mutein oligomer, a calmodulin oligomer, a compound (oligomer) that provides least two chelating groups K, wherein the at least two chelating groups are capable of binding to a transition metal ion, thereby rendering the reagent capable of binding to an oligohistidine affinity tag, multimeric glutathione-S-transferase, or a biotinylated carrier protein.

In some embodiments, the reagent is characterized by the absence of a solid support (surface) attached to the reagent. For example, in some embodiments, the reagent does not comprise or is not attached (directly or indirectly) to a particle, bead, nanoparticle, microsphere or other solid support. In some embodiments, the reagent is not rigid, inflexible or stiff or does not comprise or is not attached to a rigid, inflexible, or stiff surface. In some embodiments, the reagent is flexible or substantially flexible. In some cases, the reagent is able to adjust or adapt to the form of the surface of the cells. In some embodiments, the reagent does not or does not comprise a shape that is spherical or substantially spherical.

In some embodiments, substantially all, i.e. more than 80%, 85%, 90%, 91%, 92%, 93%, 94%, 95%, 96%, 97%, 98%, 99% or more of the reagent is, is composed of or comprises organic material. For example, in some embodiments, more than 80%, 85%, 90%, 91%, 92%, 93%, 94%, 95%, 96%, 97%, 98%, 99% or more of the reagent is, is composed of or comprises lipids, carbohydrates, proteins, peptides or mixtures thereof. In some embodiments, the reagent is, is composed of or contains an essential absence of inorganic material, an inorganic core, e.g. metal, e.g. iron, synthetic or inorganic polymers, such as styrene polymers, e.g. polystyrene, latex, silica or magnetic cores. For example, in some embodiments, the relative percentage of inorganic material of the reagent or that is comprised as part of the reagent is less than 20%, 15%, 10%, 5% or less.

In some embodiments, the majority (i.e. more than 50%), such as more than 60%, 70%, 80%, 90%, 95%, 99% or more of the total volume of the reagent in aqueous solution contains the individual protein molecules that comprise the reagent, such as oligomers or polymers of individual molecules or a complex of subunits that make up an individual molecule (e.g. tetrameric molecule). In some embodiments, the total density of the soluble reagent is less than 1.2 g/cm$^3$, 1.1 g/cm$^3$, 1.0 g/cm$^3$ or less.

In some embodiments, the soluble reagent, e.g. not being attached to a support or solid support (e.g. is not attached to a bead), has a relatively small size, such as generally less than or about less than 20 nm in size, such as less than or about less than 15 nm, less than or about less than 10 nm, less than or about less than 5 nm or smaller.

In some embodiments, the soluble reagent, e.g. not being attached to a support or solid support (e.g. is not attached to a bead), is biologically inert, i.e. it is non-toxic to living cells. In some embodiments, the reagent may be biodegradable, for example, it can be degraded by enzymatic activity or cleared by phagocytic cells.

In some embodiments, it is possible to react the reagent (e.g. a streptavidin or mutein, such as tetrameric streptavidin muteins) to a carrier, such as an organic carrier. In some aspects, in addition to a reaction with a polysaccharide, it is also possible to use physiologically or pharmaceutically acceptable proteins such as serum albumin (for example human serum albumin (HSA) or bovine serum albumin (BSA)) as carrier protein. In such a case, the reagent, such as streptavidin or a streptavidin mutein (either as individual tetramer or also in the form of oligomers), can be coupled to the carrier protein via non-covalent interaction. In some such embodiments, biotinylated BSA (which is commercially available from various suppliers such as ThermoFisher Scientific, Sigma Aldrich or Vectorlabs, to name only a few) can be reacted with the reagent (e.g. streptavidin mutein). In some aspects, some of the reagent oligomers (e.g. streptavidin oligomers) can non-covalently bind via one or more binding sites Z to the biotinylated carrier protein, leaving the majority of the binding sites Z of the oligomer available for binding the agent (e.g., receptor-binding agent or selection agent) and any further agent as described herein. Thus, by such an approach a soluble reagent with a multitude of binding sites Z can be prepared.

In other embodiments, a reagent, such as a streptavidin mutein (either as an individual tetramer or also in the form of an oligomer), can be covalently coupled to a synthetic carrier such as a polyethylene glycol (PEG) molecule. Any suitable PEG molecule can be used for this purpose, for example, and the PEG molecule and the respective reagent can be soluble. Typically, PEG molecules up to a molecular weight of 1000 Da are soluble in water or culture media that may be used in the present methods. In some cases, such PEG based reagent can be prepared using commercially available activated PEG molecules (for example, PEG-NHS derivatives available from NOF North America Corporation, Irvine, Calif., USA, or activated PEG derivatives available from Creative PEGWorks, Chapel Hills, N.C., USA) with amino groups of the streptavidin mutein.

3. Removal or Disruption of Components

In some embodiments, after incubation or other suitable time at which transduction and/or one or more other processes (e.g. selection, activation, stimulation and/or expansion) is desired to be disrupted, the binding between the binding partner C, e.g. C1 of a reversibly bound agent and the binding site Z, e.g. Z1, of the multimerization reagent is disrupted by disrupting the respective reversible bond. In some cases, the disruption may be achieved by adding a competitor to the incubation/reaction mixture containing the population of cells being bound to the multimerization reagent. For competitive disruption (which can be understood as being a competitive elution) of the reversible bond between the binding partner C, e.g. C1, of a reversibly bound agent and the binding site Z, e.g. Z1 of the multimerization reagent, the incubation mixture/population of cells can be contacted with a free first binding partner C, e.g. C1, or an analog of said first binding partner C that is capable of disrupting the bond between the first binding partner and the binding site Z, e.g. Z1. In the example of the binding partner C, e.g. C1, being a streptavidin binding peptide that binds to biotin binding site of streptavidin, the first free partner may be the corresponding free streptavidin binding peptide or an analogue that binds competitively. Such an analogue can, for example, be biotin or a biotin derivate such as desthiobiotin.

In some aspects, reversibility can be achieved because the bond between the streptavidin binding peptide (e.g. Strep-tag) and streptavidin mutein binding reagent is high, but is less than the binding affinity of the streptavidin binding reagent for biotin or a biotin analog. Hence, in some embodiments, biotin (Vitamin H) or a biotin analog can be added to compete for binding to disrupt the binding interaction between the streptavidin mutein binding reagent, e.g. present on the solid support (e.g. bead or chromatography matrix), and the streptavidin binding peptide (e.g. Strep-tag). In some embodiments, the interaction can be reversed in the presence of low concentrations of biotin or analog, such as in the presence of 0.1 mM to 10 mM, 0.5 mM to 5 mM or 1 mM to 3 mM, such as generally at least or about at least 1 mM or at least 2 mM, for example at or about 2.5 mM. In some embodiments, incubation in the presence of a competing agent, such as a biotin or biotin analog, releases the selected cell from the solid support, such as chromatography matrix or bead.

In some embodiments, due to the dissociation of the reversibly bound agent or agents from the cell surface molecule, the provided method has the added advantage that the stimulated cell population is free of binding agents (e.g. viral-binding agent, selection agent or stimulatory agent) at the end of the stimulation period. Also, in some embodiments, all other reagents used in the method, namely the agents (e.g. first or second, receptor-binding agents, e.g. stimulatory agents, or selection agents) as well as the competition reagent of the binding partner C, e.g. C1, or the analog thereof can be easily removed from the stimulated cell population.

In some embodiments, the separation/removal of components (e.g. competition reagent) can be carried out using a second stationary phase. For this purpose, a mixture comprising the target cells and/or viral particles and one or more remaining components are exposed, e.g. before or after being applied onto the first stationary phase described above, to chromatography on a suitable second stationary phase. This secondary stationary phase may be a gel filtration matrix and/or affinity chromatography matrix, wherein the gel filtration and/or affinity chromatography matrix comprises an affinity reagent. The affinity reagent comprised on the chromatography resin include a binding partner D that (specifically) binds to the binding site Z of the reagent (e.g. a streptavidin mutein, such as Strep-Tactin), thereby immobilizing the binding molecule reagent on the stationary phase. In some embodiments, the affinity reagent may, for instance, be streptavidin, a streptavidin mutein, avidin, an avidin mutein or a mixture thereof. In some embodiments the agent (e.g. first or second, receptor-binding agents, e.g. stimulatory agents, or selection agents) and/or the competition reagent bind to the affinity reagent, thereby being immobilized on the chromatography matrix. In some aspects, if a streptavidin based binding molecule reagent is used, such as Strep-Tactin) and the agent bound thereto comprises a streptavidin binding peptide (e.g. Strep-tag), the binding partner D that is comprised in the affinity reagent of this second stationary phase can be biotin. Any remaining streptavidin or of a streptavidin mutein in the composition then binds to the biotin that is usually covalently coupled to a chromatography matrix such as biotin-Sepharose™ that is commercially available.

In some such embodiments, the target cells (e.g. gene modified, such as transduced, T cells) can be recovered away from the reagent.

IAs a result the sample containing the cultured cells, such as isolated, selected, transduced, activated and/or expanded cell population, is being depleted of the agent (e.g. first agent, second agent, etc., such as viral-binding agent, selection agent or receptor-binding agents, e.g. stimulatory agents, or selection agents) and/or the competition substance. In some embodiments, the cultured composition is free of any reactants, which in some aspects is an advantageous for use in connection with certain applications, such as for any cell based therapeutic application.

In some embodiments, the competition substance used to disrupt or reverse binding between the agent and reagent can be easily removed from the stimulated cell population via a "removal cartridge" (see e.g. described in International patent application WO 2013/124474). In some cases, for example in which the reagent is immobilized on a solid support, such as a bioreactor surface or a magnetic bead, it is being held back. Thus, the use of a removal cartridge for removal of the free agent and the competition reagent, can include loading the elution sample (e.g. sample obtained after disruption of the reversible binding) onto a second chromatography column. In some embodiments, this chromatography column has a suitable stationary phase that is both an affinity chromatography matrix and, at the same time, can act as gel permeation matrix. In some aspects, this affinity chromatography matrix has an affinity reagent immobilized thereon. In some embodiments, the affinity reagent may, for instance, be streptavidin, a streptavidin mutein, avidin, an avidin mutein or a mixture thereof.

In some embodiments, the chromatography matrix is a gel filtration matrix, for example, when used in a removal cartridge as described herein. Generally, a gel filtration can be characterized by the property that it is designed to undergo. Hence, a gel filtration matrix in some aspects allows the separation of cells or other biological entities largely on the basis of their size. In some such aspects, the respective chromatography matrix is typically a particulate porous material as mentioned above. The chromatography matrix may have a certain exclusion limit, which is typically defined in terms of a molecular weight above which molecules are entirely excluded from entering the pores. In some embodiments, the respective molecular weight defining the size exclusion limit may be selected to be below the weight corresponding to the weight of a target cell. In such an embodiment, the target cell is prevented from entering the pores of the size exclusion chromatography matrix. Likewise, a stationary phase may have pores that are of a size that is smaller than the size of a chosen target cell. In illustrative embodiments chromatography matrix has a mean pore size of 0 to about 500 nm.

In some embodiments, components present in a sample such as agents (e.g., viral-binding agent, receptor-binding agents or selection agents) or a competition reagent may have a size that is below the exclusion limit of the pores and thus can enter the pores of the chromatography matrix. In some aspects, of such components that are able to partially or fully enter the pore volume, larger molecules, with less access to the pore volume can elute first, whereas the smallest molecules typically elute last. In some embodiments, the exclusion limit of the chromatography matrix is selected to be below the maximal width of the target cell. Hence, in some aspects, components that have access to the pore volume can remain longer in/on the chromatography matrix than target cell. Thus, in some cases, target cells can be collected in the eluate of a chromatography column separately from other matter/components of a sample. Therefore, in some aspects, components such as an agent (e.g., receptor-binding agent or selection agent), or where applicable a competition reagent, may elute at a later point of time from a gel filtration matrix than the target cell. In some embodiments, this effect can be further increased, such as if the gel permeation matrix comprises a reagent (such as covalently bound thereon) that comprises binding sites Z that are able to bind agents (e.g., receptor-binding agents or selection agents) and/or a competition reagent present in a sample. In some cases, the agent (e.g., receptor-binding agent or selection agent) and/or the competition reagent can be bound by the binding sites Z of the reagent and thereby immobilized on the matrix. In some aspects, this method is carried out in a removal cartridge.

In some embodiments, provided is an apparatus that comprises at least one arrangement of a first and a second stationary phase, such as chromatography column for selection of cells (a selection cartridge) and a second chromatography column (a removal cartridge) for removal of reagents. The apparatus may comprise a plurality of arrangements of first and second stationary phases (chromatography columns) being fluidly connected in series. The apparatus may comprise a sample inlet being fluidly connected to the first stationary phase of the first arrangement of the first and second stationary phases. In some embodiments, the apparatus may also comprise a sample outlet for cells, the sample outlet being fluidly connected to the second stationary phase of the last of the at least one arrangement of a first and second stationary phases for chromatography. In some aspects, the apparatus may also comprise a competition reagent container that is fluidly connected to at least one of the first stationary phases of the arrangements of the first and second stationary phases.

In some embodiments, the ability to remove the reagent and other components from the composition has the further advantage of being able to avoid any solid support such as magnetic beads. In some embodiments, this means there is no risk or minimal risk of contamination of the target cells (e.g. gene modified, such as transduced, T cells) by such magnetic beads. In some embodiments, this also means that a process that is compliant with GMP standards can be more easily established compared to other methods, such as the use of Dynabeads® in which additional measures have to be taken to ensure that the final T cell population is free of magnetic beads.

B. Binding Agents

In some embodiments the agent (e.g., receptor-binding agent, selection agent, viral vector particle-binding agent) has one or binding sites for binding to a molecule on the surface of a biological particle, such as a cell, microorganism or virus. In some embodiments, the agent (e.g. receptor-binding agent or selection agent) has one or more binding sites, B, for binding to a molecule on the surface of a cell, e.g. cell surface molecule. In some embodiments, the agent (e.g. viral vector particle-binding agent) has one or more binding sites, V, for binding to a molecule on the surface of a viral particle. Thus, in some instances, the agent (e.g., receptor-binding agent or selection agent) comprises a binding site (e.g. B or V) or a plurality of binding sites (e.g. a plurality of binding sites B or V), wherein the specific binding between the agent and the molecule on the surface of the biological particle (e.g. cells or viral particle) comprises interaction between the one or more binding site (e.g. B or V) and the molecule.

In some embodiments, the agent contains only a single binding site, i.e. is monovalent. In some embodiments the agent has at least two, such as a plurality of binding sites, including three, four or five binding sites capable of binding to the molecule. In some cases, the binding site is B, and the agent (e.g. receptor-binding agent or selection agent) contains a plurality of binding sites B, including two, three, four or five binding sites B capable of binding to the cell surface molecule (e.g. B1, B2, B3, etc.). In some such aspects, the at least two or plurality of binding sites B may be identical. In some embodiments, one or more of the at least two or plurality of binding sites B may be different (e.g. B1 and B2). In some embodiments, the binding site is V, and the agent (e.g. viral particle-binding agent) contains a plurality of binding sites V, including two, three, four or five binding sites V capable of binding to a molecule on the surface of a viral vector particle (e.g. V1, V2, V3, etc.). In some such aspects, the at least two or plurality of binding sites V may be identical. In some embodiments, one or more of the at least two or plurality of binding sites V may be different (e.g. V1 and V2). In some embodiments, the binding site (e.g. B or V) comprises an antibody combining site (e.g. one or more complementarity determining regions (CDR)) or a at least two of such antibody combining sites.

In some embodiments, one or more different agents (e.g. one or more different receptor-binding agent, selection agent or other agent that binds to a molecule on a cell) are reversibly bound to the reagent. In some embodiments, at least 2, 3, 4 or more different agents are reversibly bound to the same reagent. In some embodiments, at least two different agents are reversibly bound to the same reagent, whereby each reagent comprises a binding site B or a plurality of binding sites B for specific binding between the agent and the molecule. In some embodiments, the at least two or more agents contain the same binding site B, e.g. for the binding the same or substantially the same molecule. In some embodiments, the at least two or more agents contain different binding sites B, e.g. for the binding to different molecules. In some embodiments, a first agent (e.g. a first receptor-binding agent or a first selection agent) contains a binding site B1, B2, B3, B4, etc. and a second agent (e.g. a second receptor-binding agent or second selection agent) contains another of a binding site B1, B2, B3, B4, etc. In some embodiments, a first agent (e.g. a first selection agent) contains a binding site B1 and a second agent (e.g. second selection agent) contains a binding site B3. In some embodiments, a first agent (e.g. a first receptor-binding agent) contains a binding site B2 and a second agent (e.g. a second receptor-binding agent) contains a binding site B4. In any of such embodiments, the first agent and second agent can contain a binding partner, C1 or C2. In some embodiments, C1 and C2 can be the same. In some embodiments, C1 and C2 are different. In some embodiments, the first agent and second agent contain the same binding partner, C1.

In some cases, the dissociation constant ($K_D$) of the binding between the agent (e.g., via the binding site B) and the binding site Z of the reagent may have a value in the range from about $10^{-2}$ M to about $10^{-13}$ M or from about $10^{-3}$ M to about $10^{-12}$ M or from about $10^{-4}$ M to about $10^{-11}$ M, or from about $10^{-5}$ M to about $10^{-10}$ M. In some embodiments, the dissociation constant ($K_D$) for the binding between the binding agent and the molecule is of low affinity, for example, in the range of a $K_D$ of about $10^{-3}$ to about $10^{-7}$ M. In some embodiments, the dissociation constant ($K_D$) for the binding between the binding agent and the molecule is of high affinity, for example, in the range of a $K_D$ of about $10^{-7}$ to about $1\times10^{-10}$ M.

In some embodiments, the dissociation of the binding of the agent via the binding site, B or V, and the molecule occurs sufficiently fast, for example, to allow the biological particle (e.g. target cell or viral particle) to be only transiently stained or associated with the agent after disruption of the reversible bond between the reagent and the agent. In some cases, when expressed in terms of the $k_{off}$ rate (also called dissociation rate constant for the binding between the agent (via the binding site B) and the molecule, the $k_{off}$ rate is about $0.5\times10^{-4}$ sec$^{-1}$ or greater, about $1\times10^{-4}$ sec$^{-1}$ or greater, about $2\times10^{-4}$ sec$^{-1}$ or greater, about $3\times10^{-4}$ sec$^{-1}$ or greater, about $4\times10^{-4}$ sec$^{-1}$ of greater, about $5\times10^{-4}$ sec$^{-1}$ or greater, about $1\times10^{-3}$ sec$^{-1}$ or greater, about $1.5\times10^{-3}$ sec$^{-1}$ or greater, about $2\times10^{-3}$ sec$^{-1}$ or greater, about $3\times10^{-3}$ sec$^{-1}$ or greater, about $4\times10^{-3}$ sec$^{-1}$, about $5\times10^{-3}$ sec$^{-1}$ or greater, about $1\times10^{-2}$ sec or greater, or about $5\times10^{-1}$ sec$^{-1}$ or greater. It is within the level of a skilled artisan to empirically determine the $k_{off}$ rate range suitable for a particular agent and cell molecule interaction (see e.g. U.S. published application No. US2014/0295458). For example, an agent with a rather high $k_{off}$ rate of, for example, greater than $4.0\times10^{-4}$ sec$^{-1}$ may be used so that, after the disruption of the binding complexes, most of the agent can be removed or dissociated within one hour. In other cases, an agent with a lower $k_{off}$ rate of, for example, $1.0\times10^{-4}$ sec$^{-1}$, may be used, so that after the disruption of the binding complexes, most of the agent may be removed or dissociated from the cell within about 3 and a half hours.

In some embodiments, the $K_D$ of this bond as well as the $K_D$, $K_A$, $k_{off}$ and $k_{on}$ rate of the bond formed between the binding site (B or V) of the agent (e.g., receptor-binding agent, selection agent or viral vector particle-binding agent) and the molecule can be determined by any suitable means, for example, by fluorescence titration, equilibrium dialysis or surface plasmon resonance.

In some aspects, the molecule against which an agent (e.g., receptor-binding agent or selection agent) may be directed is a cell surface molecule. In some embodiments, the cell surface molecule is a peptide or a protein, such as a receptor, e.g., a membrane receptor protein. In some embodiments, the receptor is a lipid, a polysaccharide or a nucleic acid. In some embodiments, a cell surface molecule that is a protein may be a peripheral membrane protein or an integral membrane protein. The cell surface molecule may in some embodiments have one or more domains that span the membrane. As a few illustrative examples, a membrane protein with a transmembrane domain may be a G-protein coupled receptor, such as an odorant receptors, a rhodopsin receptor, a rhodopsin pheromone receptor, a peptide hormone receptor, a taste receptor, a GABA receptor, an opiate receptor, a serotonin receptor, a Ca$^{2+}$ receptor, melanopsin, a neurotransmitter receptor, such as a ligand gated, a voltage gated or a mechanically gated receptor, including the acetylcholine, the nicotinic, the adrenergic, the norepinephrine, the catecholamines, the L-DOPA-, a dopamine and serotonin (biogenic amine, endorphin/enkephalin) neuropeptide receptor, a receptor kinase such as serine/threonine kinase, a tyrosine kinase, a porin/channel such as a chloride channel, a potassium channel, a sodium channel, an OMP protein, an ABC transporter (ATP-Binding Cassette-Transporter) such as amino acid transporter, the Na-glucose transporter, the Na/iodide transporter, an ion transporter such as Light Harvesting Complex, cytochrome c oxidase, ATPase Na/K, H/K, Ca, a cell adhesion receptor such as metalloprotease, an integrin or a catherin.

In some embodiments, the cell surface molecule may be an antigen defining a desired cell population or subpopulation, for instance a population or subpopulation of blood cells, e.g., lymphocytes (e.g., T cells, T-helper cells, for example, CD4+T-helper cells, B cells or natural killer cells), monocytes, or stem cells, e.g. CD34-positive peripheral stem cells or Nanog or Oct-4 expressing stem cells. Examples of T-cells include cells such as CMV-specific CD8+ lymphocytes, cytotoxic T-cells, memory T-cells and regulatory T-cells (Treg). An illustrative example of Treg is CD4 CD25 CD45RA Treg cells and an illustrative example of memory T-cells is CD62L CD8+ specific central memory T-cells. The cell surface molecule may also be a marker for a tumor cell.

In some embodiments, the molecule against which an agent (e.g., viral vector particle-binding agent) may be directed is a molecule on the surface of a virus. Exemplary of such molecules are described below.

As described above, in some embodiments, in addition to the binding site, B or V, the agent (e.g., receptor-binding agent, selection agent or viral vector particle-binding agent) a binding partner C. In some aspects, this binding partner C is able to bind to a binding site Z of the reagent wherein the reagent has one or more binding sites for the binding partner C. In some embodiments, the non-covalent bond that may be formed between the binding partner C that is included in the agent (e.g., receptor-binding agent or selection agent) and the binding site(s) Z of the reagent may be of any desired strength and affinity, and may be disruptable or reversible under conditions under which the method is performed. The agent (e.g., receptor-binding agent, selection agent and/or viral particle-binding agent) may include at least one, including two, three or more, additional binding partners C and the reagent may include at least two, such as three, four, five, six, seven, eight or more binding sites Z for the binding partner C that is included in the agent (e.g., receptor-binding agent or selection agent). As described in U.S. Pat. Nos. 7,776,562, 8,298,782 or International Patent application WO 2002/054065, any combination of a binding partner C and a reagent with one or more corresponding binding sites Z can be chosen, for example, such that the binding partner C and the binding site Z are able to reversibly bind in a complex, such as to cause an avidity effect.

The binding partner C included in the agent (e.g., receptor-binding agent, selection agent or viral vector particle-binding agent) may for instance be hydrocarbon-based (including polymeric) and include nitrogen-, phosphorus-, sulphur-, carben-, halogen- or pseudohalogen groups. In some aspects, it may be an alcohol, an organic acid, an inorganic acid, an amine, a phosphine, a thiol, a disulfide, an alkane, an amino acid, a peptide, an oligopeptide, a polypeptide, a protein, a nucleic acid, a lipid, a saccharide, an oligosaccharide, or a polysaccharide. As further examples, it may also be a cation, an anion, a polycation, a polyanion, a polycation, an electrolyte, a polyelectrolyte, a carbon nanotube or carbon nanofoam. Generally, such a binding partner C has a higher affinity to the binding site of the reagent than to other matter. Examples of a respective binding partner C include, but are not limited to, a crown ether, an immunoglobulin, a fragment thereof and a proteinaceous binding molecule with antibody-like functions.

In some embodiments, the binding partner C that is included in the agent (e.g., receptor-binding agent, selection agent or viral vector particle-binding agent) includes biotin and the reagent includes a streptavidin analog or an avidin analog that reversibly binds to biotin. In some embodiments the binding partner C that is included in the agent includes a biotin analog that reversibly binds to streptavidin or avidin, and the reagent includes streptavidin, avidin, a streptavidin analog or an avidin analog that reversibly binds to the respective biotin analog. In some embodiments, the binding partner C that is included in the agent includes a streptavidin or avidin binding peptide and the reagent includes streptavidin, avidin, a streptavidin analog or an avidin analog that reversibly binds to the respective streptavidin or avidin binding peptide.

In some embodiments, the reagent is a streptavidin, such as a streptavidin mutein including any described above (e.g. set forth in SEQ ID NOS: 3-6), and the binding partner C that is included in the agent (e.g. receptor-binding agent or selection agent) may include a streptavidin-binding peptide. In some embodiments, the streptavidin-binding peptide may include a sequence with the general formula set forth in SEQ ID NO: 9, such as contains the sequence set forth in SEQ ID NO: 10. In some embodiments, the peptide sequence has the general formula set forth in SEQ ID NO: 11, such as set forth in SEQ ID NO: 12. In one example, the peptide sequence is Trp-Arg-His-Pro-Gln-Phe-Gly-Gly (also called Strep-tag®, set forth in SEQ ID NO: 7). In one example, the peptide sequence is Trp-Ser-His-Pro-Gln-Phe-Glu-Lys (also called Strep-tag® II, set forth in SEQ ID NO: 8). In some embodiments, the peptide ligand contains a sequential arrangement of at least two streptavidin-binding modules, wherein the distance between the two modules is at least 0 and not greater than 50 amino acids, wherein one binding module has 3 to 8 amino acids and contains at least the sequence His-Pro-Xaa (SEQ ID NO: 9), where Xaa is glutamine, asparagine, or methionine, and wherein the other binding module has the same or different streptavidin peptide ligand, such as set forth in SEQ ID NO: 11 (see e.g. International Published PCT Appl. No. WO02/077018; U.S. Pat. No. 7,981,632). In some embodiments, the peptide ligand contains a sequence having the formula set forth in any of SEQ ID NO: 13 or 14. In some embodiments, the peptide ligand has the sequence of amino acids set forth in any of SEQ ID NOS: 15-19. In most cases, all these streptavidin binding peptides bind to the same binding site, namely the biotin binding site of streptavidin. If one or more of such streptavidin binding peptides is used as binding partners C, e.g. C1 and C2, the multimerization reagent is typically a streptavidin mutein.

In some embodiments, the streptavidin-binding peptide may be further modified. In some embodiments, the streptavidin-binding peptide may include the peptide sequence is Trp-Ser-His-Pro-Gln-Phe-Glu-Lys (also called Strep-tag® II, set forth in SEQ ID NO: 8) conjugated with a nickel charged trisNTA (also called His-STREPPER or His/Strep-tag®II Adapter).

In some embodiment the binding partner C of the agent (e.g., receptor-binding agent, selection agent and/or viral vector particle-binding agent) includes a moiety known to the skilled artisan as an affinity tag. In such an embodiment, the reagent may include a corresponding binding partner, for example, an antibody or an antibody fragment, known to bind to the affinity tag. As a few illustrative examples of known affinity tags, the binding partner C that is included in the agent (e.g., receptor-binding agent or selection agent) may include dinitrophenol or digoxigenin, oligohistidine, polyhistidine, an immunoglobulin domain, maltose-binding protein, glutathione-S-transferase (GST), chitin binding protein (CBP) or thioredoxin, calmodulin binding peptide (CBP), FLAG-peptide, the HA-tag (sequence: Tyr-Pro-Tyr-Asp-Val-Pro-Asp-Tyr-Ala) (SEQ ID NO: 20), the VSV-G-tag (sequence: Tyr-Thr-Asp-Ile-Glu-Met-Asn-Arg-Leu-Gly-Lys) (SEQ ID NO: 21), the HSV-tag (sequence: Gln-Pro-Glu-Leu-Ala-Pro-Glu-Asp-Pro-Glu-Asp) (SEQ ID NO: 22), the T7 epitope (Ala-Ser-Met-Thr-Gly-Gly-Gln-Gln-Met-Gly) (SEQ ID NO: 23), maltose binding protein (MBP), the HSV epitope of the sequence Gln-Pro-Glu-Leu-Ala-Pro-Glu-Asp-Pro-Glu-Asp (SEQ ID NO: 24) of herpes simplex virus glycoprotein D, the "myc" epitope of the transcription factor c-myc of the sequence Glu-Gln-Lys-Leu-Ile-Ser-Glu-Glu-Asp-Leu (SEQ ID NO: 25), the V5-tag (sequence: Gly-Lys-Pro-Ile-Pro-Asn-Pro-Leu-Leu-Gly-Leu-Asp-Ser-Thr) (SEQ ID NO: 26), or glutathione-S-transferase (GST). In such embodiments, the complex formed between the one or more binding sites Z of the reagent which may be an antibody or antibody fragment, and the antigen can be disrupted competitively by adding the free antigen, i.e. the free peptide (epitope tag) or the free protein (such as MBP or CBP). In some embodiments, the affinity tag might also be an oligonucleotide tag. In some cases, such an oligonucleotide tag may, for instance, be used to hybridize to an oligonucleotide with a complementary sequence, linked to or included in the reagent.

Further examples of a suitable binding partner C include, but are not limited to, a lectin, protein A, protein G, a metal, a metal ion, nitrilo triacetic acid derivatives (NTA), RGDmotifs, a dextrane, polyethyleneimine (PEI), a redox polymer, a glycoproteins, an aptamers, a dye, amylose, maltose, cellulose, chitin, glutathione, calmodulin, gelatine, polymyxin, heparin, NAD, NADP, lysine, arginine, benzamidine, poly U, or oligo-dT. Lectins such as Concavalin A are known to bind to polysaccharides and glycosylated proteins. An illustrative example of a dye is a triazine dye such as Cibacron blue F3G-A (CB) or Red HE-3B, which specifically bind NADH-dependent enzymes. Typically, Green A binds to Co A proteins, human serum albumin, and dehydrogenases. In some cases, the dyes 7-aminoactinomycin D and 4',6-diamidino-2-phenylindole bind to DNA. Generally, cations of metals such as Ni, Cd, Zn, Co, or Cu, are typically used to bind affinity tags such as an oligohistidine containing sequence, including the hexahistidine or the His-Asn-His-Arg-His-Lys-His-Gly-Gly-Gly-Cys tag (MAT tag)(SEQ ID NO: 35), and N-methacryloyl-(L)-cysteine methyl ester.

In some embodiments the binding between the binding partner C that is included in the agent (e.g., receptor-binding agent, selection agent or viral vector particle-binding agent) and the one or more binding sites Z of the reagent occurs in the presence of a divalent, a trivalent or a tetravalent cation. In this regard, in some embodiments the reagent includes a divalent, a trivalent or a tetravalent cation, typically held, e.g. complexed, by means of a suitable chelator. In some embodiments, the binding partner C that is included in the agent (e.g., receptor-binding agent or selection agent) may include a moiety that includes, e.g. complexes, a divalent, a trivalent or a tetravalent cation. Examples of a respective metal chelator, include, but are not limited to, ethylenediamine, ethylene-diaminetetraacetic acid (EDTA), ethylene glycol tetraacetic acid (EGTA), diethylenetri-aminepentaacetic acid (DTPA), N,N-bis(carboxymethyl)glycine (also called nitrilotriacetic acid, NTA), 1,2-bis(o-aminophenoxy)ethane-N,N,N',N'-tetraacetic acid (BAPTA), 2,3-dimercapto-1-propanol (dimercaprol), porphine and heme. As an example, EDTA forms a complex with most monovalent, divalent, trivalent and tetravalent metal ions, such as e.g. silver ($Ag^+$), calcium ($Ca^{2+}$), manganese ($Mn^{2+}$), copper ($Cu^{2+}$), iron ($Fe^{2+}$), cobalt ($Co^+$) and zirconium ($Zr^{4+}$), while BAPTA is specific for $Ca^{2+}$. As an illustrative example, a standard method used in the art is the formation of a complex between an oligohistidine tag and copper ($Cu^{2+}$), nickel ($Ni^{2+}$), cobalt ($Co^{2+}$), or zinc ($Zn^{2+}$) ions, which are presented by means of the chelator nitrilotriacetic acid (NTA).

In some embodiments, the binding partner C that is included in the agent (e.g., receptor-binding agent, selection agent and/or viral vector particle-binding agent) includes a calmodulin binding peptide and the reagent includes multimeric calmodulin as described in U.S. Pat. No. 5,985,658, for example. In some embodiments, the binding partner C that is included in the agent (e.g., receptor-binding agent, selection agent and/or viral vector particle-binding agent) includes a FLAG peptide and the reagent includes an antibody that binds to the FLAG peptide, e.g. the FLAG peptide, which binds to the monoclonal antibody 4E11 as described in U.S. Pat. No. 4,851,341. In one embodiment, the binding partner C that is included in the agent (e.g., receptor-binding agent, selection agent and/or viral vector particle-binding agent) includes an oligohistidine tag and the reagent includes an antibody or a transition metal ion binding the oligohistidine tag. In some cases, the disruption of all these binding complexes may be accomplished by metal ion chelation, e.g. calcium chelation, for instance by adding EDTA or EGTA. In some embodiments, calmodulin, antibodies such as 4E11 or chelated metal ions or free chelators may be multimerized by conventional methods, e.g. by biotinylation and complexation with streptavidin or avidin or oligomers thereof or by the introduction of carboxyl residues into a polysaccharide, e.g. dextran, essentially as described in Noguchi, A, et al. Bioconjugate Chemistry (1992) 3, 132-137 in a first step and linking calmodulin or antibodies or chelated metal ions or free chelators via primary amino groups to the carboxyl groups in the polysaccharide, e.g. dextran, backbone using conventional carbodiimide chemistry in a second step. In some such embodiments, the binding between the binding partner C that is included in the agent (e.g., receptor-binding agent or selection agent) and the one or more binding sites Z of the reagent can be disrupted by metal ion chelation. The metal chelation may, for example, be accomplished by addition of EGTA or EDTA.

In some embodiments, the one or more binding sites, B or V, of the agent, which specifically bind to the molecule, may for instance be comprised by an antibody, a fragment thereof, or a proteinaceous binding molecule with antibody-like functions. In some embodiments, the binding site, B or V, of the agent is an antibody combining site, such as is or comprises one or more complementarity determining regions (CDRs) of an antibody. Examples of (recombinant) antibody fragments include, but are not limited to, Fab fragments, Fv fragments, single-chain Fv fragments (scFv), a divalent antibody fragment such as an (Fab)2'-fragment, diabodies, triabodies (Iliades, P., et al, FEB S Lett (1997) 409, 437-441), decabodies (Stone, E., et al, Journal of Immunological Methods (2007) 318, 88-94) and other domain antibodies (Holt, L. J., et al, Trends Biotechnol. (2003), 21, 11, 484-490). In some embodiments, the agent (e.g., receptor-binding agent, selection agent or viral vector particle-binding agent) may comprise a bivalent proteinaceous artificial binding molecule such as a dimeric lipocalin mutein that is also known as "duocalin".

In some embodiments, the agent (e.g., receptor-binding agent, selection agent or viral vector particle-binding agent) may have a single binding site, B or V, i.e., it may be monovalent. Examples of monovalent agents include, but are not limited to, a monovalent antibody fragment, a proteinaceous binding molecule with antibody-like binding properties or an MHC molecule. Examples of monovalent antibody fragments include, but are not limited to a Fab fragment, an Fv fragment, and a single-chain Fv fragment (scFv), including a divalent single-chain Fv fragment.

In some embodiments, the agent is an antibody or an antigen-binding fragment thereof, such as a Fab fragments, Fv fragments, single-chain Fv fragments (scFv), a divalent antibody fragment such as an (Fab)2'-fragment. In some embodiments, the agent is or is derived from a parental antibody that is known to bind to a cell molecule of interest. Various antibody molecules or fragments thereof against cell surface molecules are well known in the art and any of a variety of such can be used as agents in the methods herein. In some embodiments, the agent is an antibody or fragment thereof that contains one or more amino acid replacements in the variable heavy chain of a parental or reference antibody, for example, to generate an antibody with an altered affinity or that exhibits a sufficiently fast off-rate as described above. For example, exemplary of such mutations are known in the context of mutants of the anti-CD4 antibody 13B8.2 (see e.g., U.S. Pat. No. 7,482,000, U.S. Patent Appl. No. US2014/0295458 or International Patent Application No. WO2013/124474), and any of such mutations can be generated in another parental or reference antibody.

In some aspects, the agent (e.g., receptor-binding agent, selection agent or viral vector particle-binding agent) that can be monovalent, for example comprise a monovalent antibody fragment or a monovalent artificial binding molecule (proteinaceous or other) such as a mutein based on a polypeptide of the lipocalin family (also known as "Anticalin®"), or a bivalent molecule such as an antibody or a fragment in which both binding sites are retained such as an F(ab')$_2$ fragment.

An example of a proteinaceous binding molecule with antibody-like functions includes a mutein based on a polypeptide of the lipocalin family (see for example, WO 03/029462, Beste et al, Proc. Natl. Acad. Sci. U.S.A. (1999) 96, 1898-1903). Generally, lipocalins, such as the bilin binding protein, the human neutrophil gelatinase-associated lipocalin, human Apo lipoprotein D or human tear lipocalin possess natural ligand-binding sites that can be modified so that they bind a given target. Further examples of a proteinaceous binding molecule with antibody-like binding properties that can be used as agent (e.g., receptor-binding agent or selection agent) that specifically binds to the cell surface molecule include, but are not limited to, the so-called glubodies (see e.g. international patent application WO 96/23879), proteins based on the ankyrin scaffold (Mosavi, L. K., et al, Protein Science (2004) 13, 6, 1435-1448) or crystalline scaffold (e.g. international patent application WO 01/04144) the proteins described in Skerra, J. Mol. Recognit. (2000) 13, 167-187, AdNectins, tetranectins and avimers. Generally, avimers, including multivalent avimer proteins evolved by exon shuffling of a family of human receptor domains, contain so called A-domains that occur as strings of multiple domains in several cell surface receptors (Silverman, J., et al, Nature Biotechnology (2005) 23, 1556-1561). Adnectins, generally derived from a domain of human fibronectin, typically contain three loops that can be engineered for immunoglobulin-like binding to targets (Gill, D. S. & Damle, N. K., Current Opinion in Biotechnology (2006) 17, 653-658). Tetranectins, generally derived from the respective human homotrimeric protein, likewise typically contain loop regions in a C-type lectin domain that can be engineered for desired binding. Peptoids, which can, in some cases, act as protein ligands, typically are oligo(N-alkyl) glycines that differ from peptides in that the side chain is connected to the amide nitrogen rather than the carbon atom. Peptoids are typically resistant to proteases and other modifying enzymes and can have a much higher cell permeability than peptides (see e.g. Kwon, Y.-U., and Kodadek, T., J. Am. Chem. Soc. (2007) 129, 1508-1509).

Further examples of suitable proteinaceous binding molecules include, but are not limited to, an EGF-like domain, a Kringle-domain, a fibronectin type I domain, a fibronectin type II domain, a fibronectin type III domain, a PAN domain, a Gla domain, a SRCR domain, a Kunitz/Bovine pancreatic trypsin Inhibitor domain, tendamistat, a Kazal-type serine protease inhibitor domain, a Trefoil (P-type) domain, a von Willebrand factor type C domain, an Anaphylatoxin-like domain, a CUB domain, a thyroglobulin type I repeat, LDL-receptor class A domain, a Sushi domain, a Link domain, a Thrombospondin type I domain, an immunoglobulin domain or a an immunoglobulin-like domain (for example, domain antibodies or camel heavy chain antibodies), a C-type lectin domain, a MAM domain, a von Willebrand factor type A domain, a Somatomedin B domain, a WAP-type four disulfide core domain, a F5/8 type C domain, a Hemopexin domain, an SH2 domain, an SH3 domain, a Laminin-type EGF-like domain, a C2 domain, "Kappabodies" (Ill et al. Protein Eng (1997) 10, 949-57, a so called "minibody" (Martin et al, EMBO J (1994) 13, 5303-5309), a diabody (Holliger et al, PNAS USA (1993)90, 6444-6448), a so called "Janusis" (Traunecker et al, EMBO J (1991) 10, 3655-3659, or Traunecker et al, Int J Cancer (1992) Suppl 7, 51-52), a nanobody, a microbody, an affilin, an affibody, a knottin, ubiquitin, a zinc-finger protein, an autofluorescent protein or a leucine-rich repeat protein. In some embodiments, a nucleic acid molecule with antibody-like functions can be an aptamer. Generally, an aptamer folds into a defined three-dimensional motif and shows high affinity for a given target structure.

I. Receptor-Binding Agents

In some embodiments, the agent is a receptor-binding agent. In some embodiments, the receptor-binding agent binds to a molecule (e.g. receptor) on the surface of a cell, which binding between the agent and the molecule is capable of inducing or modulating a signal in the cells. In some instances, the cell surface molecule (e.g. receptor) is a signaling molecule. In some such cases, the receptor-binding agent is capable of specifically binding to a signaling molecule expressed by one or more of the cells. In some instances, the receptor-binding agent is a stimulatory agent, which can be any agent that is capable of inducing a signal in a cell (e.g. a T cell) upon binding to a cell surface molecule (e.g. such as a receptor. In some embodiments, the signal can be immunostimulatory, in which case the receptor-binding agent or stimulatory agent is capable of inducing or modulating a signal that is involved in or that does stimulate an immune response by the cell (e.g. T cell), e.g. increase immune cell proliferation or expansion, immune cell activation, immune cell differentiation, cytokine secretion, cytotoxic activity or one or more other functional activities of an immune cell. In some embodiment, the signal can be inhibitory, in which case the receptor-binding agent or stimulatory agent is capable of inducing or modulating a signal in the cell (e.g. T cell) that is involved in or that does inhibit an immune response, e.g. inhibits or decreases immune cell proliferation or expansion, immune cell activation, immune cell differentiation, cytokine secretion, cytotoxic activity or one or more other functional activities of an immune cell.

In some embodiments, the receptor-binding agent is a first receptor-binding agent. In some aspects, the first receptor-binding agent binds to a receptor molecule on the surface of the cells. Thus, in some cases, the first receptor-binding agent induces or modulates a signal. In some aspects, the inducing or modulating of a signal by the first receptor-binding agent effects the activation, stimulation, and/or expansion (proliferation) of the cells. Thus, in some cases, the first receptor-binding agent provides a primary activation signal to the cells, thereby activating the cells.

In some embodiments the cell population may be a population of lymphocytes including, but not limited a population of B cells, a population of T cells or a population of natural killer cells. Illustrative examples of cell populations are B cells carrying CD40 or CD137 (both cell population can be proliferated upon binding of only a first agent that provides an activation signal, for example 4-1BB ligand; or an αCD40 antibody molecule or an αCD137 antibody molecule (see for example Zhang et al., 2010, J Immunol, 184:787-795)). Other illustrative examples for agents (either first or second) that may be used for the expansion of B cells are agents that bind to IgG, CD19, CD28 or CD14, for example αCD19, αIgG, αCD28, or αCD14 antibody molecules. It is also envisioned that first or second agents for the expansion of B cell may comprise ligands for toll like receptors or interleukins, such as IL-21

(see for example Dienz O, et al. 2009. J. Exp. Med. 206:69). It is noted that lipopolysaccharide dependent activation of B cells is also encompassed in the present invention, as a lipopolysaccharide can also be used as first agent and can be equipped with a binding partner C1 as used herein.

Other illustrative examples of suitable cell populations include T cell population that expand after being activated by binding of a first agent to TCR/CD3 and binding of a second agent to an accessory molecule on the T cell such as CD28. In this case, the first agent stimulates a TCR/CD3 complex-associated signal in the T cells and the second agent provides a secondary stimulus by binding CD28 as accessory molecule. Agents that can be used for the expansion of T cells may also include interleukins, such as IL-2, IL-7, IL-15, or IL-21 (see for example Cornish et al. 2006, Blood. 108(2):600-8, Bazdar and Sieg, 2007, Journal of Virology, 2007, 81(22):12670-12674, Battalia et al, 2013, Immunology, 139(1):109-120). Other illustrative examples for agents that may be used for the expansion of T cells are agents that bind to CD8, CD45 or CD90, such as αCD8, αCD45 or αCD90 antibodies. Illustrative examples of T cell population including antigen-specific T cells, T helper cells, cytotoxic T cells, memory T cell (an illustrative example of memory T-cells are CD62L$^+$CD8$^+$ specific central memory T cells) or regulatory T cells (an illustrative example of Treg are CD4$^+$CD25$^+$CD45RA+ Treg cells).

Another illustrative example of a suitable cell population includes natural killer cells (NK cells), which may for example be expanded with agents that bind to CD16 or CD56, such as for example αCD16 or αCD56 antibodies. In illustrative example for such an αCD16 antibody is the antibody 3G8 with a VH sequence set forth in SEQ ID NO: 36 and a VL sequence set forth in SEQ ID NO: 37 (see for example Hoshino et al, Blood. 1991 Dec. 15; 78(12):3232-40.). Another agent that may be used for expansion of NK cells may be IL-15 (see for example Vitale et al. 2002. The Anatomical Record. 266:87-92). Yet another illustrative example of a suitable cell population includes monocytes, which may for instance be expanded using an agent that binds to CD14, such as an αCD14 antibody molecule.

In some embodiments, the first receptor-binding agent may stimulate a TCR/CD3 complex-associated signal in the cells, e.g., T cells. In some aspects, the first receptor-binding agent may be a binding agent that specifically binds CD3. In some cases, a first receptor-binding agent that specifically binds CD3 may be selected from the group consisting of an anti-CD3-antibody, a divalent antibody fragment of an anti-CD3 antibody, a monovalent antibody fragment of an anti-CD3-antibody, and a proteinaceous CD3 binding molecule with antibody-like binding properties. The divalent antibody fragment may be a (Fab')$_2$-fragment, or a divalent single-chain Fv fragment while the monovalent antibody fragment may be selected from the group consisting of a Fab fragment, an Fv fragment, and a single-chain Fv fragment (scFv). In some cases, a proteinaceous CD3 binding molecule with antibody-like binding properties may be an aptamer, a mutein based on a polypeptide of the lipocalin family, a glubody, a protein based on the ankyrin scaffold, a protein based on the crystalline scaffold, an adnectin, or an avimer.

In some embodiments, an anti-CD3 Fab fragment can be derived from the CD3 binding monoclonal antibody produced by the hybridoma cell line OKT3 (ATCC® CRL-8001™; see also U.S. Pat. No. 4,361,549). The variable domain of the heavy chain and the variable domain of the light chain of the anti-CD3 antibody OKT3 are described in Arakawa et al J. Biochem. 120, 657-662 (1996) and comprise the amino acid sequences set forth in SEQ ID NO: 31 and 32, respectively.

In some aspects, the receptor-binding agent is a second receptor-binding agent. In some cases, the second receptor-binding agent binds to a molecule on the surface of the cells, such as a cell surface molecule, e.g., receptor molecule. In some embodiments, the second receptor-binding agent is capable of enhancing, dampening, or modifying a signal delivered through the first molecule. In some embodiments, the second receptor-binding agent induces or modulates a signal, e.g., a second or an additional signal. In some aspects, the second receptor-binding agent may enhance or potentiate a signal induced by the first receptor-binding agent. In some embodiments, the second receptor-binding agent binds to an accessory molecule and/or can stimulate or induce an accessory or secondary signal in the cell. In some aspects, the second receptor-binding agent binds to a co-stimulatory molecule and/or provides a costimulatory signal.

In some embodiments, the receptor-binding agent, which can be the second receptor-binding agent, binds, e.g. specifically binds, to a second molecule that can be a costimulatory molecule, an accessory molecule, a cytokine receptor, a chemokine receptor, an immune checkpoint molecule, or a member of the TNF family or the TNF receptor family.

In some embodiments, the molecule on the cell, e.g., T cell, may be CD28 and the receptor-binding agent (e.g. which can be the second receptor-binding agent) specifically binds CD28. In some aspects, the receptor-binding agent (e.g. which can be the second receptor-binding agent) that specifically binds CD28 may be selected from the group consisting of an anti-CD28-antibody, a divalent antibody fragment of an anti-CD28 antibody, a monovalent antibody fragment of an anti-CD28-antibody, and a proteinaceous CD28 binding molecule with antibody-like binding properties. The divalent antibody fragment may be an (Fab')$_2$-fragment, or a divalent single-chain Fv fragment while the monovalent antibody fragment may be selected from the group consisting of a Fab fragment, an Fv fragment, and a single-chain Fv fragment (scFv). A proteinaceous CD28 binding molecule with antibody-like binding properties may be an aptamer, a mutein based on a polypeptide of the lipocalin family, a glubody, a protein based on the ankyrin scaffold, a protein based on the crystalline scaffold, an adnectin, and an avimer.

In some embodiments, an anti-CD28 Fab fragment can be derived from antibody CD28.3 (deposited as a synthetic single chain Fv construct under GenBank Accession No. AF451974.1; see also Vanhove et al, BLOOD, 15 Jul. 2003, Vol. 102, No. 2, pages 564-570) the heavy and light chain of which comprise SEQ ID NO: 33 and 34, respectively.

In some embodiments, the molecule on the cell, e.g., T cell or B cell, may be CD137 and the receptor-binding agent (e.g. which can be the second receptor-binding agent) specifically binds CD137. In some aspects, the receptor-binding agent (e.g. which can be the second receptor-binding agent) that specifically binds CD137 may be selected from the group consisting of an anti-CD137-antibody, a divalent antibody fragment of an anti-CD137 antibody, a monovalent antibody fragment of an anti-CD137-antibody, and a proteinaceous CD137 binding molecule with antibody-like binding properties.

In some embodiments, the molecule on the cell, e.g. B cell, may be CD40 and the receptor-binding agent (e.g. which can be the second receptor-binding agent) specifically binds CD40. In some aspects, the receptor-binding agent (which can be the second receptor-binding agent) that specifically binds CD40 may be selected from the group consisting of an anti-CD40-antibody, a divalent antibody fragment of an anti-CD40 antibody, a monovalent antibody fragment of an anti-CD40-antibody, and a proteinaceous CD40 binding molecule with antibody-like binding properties.

In any of the above examples, the divalent antibody fragment may be an (Fab')$_2$-fragment, or a divalent single-chain Fv fragment while the monovalent antibody fragment may be selected from the group consisting of a Fab fragment, an Fv fragment, and a single-chain Fv fragment (scFv). In any of the above examples, the proteinaceous binding molecule with antibody-like binding properties may be an aptamer, a mutein based on a polypeptide of the lipocalin family, a glubody, a protein based on the ankyrin scaffold, a protein based on the crystalline scaffold, an adnectin, and an avimer.

In some aspects, the receptor-binding agent, e.g., stimulatory agent, specifically targets a molecule expressed on the surface of the target cells in which the molecule is a TCR or a chimeric antigen receptor. For example, the molecule expressed on the surface of the target cell is selected from a T cell or B cell antigen receptor complex, a CD3 chain, a CD3 zeta, an antigen-binding portion of a T cell receptor or a B cell receptor, or a chimeric antigen receptor. In some cases, the receptor binding agent targets peptide:MHC class I complexes.

In some embodiments, the stimulatory agent binds to a His-tagged extracellular domain of a molecule expressed on the surface of the target cells. In some cases, the stimulator agent contains the peptide sequence Trp-Ser-His-Pro-Gln-Phe-Glu-Lys (also called Strep-tag® II, set forth in SEQ ID NO: 8) conjugated with a nickel charged trisNTA (also called His-STREPPER or His/Strep-tag®II Adapter). In some embodiments, the molecule expressed on the surface of the target cells that is His-tagged is CD19.

In some aspects, the receptor-binding agent, e.g., stimulatory agent, specifically binds to the antibody portion of the recombinant receptor, e.g., CAR. In some cases, the antibody portion of the recombinant receptor includes at least a portion of an immunoglobulin constant region, such as a hinge region, e.g., an IgG4 hinge region, and/or a CH1/CL and/or Fc region. In some embodiments, the constant region or portion is of a human IgG, such as IgG4 or IgG1. In some cases, the reagent is loaded with αIgG that recognizes the IgG4 spacer.

2. Selection Agents

In some embodiments, the agent is a selection agent. In some embodiments, the selection agent binds to a molecule on the surface of a cell, such as a cell surface molecule. In some instances, the cell surface molecule is a selection marker. In some such cases, the selection agent is capable of specifically binding to a selection marker expressed by one or more of the cells. In some embodiments, a selection agent or agents that are reversibly bound to a reagent can be used to facilitate selection or isolation of cells.

In some aspects, the cell surface molecule, e.g., selection marker, may be an antigen defining a desired cell population or subpopulation, for instance a population or subpopulation of blood cells, e. g. lymphocytes (e.g. T cells, T-helper cells, for example, CD4+T-helper cells, B cells or natural killer cells), monocytes, or stem cells, e.g. CD34-positive peripheral stem cells or Nanog or Oct-4 expressing stem cells. In some embodiments, the selection marker can be a marker expressed on the surface of T cells or a subset of T cells, such as CD25, CD28, CD62L, CCR7, CD27, CD127, CD3, CD4, CD8, CD45RA, and/or CD45RO Examples of T-cells include cells such as CMV-specific CD8+T-lymphocytes, cytotoxic T-cells, memory T-cells and regulatory T-cells (Treg). An illustrative example of Treg includes CD4 CD25 CD45RA Treg cells and an illustrative example of memory T-cells includes CD62L CD8+ specific central memory T-cells. The cell surface molecule, e.g., selection marker, may also be a marker for a tumor cell.

In some embodiments, the selection marker may be CD4 and the selection agent specifically binds CD4. In some aspects, the selection agent that specifically binds CD4 may be selected from the group consisting of an anti-CD4-antibody, a divalent antibody fragment of an anti-CD4 antibody, a monovalent antibody fragment of an anti-CD4-antibody, and a proteinaceous CD4 binding molecule with antibody-like binding properties. In some embodiments, an anti-CD4-antibody, such as a divalent antibody fragment or a monovalent antibody fragment (e.g. CD4 Fab fragment) can be derived from antibody 13B8.2 or a functionally active mutant of 13B8.2 that retains specific binding for CD4. For example, exemplary mutants of antibody 13B8.2 or m13B8.2 are described in U.S. Pat. No. 7,482,000, U.S. Patent Appl. No. US2014/0295458 or International Patent Application No. WO2013/124474; and Bes, C, et al. J Biol Chem 278, 14265-14273 (2003). The mutant Fab fragment termed "m13B8.2" carries the variable domain of the CD4 binding murine antibody 13B8.2 and a constant domain containing constant human CH1 domain of type gamma for the heavy chain and the constant human light chain domain of type kappa, as described in U.S. Pat. No. 7,482,000. In some embodiments, the anti-CD4 antibody, e.g. a mutant of antibody 13B8.2, contains the amino acid replacement H91A in the variable light chain, the amino acid replacement Y92A in the variable light chain, the amino acid replacement H35A in the variable heavy chain and/or the amino acid replacement R53A in the variable heavy chain, each by Kabat numbering. In some aspects, compared to variable domains of the 13B8.2 Fab fragment in m13B8.2 the His residue at position 91 of the light chain (position 93 in SEQ ID NO: 30) is mutated to Ala and the Arg residue at position 53 of the heavy chain (position 55 in SEQ ID NO: 29) is mutated to Ala. In some embodiments, the reagent that is reversibly bound to anti-CD4 or a fragment thereof is commercially available or derived from a reagent that is commercially available (e.g. catalog No. 6-8000-206 or 6-8000-205 or 6-8002-100; IBA GmbH, Gottingen, Germany).

In some embodiments, the selection marker may be CD8 and the selection agent specifically binds CD8. In some aspects, the selection agent that specifically binds CD8 may be selected from the group consisting of an anti-CD8-antibody, a divalent antibody fragment of an anti-CD8 antibody, a monovalent antibody fragment of an anti-CD8-antibody, and a proteinaceous CD8 binding molecule with antibody-like binding properties. In some embodiments, an anti-CD8-antibody, such as a divalent antibody fragment or a monovalent antibody fragment (e.g. CD8 Fab fragment) can be derived from antibody OKT8 (e.g. ATCC CRL-8014) or a functionally active mutant thereof that retains specific binding for CD8. In some embodiments, the reagent that is reversibly bound to anti-CD8 or a fragment thereof is commercially available or derived from a reagent that is commercially available (e.g. catalog No. 6-8003 or 6-8000-201; IBA GmbH, Gottingen, Germany).

In some embodiments, the selection marker may be CD3 and the selection agent specifically binds CD3. In some aspects, the selection agent that specifically binds CD3 may be selected from the group consisting of an anti-CD3- antibody, a divalent antibody fragment of an anti-CD3 antibody, a monovalent antibody fragment of an anti-CD3-antibody, and a proteinaceous CD3 binding molecule with antibody-like binding properties. In some embodiments, an anti-CD3-antibody, such as a divalent antibody fragment or a monovalent antibody fragment (e.g. CD3 Fab fragment) can be derived from antibody OKT3 (e.g. ATCC CRL-8001; see e.g., Stemberger et al. PLoS One. 2012; 7(4): e35798) or a functionally active mutant thereof that retains specific binding for CD3. In some embodiments, the reagent that is reversibly bound to anti-CD3 or a fragment thereof is commercially available or derived from a reagent that is commercially available (e.g. catalog No. 6-8000-201, 6-8001-100; IBA GmbH, Gottingen, Germany).

In some embodiments, the selection marker may be CD25 and the selection agent specifically binds CD25. In some aspects, the selection agent that specifically binds CD25 may be selected from the group consisting of an anti-CD25-antibody, a divalent antibody fragment of an anti-CD25 antibody, a monovalent antibody fragment of an anti-CD25-antibody, and a proteinaceous CD25 binding molecule with antibody-like binding properties. In some embodiments, an anti-CD25-antibody, such as a divalent antibody fragment or a monovalent antibody fragment (e.g. CD25 Fab fragment) can be derived from antibody FRT5 (See e.g., Stemberger et al. 20128) or a functionally active mutant thereof that retains specific binding for CD25. In some embodiments, the reagent that is reversibly bound to anti-CD4 or a fragment thereof is commercially available or derived from a reagent that is commercially available (e.g. catalog No. 6-8000-205 or 6-8000-207 or 6-8004-050; IBA GmbH, Gottingen, Germany).

In some embodiments, the selection marker may be CD62L and the selection agent specifically binds CD62L. In some aspects, the selection agent that specifically binds CD62L may be selected from the group consisting of an anti-CD62L-antibody, a divalent antibody fragment of an anti-CD62L antibody, a monovalent antibody fragment of an anti-CD62L-antibody, and a proteinaceous CD62L binding molecule with antibody-like binding properties. In some embodiments, an anti-CD62L-antibody, such as a divalent antibody fragment or a monovalent antibody fragment (e.g. CD62L Fab fragment) can be derived from antibody DREG56 (e.g. ATCC HB300; see e.g. Stemberger et al. 2012) or a functionally active mutant thereof that retains specific binding for CD62L. In some embodiments, the reagent that is reversibly bound to anti-CD62L or a fragment thereof is commercially available or derived from a reagent that is commercially available (e.g. catalog No. 6-8000-204 or 6-8005-050; IBA GmbH, Gottingen, Germany).

In some embodiments, the selection marker may be CD45RA and the selection agent specifically binds CD45RA. In some aspects, the selection agent that specifically binds CD45RA may be selected from the group consisting of an anti-CD45RA-antibody, a divalent antibody fragment of an anti-CD45RA antibody, a monovalent antibody fragment of an anti-CD45RA-antibody, and a proteinaceous CD45RA binding molecule with antibody-like binding properties. In some embodiments, an anti-CD45RA-antibody, such as a divalent antibody fragment or a monovalent antibody fragment (e.g. CD45RA Fab fragment) can be derived from antibody MEM56 (e.g. Millipore 05-1413; see e.g. Stemberger et al. 2012) or a functionally active mutant thereof that retains specific binding for CD45RA. In some embodiments, the reagent that is reversibly bound to anti-CD45RA or a fragment thereof is commercially available or derived from a reagent that is commercially available (e.g. catalog No. 6-8000-208 or 6-8007-050; IBA GmbH, Gottingen, Germany).

In some embodiments, the selection marker may be CD45RO and the selection agent specifically binds CD45RO. In some aspects, the selection agent that specifically binds CD45RO may be selected from the group consisting of an anti-CD45RO-antibody, a divalent antibody fragment of an anti-CD45RO antibody, a monovalent antibody fragment of an anti-CD45RO-antibody, and a proteinaceous CD45RO binding molecule with antibody-like binding properties. In some embodiments, the reagent that is reversibly bound to anti-CD45RO or a fragment thereof is commercially available or derived from a reagent that is commercially available (e.g. catalog No. 6-8000-209 or 6-8012-020; IBA GmbH, Gottingen, Germany).

In some embodiments, the selection marker may be CD154 and the selection agent specifically binds CD154. In some aspects, the selection agent that specifically binds CD154 may be selected from the group consisting of an anti-CD154-antibody, a divalent antibody fragment of an anti-CD154 antibody, a monovalent antibody fragment of an anti-CD154-antibody, and a proteinaceous CD154 binding molecule with antibody-like binding properties. In some embodiments, the reagent that is reversibly bound to anti-CD154 or a fragment thereof is commercially available or derived from a reagent that is commercially available (e.g. catalog No. 6-8000-202 or 6-5510-050; IBA GmbH, Gottingen, Germany).

3. Viral Vector Particle-Binding Agent

In some embodiments, the agent is a viral vector particle-binding agent (also called a viral particle binding-agent or similar variations thereof) that binds to a molecule on the surface of a viral particle. In some embodiments, the reagent, which can be an oligomer or polymer, e.g. a multimerization reagent, is reversibly bound to a viral particle-binding agent via a binding partner. In some embodiments, the binding partner is binding partner C (e.g. C1), which reversibly binds to a binding site Z (e.g. Z1) present on the reagent. In some embodiments, the viral particle-binding agent comprises a binding site V (e.g. V1) that binds to the molecule on the surface of the viral particle.

In some embodiments, a viral particle-binding agent is not required, such that the viral particle can be directly reversibly bound to the reagent. In some embodiments, the viral particle contains a binding partner C (e.g. C1) that is expressed directly on the surface of the virus, which can reversibly bind to a binding site Z (e.g. Z1) present on the reagent.

In some embodiments, the reagent to which is reversibly bound a viral vector particle-binding agent can further be reversibly bound by another agent, such as a receptor-binding agent and/or a selection agent, that is capable of binding to a molecule on the surface of a cell desired to be transduced with the viral vector particle. Thus, in some embodiments, the reagent is capable of bringing into close contact a viral particle bound by the viral vector particle-binding agent and a cell bound by the receptor-binding agent or selection agent, thereby facilitating transduction of the cell.

In some embodiments, a molecule on the surface of the viral particle binds to binding site V1 present on the viral particle-binding agent.

In some embodiments, the molecule on the surface of the viral particle comprises a viral envelope protein, or a variant or a portion of a viral envelope protein of a virus, or a chimeric envelope protein. In some embodiments, the viral particle is a retroviral particle, such as a lentiviral particle.

In some embodiments, the viral envelope protein, such as viral glycoprotein, is one that is natural or native to a particular virus strain or species, such as is naturally associated with a retroviral (e.g. lentiviral) strain. In some embodiments, the viral envelope protein, such as a viral glycoprotein, is one that is not natural or native to the particular virus strain. For example, in some embodiments, the viral particle, such as a retroviral particle (e.g. lentiviral particle) is pseudotyped to contain an envelope glycoprotein derived from a different virus, for example, to increase or alter cell tropism of the virus. For example, in some cases, retroviruses, including lentiviruses, normally have a narrow tropism, since the surface glycoprotein encoded by the env gene is only capable of binding to a receptor on a limited number of cell types. Thus, in some embodiments, the retroviral vector (e.g. lentiviral vector) is pseudotyped with an envelope protein, such as an envelope glycoprotein or chimeric glycoprotein, derived from the vesicular stomatitis virus (VSV), leukemia virus gibbon (GALV, gibbon ape leukemia virus), murine leukemia virus (MLV), Moloney murine leukemia virus (MoMuLV or MMLV), Sindbis virus, Harvey murine sarcoma virus (HaMuSV or HSV), murine mammary tumor virus (MuMTV or MMTV), human immunodeficiency virus (HIV), Rous sarcoma virus (RSV), RD114 virus, or Human T-cell lymphotropic virus type 1 (HTLV-1), or other viral envelope glycoprotein known in the art (see e.g., Frecha et al. 2008 and WO2015/036713).

Thus, in some embodiments, the molecule on the surface of a viral particle can be or include a viral envelope protein (e.g. a viral envelope glycoprotein) or a variant, portion or chimera thereof for which the viral particle is pseduotyped. Exemplary viral envelope proteins (e.g. viral envelope glycoproteins) include or are derived from, for example, VSV glycoprotetins (VSVG or VSV-G), Sindbis glycoprotein (e.g. SIN), MMLV glycoprotein, HSV glycoproteins, MMTV glycoproteins, GALV glycoproteins, HIV glycoprotein, including gp160, gp120 and/or gp41, or RSV glycoproteins, including gp85 and/or gp37, or are variants, portions or chimeras thereof. In some embodiments, the viral particle containing the viral envelope protein is a lentiviral particle.

In some embodiments, the viral envelope protein is a vesicular stomatitis virus-G (VSVG or VSV-G) protein or variants thereof. In some embodiments, the VSVG is polyethylene glycol-modified (PEGylated) or covalently modified using monomethoxypoly(ethylene).

In some embodiments, the molecule on the surface of the viral particle is a viral capsid protein or variant thereof. Exemplary capsid proteins include the p24 capsid protein.

In some embodiments, the molecule on the surface of the viral particle is a viral matrix protein or variant thereof. Exemplary matrix proteins include the p17 matrix protein.

In some embodiments, the viral particle-binding agent does not neutralize or substantially neutralize the viral particle, i.e. is a non-neutralizing viral particle-binding agent. In some embodiments, the viral particle-binding agent does not or does not substantially interfere with virion binding to cells receptors for uptake, virion uptake into the cells, uncoating of the genomes in endosomes, aggregation of virus particles and/or lysis of enveloped viruses, e.g. such as alters or change such feature no more than 2-fold or no more than 1.5-fold compared to the respective feature as occurs in the absence of the viral particle-binding agent. In some embodiments, the degree of virion binding to cell receptors for uptake and/or virion uptake into cells is not reduced or is not substantially reduced in the presence of the viral particle-binding agent compared to virion binding to receptors and/or virion uptake by cells that occurs in the absence of the presence of the viral particle-binding agent. In some embodiments, the degree or level of virion binding to cell receptors for uptake and/or virion uptake into cells is at least 50% or greater, e.g. at least 60%, at least 70%, at least 80%, at least 90%, at least 95% or greater, of the degree or level of the virion binding to cell receptors for uptake and/or virion uptake into cells in the absence of the viral particle-binding agent.

In some embodiments, the viral particle-binding agent is an antibody or antigen binding fragment thereof. In some embodiments, viral particle-binding agent can be monovalent (for example a monovalent antibody fragment or a monovalent artificial binding molecule (proteinaceous or other) such as a mutein based on a polypeptide of the lipocalin family (also known as "Anticalin®"), or a bivalent molecule such as an antibody or a fragment in which both binding sites are retained such as an F(ab')2 fragment.

In some embodiments, the viral particle-binding agent can be an anti-VSV-G-antibody, an anti-Sindbis glycoprotein antibody (e.g. anti-SIN antibody), and anti-MMLV glycoprotein antibody, an anti-HSV glycoprotein antibody, an anti-MMTV glycoprotein antibody, an anti-GALV glycoprotein antibody, an anti-HIV glycoprotein antibody or an anti-RSV glycoprotein antibody, or antigen-binding fragments thereof such as a divalent antibody fragment, e.g. a F(ab')2 fragment or a divalent single-chain Fv fragment, or a monovalent antibody fragment, e.g. a Fab fragment, an Fv fragment, and a single-chain Fv fragment (scFv). In some embodiments, the viral particle-binding agent can be an anti-gp160 antibody, an anti-gp120 antibody, an anti-gp41 antibody, an anti-gp85 antibody or an anti-pg37 antibody, or antigen-binding fragments thereof such as a divalent antibody fragment, e.g. a F(ab')2 fragment or a divalent single-chain Fv fragment, or a monovalent antibody fragment, e.g. a Fab fragment, an Fv fragment, and a single-chain Fv fragment (scFv). In some embodiments, the antibody is a Fab fragment.

In some embodiments, the antibody is an anti-VSV-G antibody or an antigen-binding fragment thereof, such as a divalent antibody fragment, e.g. a F(ab')2 fragment or a divalent single-chain Fv fragment, or a monovalent antibody fragment, e.g. a Fab fragment, an Fv fragment, and a single-chain Fv fragment (scFv). In some embodiments, the anti-VSV-G antibody or antigen-binding fragment thereof is or is derived from an anti-VSV-G antibody described in Lefrancois, J Virol. 1984 July; 51(1):208-14 or other anti-VSV-G antibody known to a skilled artisan.

In some embodiments, the antibody is an anti-gp120 antibody or an antigen-binding fragment thereof, such as a divalent antibody fragment, e.g. a F(ab')2 fragment or a divalent single-chain Fv fragment, or a monovalent antibody fragment, e.g. a Fab fragment, an Fv fragment, and a single-chain Fv fragment (scFv). In some embodiments, the antibody is an anti-gp41 antibody or an antigen-binding fragment thereof, such as a divalent antibody fragment, e.g. a F(ab')2 fragment or a divalent single-chain Fv fragment, or a monovalent antibody fragment, e.g. a Fab fragment, an Fv fragment, and a single-chain Fv fragment (scFv). In some embodiments, the antibody is an anti-gp160 antibody or an antigen-binding fragment thereof, such as a divalent antibody fragment, e.g. a F(ab')2 fragment or a divalent single-chain Fv fragment, or a monovalent antibody fragment, e.g. a Fab fragment, an Fv fragment, and a single-chain Fv fragment (scFv). In some embodiments, the anti-gp120 antibody, anti-gp160 antibody or anti-gp41 antibody or antigen-binding fragments thereof are or are derived from antibodies that bind to gp120, gp41, and gp160 described by Holl et al., J Virol. 2006 June; 80(12):6177-81 or known to a skilled artisan.

In some embodiments the viral particle-binding agents binds to a molecule on the surface of the viral particle that is a non-viral recombinant molecule heterologous to the virus. In some embodiments, methods for surface modification of viral particles include, for example, pseudotyping, generation of fusion proteins, post translational modification of proteins with lipophilic residues, such as GPI anchor modification, utilization of adaptor molecules or direct chemical modification (Metzner and Dangerfield, Ch. 3 "Surface Modification of Retroviral Vectors for Gene Therapy, in "Viral Gene Therapy", published Jul. 20, 2011).

In some aspects, surface modification of viral particles is achieved by the same processes used to prepare and produce viral particles. In some cases, co-transfection of plasmid vectors carrying genes for production of the viral particle with constructs comprising a nucleic acid encoding the non-viral recombinant molecule of interest can lead to the formation of viral particles displaying the non-viral recombinant molecule of interest (Metzner and Dangerfield). Observations indicate that cells used to produce viral particles, e.g. viral particles for transduction of target cells to express a recombinant molecule of interest, may express the recombinant molecule (e.g. chimeric antigen receptor) during production of the viral particles. Accordingly, it is contemplated that viral particles produced in such producer cells (e.g. producer cells for producing viral particles containing a heterologus nucleic acid encoding an antigen receptor, such as a chimeric antigen receptor (CAR)), may display the recombinant molecule (e.g. CAR) on the surface of the viral particle. Thus, in some aspects, a viral particle-binding agent can be one that specifically binds to an antigen receptor (e.g. CAR) itself on the surface of the viral particles being used to transduce cells to express the antigen receptor. In some embodiments, the viral particle-binding agent is or comprises an antibody or antigen-binding fragment directed against an extracellular region of the antigen receptor (e.g. CAR). In some embodiments, the antibody or antigen-binding fragment specifically binds the antigen-binding fragment (e.g. scFv) of the CAR. In some embodiments, the viral particle-binding agent is an anti-idiotype antibody. In some embodiments, the antibody or antigen-binding fragment specifically binds to the hinge region of the antigen receptor (e.g. CAR), such as an IgG hinge region, including any as described or known. Similar methods can be employed for other recombinant heterologous molecules.

In some embodiments, the surface of the viral particle comprises a synthetic moiety, such as a peptide, which, in some cases, can be a tag (e.g. an affinity tag). In some embodiments, the viral vector particle is engineered to express such moiety, such as a peptide or tag (e.g. affinity tag) on its surface. For example, in some aspects, a molecule on the surface of the virus, such as a viral glycoprotein, is engineered as a fusion protein for expression of the synthetic moiety, such as a peptide or tag (e.g. affinity tag). In such an embodiment, the viral particle-binding agent includes a binding site V (e.g. V1) that specifically binds to the synthetic moiety, peptide or tag expressed on the surface of the viral particle.

Exemplary synthetic moieties, peptides or tags (e.g. affinity tags) can include: dinitrophenol or digoxigenin, oligohistidine, polyhistidine, an immunoglobulin domain, maltose-binding protein, glutathione-S-transferase (GST), chitin binding protein (CBP) or thioredoxin, calmodulin binding peptide (CBP), FLAG-peptide, the hemagglutinin peptide (HA-tag)(YPYDVPDYA, SEQ ID No: 20), the VSV-G-tag, the HSV-tag, the T7 epitope, maltose binding protein (MBP), the HSV epitope, the "myc" epitope, the V5-tag, glutathione-S-transferase (GST), a streptavidin-binding peptide (e.g. Strep-Tag®), an oligonucleotide, a dye, a cation, a polycation.

As a few illustrative examples of known affinity tags, include, for example, dinitrophenol or digoxigenin, oligohistidine, polyhistidine, an immunoglobulin domain, maltose-binding protein, glutathione-S-transferase (GST), chitin binding protein (CBP) or thioredoxin, calmodulin binding peptide (CBP), FLAG-peptide, the HA-tag (sequence: Tyr-Pro-Tyr-Asp-Val-Pro-Asp-Tyr-Ala) (SEQ ID NO: 20), the VSV-G-tag (sequence: Tyr-Thr-Asp-Ile-Glu-Met-Asn-Arg-Leu-Gly-Lys) (SEQ ID NO: 21), the HSV-tag (sequence: Gln-Pro-Glu-Leu-Ala-Pro-Glu-Asp-Pro-Glu-Asp) (SEQ ID NO: 22), the T7 epitope (Ala-Ser-Met-Thr-Gly-Gly-Gln-Gln-Met-Gly) (SEQ ID NO: 23), maltose binding protein (MBP), the HSV epitope of the sequence Gln-Pro-Glu-Leu-Ala-Pro-Glu-Asp-Pro-Glu-Asp (SEQ ID NO: 24) of herpes simplex virus glycoprotein D, the "myc" epitope of the transcription factor c-myc of the sequence Glu-Gln-Lys-Leu-Ile-Ser-Glu-Glu-Asp-Leu (SEQ ID NO: 25), the V5-tag (sequence: Gly-Lys-Pro-Ile-Pro-Asn-Pro-Leu-Leu-Gly-Leu-Asp-Ser-Thr) (SEQ ID NO: 26), or glutathione-S-transferase (GST).

Exemplary corresponding binding agents, which would be the viral particle-binding agent in this context, and include any of the known antibodies or antigen binding fragments against such synthetic moieties, such as peptides or tags (e.g. affinity tags).

In some embodiments, the reagent is directly bound to a synthetic moiety, such as a peptide or tag (e.g. affinity tag), present on the surface of the viral vector particle. Thus, in some embodiments, there is no viral particle-binding agent that facilitates interaction between the viral vector particle and the reagent. In some embodiments, a molecule on the surface of the viral particle comprises binding partner C1. In some embodiments the reagent is reversibly bound directly to the particle via an interaction between the binding site Z (e.g. Z1) and a binding partner C (e.g. C1) present on the surface of the viral particle.

In some embodiments, the molecule on the surface of the viral particle comprises a viral envelope protein, a variant thereof, or a portion thereof that is conjugated to, directly or indirectly, to a synthetic moiety, such as a peptide or tag (e.g. an affinity tag) that is able to reversibly bind to the binding site Z (e.g. Z1) on the reagent. In some embodiments, the synthetic moiety, such as a peptide, is a streptavidin-binding peptide. Exemplary viral envelope proteins are discussed above, and include the env-glycoprotein complex of a lentiviral particle, including gp160, gp120, or gp41, vesicular stomatitis virus-G (VSVG or VSV-G), Sindbis virus envelope, Moloney murine leukemia virus (MoMuLV or MMLV), Harvey murine sarcoma virus (HaMuSV or HSV), murine mammary tumor virus (MuMTV or MMTV), gibbon ape leukemia virus (GaLV or GALV), human immunodeficiency virus (HIV) or Rous sarcoma virus (RSV) proteins or variants thereof.

In some embodiments, the reagent is a streptavidin, such as a streptavidin mutein including any described above (e.g. set forth in SEQ ID NOS: 3-6), and the binding partner C (e.g. C1) that is included in the viral particle and/or viral envelope protein or variant thereof can be a streptavidin-binding peptide. In some embodiments, the streptavidin-binding peptide may include a sequence with the general formula set forth in SEQ ID NO: 9, such as contains the sequence set forth in SEQ ID NO: 10. In some embodiments, the peptide sequence has the general formula set forth in SEQ ID NO: 11, such as set forth in SEQ ID NO: 12. In one example, the peptide sequence is Trp-Arg-His-Pro-Gln-Phe-Gly-Gly (also called Strep-tag®, set forth in SEQ ID NO: 7). In one example, the peptide sequence is Trp-Ser-His-Pro-Gln-Phe-Glu-Lys (also called Strep-tag® II, set forth in SEQ ID NO: 8). In some embodiments, the peptide ligand contains a sequential arrangement of at least two streptavidin-binding modules, wherein the distance between the two modules is at least 0 and not greater than 50 amino acids, wherein one binding module has 3 to 8 amino acids and contains at least the sequence His-Pro-Xaa (SEQ ID NO: 9), where Xaa is glutamine, asparagine, or methionine, and wherein the other binding module has the same or different streptavidin peptide ligand, such as set forth in SEQ ID NO: 11 (see e.g. International Published PCT Appl. No. WO02/077018; U.S. Pat. No. 7,981,632). In some embodiments, the peptide ligand contains a sequence having the formula set forth in any of SEQ ID NO: 13 or 14. In some embodiments, the peptide ligand has the sequence of amino acids set forth in any of SEQ ID NOS: 15-19.

Methods of engineering a molecule present on the surface of a viral particle, including lentiviral particles, to contain a synthetic moiety or tag (e.g. affinity tag) are known in the art. In some embodiments the molecule present on the surface of a viral particle is a protein (e.g. glycoprotein) that is a fusion protein containing the affinity tag and a viral envelope protein or variant thereof. The synthetic moiety, such as a peptide or tag (e.g. affinity tag) can be present at the carboxy terminus of a viral envelope protein or variant thereof, the amino terminus of a viral envelope protein or variant thereof, and/or contained within the viral envelope protein sequence or variant thereof.

Standard recombinant molecular techniques can be used to introduce such moieties into viral envelope protein sequences, including VSV-G, for expression on viral particles, including lentiviral particles. For example, in some embodiments, VSV-G contains the VSV-G tag "YTDI-EMNRLGK" (SEQ ID NO: 46) native to the VSV-G protein. In some embodiments, VSV-G contains a synthetic moiety or tag inserted at a site corresponding to amino acid position 24 of the native VSV-G molecule (see e.g. Guibinga et al. Molecular Therapy (2004) 9, 76-84, exemplifying insertion of a 10 amino acid tag "WREPGRMELN" (SEQ ID NO: 47) from the collagen-binding domain of von Willebrand factor). In some embodiments, the synthetic moiety, such as a peptide or tag (e.g. affinity moiety) can be fused to the N-terminus of VSV-G (see e.g. Kameyama et al., J Virol Methods. 2008 October; 153(1):49-54.). As another example, the MLV env gene and resulting protein can be modified by fusing an affinity tag or protein to the +1 position of the surface subunit, as described in Verhoeyen et al., Blood. 2003 Mar. 15; 101(6): 2167-2174. In some embodiments, the E2 transmembrane domain of the Sindbis virus glycoprotein (SIN) can be engineered to include a synthetic peptide or tag, which, in some cases, can be inserted between amino acids 70 and 74 of the E2 protein (see, e.g. Yang et al., Proc Natl Acad Sci USA. 2006 Aug. 1; 103(31):11479-84, and Morizono et al., J Gene Med. 2009 August; 11(8): 655-663.) In some embodiments, the tag is an HA-tag located between amino acids 71-74 of the E2 protein (see Yang). In some embodiments, the tag is a biotin-adapter peptide inserted at amino acid 70 of E2 (see Morizono). In some embodiments, the synthetic moiety, such as a peptide or tag (e.g. affinity tag), can further contain one or more linker peptides, including flexible linker peptides, including linker peptides with the sequence "GGGS" (SEQ ID NO: 48)(see Morizono). Similar techniques can be used for generating fusion proteins of a virus glycoprotein with any desired synthetic moiety, such as a peptide or tag (e.g. affinity tag).

In some embodiments, the viral particle-binding agent is or includes a polycation or cationic lipid that can facilitate, such as enhance, viral transduction. Exemplary polycations include protamine (e.g. protamine sulfate), hexadimethrine bromide (POLYBRENE®, Abbott Laboratories Corp), and CH-296 (RETRONECTIN®, Clontech). In some embodiments, the polycation is linked, directly or indirectly, to a binding partner C (e.g. C1) for reversibly binding to the binding site Z (e.g. Z1) on the reagent. In some embodiments, the polycation can serve as an electrostatic bridge between the virus and the cells. In some embodiments, the polycation does not contain a binding site V (e.g. V1) that specifically binds to a molecule on the surface of the viral particle, but nonetheless is able to interact with the surface of the viral particle to bridge the interaction with the cells.

III. METHODS OF TRANSDUCING CELLS

Provided are methods for transfer of viral vectors into cells using an oligomeric protein (e.g. streptavidin mutein) reagent. In some embodiments, the oligomeric protein reagent used in accord with the provided transduction methods is a multimerization reagent. In some embodiments, the cells are for use in cell therapy, such as primary cells prepared for autologous or allogeneic transfer, e.g., in adoptive cell therapy. In some embodiments, the reagent also can be exploited in the methods to facilitate one or more other processing step associated with preparing an engineered cell composition, such as one or more of selection, activation and/or stimulation of cells. The methods may include additional cell processing steps, such as cell washing, isolation, separation, formulation or other steps related to producing a cell composition.

In some embodiments, the provided methods are used to introduce viral vector particles, such as retroviral vector particles, into cells, such immune cells, including T cells. In some embodiments, the viral vector particles have a genome that contains a nucleic acid encoding an antigen receptor, such as a chimeric antigen receptor (CAR) or transgenic T cell receptor (TCR). Hence, in some embodiments, the provided methods can be used for expressing in immune cells, such as T cells, a genetically engineered antigen receptor, such as a transgenic TCR or a CAR. Also provided are cells transduced by such particles and methods and compositions containing such cells, and methods for using the same.

In some embodiments, the retroviral vector particles and methods include features that result in an increased transduction of immune cells and/or certain populations and/or subpopulations thereof, desirable for use in adoptive immunotherapy. In some embodiments of the provided transduction methods and viral vector particles, cells, e.g., T cells, in the populations being transduced are not or need not be stimulated and/or activated prior to and/or in conjunction with contacting or incubating the cells with the provided retroviral vector particle.

A. Incubating Cells with Viral Vector Particles

In some embodiments, the provided methods involve methods of transducing cells by contacting, e.g. incubating, a cell composition comprising a plurality of cells (hereinafter also called an "input composition") with a (1) an oligomeric protein (e.g. streptavidin mutein) reagent, such as a multimerization reagent and (2) a viral particle. In some embodiments, the method involves admixing the cells with the reagent and with the viral particles simultaneously or sequentially. In some embodiments, the method involves premixing the viral particles and the reagent together and then contacting the cell composition with the mixture of viral particles associated with the reagent. In some embodiments, the contacting is for 30 minutes to 72 hours, such as 30 minute to 48 hours, 30 minutes to 24 hours or 1 hour to 24 hours, such as at least or about at least 30 minutes, 1 hour, 2 hours, 6 hours, 12 hours, 24 hours, 36 hours or more.

In some embodiments of any of the methods provided herein, (i) the incubating includes admixing the target cells with the reagent, and/or admixing the target cells with the viral particle, sequentially, in either order, optionally wherein the admixing in (a) and the admixing in (b) are carried out within a period of no more than 1 hour, 2 hours, 3 hours, 4 hours, 5 hours, 6 hours, 7 hours, 8 hours, 9 hours, 10 hours, 11 hours, 12 hours, 18 hours, 24 hours, 36 hours, 48 hours, or 72 hours and/or the admixing in (a) is carried out no more than 1 hour, 2 hours, 3 hours, 4 hours, 5 hours, 6 hours, 7 hours, 8 hours, 9 hours, 10 hours, 11 hours, 12 hours, 18 hours, 24 hours, 36 hours, or 48 hours apart from the admixing in (b); (ii) the incubating includes admixing the target cells, the reagent, and the viral particle, said admixing carried out simultaneously or substantially simultaneously; (iii) the incubating includes admixing a composition that contains the target cells and the viral particles, and not including the reagent, optionally wherein: no more than 5%, 10%, 20%, 30%, or 40% of the target cells in the composition including the target cells and the reagent are activated cells, express a surface marker selected from the group consisting of HLA-DR, CD25, CD69, CD71, CD40L and 4-1BB; includes intracellular expression of a cytokine selected from the group consisting of IL-2, IFNgamma, TNF-alpha, and/or are capable of proliferating; and/or the admixing is carried out no more than 1 hour, 2 hours, 3 hours, 4 hours, 5 hours, 6 hours, 7 hours, 8 hours, 9 hours, 10 hours, 11 hours, 12 hours, 18 hours, 24 hours, 36 hours, or 48 hours following an admixing of the target cells and the viral particles in the composition; (iv) the incubation includes admixing a composition that contains the target cells and the reagent, and not including the viral particle, with the viral particle, optionally wherein: no more than 5%, 10%, 20%, 30%, or 40% of the target cells in the composition including the target cells and the reagent activated cells, express a surface marker selected from the group consisting of HLA-DR, CD25, CD69, CD71, CD40L and 4-1BB; including intracellular expression of a cytokine selected from the group consisting of IL-2, IFNgamma, TNF-alpha, and/or are capable of proliferating; and/or the admixing is carried out no more than 1 hour, 2 hours, 3 hours, 4 hours, 5 hours, 6 hours, 7 hours, 8 hours, 9 hours, 10 hours, 11 hours, 12 hours, 18 hours, 24 hours, 36 hours, or 48 hours following an admixing of the target cells and the viral particles in the composition; and/or (v) the incubation includes admixing a composition including the viral particles and the reagent with a composition that contains the target cells and not the viral particle and/or not the reagent, optionally wherein: no more than 5%, 10%, 20%, 30%, or 40% of the target cells in the composition including the target cells and the reagent are activated cells express a surface marker selected from the group consisting of HLA-DR, CD25, CD69, CD71, CD40L and 4-1BB; includes intracellular expression of a cytokine selected from the group consisting of IL-2, IFNgamma, TNF-alpha, and/or are capable of proliferating.

In some embodiments, the incubating includes admixing the cell with the reagent and with the viral particle, simultaneously or sequentially, in either order. In some embodiments, during at least a portion of the incubating, the reagent and viral particle are in the presence of or contacted with the cell simultaneously.

In some embodiments, the provided methods involve (a) contacting a viral particle with an oligomeric protein reagent, thereby generating a composition including viral particles and the reagent, wherein the viral particles are optionally associated with the reagent; and (b) incubating the composition in (a) with a plurality of cells including target cells, wherein the method produces an output composition including one or more cells transduced with the viral particle.

In some embodiments, the provided methods involve admixing a composition containing viral particles and an oligomeric protein reagent with a plurality of cells including target cells, wherein the method produces an output composition including one or more cells transduced with the viral particle.

In some embodiments, the provided methods involve (a) contacting a viral particle with a protein reagent including a streptavidin, an avidin, a streptavidin analog or mutein, an avidin analog, a mutein or a biologically active fragment of any of the foregoing, and/or multiple subunits of any of the foregoing, thereby generating a composition including viral particles and the reagent, wherein the viral particles are optionally associated with the reagent; and (b) incubating the composition in (a) with a plurality of cells, wherein the method produces an output composition including one or more cells transduced with the viral particle.

In some embodiments, the provided methods involve admixing a composition containing viral particles and a protein reagent with a plurality of cells including target cells, wherein: the protein reagent includes a streptavidin, an avidin, a streptavidin analog or mutein, an avidin analog, a mutein or a biologically active fragment of any of the foregoing, and/or multiple subunits of any of the foregoing; and the method produces an output composition including one or more cells transduced with the viral particle. In some embodiments, the reagent and/or each of the monomeric units and/or each of the multimeric units, has a net positive charge or an overall positive charge.

In some embodiments, the provided methods involve incubating a plurality of cells including target cells with: 1) an oligomeric protein reagent including a plurality of binding sites capable of reversibly binding to a binding agent, wherein one or more binding sites are reversibly bound to the binding agent; and 2) a viral particle, wherein at least a portion of the incubation in (1) occurs simultaneously with (2) and wherein the method produces an output composition including one or more cells transduced with the viral particle.

In some embodiments, the provided methods involve (1) contacting (a) a composition including one or more viral particles and (b) a binding agent that is a viral-binding agent that (i) is capable of specifically binding to a molecule on the surface of the viral particle and ii) is reversibly bound to a reagent including a plurality of binding sites capable of reversibly binding to the viral-binding agent; and (2) incubating at least a plurality of cells including target cells in the presence of the one or more viral particles, wherein the contacting in (1) and the incubating in (2) are carried out simultaneously or sequentially, in either order, wherein the method generates an output composition including a plurality of cells transduced with the viral particle.

In some embodiments of any of the methods provided herein, the contacting in (1) and the incubating in (2) are carried out within a period of no more than 1 hour, 2 hours, 3 hours, 4 hours, 5 hours, 6 hours, 7 hours, 8 hours, 9 hours, 10 hours, 11 hours, 12 hours, 18 hours, 24 hours, 36 hours, 48 hours, or 72 hours and/or the admixing in (a) is carried out no more than 1 hour, 2 hours, 3 hours, 4 hours, 5 hours, 6 hours, 7 hours, 8 hours, 9 hours, 10 hours, 11 hours, 12 hours, 18 hours, 24 hours, 36 hours, or 48 hours apart from the incubating in (b). In some embodiments, the viral vector particle comprises a genome encoding a recombinant antigen receptor, optionally a chimeric antigen receptor.

The composition that contains the viral vector particles and cells during the transduction step may further include one or more additional agents, such as those to promote transduction efficiency, such as polycations including protamine (e.g. protamine sulfate), hexadimethrine bromide (POLYBRENE®, Abbott Laboratories Corp), and CH-296 (RETRONECTIN®, Clontech). In some embodiments, the polycation can be present in the input composition at a final concentration of 1 μg/mL to 100 μg/mL, such as 5 μg/mL to 50 μg/mL. The composition may also include media, including cell culture medium including medium designed for culture of the cell type to be processed, such as hematopoietic stem cell medium, e.g., serum free medium.

In some embodiments, the concentration of cells of the input composition is from or from about $1.0 \times 10^5$ cells/mL to $1.0 \times 10^8$ cells/mL, such as at least or about at least or about $1.0 \times 10^5$ cells/mL, $5 \times 10^5$ cells/mL, $1 \times 10^6$ cells/mL, $5 \times 10^6$ cells/mL, $1 \times 10^7$ cells/mL, $5 \times 10^7$ cells/mL or $1 \times 10^8$ cells/mL.

In some embodiments, the viral particles are provided at a certain ratio of copies of the viral vector particles or infectious units (IU) thereof, per total number of cells (IU/cell) in the input composition or total number of cells to be transduced. For example, in some embodiments, the viral particles are present during the contacting at or about or at least at or about 0.5, 1, 2, 3, 4, 5, 10, 15, 20, 30, 40, 50, or 60 IU of the viral vector particles per one of the cells.

In some embodiments, the titer of viral vector particles is between or between about $1 \times 10^6$ IU/mL and $1 \times 10^8$ IU/mL, such as between or between about $5 \times 10^6$ IU/mL and $5 \times 10^7$ IU/mL, such as at least $6 \times 10^6$ IU/mL, $7 \times 10^6$ IU/mL, $8 \times 10^6$ IU/mL, $9 \times 10^6$ IU/mL, $1 \times 10^7$ IU/mL, $2 \times 10^7$ IU/mL, $3 \times 10^7$ IU/mL, $4 \times 10^7$ IU/mL, or $5 \times 10^7$ IU/mL.

In some embodiments, transduction can be achieved at a multiplicity of infection (MOI) of less than 100, such as generally less than 60, 50, 40, 30, 20, 10, 5 or less.

In some embodiments, contacting is performed in solution, such as using a soluble oligomeric protein (e.g. streptavidin mutein) reagent or multimerization reagent. In some embodiments, the cells, oligomeric reagent and viral particles are contacted in a volume of from or from about 0.5 mL to 500 mL, such as from or from about 0.5 mL to 200 mL, 0.5 mL to 100 mL, 0.5 mL to 50 mL, 0.5 mL to 10 mL, 0.5 mL to 5 mL, 5 mL to 500 mL, 5 mL to 200 mL, 5 mL to 100 mL, 5 mL to 50 mL, 5 mL to 10 mL, 10 mL to 500 mL, 10 mL to 200 mL, 10 mL to 100 mL, 10 mL to 50 mL, 50 mL to 500 mL, 50 mL to 200 mL, 50 mL to 100 mL, 100 mL to 500 mL, 100 mL to 200 mL or 200 mL to 500 mL.

In some embodiments, when the contacting is carried out in solution, e.g. using a soluble oligomeric protein (e.g. streptavidin mutein) reagent, the contacting can be carried out in which at least a portion of the contacting is with centrifugation, such as spinoculation (e.g. centrifugal inoculation). In some embodiments, the composition containing cells, viral particles and reagent can be rotated, generally at relatively low force or speed, such as speed lower than that used to pellet the cells, such as from or from about 600 rpm to 1700 rpm (e.g. at or about or at least 600 rpm, 1000 rpm, or 1500 rpm or 1700 rpm). In some embodiments, the rotation is carried at a force, e.g., a relative centrifugal force, of from or from about 100 g to 3200 g (e.g. at or about or at least at or about 100 g, 200 g, 300 g, 400 g, 500 g, 1000 g, 1500 g, 2000 g, 2500 g, 3000 g or 3200 g), as measured for example at an internal or external wall of the chamber or cavity. The term "relative centrifugal force" or RCF is generally understood to be the effective force imparted on an object or substance (such as a cell, sample, or pellet and/or a point in the chamber or other container being rotated), relative to the earth's gravitational force, at a particular point in space as compared to the axis of rotation. The value may be determined using well-known formulas, taking into account the gravitational force, rotation speed and the radius of rotation (distance from the axis of rotation and the object, substance, or particle at which RCF is being measured).

In some embodiments, the oligomeric reagent, such as multimerization reagent, is not bound to a support, such as not bound to a solid surface or stationary phase.

In some embodiments, the oligomeric reagent, such as multimerization reagent, is immobilized on a support, such as a solid surface or stationary phase. In some embodiments, the contacting is performed in a stationary phase, such as using a chromatography matrix in which is immobilized thereon the protein (streptavidin mutein), such as an oligomeric protein (e.g. streptavidin mutein) reagent. Exemplary of such formats for use in connection with the provided methods are described herein. Thus, in some embodiments, an on-column transduction can be performed in accord with the provided methods.

In some embodiments, the input composition that is contacted with the cells comprises activated cells. In some embodiments, at least 40%, 50%, 60%, 70%, 80%, 90% or more of the cells, e.g. T cells, in the input composition are activated, such as, in some cases, are surface positive for one or more of HLA-DR, CD25, CD69, CD71, CD40L and/or 4-1BB. In some embodiments, cells are activated with an activating agent, such as in the presence of anti-CD3/anti-CD28, prior to initiation of the contacting, e.g. prior to initiation of transduction. Methods of expanding T cell populations in vitro in the absence of exogenous growth factors or low amounts of exogenous growth factors are known in the art (see e.g. U.S. Pat. No. 6,352,694 B1 and European Patent EP 0 700 430 B1). In general, such methods employ a solid phase surfaces of greater than 1 μM to which various bind agents (e.g. anti-CD3 antibody and/or anti-CD28 antibody) are immobilized. For example, Dynabeads® CD3/CD28 (Invitrogen) are commercially available reagents for T cell expansion, which are uniform, 4.5 μm superparamagnetic, sterile, non-pyrogenic polystyrene beads coated with a mixture of affinity purified monoclonal antibodies against the CD3 and CD28 cell surface molecules on human T cells In some embodiments, the activating agent, e.g. anti-CD3 and/or anti-CD28, can be immobilized on beads, such as magnetic beads.

In some embodiments, the cell activation is also performed in the presence IL-2 (e.g. from or from about 50 IU/mL to 200 IU/mL, such as or about 100 IU/mL). In some embodiments, the activation is carried out between or between about 1 hour and 96 hours, 1 hour and 72 hours, 1 hour and 48 hours, 4 hours and 36 hours, 8 hours and 30 hours or 12 hours and 24 hours, such as at least or about at least 6 hours, 12 hours, 18 hours, 24 hours, 36 hours or 72 hours. In some embodiments, the activation is carried out at a temperature greater than or greater than about 25° C., such as generally greater than or greater than about 32° C., 35° C. or 37° C., for example at or about 37° C.±2° C., such as at a temperature of at or about 37° C.

In some embodiments, cells are not activated with an activating agent, such as in the presence of anti-CD3/anti-CD28, prior to initiation of the contacting, e.g. prior to initiation of transduction. In some embodiments, the input composition that is contacted with the cells comprises a plurality of resting cells. In some embodiments, at least 40%, 50%, 60%, 70%, 80%, 90% or more of the T cells in the population are resting T cells, such as T cells that lack a T cell activation marker, such as a surface marker or intracellular cytokine or other marker, and/or T cells that are in the $G_0$ or $G_0G_{1a}$ stage of the cell cycle.

In particular aspects, the provided methods allow transduction to happen in T cells without the need for activation prior to the contacting and/or incubation with the oligomeric protein reagent, such as multimerization reagent. In some embodiments, the methods include transducing a population of T cells that contain resting or naïve T cells with a viral vector in the presence of an oligomeric protein (e.g. streptavidin) reagent in accord with the provided methods, without first, i.e. prior to the transduction, activating and/or stimulating the T cells. In some such embodiments, the provided methods can be used to prepare immune cells, such as T cells, for adoptive therapy, that do not include a step of activating and/or stimulating T cells.

In some embodiments, the oligomeric protein (e.g. streptavidin mutein) is naked.

In some embodiments, the oligomeric protein (e.g. streptavidin mutein) is a multimerization reagent that has bound thereto one or more binding agent that is capable of binding to a molecule on the surface of targets cells (e.g. T cells) or, in some cases, on the surface of viral particles in the composition. In some embodiments, the binding agent is reversibly bound to a reagent containing a plurality of binding sites capable of reversibly binding to the agent. In some embodiments, the incubation is performed under conditions in which the agent binds, such as specifically binds, to the molecule on the cell or viral particle. In some embodiments as described, the oligomeric reagent has reversibly immobilized thereon (bound thereto) an agent or agents (e.g. first or second or third, etc.), which can include receptor-binding, e.g. stimulatory agent or accessory agents, selection agent or viral-binding agents, which can be used for the selection, stimulation, expansion and/or differentiation of cells or modulation of transduction of cells.

In some cases, for certain receptor-binding agents (e.g. stimulatory agents or accessory agents), such binding can induce or modulate a signal in target cells (e.g. T cells) in the compositions, such as a primary signal or accessory signal as described. In some embodiments, binding of the agent to the molecule results in one or more of the stimulation, activation, expansion (proliferation) and/or differentiation of target cells in the composition. In some embodiments, the reagent comprises a stimulatory agent that provides a primary activation signal to the cells, wherein the stimulatory agent comprises at least one binding partner C (e.g. C1, C2 or C3, etc), wherein the binding partner C is able of reversibly binding to the binding site Z1 of the oligomeric reagent reagent for reversible binding of the agent. In some embodiments, the reagent comprises an accessory agent that provides an accessory signal to the cells, wherein the accessory agent comprises at least one binding partner C (e.g. C1, C2 or C3, etc), wherein the binding partner C is able of reversibly binding to the binding site Z1 of the oligomeric reagent reagent for reversible binding of the agent. In some embodiments, the reagent comprises a selection agent that specifically targets binding to a particular cell surface molecule or marker, wherein the selection agent comprises at least one binding partner C (e.g. C1, C2 or C3, etc), wherein the binding partner C is able of reversibly binding to the binding site Z1 of the oligomeric reagent reagent, for reversible binding of the agent.

In some embodiments, activation of the cells in the input composition is initiated during the contacting of cells of the input composition with the oligomeric protein reagent and/or viral particle. In such instances, the oligomeric protein reagent can have immobilized thereon a receptor binding agent, e.g. stimulatory agent and/or accessory agent, capable of inducing or modulating a signal in the cells, such as T cells. In some embodiments, the stimulatory agent comprises an MHC I:peptide complex or functional portion thereof, an MHCII:peptide complex or functional portion thereof, and/or is capable of delivering a stimulatory signal through a TCR/CD3 complex in a T cell, a CD3-containing complex in a T cell, and/or an ITAM-containing molecule in a T cell. In some embodiments, the oligomeric reagent can have immobilized thereon an accessory agent capable of provided an accessory signal to the cells, such as T cells. In some embodiments, the receptor binding agent, e.g. stimulatory agent and/or accessory agent, is any agent as described herein, such as anti-CD3 and/or anti-CD28 antibody (e.g. Fabs). Alternatively, it is also possible to use as the stimulatory agent a ligand, such as a natural ligand, of a receptor that triggers of cell expansion. For example, the extracellular domain of CD19 can be used to cause the activation of intracellular signaling cascades of cells transduced to express chimeric CD19 binding antigen receptor (CAR). In some embodiments, the oligomeric protein (e.g. streptavidin) reagent is able to both modulate cell transduction and activate, such as stimulate cells, during the contacting and, optionally the further incubation. In some embodiments, binding of the oligomeric reagent comprising the stimulating agent is reversible, such as in the presence of a competing agent, e.g. biotin.

In some embodiments, the provided method can be used for selectively inducing transduction and/or ex vivo expansion of a specific population of cells such as B cells, T cells or natural killer cells. In some embodiments, the oligomeric protein (e.g. streptavidin mutein) reagent is a multimerization reagent that can include at least one selection agent reversibly bound to the same reagent used for modulating transduction. In some embodiments, the oligomeric (e.g. streptavidin mutein) reagent is a multimerization reagent that can contain the selection agent and one or both of the first or second receptor binding agents (e.g. stimulatory agent or accessory agent) on the same reagent. In some embodiments, the oligomeric protein (e.g. streptavidin) reagent, such as multimerization reagent, is able to both modulate cell transduction and preferentially target the transduction to a particular subpopulation of selected or targeted cells. In some embodiments, the oligomeric protein (e.g. streptavidin) reagent, such as multimerization reagent, is able to modulate cell transduction, such as preferentially target the transduction to a particular subpopulation of selected or targeted cells, and activate, such as stimulate cells, during the contacting and, optionally the further incubation.

In some embodiments, binding of the oligomeric reagent comprising the binding agents, e.g. selection agent and/or stimulatory agent, is reversible, such as in the presence of a competing agent, e.g. biotin. As described below, in some aspects, the method includes adding or incubating the composition containing cells, viral particles and oligomeric reagent (e.g. multimerization reagent bound to one or more binding agent) with a competition substance to reverse, dissociate or disrupt binding of the one or more binding agent to the cell or viral particles. In some embodiments, following the reversal, dissociation or disruption, one or more components of the composition can be removed, such as the dissociated oligomeric reagent, one or more binding agent and/or the competition substance. Exemplary of such methods are described below.

In some embodiments, cells produced from the provided method (hereinafter also called "output composition" or "incubated composition") include those transduced with the viral vector, such as a viral vector containing nucleotides encoding a heterologous protein, such as a recombinant receptor, e.g. a CAR. By heterologous in this context refers to a protein that is not normally expressed from a virus and/or not encoded by a viral genome. In some embodiments, integration of a viral vector into a host genome can be assessed by measuring the level of expression of a recombinant protein, such as a heterologous protein, encoded by a nucleic acid contained in the genome of the viral vector particle following incubation. A number of well-known methods for assessing expression level of recombinant molecules may be used, such as detection by affinity-based methods, e.g., immunoaffinity-based methods, e.g., in the context of cell surface proteins, such as by flow cytometry. In some examples, the expression is measured by detection of a transduction marker and/or reporter construct. In some embodiments, nucleic acid encoding a truncated surface protein is included within the vector and used as a marker of expression and/or enhancement thereof.

Cells

In some embodiments, a composition containing target cells is transduced with a viral vector particle, such as in accord with the described methods.

In some embodiments, the cells generally are eukaryotic cells, such as mammalian cells, and typically are human cells. In some embodiments, the cells are derived from the blood, bone marrow, lymph, or lymphoid organs, or are cells of the immune system, such as cells of the innate or adaptive immunity, e.g., myeloid or lymphoid cells, including lymphocytes, typically T cells and/or NK cells. Other exemplary cells include stem cells, such as multipotent and pluripotent stem cells, including induced pluripotent stem cells (iPSCs). The cells typically are primary cells, such as those isolated directly from a subject and/or isolated from a subject and frozen. In some embodiments, the cells include one or more subsets of T cells or other cell types, such as whole T cell populations, CD4+ cells, CD8+ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. With reference to the subject to be treated, the cells may be allogeneic and/or autologous. Among the methods include off-the-shelf methods. In some aspects, such as for off-the-shelf technologies, the cells are pluripotent and/or multipotent, such as stem cells, such as induced pluripotent stem cells (iPSCs). In some embodiments, the methods include isolating cells from the subject, preparing, processing, culturing, and/or engineering them, as described herein, and re-introducing them into the same patient, before or after cryopreservation.

Among the sub-types and subpopulations of T cells and/or of CD4+ and/or of CD8+ T cells are naïve T ($T_N$) cells, effector T cells ($T_{EFF}$), memory T cells and sub-types thereof, such as stem cell memory T ($T_{SCM}$), central memory T ($T_{CM}$), effector memory T ($T_{EM}$), or terminally differentiated effector memory T cells, tumor-infiltrating lymphocytes (TIL), immature T cells, mature T cells, helper T cells, cytotoxic T cells, mucosa-associated invariant T (MATT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells.

In some embodiments, the cells are natural killer (NK) cells. In some embodiments, the cells are monocytes or granulocytes, e.g., myeloid cells, macrophages, neutrophils, dendritic cells, mast cells, eosinophils, and/or basophils.

In some embodiments, preparation of the cells includes one or more culture and/or preparation steps. The cells may be isolated from a sample, such as a biological sample, e.g., one obtained from or derived from a subject. In some embodiments, the subject from which the cells are isolated is one having the disease or condition or in need of a cell therapy or to which cell therapy will be administered. The subject in some embodiments is a human in need of a particular therapeutic intervention, such as the adoptive cell therapy for which cells are being isolated, processed, and/or engineered.

Accordingly, the cells in some embodiments are primary cells, e.g., primary human cells. The samples include tissue, fluid, and other samples taken directly from the subject, as well as samples resulting from one or more processing steps, such as separation, centrifugation, genetic engineering (e.g. transduction with viral vector), washing, and/or incubation. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom.

In some aspects, the sample from which the cells are derived or isolated is blood or a blood-derived sample, or is or is derived from an apheresis or leukapheresis product. Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples include, in the context of cell therapy, e.g., adoptive cell therapy, samples from autologous and allogeneic sources.

In some embodiments, the cells are derived from cell lines, e.g., T cell lines. The cells in some embodiments are obtained from a xenogeneic source, for example, from mouse, rat, non-human primate, or pig.

In some embodiments, isolation of the cells includes one or more preparation and/or non-affinity based cell separation steps. In some examples, cells are washed, centrifuged, and/or incubated in the presence of one or more reagents, for example, to remove unwanted components, enrich for desired components, lyse or remove cells sensitive to particular reagents. In some examples, cells are separated based on one or more property, such as density, adherent properties, size, sensitivity and/or resistance to particular components.

In some examples, cells from the circulating blood of a subject are obtained, e.g., by apheresis or leukapheresis. The samples, in some aspects, contain lymphocytes, including T cells, monocytes, granulocytes, B cells, other nucleated white blood cells, red blood cells, and/or platelets, and in some aspects contains cells other than red blood cells and platelets.

In some embodiments, the blood cells collected from the subject are washed, e.g., to remove the plasma fraction and to place the cells in an appropriate buffer or media for subsequent processing steps. In some embodiments, the cells are washed with phosphate buffered saline (PBS). In some embodiments, the wash solution lacks calcium and/or magnesium and/or many or all divalent cations. In some aspects, a washing step is accomplished a semi-automated "flow-through" centrifuge (for example, the Cobe 2991 cell processor, Baxter) according to the manufacturer's instructions. In some aspects, a washing step is accomplished by tangential flow filtration (TFF) according to the manufacturer's instructions. In some embodiments, the cells are resuspended in a variety of biocompatible buffers after washing, such as, for example, $Ca^{++}/Mg^{++}$ free PBS. In certain embodiments, components of a blood cell sample are removed and the cells directly resuspended in culture media.

In some embodiments, the methods include density-based cell separation methods, such as the preparation of white blood cells from peripheral blood by lysing the red blood cells and centrifugation through a Percoll or Ficoll gradient.

In some embodiments, it is not necessary to enrich or select cells prior to performing the provided method. In some embodiments, the reagent, such as the oligomeric reagent, e.g. multimerization reagent, can contain reversibly bound thereto one or more selection agents that is capable of binding to or that does bind to a molecule on the surface of the cell. In some embodiments, such a reagent is the same reagent employed for mediating transduction or is a different reagent. In some embodiments, carrying out at least a portion of the incubation of the cells and viral particles in the presence of such a reagent can result in selective transduction of a cell population without prior selection or enrichment of cells.

In some embodiments, the isolation methods include the separation of different cell types based on the expression or presence in the cell of one or more specific molecules, such as surface markers, e.g., surface proteins, intracellular markers, or nucleic acid. In some embodiments, any known method for separation based on such markers may be used. Separation methods may include any of those disclosed herein, including methods using reversible reagent systems, e.g., agents (such as receptor binding agents or selection agents) and reagents as described herein.

In some embodiments, the separation is affinity- or immunoaffinity-based separation. For example, the isolation in some aspects includes separation of cells and cell populations based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner.

Such separation steps can be based on positive selection, in which the cells having bound the reagents are retained for further use, and/or negative selection, in which the cells having not bound to the antibody or binding partner are retained. In some examples, both fractions are retained for further use. In some aspects, negative selection can be particularly useful where no antibody is available that specifically identifies a cell type in a heterogeneous population, such that separation is best carried out based on markers expressed by cells other than the desired population.

The separation need not result in 100% enrichment or removal of a particular cell population or cells expressing a particular marker. For example, positive selection of or enrichment for cells of a particular type, such as those expressing a marker, refers to increasing the number or percentage of such cells, but need not result in a complete absence of cells not expressing the marker. Likewise, negative selection, removal, or depletion of cells of a particular type, such as those expressing a marker, refers to decreasing the number or percentage of such cells, but need not result in a complete removal of all such cells.

In some examples, multiple rounds of separation steps are carried out, where the positively or negatively selected fraction from one step is subjected to another separation step, such as a subsequent positive or negative selection. In some examples, a single separation step can deplete cells expressing multiple markers simultaneously, such as by incubating cells with a plurality of antibodies or binding partners, each specific for a marker targeted for negative selection. Likewise, multiple cell types can simultaneously be positively selected by incubating cells with a plurality of antibodies or binding partners expressed on the various cell types.

For example, in some aspects, specific subpopulations of T cells, such as cells positive or expressing high levels of one or more surface markers, e.g., $CD28^+$, $CD62L^+$, $CCR7^+$, $CD27^+$, $CD127^+$, $CD4^+$, $CD8^+$, $CD45RA^+$, and/or $CD45RO^+$ T cells, are isolated by positive or negative selection techniques.

For example, $CD3^+$, $CD28^+$ T cells can be positively selected using CD3/CD28 conjugated magnetic beads (e.g., DYNABEADS® M-450 CD3/CD28 T Cell Expander).

In some embodiments, isolation is carried out by enrichment for a particular cell population by positive selection, or depletion of a particular cell population, by negative selection. In some embodiments, positive or negative selection is accomplished by incubating cells with one or more antibodies or other binding agent that specifically bind to one or more surface markers expressed or expressed (marker$^+$) at a relatively higher level (marker$^{high}$) on the positively or negatively selected cells, respectively.

In some embodiments, T cells are separated from a PBMC sample by negative selection of markers expressed on non-T cells, such as B cells, monocytes, or other white blood cells, such as CD14. In some aspects, a $CD4^+$ or $CD8^+$ selection step is used to separate $CD4^+$ helper and $CD8^+$ cytotoxic T cells. Such $CD4^+$ and $CD8^+$ populations can be further sorted into sub-populations by positive or negative selection for markers expressed or expressed to a relatively higher degree on one or more naive, memory, and/or effector T cell subpopulations.

In some embodiments, $CD8^+$ cells are further enriched for or depleted of naive, central memory, effector memory, and/or central memory stem cells, such as by positive or negative selection based on surface antigens associated with the respective subpopulation. In some embodiments, enrichment for central memory T ($T_{CM}$) cells is carried out to increase efficacy, such as to improve long-term survival, expansion, and/or engraftment following administration, which in some aspects is particularly robust in such sub-populations. See Terakura et al. (2012) Blood. 1:72-82; Wang et al. (2012) *J Immunother.* 35(9):689-701. In some embodiments, combining $T_{CM}$-enriched CD8$^+$ T cells and CD4$^+$ T cells further enhances efficacy.

In embodiments, memory T cells are present in both CD62L$^+$ and CD62L$^-$ subsets of CD8$^+$ peripheral blood lymphocytes. PBMC can be enriched for or depleted of CD62L$^-$CD8$^+$ and/or CD62L$^+$CD8$^+$ fractions, such as using anti-CD8 and anti-CD62L antibodies.

In some embodiments, the enrichment for central memory T ($T_{CM}$) cells is based on positive or high surface expression of CD45RO, CD62L, CCR7, CD28, CD3, and/or CD 127; in some aspects, it is based on negative selection for cells expressing or highly expressing CD45RA and/or granzyme B. In some aspects, isolation of a CD8$^+$ population enriched for $T_{CM}$ cells is carried out by depletion of cells expressing CD4, CD14, CD45RA, and positive selection or enrichment for cells expressing CD62L. In one aspect, enrichment for central memory T ($T_{CM}$) cells is carried out starting with a negative fraction of cells selected based on CD4 expression, which is subjected to a negative selection based on expression of CD14 and CD45RA, and a positive selection based on CD62L. Such selections in some aspects are carried out simultaneously and in other aspects are carried out sequentially, in either order. In some aspects, the same CD4 expression-based selection step used in preparing the CD8$^+$ cell population or subpopulation, also is used to generate the CD4$^+$ cell population or sub-population, such that both the positive and negative fractions from the CD4-based separation are retained and used in subsequent steps of the methods, optionally following one or more further positive or negative selection steps.

In a particular example, a sample of PBMCs or other white blood cell sample is subjected to selection of CD4$^+$ cells, where both the negative and positive fractions are retained. The negative fraction then is subjected to negative selection based on expression of CD14 and CD45RA or CD19, and positive selection based on a marker characteristic of central memory T cells, such as CD62L or CCR7, where the positive and negative selections are carried out in either order.

CD4$^+$ T helper cells are sorted into naïve, central memory, and effector cells by identifying cell populations that have cell surface antigens. CD4$^+$ lymphocytes can be obtained by standard methods. In some embodiments, naive CD4$^+$ T lymphocytes are CD45RO$^-$, CD45RA$^+$, CD62L$^+$, CD4$^+$ T cells. In some embodiments, central memory CD4$^+$ cells are CD62L$^+$ and CD45RO$^+$. In some embodiments, effector CD4$^+$ cells are CD62L$^-$ and CD45RO$^-$.

In one example, to enrich for CD4$^+$ cells by negative selection, a monoclonal antibody cocktail typically includes antibodies to CD14, CD20, CD11b, CD16, HLA-DR, and CD8. In some embodiments, the antibody or binding partner is bound to a solid support or matrix, such as a magnetic bead or paramagnetic bead, to allow for separation of cells for positive and/or negative selection. For example, in some embodiments, the cells and cell populations are separated or isolated using immunomagnetic (or affinitymagnetic) separation techniques (reviewed in Methods in Molecular Medicine, vol. 58: Metastasis Research Protocols, Vol. 2: Cell Behavior In Vitro and In Vivo, p 17-25 Edited by: S. A. Brooks and U. Schumacher © Humana Press Inc., Totowa, N.J.).

In some aspects, the sample or composition of cells to be separated is incubated with small, magnetizable or magnetically responsive material, such as magnetically responsive particles or microparticles, such as paramagnetic beads (e.g., such as Dynalbeads or MACS beads). The magnetically responsive material, e.g., particle, generally is directly or indirectly attached to a binding partner, e.g., an antibody, that specifically binds to a molecule, e.g., surface marker, present on the cell, cells, or population of cells that it is desired to separate, e.g., that it is desired to negatively or positively select.

In some embodiments, the magnetic particle or bead contains a magnetically responsive material bound to a specific binding member, such as an antibody or other binding partner. There are many well-known magnetically responsive materials used in magnetic separation methods. Suitable magnetic particles include those described in Molday, U.S. Pat. No. 4,452,773, and in European Patent Specification EP 452342 B, which are hereby incorporated by reference. Colloidal sized particles, such as those described in Owen U.S. Pat. No. 4,795,698, and Liberti et al., U.S. Pat. No. 5,200,084 are other examples.

The incubation generally is carried out under conditions whereby the antibodies or binding partners, or molecules, such as secondary antibodies or other reagents, which specifically bind to such antibodies or binding partners, which are attached to the magnetic particle or bead, specifically bind to cell surface molecules if present on cells within the sample.

In some aspects, the sample is placed in a magnetic field, and those cells having magnetically responsive or magnetizable particles attached thereto will be attracted to the magnet and separated from the unlabeled cells. For positive selection, cells that are attracted to the magnet are retained; for negative selection, cells that are not attracted (unlabeled cells) are retained. In some aspects, a combination of positive and negative selection is performed during the same selection step, where the positive and negative fractions are retained and further processed or subject to further separation steps.

In certain embodiments, the magnetically responsive particles are coated in primary antibodies or other binding partners, secondary antibodies, lectins, enzymes, or streptavidin. In certain embodiments, the magnetic particles are attached to cells via a coating of primary antibodies specific for one or more markers. In certain embodiments, the cells, rather than the beads, are labeled with a primary antibody or binding partner, and then cell-type specific secondary antibody- or other binding partner (e.g., streptavidin)-coated magnetic particles, are added. In certain embodiments, streptavidin-coated magnetic particles are used in conjunction with biotinylated primary or secondary antibodies.

In some embodiments, the magnetically responsive particles are left attached to the cells that are to be subsequently incubated, cultured and/or engineered; in some aspects, the particles are left attached to the cells for administration to a patient. In some embodiments, the magnetizable or magnetically responsive particles are removed from the cells. Methods for removing magnetizable particles from cells are known and include, e.g., the use of competing non-labeled antibodies, magnetizable particles or antibodies conjugated to cleavable linkers, etc. In some embodiments, the magnetizable particles are biodegradable.

In some embodiments, the affinity-based selection is via magnetic-activated cell sorting (MACS) (Miltenyi Biotech, Auburn, Calif.). Magnetic Activated Cell Sorting (MACS) systems are capable of high-purity selection of cells having magnetized particles attached thereto. In certain embodiments, MACS operates in a mode wherein the non-target and target species are sequentially eluted after the application of the external magnetic field. That is, the cells attached to magnetized particles are held in place while the unattached species are eluted. Then, after this first elution step is completed, the species that were trapped in the magnetic field and were prevented from being eluted are freed in some manner such that they can be eluted and recovered. In certain embodiments, the non-target cells are labelled and depleted from the heterogeneous population of cells.

In certain embodiments, the isolation or separation is carried out using a system, device, or apparatus that carries out one or more of the isolation, cell preparation, separation, processing, incubation, culture, and/or formulation steps of the methods. In some aspects, the system is used to carry out each of these steps in a closed or sterile environment, for example, to minimize error, user handling and/or contamination. In one example, the system is a system as described in International Patent Application, Publication Number WO2009/072003, or US 20110003380 A1.

In some embodiments, the system or apparatus carries out one or more, e.g., all, of the isolation, processing, engineering, and formulation steps in an integrated or self-contained system, and/or in an automated or programmable fashion. In some aspects, the system or apparatus includes a computer and/or computer program in communication with the system or apparatus, which allows a user to program, control, assess the outcome of, and/or adjust various aspects of the processing, isolation, engineering, and formulation steps.

In some aspects, the separation and/or other steps is carried out using CliniMACS system (Miltenyi Biotic), for example, for automated separation of cells on a clinical-scale level in a closed and sterile system. Components can include an integrated microcomputer, magnetic separation unit, peristaltic pump, and various pinch valves. The integrated computer in some aspects controls all components of the instrument and directs the system to perform repeated procedures in a standardized sequence. The magnetic separation unit in some aspects includes a movable permanent magnet and a holder for the selection column. The peristaltic pump controls the flow rate throughout the tubing set and, together with the pinch valves, ensures the controlled flow of buffer through the system and continual suspension of cells.

The CliniMACS system in some aspects uses antibody-coupled magnetizable particles that are supplied in a sterile, non-pyrogenic solution. In some embodiments, after labelling of cells with magnetic particles the cells are washed to remove excess particles. A cell preparation bag is then connected to the tubing set, which in turn is connected to a bag containing buffer and a cell collection bag. The tubing set consists of pre-assembled sterile tubing, including a pre-column and a separation column, and are for single use only. After initiation of the separation program, the system automatically applies the cell sample onto the separation column. Labelled cells are retained within the column, while unlabeled cells are removed by a series of washing steps. In some embodiments, the cell populations for use with the methods described herein are unlabeled and are not retained in the column. In some embodiments, the cell populations for use with the methods described herein are labeled and are retained in the column. In some embodiments, the cell populations for use with the methods described herein are eluted from the column after removal of the magnetic field, and are collected within the cell collection bag.

In certain embodiments, separation and/or other steps are carried out using the CliniMACS Prodigy system (Miltenyi Biotec). The CliniMACS Prodigy system in some aspects is equipped with a cell processing unity that permits automated washing and fractionation of cells by centrifugation. The CliniMACS Prodigy system can also include an onboard camera and image recognition software that determines the optimal cell fractionation endpoint by discerning the macroscopic layers of the source cell product. For example, peripheral blood may be automatically separated into erythrocytes, white blood cells and plasma layers. The CliniMACS Prodigy system can also include an integrated cell cultivation chamber which accomplishes cell culture protocols such as, e.g., cell differentiation and expansion, antigen loading, and long-term cell culture. Input ports can allow for the sterile removal and replenishment of media and cells can be monitored using an integrated microscope. See, e.g., Klebanoff et al. (2012) *J Immunother.* 35(9): 651-660, Terakura et al. (2012) Blood. 1:72-82, and Wang et al. (2012) *J Immunother.* 35(9):689-701.

In some embodiments, a cell population described herein is collected and enriched (or depleted) via flow cytometry, in which cells stained for multiple cell surface markers are carried in a fluidic stream. In some embodiments, a cell population described herein is collected and enriched (or depleted) via preparative scale (FACS)-sorting. In certain embodiments, a cell population described herein is collected and enriched (or depleted) by use of microelectromechanical systems (MEMS) chips in combination with a FACS-based detection system (see, e.g., WO 2010/033140, Cho et al. (2010) Lab Chip 10, 1567-1573; and Godin et al. (2008) J Biophoton. 1(5):355-376. In both cases, cells can be labeled with multiple markers, allowing for the isolation of well-defined T cell subsets at high purity.

In some embodiments, the antibodies or binding partners are labeled with one or more detectable marker, to facilitate separation for positive and/or negative selection. For example, separation may be based on binding to fluorescently labeled antibodies. In some examples, separation of cells based on binding of antibodies or other binding partners specific for one or more cell surface markers are carried in a fluidic stream, such as by fluorescence-activated cell sorting (FACS), including preparative scale (FACS) and/or microclectromechanical systems (MEMS) chips, e.g., in combination with a flow-cytometric detection system. Such methods allow for positive and negative selection based on multiple markers simultaneously.

In some embodiments, the preparation methods include steps for freezing, e.g., cryopreserving, the cells, either before or after isolation, incubation, and/or engineering. In some embodiments, the freeze and subsequent thaw step removes granulocytes and, to some extent, monocytes in the cell population. In some embodiments, the cells are suspended in a freezing solution, e.g., following a washing step to remove plasma and platelets. Any of a variety of known freezing solutions and parameters in some aspects may be used. One example involves using PBS containing 20% DMSO and 8% human serum albumin (HSA), or other suitable cell freezing media. This is then diluted 1:1 with media so that the final concentration of DMSO and HSA are 10% and 4%, respectively. The cells are then frozen to $-80°$ C. at a rate of 1° per minute and stored in the vapor phase of a liquid nitrogen storage tank.

In some embodiments, the cells are incubated and/or cultured prior to or in connection with genetic engineering, such as prior to or in connection with transduction in accord with the provided methods. The incubation steps can include culture, cultivation, stimulation, activation, and/or propagation. In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a recombinant antigen receptor.

The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

In some embodiments, the stimulating conditions or agents include one or more agent, e.g., ligand, which is capable of activating an intracellular signaling domain of a TCR complex. In some aspects, the agent turns on or initiates TCR/CD3 intracellular signaling cascade in a T cell. Such agents can include antibodies, such as those specific for a TCR component and/or costimulatory receptor, e.g., anti-CD3, anti-CD28, for example, bound to solid support such as a bead, and/or one or more cytokines. Optionally, the expansion method may further comprise the step of adding anti-CD3 and/or anti CD28 antibody to the culture medium (e.g., at a concentration of at least about 0.5 ng/ml). In some embodiments, the stimulating agents include IL-2 and/or IL-15, for example, an IL-2 concentration of at least about 10 units/mL.

In some aspects, incubation is carried out in accordance with techniques such as those described in U.S. Pat. No. 6,040,177 to Riddell et al., Klebanoff et al. (2012) J Immunother. 35(9): 651-660, Terakura et al. (2012) Blood. 1:72-82, and/or Wang et al. (2012) J Immunother. 35(9):689-701.

In some embodiments, the T cells are expanded by adding to the culture-initiating composition feeder cells, such as non-dividing peripheral blood mononuclear cells (PBMC), (e.g., such that the resulting population of cells contains at least about 5, 10, 20, or 40 or more PBMC feeder cells for each T lymphocyte in the initial population to be expanded); and incubating the culture (e.g. for a time sufficient to expand the numbers of T cells). In some aspects, the non-dividing feeder cells can comprise gamma-irradiated PBMC feeder cells. In some embodiments, the PBMC are irradiated with gamma rays in the range of about 3000 to 3600 rads to prevent cell division. In some aspects, the feeder cells are added to culture medium prior to the addition of the populations of T cells.

In some embodiments, the stimulating conditions include temperature suitable for the growth of human T lymphocytes, for example, at least about 25 degrees Celsius, generally at least about 30 degrees, and generally at or about 37 degrees Celsius. Optionally, the incubation may further comprise adding non-dividing EBV-transformed lymphoblastoid cells (LCL) as feeder cells. LCL can be irradiated with gamma rays in the range of about 6000 to 10,000 rads. The LCL feeder cells in some aspects is provided in any suitable amount, such as a ratio of LCL feeder cells to initial T lymphocytes of at least about 10:1.

In embodiments, antigen-specific T cells, such as antigen-specific CD4+ and/or CD8+ T cells, are obtained by stimulating naive or antigen specific T lymphocytes with antigen. For example, antigen-specific T cell lines or clones can be generated to cytomegalovirus antigens by isolating T cells from infected subjects and stimulating the cells in vitro with the same antigen.

In some cases, a viral vector particle may be used that does not require that the cells, e.g., T cells, are activated. In some such instances, the cells may be selected and/or transduced prior to activation and or in the absence of activation.

B. Reversible Binding or Disruption and Removal of Components

In some embodiments, the method further includes contacting the cells contacted, incubated or cultured with the oligomeric protein reagent, such as a multimerization reagent, with (i) a competition reagent (e.g. free binding partner C, e.g. C1) or an analog thereof capable of disrupting the bond between the first binding partner, e.g. C1 and the binding site Z, e.g. Z1 and/or (such as if necessary). Any of the exemplary competition reagents as described herein can be employed. In some embodiments, one or more further second competition reagents can be added dependent on the nature of the particular binding partner C and its interaction with the binding site Z. By so doing the reversible bond between said binding partner and said binding site of the oligomeric reagent is disrupted, thereby releasing in an eluate the cells, e.g. T cells, bound to the oligomeric reagent (e.g. output composition).

In some embodiments, the addition of the free partner or the analog thereof results in displacement of the binding partner C, e.g. C1, from the multimerization reagent and thus, since the binding partner is comprised in the reversibly bound agent, displacement of such agent from the multimerization reagent is achieved. This displacement of the agent in turn results in a dissociation of the first agent from the cell surface molecule, in particular if the binding affinity of the bond between the first agent and the cell surface receptor has a dissociation constant ($K_D$) in the range of $10^{-2}$ M to $10^{-13}$ M and is thus also reversible. Due to this dissociation, in some aspects, the transduction, selection, activation, stimulation and/or activation of the cell population is also terminated.

In some embodiments, the method can further include removing one or more components following the reversible dissociation or disruption. Any of the methods as described herein above for disruption and/or removal of components can be employed. In some embodiments, any unbound or residual competition reagent (e.g. biotin) in the cultured target cells (e.g. T cells) can be separated or removed. In some embodiments, the oligomerization reagent is removed, reduced or separated from the cells in the cell composition (e.g. output composition). In some embodiments, one or more of the binding agent is removed, reduced or separated from the cells in the cell composition (e.g. output composition). In some embodiments, the competition substance is removed or reduced or separated from the cells in the composition (e.g. output composition). In some embodiments, the methods employ a soluble oligomerization reagent, e.g. multimerization reagent, such that the reagent, and one or more other components, can be easily removed from the cell composition, since the cells can be simple sedimented by centrifugation and the supernatant, including the soluble multimerization agent and/or other components can be discarded. Alternatively, the soluble multimerization agent can be removed from the cell composition in a gel permeations matrix of the removal cartridge, such as described herein (e.g. International patent application WO 2013/124474).

For example, in some embodiments, the separation/removal can be carried out using a second stationary phase. For this purpose, a mixture comprising the target cells (e.g. T cells) and the oligomerization reagent, such as can remain present in the output composition, are exposed, to a suitable stationary phase, which can be a second stationary phase. This stationary phase may be a gel filtration matrix and/or affinity chromatography matrix, wherein the gel filtration and/or affinity chromatography matrix comprises an affinity reagent. The affinity reagent comprised on the chromatography resin include a binding partner D that (specifically) binds to the binding site Z1 and/or binding site Z2, if present, of the oligomeric reagent, thereby immobilizing the oligomeric reagent on the stationary phase. If a streptavidin based oligomeric reagent is used and the binding agents have a streptavidin binding peptide as binding partner C1 or C2, the binding partner D that is comprised in the affinity reagent of this stationary phase can be biotin. The soluble oligomer of streptavidin or of a streptavidin mutein that is used as an oligomerization reagent then binds to the biotin that is usually covalently coupled to a chromatography matrix such as biotin-Sepharose™ that is commercially available. In some such embodiments, the cells (e.g. output composition) can be recovered away from the oligomerization reagent.

In some embodiments, the ability to remove the reagent and other components form the composition has the further advantage of being able to avoid any solid support such as magnetic beads. In some embodiments, this means there is no risk or minimal risk of contamination of the activated T cells by such magnetic beads. In some embodiments, this also means that a process that is compliant with GMP standards can be more easily established compared to other methods, such as the use of Dynabeads® in which additional measures have to be taken to ensure that the final expanded T cell population is free of magnetic beads. In some embodiments, since no solid phase (e.g. magnetic beads) are present, the present invention also provides for an automated closed system for expansion of the cells that can be integrated into known cell expansion systems such as the Xuri Cell Expansion System W25 and WAVE Bioreactor 2/10 System, available from GE Healthcare (Little Chalfont, Buckinghamshire, United Kingdom) or the Quantum® Cell Expansion System, available from TerumoBCT Inc. (Lakewood, Colo., USA).

C. Further Processing

In some embodiments, the processing steps for transduction, such as in connection with cell engineering, can additionally include culture, cultivation, stimulation, activation, and/or propagation of cells. In some embodiments, the input and/or output compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for activating the cells for transduction with the viral vector.

In some embodiments, optionally, the method includes an incubation in which a further portion of the incubation, e.g. a further portion subsequent to the contacting of the cells with the oligomeric reagent, such as multimerization reagent, and viral vector particles. In some embodiments, the further incubation is carried out subsequent to disruption of the viral particle-binding agent and the reagent and/or the selection agent and the reagent. In some embodiments, the further incubation is carried out without rotation or centrifugation, which generally is carried out subsequent to the at least portion of the incubation done under rotation, e.g. in connection with centrifugation or spinoculation. In some embodiments, the further incubation is carried out outside of a stationary phase, such as outside of a chromatography matrix, for example, in solution. In some such embodiments, the further incubation is effected under conditions to result in integration of the viral vector into a host genome of one or more of the cells.

It is within the level of a skilled artisan to assess or determine if the incubation has resulted in integration of viral vector particles into a host genome, and hence to empirically determine the conditions for a further incubation. In some embodiments, integration of a viral vector into a host genome can be assessed by measuring the level of expression of a recombinant protein, such as a heterologous protein, encoded by a nucleic acid contained in the genome of the viral vector particle following incubation. A number of well-known methods for assessing expression level of recombinant molecules may be used, such as detection by affinity-based methods, e.g., immunoaffinity-based methods, e.g., in the context of cell surface proteins, such as by flow cytometry. In some examples, the expression is measured by detection of a transduction marker and/or reporter construct. In some embodiments, nucleic acid encoding a truncated surface protein is included within the vector and used as a marker of expression and/or enhancement thereof.

In some embodiments, the further incubation is carried out in the same container or apparatus in which the contacting occurred. In some embodiments, the further incubation is carried out in a different container or apparatus from that in which the contacting occurred, such as by transfer, e.g. automatic transfer, of the cell composition into a different container or apparatus subsequent to contacting with the viral particles and reagent. In some embodiments, the further incubation is carried out without removing the reagent from the input composition prior to the incubation. In some embodiments, the further incubation is carried out without removing the reagent during the further incubation. In some embodiments, the reagent is included during at least a portion of the further incubation, such as for at least half of the further incubation, but then is removed from the composition prior to one or more further processing steps. In some embodiments, subsequent to the further incubation, the process for preparing the cells can further include washing or formulating the cells.

In some embodiments, the further incubation is performed under conditions for stimulation and/or activation of cells, which conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

In some embodiments, the stimulating conditions or agents include one or more agent (e.g. stimulatory and/or accessory agents), e.g., ligand, which is capable of activating an intracellular signaling domain of a TCR complex. In some aspects, the agent turns on or initiates TCR/CD3 intracellular signaling cascade in a T cell, such as agents suitable to deliver a primary signal, e.g., to initiate activation of an ITAM-induced signal, such as those specific for a TCR component, and/or an agent that promotes a costimulatory signal, such as one specific for a T cell costimulatory receptor, e.g., anti-CD3, anti-CD28, or anti-41-BB, for example, bound to solid support such as a bead, and/or one or more cytokines. Among the stimulating agents are anti-CD3/anti-CD28 beads (e.g., DYNABEADS® M-450 CD3/CD28 T Cell Expander, and/or ExpACT® beads). Optionally, the expansion method may further comprise the step of adding anti-CD3 and/or anti-CD28 antibody to the culture medium. In some embodiments, the stimulating agents include IL-2 and/or IL-15, for example, an IL-2 concentration of at least about 10 units/mL. In some embodiments, incubation is carried out in accordance with techniques such as those described in U.S. Pat. No. 6,040,177 to Riddell et al., Klebanoff et al. (2012) J Immunother. 35(9): 651-660, Terakura et al. (2012) Blood. 1:72-82, and/or Wang et al. (2012) J Immunother. 35(9):689-701.

In some embodiments, the further incubation is effected in the presence of a stimulating agent (e.g. a cytokine, such as IL-2).

In some embodiments, the further incubation is carried out at temperatures greater than room temperature, such as greater than or greater than about 25° C., such as generally greater than or greater than about 32° C., 35° C. or 37° C. In some embodiments, the further incubation is carried out at a temperature of at or about 37° C.±2° C., such as at a temperature of at or about 37° C.

In some embodiments, the total duration of the incubation, such as incubation with one or more stimulating agent, is between or between about 1 hour and 96 hours, 1 hour and 72 hours, 1 hour and 48 hours, 4 hours and 36 hours, 8 hours and 30 hours or 12 hours and 24 hours, such as at least or about at least 6 hours, 12 hours, 18 hours, 24 hours, 36 hours or 72 hours. In some embodiments, the further incubation is for a time between or about between 1 hour and 48 hours, 4 hours and 36 hours, 8 hours and 30 hours or 12 hours and 24 hours, inclusive.

In some embodiments, the further incubation occurs in a closed system. In some embodiments, after elution of cells from the reagent, such as into a container, e.g. bag, tube, or vessel, the container containing the eluted composition is incubated for a further portion of time. In some embodiments, the container is incubated at a temperature of at or about 37° C.±2° C. for a time between or about between 1 hour and 48 hours, 4 hours and 36 hours, 8 hours and 30 hours or 12 hours and 24 hours, inclusive.

D. Exemplary Feature of Transduced Cells

In some embodiments, the methods result in transduction of a certain number or percentage of the cells in the output composition (e.g. the eluted composition) or subset thereof. For example, in some embodiments, at least 2.5%, at least 5%, at least 6%, at least 8%, at least 10%, at least 20%, at least 25%, at least 30%, at least 40%, at least 50%, or at least 75% of the total cells (or of a particular target cell type, such as T cells) in the output composition, e.g. eluted composition, are transduced with said viral vector and/or express the recombinant gene product encoded thereby. In some embodiments, the methods of transduction result in an output composition, e.g. eluted composition, in which at least 2.5%, at least 5%, at least 6%, at least 8%, at least 10%, at least 20%, at least 25%, at least 30%, at least 40%, at least 50%, or at least 75% of the total cells, such as T cells, in the composition are transduced with the viral vector and/or express the recombinant gene product encoded thereby. Transduction of the cells may be detected by detecting the presence of recombinant nucleic acid, e.g., transgene, included in the vector or product thereof in the cell. In some embodiments, the product is detected on the surface of the cell, indicating the cell has been successfully transduced. In some embodiments, detection of transduction involves detection of a transduction marker, such as another transgene or product included for the purposes of marking transduced cells, and/or other selection marker.

In some embodiments, the methods are capable of achieving such at least a particular transduction efficiency under certain conditions. For example, in some embodiments, where the input composition includes the virus and cells at a ratio of from or from about 1 infectious unit (IU) per one of the cells to 10 IU per one of the cells, such as at least or at or about 1 infectious units (IU) per one of the cells, or at least or at or about 2 IU per one of the cells, at least or at or about 5 IU per one of the cells, or at least or at or about 10 IU per one of the cells, the method is capable of producing an output composition in which at least 10%, at least 25%, at least 30%, at least 40%, at least 50%, or at least 75% of the cells in the composition generated by the method comprise, e.g., have been transduced with, the recombinant viral vector.

In some embodiments, the output composition, e.g. eluted composition, resulting from the transduction methods includes a particular average or mean number of copies of the transduced vector per cell (vector copy number (VCN)). VCN may be expressed in terms of the number of copies in a single cell. Alternatively, it may be expressed as an average number over a total cell population or composition, such as the output or transduced composition (including any non-transduced cells within the composition, which would not include any copies of the vector). Alternatively, VCN may be expressed in terms of average copy number only among the transduced cells. In some embodiments, among all the cells in the transduced or eluted composition produced by the methods, the average VCN is no more than at or about 10, 5, 4, 2.5, 1.5, or 1. In some embodiments, among the cells in the transduced or eluted composition that contain the recombinant viral vector or express the recombinant gene product, the average VCN is no more than at or about 4, 3, 2, 2.5, 1.5, or 1.

In some aspects, using the provided methods it is possible to enhance or increase transduction in a subset of cells, such as T cells, which can be reversibly selected in the presence of the at least one or more selection agent in an incubation or culture that occurs during at least a portion of the contacting (e.g. transducing) of cells with the oligomeric reagent and viral particles. In some embodiments, transduction can be increased at least 1.5-fold, at least 2.0-fold, at least 3.0-fold, at least 4.0-fold, at least 5.0-fold, at least 6.0-fold, at least 7.0-fold, at least 8.0-fold, at least 9.0-fold, at least 10-fold or more in a subset of cells, such as T cells, in the output composition that are positive for a selection marker when contacted, such as incubated, in the presence of the selection agent that specifically binds to the selection marker compared to the contacting, such as incubation, in the presence of the reagent not including the selection agent. In some embodiments, the selection marker can be any selection marker as described herein. In some embodiments, the selection marker is selected from among CD25, CD28, CD62L, CCR7, CD27, CD127, CD3, CD4, CD8, CD45RA, and/or CD45RO. In some embodiments, the ability to selectively or preferentially target transduction of cells means that transduction can be performed in a mixed population of cells without first isolating or selecting cells prior to the initiation of the processes for cell engineering, e.g. activation and/or transducing cells. In some embodiments, the provided methods do not include a step of selecting or isolating cells by immunoaffinity based methods prior to activation of the cells or prior to the initiation of transduction of the cells.

Also provided are compositions produced by any of the above methods. In some embodiments, the compositions contain at least $1 \times 10^7$ cells or $5 \times 10^7$ cells, such as at least $1 \times 10^8$ cells, $2 \times 10^8$ cells, $4 \times 10^8$ cells, $6 \times 10^8$, $8 \times 10^8$ cells or $1 \times 10^9$ cells, in which at least a plurality of cells are transduced with the recombinant viral vector. In some embodiments, the cells are T cells.

IV. VIRAL VECTOR PARTICLES

In some embodiments, the methods involve contacting a cell composition, such as an input composition, with a viral particle (also referred to as "viral vector particles") in the presence of an oligomeric reagent, such as multimerization reagent as described. In some aspects, a cell composition containing a plurality of viral vector particles is contacted with a viral particle-binding agent reversibly bound to a reagent or to a reagent to which the viral vector particles can reversibly bind.

In some embodiments, the viral vector particles are retroviral vector particles, such as lentiviral or gammaretroviral vectors particles, containing a nucleic acid encoding a recombinant and/or heterologous molecule, e.g., recombinant or heterologous protein, such as a recombinant and/or heterologous receptor, such as chimeric antigen receptor (CAR) or other antigen receptor, in a genome of the viral vector. The genome of the viral vector particle typically includes sequences in addition to the nucleic acid encoding the recombinant molecule. Such sequences may include sequences that allow the genome to be packaged into the virus particle and/or sequences that promote expression of a nucleic acid encoding a recombinant receptor, such as a CAR.

In some embodiments, the retroviral vector particle is an HIV-1 lentiviral vector particle. In some embodiments, the viral vector particle, such as retroviral vector particle, is pseudotyped with VSV-G or other viral envelope glycoprotein. In some embodiments, the viral vector particle contains on its surface a synthetic moiety, such as a peptide or tag (e.g. affinity tag), fused or conjugated to a viral envelope glycoprotein as described.

A. Viral Vector

The provided viral vector particles contain a genome derived from a retroviral genome based vector, such as derived from a gammaretroviral or lentiviral genome based vector. Any of a large number of such suitable vector genomes are known ((see, e.g., Koste et al. (2014) Gene Therapy 2014 Apr. 3. doi: 10.1038/gt.2014.25; Carlens et al. (2000) Exp Hematol 28(10): 1137-46; Alonso-Camino et al. (2013) Mol Ther Nucl Acids 2, e93; Park et al., Trends Biotechnol. 2011 Nov. 29(11): 550-557; Pfeifer and Verma (2001) Annu. Rev. Genomics Hum. Genet., 2:177-211). In some aspects of the provided viral vectors, the heterologous nucleic acid encoding a recombinant receptor, such as an antigen receptor, such as a CAR, is contained and/or located between the 5' LTR and 3' LTR sequences of the vector genome.

In some embodiments, the viral vector genome is a lentivirus genome, such as an HIV-1 genome or an SIV genome. For example, lentiviral vectors have been generated by multiply attenuating virulence genes, for example, the genes env, vif, vpu and nef can be deleted, making the vector safer for therapeutic purposes. Lentiviral vectors are known. See Naldini et al., (1996 and 1998); Zufferey et al., (1997); Dull et al., 1998, U.S. Pat. Nos. 6,013,516; and 5,994,136). In some embodiments, these viral vectors are plasmid-based or virus-based, and are configured to carry the essential sequences for incorporating foreign nucleic acid, for selection, and for transfer of the nucleic acid into a host cell. Known lentiviruses can be readily obtained from depositories or collections such as the American Type Culture Collection ("ATCC"; 10801 University Blvd., Manassas, Va. 20110-2209), or isolated from known sources using commonly available techniques.

Non-limiting examples of lentiviral vectors include those derived from a lentivirus, such as Human Immunodeficiency Virus 1 (HIV-1), HIV-2, an Simian Immunodeficiency Virus (SIV), Human T-lymphotropic virus 1 (HTLV-1), HTLV-2 or equine infection anemia virus (E1AV). For example, lentiviral vectors have been generated by multiply attenuating the HIV virulence genes, for example, the genes env, vif, vpr, vpu and nef are deleted, making the vector safer for therapeutic purposes. Lentiviral vectors are known in the art, see Naldini et al., (1996 and 1998); Zufferey et al., (1997); Dull et al., 1998, U.S. Pat. Nos. 6,013,516; and 5,994,136). In some embodiments, these viral vectors are plasmid-based or virus-based, and are configured to carry the essential sequences for incorporating foreign nucleic acid, for selection, and for transfer of the nucleic acid into a host cell. Known lentiviruses can be readily obtained from depositories or collections such as the American Type Culture Collection ("ATCC"; 10801 University Blvd., Manassas, Va. 20110-2209), or isolated from known sources using commonly available techniques.

In some embodiments, the viral genome vector can contain sequences of the 5' and 3' LTRs of a retrovirus, such as a lentivirus. In some aspects, the viral genome construct may contain sequences from the 5' and 3' LTRs of a lentivirus, and in particular can contain the R and U5 sequences from the 5' LTR of a lentivirus and an inactivated or self-inactivating 3' LTR from a lentivirus. The LTR sequences can be LTR sequences from any lentivirus from any species. For example, they may be LTR sequences from HIV, SIV, FIV or BIV. Typically, the LTR sequences are HIV LTR sequences.

In some embodiments, the nucleic acid of a viral vector, such as an HIV viral vector, lacks additional transcriptional units. The vector genome can contain an inactivated or self-inactivating 3' LTR (Zufferey et al. J Virol 72: 9873, 1998; Miyoshi et al., J Virol 72:8150, 1998). For example, deletion in the U3 region of the 3' LTR of the nucleic acid used to produce the viral vector RNA can be used to generate self-inactivating (SIN) vectors. This deletion can then be transferred to the 5' LTR of the proviral DNA during reverse transcription. A self-inactivating vector generally has a deletion of the enhancer and promoter sequences from the 3' long terminal repeat (LTR), which is copied over into the 5' LTR during vector integration. In some embodiments enough sequence can be eliminated, including the removal of a TATA box, to abolish the transcriptional activity of the LTR. This can prevent production of full-length vector RNA in transduced cells. In some aspects, the U3 element of the 3' LTR contains a deletion of its enhancer sequence, the TATA box, Sp1 and NF-kappa B sites. As a result of the self-inactivating 3' LTR, the provirus that is generated following entry and reverse transcription contains an inactivated 5' LTR. This can improve safety by reducing the risk of mobilization of the vector genome and the influence of the LTR on nearby cellular promoters. The self-inactivating 3' LTR can be constructed by any method known in the art. In some embodiments, this does not affect vector titers or the in vitro or in vivo properties of the vector.

Optionally, the U3 sequence from the lentiviral 5' LTR can be replaced with a promoter sequence in the viral construct, such as a heterologous promoter sequence. This can increase the titer of virus recovered from the packaging cell line. An enhancer sequence can also be included. Any enhancer/promoter combination that increases expression of the viral RNA genome in the packaging cell line may be used. In one example, the CMV enhancer/promoter sequence is used (U.S. Pat. Nos. 5,385,839 and 5,168,062).

In certain embodiments, the risk of insertional mutagenesis can be minimized by constructing the retroviral vector genome, such as lentiviral vector genome, to be integration defective. A variety of approaches can be pursued to produce a non-integrating vector genome. In some embodiments, a mutation(s) can be engineered into the integrase enzyme component of the pol gene, such that it encodes a protein with an inactive integrase. In some embodiments, the vector genome itself can be modified to prevent integration by, for example, mutating or deleting one or both attachment sites, or making the 3' LTR-proximal polypurine tract (PPT) non-functional through deletion or modification. In some embodiments, non-genetic approaches are available; these include pharmacological agents that inhibit one or more functions of integrase. The approaches are not mutually exclusive; that is, more than one of them can be used at a time. For example, both the integrase and attachment sites can be non-functional, or the integrase and PPT site can be non-functional, or the attachment sites and PPT site can be non-functional, or all of them can be non-functional. Such methods and viral vector genomes are known and available (see Philpott and Thrasher, *Human Gene Therapy* 18:483, 2007; Engelman et al. J Virol 69:2729, 1995; Brown et al *J Virol* 73:9011 (1999); WO 2009/076524; McWilliams et al., *J Virol* 77:11150, 2003; Powell and Levin *J Virol* 70:5288, 1996).

In some embodiments, the vector contains sequences for propagation in a host cell, such as a prokaryotic host cell. In some embodiments, the nucleic acid of the viral vector contains one or more origins of replication for propagation in a prokaryotic cell, such as a bacterial cell. In some embodiments, vectors that include a prokaryotic origin of replication also may contain a gene whose expression confers a detectable or selectable marker such as drug resistance.

B. Nucleic Acid

I. Recombinant Receptor, e.g. Chimeric Antigen Receptor

In some embodiments, the viral vector contains a nucleic acid that encodes a heterologous recombinant molecule. In some embodiments, the heterologous recombinant molecule is or includes a recombinant receptor, e.g. anantigen receptor, SB-transposons, e.g. for gene silencing, capsid-enclosed transposons, homologous double stranded nucleic acid, e.g. for genomic recombination or reporter genes (e.g. fluorescent proteins, such as GFP) or luciferase).

In some embodiments, the heterologous recombinant molecule is a recombinant receptor, such as a chimeric receptor. The recombinant receptor, such as heterologous receptor, may include antigen receptors, such as functional non-TCR antigen receptors, including chimeric antigen receptors (CARs), and other antigen-binding receptors such as transgenic T cell receptors (TCRs). The receptors may also include other receptors, such as other chimeric receptors, such as receptors that bind to particular ligands and having transmembrane and/or intracellular signaling domains similar to those present in a CAR.

In any of such examples, the nucleic acid is inserted or located in a region of the viral vector, such as generally in a non-essential region of the viral genome. In some embodiments, the nucleic acid is inserted into the viral genome in the place of certain viral sequences to produce a virus that is replication defective.

In some embodiments, the encoded recombinant antigen receptor, e.g., CAR, is one that is capable of specifically binding to one or more ligand on a cell or disease to be targeted, such as a cancer, infectious disease, inflammatory or autoimmune disease, or other disease or condition, including those described herein for targeting with the provided methods and compositions. Exemplary antigens are orphan tyrosine kinase receptor ROR1, tEGFR, Her2, L1-CAM, CD19, CD20, CD22, mesothelin, CEA, and hepatitis B surface antigen, anti-folate receptor, CD23, CD24, CD30, CD33, CD38, CD44, EGFR, EGP-2, EGP-4, OEPHa2, ErbB2, 3, or 4, FBP, fetal acethycholine e receptor, GD2, GD3, HMW-MAA, IL-22R-alpha, IL-13R-alpha2, kdr, kappa light chain, Lewis Y, L1-cell adhesion molecule, MAGE-A1, mesothelin, MUC1, MUC16, PSCA, NKG2D Ligands, NY-ESO-1, MART-1, gp100, oncofetal antigen, ROR1, TAG72, VEGF-R2, carcinoembryonic antigen (CEA), prostate specific antigen, PSMA, Her2/neu, estrogen receptor, progesterone receptor, ephrinB2, CD123, CS-1, c-Met, GD-2, and MAGE A3, CE7, Wilms Tumor 1 (WT-1), a cyclin, such as cyclin A1 (CCNA1), and/or biotinylated molecules, and/or molecules expressed by and/or characteristic of or specific for HIV, HCV, HBV, HPV, and/or other pathogens and/or oncogenic versions thereof.

Antigen receptors, including CARs and recombinant TCRs, and production and introduction thereof, in some embodiments include those described, for example, in international patent application publication numbers WO200014257, WO2013126726, WO2012/129514, WO2014031687, WO2013/166321, WO2013/071154, WO2013/123061 U.S. patent application publication numbers US2002131960, US2013287748, US20130149337, U.S. Pat. Nos. 6,451,995, 7,446,190, 8,252,592, 8,339,645, 8,398,282, 7,446,179, 6,410,319, 7,070,995, 7,265,209, 7,354,762, 7,446,191, 8,324,353, and 8,479,118, and European patent application number EP2537416, and/or those described by Sadelain et al., Cancer Discov. 2013 April; 3(4): 388-398; Davila et al. (2013) *PLoS ONE* 8(4): e61338; Turtle et al., *Curr. Opin. Immunol.*, 2012 October; 24(5): 633-39; Wu et al., *Cancer,* 2012 Mar. 18(2): 160-75.

a. Chimeric Antigen Receptors

In some embodiments, the nucleic acid contained in a genome of the viral vector encodes a chimeric antigen receptor (CAR). The CAR is generally a genetically engineered receptor with an extracellular ligand binding domain, such as an extracellular portion containing an antibody or fragment thereof, linked to one or more intracellular signaling components. In some embodiments, the chimeric antigen receptor includes a transmembrane domain and/or intracellular domain linking the extracellular domain and the intracellular signaling domain. Such molecules typically mimic or approximate a signal through a natural antigen receptor and/or signal through such a receptor in combination with a costimulatory receptor.

In some embodiments, CARs are constructed with a specificity for a particular marker, such as a marker expressed in a particular cell type to be targeted by adoptive therapy, e.g., a cancer marker and/or any of the antigens described. Thus, the CAR typically includes one or more antigen-binding fragment, domain, or portion of an antibody, or one or more antibody variable domains, and/or antibody molecules. In some embodiments, the CAR includes an antigen-binding portion or portions of an antibody molecule, such as a variable heavy chain (VH) or antigen-binding portion thereof, or a single-chain antibody fragment (scFv) derived from the variable heavy (VH) and variable light (VL) chains of a monoclonal antibody (mAb).

In some embodiments, the extracellular portion of the CAR, such as an antibody portion thereof, further includes a spacer, such as a spacer region between the antigen-recognition component, e.g. scFv, and a transmembrane domain. The spacer may be or include at least a portion of an immunoglobulin constant region or variant or modified version thereof, such as a hinge region, e.g., an IgG4 hinge region, and/or a CH1/CL and/or Fc region. In some embodiments, the constant region or portion is of a human IgG, such as IgG4 or IgG1. The spacer can be of a length that provides for increased responsiveness of the cell following antigen binding, as compared to in the absence of the spacer. In some examples, the spacer is at or about 12 amino acids in length or is no more than 12 amino acids in length. Exemplary spacers include those having at least about 10 to 229 amino acids, about 10 to 200 amino acids, about 10 to 175 amino acids, about 10 to 150 amino acids, about 10 to 125 amino acids, about 10 to 100 amino acids, about 10 to 75 amino acids, about 10 to 50 amino acids, about 10 to 40 amino acids, about 10 to 30 amino acids, about 10 to 20 amino acids, or about 10 to 15 amino acids, and including any integer between the endpoints of any of the listed ranges. In some embodiments, a spacer region has about 12 amino acids or less, about 119 amino acids or less, or about 229 amino acids or less. Exemplary spacers include IgG4 hinge alone, IgG4 hinge linked to CH2 and CH3 domains, or IgG4 hinge linked to the CH3 domain. Exemplary spacers include, but are not limited to, those described in Hudecek et al. (2013) Clin. Cancer Res., 19:3153 or international patent application publication number WO2014031687.

The extracellular ligand binding, such as antigen recognition domain, generally is linked to one or more intracellular signaling components, such as signaling components that mimic activation through an antigen receptor complex, such as a TCR complex, in the case of a CAR, and/or signal via another cell surface receptor. In some embodiments, a transmembrane domain links the extracellular ligand binding and intracellular signaling domains. In some embodiments, the CAR includes a transmembrane domain fused to the extracellular domain. In one embodiment, a transmembrane domain that naturally is associated with one of the domains in the receptor, e.g., CAR, is used. In some instances, the transmembrane domain is selected or modified by amino acid substitution to avoid binding of such domains to the transmembrane domains of the same or different surface membrane proteins to minimize interactions with other members of the receptor complex.

The transmembrane domain in some embodiments is derived either from a natural or from a synthetic source. Where the source is natural, the domain in some aspects is derived from any membrane-bound or transmembrane protein. Transmembrane regions include those derived from (i.e. comprise at least the transmembrane region(s) of) the alpha, beta or zeta chain of the T-cell receptor, CD28, CD3 epsilon, CD45, CD4, CD5, CD8, CD9, CD 16, CD22, CD33, CD37, CD64, CD80, CD86, CD 134, CD137, CD 154. The transmembrane domain in some embodiments is synthetic. In some aspects, the synthetic transmembrane domain comprises predominantly hydrophobic residues such as leucine and valine. In some aspects, a triplet of phenylalanine, tryptophan and valine will be found at each end of a synthetic transmembrane domain. In some embodiments, the linkage is by linkers, spacers, and/or transmembrane domain(s).

In some embodiments, a short oligo- or polypeptide linker, for example, a linker of between 2 and 10 amino acids in length, such as one containing glycines and serines, e.g., glycine-serine doublet, is present and forms a linkage between the transmembrane domain and the cytoplasmic signaling domain of the CAR.

The receptor, e.g., the CAR, generally includes at least one intracellular signaling component or components. In some embodiments, the receptor includes an intracellular component of a TCR complex, such as a TCR CD3 chain that mediates T-cell activation and cytotoxicity, e.g., CD3 zeta chain. Thus, in some aspects, the antigen-binding portion is linked to one or more cell signaling modules. In some embodiments, cell signaling modules include CD3 transmembrane domain, CD3 intracellular signaling domains, and/or other CD transmembrane domains. In some embodiments, the receptor, e.g., CAR, further includes a portion of one or more additional molecules such as Fc receptor γ, CD8, CD4, CD25, or CD16. For example, in some aspects, the CAR or other chimeric receptor includes a chimeric molecule between CD3-zeta (CD3-ζ) or Fc receptor γ and CD8, CD4, CD25 or CD16.

In some embodiments, upon ligation of the CAR or other chimeric receptor, the cytoplasmic domain or intracellular signaling domain of the receptor activates at least one of the normal effector functions or responses of the immune cell, e.g., T cell engineered to express the CAR. For example, in some contexts, the CAR induces a function of a T cell such as cytolytic activity or T-helper activity, such as secretion of cytokines or other factors. In some embodiments, a truncated portion of an intracellular signaling domain of an antigen receptor component or costimulatory molecule is used in place of an intact immunostimulatory chain, for example, if it transduces the effector function signal. In some embodiments, the intracellular signaling domain or domains include the cytoplasmic sequences of the T cell receptor (TCR), and in some aspects also those of co-receptors that in the natural context act in concert with such receptors to initiate signal transduction following antigen receptor engagement, and/or any derivative or variant of such molecules, and/or any synthetic sequence that has the same functional capability.

In the context of a natural TCR, full activation generally requires not only signaling through the TCR, but also a costimulatory signal. Thus, in some embodiments, to promote full activation, a component for generating secondary or co-stimulatory signal is also included in the CAR. In other embodiments, the CAR does not include a component for generating a costimulatory signal. In some aspects, an additional CAR is expressed in the same cell and provides the component for generating the secondary or costimulatory signal.

T cell activation is in some aspects described as being mediated by two classes of cytoplasmic signaling sequences: those that initiate antigen-dependent primary activation through the TCR (primary cytoplasmic signaling sequences), and those that act in an antigen-independent manner to provide a secondary or co-stimulatory signal (secondary cytoplasmic signaling sequences). In some aspects, the CAR includes one or both of such signaling components.

In some aspects, the CAR includes a primary cytoplasmic signaling sequence that regulates primary activation of the TCR complex. Primary cytoplasmic signaling sequences that act in a stimulatory manner may contain signaling motifs which are known as immunoreceptor tyrosine-based activation motifs or ITAMs. Examples of ITAM containing primary cytoplasmic signaling sequences include those derived from TCR zeta, FcR gamma, FcR beta, CD3 gamma, CD3 delta, CD3 epsilon, CD8, CD22, CD79a, CD79b, and CD66d. In some embodiments, cytoplasmic signaling molecule(s) in the CAR contain(s) a cytoplasmic signaling domain, portion thereof, or sequence derived from CD3 zeta.

In some embodiments, the CAR includes a signaling domain and/or transmembrane portion of a costimulatory receptor, such as CD28, 4-1BB, OX40, CD27, DAP10, and ICOS. In some aspects, the same CAR includes both the activating and costimulatory components.

In some embodiments, the activating domain is included within one CAR, whereas the costimulatory component is provided by another CAR recognizing another antigen. In some embodiments, the CARs include activating or stimulatory CARs, and costimulatory CARs, both expressed on the same cell (see WO2014/055668). In some aspects, the CAR is the stimulatory or activating CAR; in other aspects, it is the costimulatory CAR. In some embodiments, the cells further include inhibitory CARs (iCARs, see Fedorov et al., *Sci. Transl. Medicine*, 5(215) (December, 2013), such as a CAR recognizing a different antigen, whereby an activating signal delivered through a CAR recognizing a first antigen is diminished or inhibited by binding of the inhibitory CAR to its ligand, e.g., to reduce off-target effects.

In certain embodiments, the intracellular signaling domain comprises a CD28 transmembrane and signaling domain linked to a CD3 intracellular domain. In some embodiments, the intracellular signaling domain comprises a chimeric CD28 and CD137 co-stimulatory domains, linked to a CD3 intracellular domain.

In some embodiments, a CAR can also include a transduction marker (e.g., tEGFR). In some embodiments, the intracellular signaling domain of the $CD8^+$ cytotoxic T cells is the same as the intracellular signaling domain of the $CD4^+$ helper T cells. In some embodiments, the intracellular signaling domain of the $CD8^+$ cytotoxic T cells is different than the intracellular signaling domain of the $CD4^+$ helper T cells.

In some embodiments, the CAR encompasses one or more, e.g., two or more, costimulatory domains and an activation domain, e.g., primary activation domain, in the cytoplasmic portion. Exemplary CARs include intracellular components of CD3-zeta, CD28, and 4-1BB.

In some embodiments, the recombinant receptor(s), e.g. CAR, encoded by nucleic acid(s) within the provided viral vectors further include one or more marker, e.g., for purposes of confirming transduction or engineering of the cell to express the receptor and/or selection and/or targeting of cells expressing molecule(s) encoded by the polynucleotide. In some aspects, such a marker may be encoded by a different nucleic acid or polynucleotide, which also may be introduced during the genetic engineering process, typically via the same method, e.g., transduction by the same vector or type of vector.

In some aspects, the marker, e.g., transduction marker, is a protein and/or is a cell surface molecule. Exemplary markers are truncated variants of a naturally-occurring, e.g., endogenous markers, such as naturally-occurring cell surface molecules. In some aspects, the variants have reduced immunogenicity, reduced trafficking function, and/or reduced signaling function compared to the natural or endogenous cell surface molecule. In some embodiments, the marker is a truncated version of a cell surface receptor, such as truncated EGFR (tEGFR). In some aspects, the marker includes all or part (e.g., truncated form) of CD34, a NGFR, or epidermal growth factor receptor (e.g., tEGFR). In some embodiments, the nucleic acid encoding the marker is operably linked to a polynucleotide encoding for a linker sequence, such as a cleavable linker sequence, e.g., T2A. See WO2014031687.

In some embodiments, the marker is a molecule, e.g., cell surface protein, not naturally found on T cells or not naturally found on the surface of T cells, or a portion thereof.

In some embodiments, the molecule is a non-self molecule, e.g., non-self protein, i.e., one that is not recognized as "self" by the immune system of the host into which the cells will be adoptively transferred.

In some embodiments, the marker serves no therapeutic function and/or produces no effect other than to be used as a marker for genetic engineering, e.g., for selecting cells successfully engineered. In other embodiments, the marker may be a therapeutic molecule or molecule otherwise exerting some desired effect, such as a ligand for a cell to be encountered in vivo, such as a costimulatory or immune checkpoint molecule to enhance and/or dampen responses of the cells upon adoptive transfer and encounter with ligand.

In some cases, CARs are referred to as first, second, and/or third generation CARs. In some aspects, a first generation CAR is one that solely provides a CD3-chain induced signal upon antigen binding; in some aspects, a second-generation CARs is one that provides such a signal and costimulatory signal, such as one including an intracellular signaling domain from a costimulatory receptor such as CD28 or CD137; in some aspects, a third generation CAR in some aspects is one that includes multiple costimulatory domains of different costimulatory receptors.

In some embodiments, the chimeric antigen receptor includes an extracellular ligand-binding portion, such as an antigen-binding portion, such as an antibody or fragment thereof and in intracellular domain. In some embodiments, the antibody or fragment includes an scFv or a single-domain $V_H$ antibody and the intracellular domain contains an ITAM. In some aspects, the intracellular signaling domain includes a signaling domain of a zeta chain of a CD3-zeta (CD3ζ) chain. In some embodiments, the chimeric antigen receptor includes a transmembrane domain linking the extracellular domain and the intracellular signaling domain. The extracellular domain and transmembrane can be linked directly or indirectly. In some embodiments, the extracellular domain and transmembrane are linked by a spacer, such as any described herein. In some embodiments, the chimeric antigen receptor contains an intracellular domain of a T cell costimulatory molecule, such as between the transmembrane domain and intracellular signaling domain. In some aspects, the T cell costimulatory molecule is CD28 or 41BB.

In some embodiments, the transmembrane domain of the receptor, e.g., the CAR, is a transmembrane domain of human CD28 or variant thereof, e.g., a 27-amino acid transmembrane domain of a human CD28 (Accession No.: P10747.1). In some embodiments, the intracellular domain comprises an intracellular costimulatory signaling domain of human CD28 or functional variant thereof, such as a 41 amino acid domain thereof and/or such a domain with an LL to GG substitution at positions 186-187 of a native CD28 protein. In some embodiments, the intracellular domain comprises an intracellular costimulatory signaling domain of 41BB or functional variant thereof, such as a 42-amino acid cytoplasmic domain of a human 4-1BB (Accession No. Q07011.1). In some embodiments, the intracellular signaling domain comprises a human CD3 zeta stimulatory signaling domain or functional variant thereof, such as an 112 AA cytoplasmic domain of isoform 3 of human CD3ζ (Accession No.: P20963.2) or a CD3 zeta signaling domain as described in U.S. Pat. No. 7,446,190. In some aspects, the spacer contains only a hinge region of an IgG, such as only a hinge of IgG4 or IgG1. In other embodiments, the spacer is an Ig hinge, e.g., and IgG4 hinge, linked to a CH2 and/or CH3 domains. In some embodiments, the spacer is an Ig hinge, e.g., an IgG4 hinge, linked to CH2 and CH3 domains. In some embodiments, the spacer is an Ig hinge, e.g., an IgG4 hinge, linked to a CH3 domain only. In some embodiments, the spacer is or comprises a glycine-serine rich sequence or other flexible linker such as known flexible linkers.

For example, in some embodiments, the CAR includes: an extracellular ligand-binding portion, such as an antigen-binding portion, such as an antibody or fragment thereof, including sdAbs and scFvs, that specifically binds an antigen, e.g. an antigen described herein; a spacer such as any of the Ig-hinge containing spacers; a transmembrane domain that is a portion of CD28 or a variant thereof; an intracellular signaling domain containing a signaling portion of CD28 or functional variant thereof; and a signaling portion of CD3 zeta signaling domain or functional variant thereof. In some embodiments, the CAR includes: an extracellular ligand-binding portion, such as an antigen-binding portion, such as an antibody or fragment thereof, including sdAbs and scFvs, that specifically binds an antigen, e.g. an antigen described herein; a spacer such as any of the Ig-hinge containing spacers; a transmembrane domain that is a portion of CD28 or a variant thereof; an intracellular signaling domain containing a signaling portion of 4-1BB or functional variant thereof; and a signaling portion of CD3 zeta signaling domain or functional variant thereof. In some embodiments, such CAR constructs further includes a T2A ribosomal skip element and/or a tEGFR sequence, e.g., downstream of the CAR.

b. T Cell Receptors (TCRs)

In some embodiments, the recombinant molecule(s) encoded by the nucleic acid(s) is or include a recombinant T cell receptor (TCR). In some embodiments, the recombinant TCR is specific for an antigen, generally an antigen present on a target cell, such as a tumor-specific antigen, an antigen expressed on a particular cell type associated with an autoimmune or inflammatory disease, or an antigen derived from a viral pathogen or a bacterial pathogen.

In some embodiments, the TCR is one that has been cloned from naturally occurring T cells. In some embodiments, a high-affinity T cell clone for a target antigen (e.g., a cancer antigen) is identified and isolated from a patient. In some embodiments, the TCR clone for a target antigen has been generated in transgenic mice engineered with human immune system genes (e.g., the human leukocyte antigen system, or HLA). See, e.g., tumor antigens (see, e.g., Parkhurst et al. (2009) *Clin Cancer Res.* 15:169-180 and Cohen et al. (2005) *J Immunol.* 175:5799-5808. In some embodiments, phage display is used to isolate TCRs against a target antigen (see, e.g., Varela-Rohena et al. (2008) *Nat Med.* 14:1390-1395 and Li (2005) *Nat Biotechnol.* 23:349-354.

In some embodiments, after the T-cell clone is obtained, the TCR alpha and beta chains are isolated and cloned into a gene expression vector. In some embodiments, the TCR alpha and beta genes are linked via a picornavirus 2A ribosomal skip peptide so that both chains are coexpression. In some embodiments, the nucleic acid encoding a TCR further includes a marker to confirm transduction or engineering of the cell to express the receptor.

2. Other Regulatory Elements

In some embodiments, the nucleic acid sequence contained in the viral vector genome encoding an recombinant receptor, such as an antigen receptor, for example a CAR, is operably linked in a functional relationship with other genetic elements, for example transcription regulatory sequences including promoters or enhancers, to regulate expression of the sequence of interest in a particular manner. In certain instances, such transcriptional regulatory sequences are those that are temporally and/or spatially regulated with respect to activity. Expression control elements that can be used for regulating the expression of the components are known and include, but are not limited to, inducible promoters, constitutive promoters, secretion signals, enhancers and other regulatory elements.

In some embodiments, the nucleic acid sequence encoding a recombinant receptor, such as an antigen receptor, for example a CAR, is operably linked with internal promoter/enhancer regulatory sequences. The promoters employed may be constitutive, tissue-specific, inducible, and/or useful under the appropriate conditions to direct high level expression of the introduced DNA segment. The promoter may be heterologous or endogenous. In some embodiments, a promoter and/or enhancer is produced synthetically. In some embodiments, a promoter and/or enhancer is produced using recombinant cloning and/or nucleic acid amplification technology.

In some embodiments a promoter and/or enhancer may be one that is naturally associated with a nucleic acid sequence, as may be obtained by isolating the 5' non-coding sequences located upstream of the coding segment and/or exon. Alternatively, in some embodiments the coding nucleic acid segment may be positioned under the control of a recombinant and/or heterologous promoter and/or enhancer, which is not normally associated with the coding nucleic acid sequence in the natural setting. For example, exemplary promoters used in recombinant DNA construction include, but are not limited to, the β-lactamase (penicillinase), lactose, tryptophan (trp), RNA polymerase (pol) III promoters including, the human and murine U6 pol III promoters as well as the human and murine H1 RNA pol III promoters; RNA polymerase (pol) II promoters; cytomegalovirus immediate early promoter (pCMV), elongation factor-1 alpha (EF-1 alpha), and the Rous Sarcoma virus long terminal repeat promoter (pRSV) promoter systems. In some embodiments, the promoter may be obtained, for example, from the genomes of viruses such as polyoma virus, fowlpox virus, adenovirus, bovine papilloma virus, avian sarcoma virus, cytomegalovirus, a retrovirus, hepatitis-B virus and Simian Virus 40 (SV40). The promoter may also be, for example, a heterologous mammalian promoter, e.g., the actin promoter or an immunoglobulin promoter, a heat-shock promoter, or the promoter normally associated with the native sequence, provided such promoters are compatible with the target cell. In one embodiment, the promoter is the naturally occurring viral promoter in a viral expression system.

In some embodiments, the promoter may be constitutively active. Non-limiting examples of constitutive promoters that may be used include the promoter for ubiquitin (U.S. Pat. No. 5,510,474; WO 98/32869), CMV (Thomsen et al., PNAS 81:659, 1984; U.S. Pat. No. 5,168,062), beta-actin (Gunning et al. 1989 *Proc. Natl. Acad. Sci. USA* 84:4831-4835) and pgk (see, for example, Adra et al. 1987 *Gene* 60:65-74; Singer-Sam et al. 1984 *Gene* 32:409-417; and Dobson et al. 1982 *Nucleic Acids Res.* 10:2635-2637).

In some embodiments, the promoter may be a tissue specific promoter and/or a target cell-specific promoter. In some embodiments, the promoters may be selected to allow for inducible expression of the sequence of interest. A number of systems for inducible expression are known, including the tetracycline responsive system, the lac operator-repressor system, as well as promoters responsive to a variety of environmental or physiological changes, including heat shock, metal ions, such as metallothionein promoter, interferons, hypoxia, steroids, such as progesterone or glucocorticoid receptor promoter, radiation, such as VEGF promoter. In some embodiments, the tetracycline-(tet)-regulatable system, which is based on the inhibitory action of the tet repression (tetr) of *Escherichia coli* on the tet operator sequence (TECO), can be modified for use in mammalian systems and used as a regulatable element for expression cassettes. These systems are well known. (See, Goshen and Badgered, Proc. Natl. Acad. Sci. USA 89: 5547-51 (1992), Shockett et al., Proc. Natl. Acad. Sci. USA 92:6522-26 (1996), Lindemann et al., Mol. Med. 3:466-76 (1997)).

A combination of promoters may also be used to obtain the desired expression of the gene of interest. The artisan of ordinary skill will be able to select a promoter based on the desired expression pattern of the gene in the organism or the target cell of interest.

In some embodiments, an enhancer may also be present in the viral construct to increase expression of the gene of interest. Enhancers are typically cis-acting nucleic acid elements, usually about 10 to 300 by in length, that act on a promoter to increase its transcription. Many enhancers in viral genomes, such as HIV or CMV are known. For example, the CMV enhancer (Boshart et al. *Cell,* 41:521, 1985) can be used. Other examples include, for example, the SV40 enhancer on the late side of the replication origin (bp 100-270), the cytomegalovirus early promoter enhancer, the polyoma enhancer on the late side of the replication origin, and adenovirus enhancers. In some cases, an enhancer is from a mammalian gene, such as an enhancer from a globin, elastase, albumin, alpha-fetoprotein or insulin). An enhancer can be used in combination with a heterologous promoter. The enhancer may be spliced into the vector at a position 5' or 3' to the polynucleotide sequence encoding the gene of interest, but is generally located at a site 5' from the promoter. One of ordinary skill in the art will be able to select the appropriate enhancer based on the desired expression pattern.

The viral vector genome may also contain additional genetic elements. The types of elements that can be included in the constructs are not limited in any way and can be chosen by one with skill in the art.

For example, a signal that facilitates nuclear entry of the viral genome in the target cell may be included. An example of such a signal is the HIV-1 flap signal. In addition, the vector genome may contain one or more genetic elements designed to enhance expression of the gene of interest. In some embodiments, the genome contains a post-transcriptional regulatory element (PRE) or modified form thereof that exhibits post-transcriptional activity. For example, in some embodiments, a woodchuck hepatitis virus posts-transcriptional responsive element (WPRE) may be placed into the construct (Zufferey et al. 1999. *J. Virol.* 74:3668-3681; Deglon et al. 2000. *Hum. Gene Ther.* 11:179-190).

In some instances, more than one open reading frame encoding separate heterologous proteins can be included. For example, in some embodiments, if a reporter and/or detectable and/or selectable gene is included in the expression construct, an internal ribosomal entry site (IRES) sequence can be included. Typically, the additional genetic elements are operably linked with and controlled by an independent promoter/enhancer. The additional genetic element can be a reporter gene, a selectable marker or other desired gene.

In some embodiments, other various regulatory elements can include a transcription initiation region and/or a termination region. Expression vectors may also contain sequences for the termination of transcription and for stabilizing the mRNA. Such sequences are known and are often found naturally in the 5' and, occasionally 3', untranslated regions of eukaryotic or viral DNAs or cDNAs. Examples of transcription termination region include, but are not limited to, polyadenylation signal sequences. Examples of polyadenylation signal sequences include, but are not limited to, Bovine growth hormone (BGH) poly(A), SV40 late poly(A), rabbit beta-globin (RBG) poly(A), thymidine kinase (TK) poly(A) sequences, and any variants thereof.

C. Preparation of Viral Vector Particles

The viral vector genome is typically constructed in a plasmid form that can be transfected into a packaging or producer cell line. Any of a variety of known methods can be used to produce retroviral particles whose genome contains an RNA copy of the viral vector genome. In some embodiments, at least two components are involved in making a virus-based gene delivery system: first, packaging plasmids, encompassing the structural proteins as well as the enzymes necessary to generate a viral vector particle, and second, the viral vector itself, i.e., the genetic material to be transferred. Biosafety safeguards can be introduced in the design of one or both of these components.

In some embodiments, the packaging plasmid can contain all retroviral, such as HIV-1, proteins other than envelope proteins (Naldini et al., 1998). In other embodiments, viral vectors can lack additional viral genes, such as those that are associated with virulence, e.g. vpr, vif, vpu and nef, and/or Tat, a primary transactivator of HIV. In some embodiments, lentiviral vectors, such as HIV-based lentiviral vectors, comprise only three genes of the parental virus: gag, pol and rev, which reduces or eliminates the possibility of reconstitution of a wild-type virus through recombination.

In some embodiments, the viral vector genome is introduced into a packaging cell line that contains all the components necessary to package viral genomic RNA, transcribed from the viral vector genome, into viral particles. Alternatively, the viral vector genome may comprise one or more genes encoding viral components in addition to the one or more sequences, e.g., recombinant nucleic acids, of interest. In some aspects, in order to prevent replication of the genome in the target cell, however, endogenous viral genes required for replication are removed and provided separately in the packaging cell line.

In some embodiments, a packaging cell line is transfected with one or more plasmid vectors containing the components necessary to generate the particles. In some embodiments, a packaging cell line is transfected with a plasmid containing the viral vector genome, including the LTRs, the cis-acting packaging sequence and the sequence of interest, i.e. a nucleic acid encoding an antigen receptor, such as a CAR; and one or more helper plasmids encoding the virus enzymatic and/or structural components, such as Gag, pol and/or rev. In some embodiments, multiple vectors are utilized to separate the various genetic components that generate the retroviral vector particles. In some such embodiments, providing separate vectors to the packaging cell reduces the chance of recombination events that might otherwise generate replication competent viruses. In some embodiments, a single plasmid vector having all of the retroviral components can be used.

In some embodiments, the retroviral vector particle, such as lentiviral vector particle, is pseudotyped to increase the transduction efficiency of host cells. For example, a retroviral vector particle, such as a lentiviral vector particle, in some embodiments is pseudotyped with a VSV-G glycoprotein, which provides a broad cell host range extending the cell types that can be transduced. In some embodiments, a packaging cell line is transfected with a plasmid or polynucleotide encoding a non-native envelope glycoprotein, such as to include xenotropic, polytropic or amphotropic envelopes, such as Sindbis virus envelope, GALV or VSV-G.

In some embodiments, the packaging cell line provides the components, including viral regulatory and structural proteins, that are required in trans for the packaging of the viral genomic RNA into lentiviral vector particles. In some embodiments, the packaging cell line may be any cell line that is capable of expressing lentiviral proteins and producing functional lentiviral vector particles. In some aspects, suitable packaging cell lines include 293 (ATCC CCL X), 293T, HeLA (ATCC CCL 2), D17 (ATCC CCL 183), MDCK (ATCC CCL 34), BHK (ATCC CCL-10) and Cf2Th (ATCC CRL 1430) cells.

In some embodiments, the packaging cell line stably expresses the viral protein(s). For example, in some aspects, a packaging cell line containing the gag, pol, rev and/or other structural genes but without the LTR and packaging components can be constructed. In some embodiments, a packaging cell line can be transiently transfected with nucleic acid molecules encoding one or more viral proteins along with the viral vector genome containing a nucleic acid molecule encoding a heterologous protein, and/or a nucleic acid encoding an envelope glycoprotein.

In some embodiments, the viral vectors and the packaging and/or helper plasmids are introduced via transfection or infection into the packaging cell line. The packaging cell line produces viral vector particles that contain the viral vector genome. Methods for transfection or infection are well known. Non-limiting examples include calcium phosphate, DEAE-dextran and lipofection methods, electroporation and microinjection.

When a recombinant plasmid and the retroviral LTR and packaging sequences are introduced into a special cell line (e.g., by calcium phosphate precipitation for example), the packaging sequences may permit the RNA transcript of the recombinant plasmid to be packaged into viral particles, which then may be secreted into the culture media. The media containing the recombinant retroviruses in some embodiments is then collected, optionally concentrated, and used for gene transfer. For example, in some aspects, after cotransfection of the packaging plasmids and the transfer vector to the packaging cell line, the viral vector particles are recovered from the culture media and titered by standard methods used by those of skill in the art.

In some embodiments, a retroviral vector, such as a lentiviral vector, can be produced in a packaging cell line, such as an exemplary HEK 293T cell line, by introduction of plasmids to allow generation of lentiviral particles. In some embodiments, a packaging cell is transfected and/or contains a polynucleotide encoding gag and pol, and a polynucleotide encoding a recombinant receptor, such as an antigen receptor, for example, a CAR. In some embodiments, the packaging cell line is optionally and/or additionally transfected with and/or contains a polynucleotide encoding a rev protein. In some embodiments, the packaging cell line is optionally and/or additionally transfected with and/or contains a polynucleotide encoding a non-native envelope glycoprotein, such as VSV-G. In some such embodiments, approximately two days after transfection of cells, e.g. HEK 293T cells, the cell supernatant contains recombinant lentiviral vectors, which can be recovered and titered.

Recovered and/or produced retroviral vector particles can be used to transduce target cells using the methods as described. Once in the target cells, the viral RNA is reverse-transcribed, imported into the nucleus and stably integrated into the host genome. One or two days after the integration of the viral RNA, the expression of the recombinant protein, e.g. antigen receptor, such as CAR, can be detected.

V. COMPOSITIONS, FORMULATIONS AND METHODS OF ADMINISTRATION

Also provided are compositions containing the engineered receptor (e.g., engineered antigen receptor), such as CAR or TCR, and compositions containing the engineered cells, including pharmaceutical compositions and formulations. Also provided are methods of using and uses of the compositions, such as in the treatment of diseases, conditions, and disorders in which the antigen is expressed, or in detection, diagnostic, and prognostic methods.

A. Compositions/Formulations

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

In some aspects, the choice of carrier is determined in part by the particular cell and/or by the method of administration. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001% to about 2% by weight of the total composition. Carriers are described, e.g., by Remington's Pharmaceutical Sciences 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Buffering agents in some aspects are included in the compositions. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

The formulation or composition may also contain more than one active ingredients useful for the particular indication, disease, or condition being treated with the cells, preferably those with activities complementary to the cell, where the respective activities do not adversely affect one another. Such active ingredients are suitably present in combination in amounts that are effective for the purpose intended. Thus, in some embodiments, the pharmaceutical composition further includes other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc. In some embodiments, the cells or antibodies are administered in the form of a salt, e.g., a pharmaceutically acceptable salt. Suitable pharmaceutically acceptable acid addition salts include those derived from mineral acids, such as hydrochloric, hydrobromic, phosphoric, metaphosphoric, nitric, and sulphuric acids, and organic acids, such as tartaric, acetic, citric, malic, lactic, fumaric, benzoic, glycolic, gluconic, succinic, and arylsulphonic acids, for example, p-toluenesulphonic acid.

Active ingredients may be entrapped in microcapsules, in colloidal drug delivery systems (for example, liposomes, albumin microspheres, microemulsions, nano-particles and nanocapsules) or in macroemulsions. In certain embodiments, the pharmaceutical composition is formulated as an inclusion complex, such as cyclodextrin inclusion complex, or as a liposome. Liposomes can serve to target the host cells (e.g., T-cells or NK cells) to a particular tissue. Many methods are available for preparing liposomes, such as those described in, for example, Szoka et al., Ann. Rev. Biophys. Bioeng., 9: 467 (1980), and U.S. Pat. Nos. 4,235,871, 4,501,728, 4,837,028, and 5,019,369.

The pharmaceutical composition in some aspects can employ time-released, delayed release, and sustained release delivery systems such that the delivery of the composition occurs prior to, and with sufficient time to cause, sensitization of the site to be treated. Many types of release delivery systems are available and known. Such systems can avoid repeated administrations of the composition, thereby increasing convenience to the subject and the physician.

The pharmaceutical composition in some embodiments contains cells in amounts effective to treat or prevent the disease or condition, such as a therapeutically effective or prophylactically effective amount. Therapeutic or prophylactic efficacy in some embodiments is monitored by periodic assessment of treated subjects. For repeated administrations over several days or longer, depending on the condition, the treatment is repeated until a desired suppression of disease symptoms occurs. However, other dosage regimens may be useful and can be determined. The desired dosage can be delivered by a single bolus administration of the composition, by multiple bolus administrations of the composition, or by continuous infusion administration of the composition.

The cells may be administered using standard administration techniques, formulations, and/or devices. Provided are formulations and devices, such as syringes and vials, for storage and administration of the compositions. Administration of the cells can be autologous or heterologous. For example, immunoresponsive cells or progenitors can be obtained from one subject, and administered to the same subject or a different, compatible subject. Peripheral blood derived immunoresponsive cells or their progeny (e.g., in vivo, ex vivo or in vitro derived) can be administered via localized injection, including catheter administration, systemic injection, localized injection, intravenous injection, or parenteral administration. When administering a therapeutic composition (e.g., a pharmaceutical composition containing a genetically modified immunoresponsive cell), it will generally be formulated in a unit dosage injectable form (solution, suspension, emulsion).

Formulations include those for oral, intravenous, intraperitoneal, subcutaneous, pulmonary, transdermal, intramuscular, intranasal, buccal, sublingual, or suppository administration. In some embodiments, the cell populations are administered parenterally. The term "parenteral," as used herein, includes intravenous, intramuscular, subcutaneous, rectal, vaginal, and intraperitoneal administration. In some embodiments, the cell populations are administered to a subject using peripheral systemic delivery by intravenous, intraperitoneal, or subcutaneous injection.

Compositions in some embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyoi (for example, glycerol, propylene glycol, liquid polyethylene glycol) and suitable mixtures thereof.

Sterile injectable solutions can be prepared by incorporating the cells in a solvent, such as in admixture with a suitable carrier, diluent, or excipient such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts may in some aspects be consulted to prepare suitable preparations.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, aluminum monostearate and gelatin.

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

B. Methods of Administration

Provided are methods of administering the cells, populations, and compositions, and uses of such cells, populations, and compositions to treat or prevent diseases, conditions, and disorders, including cancers. In some embodiments, the cells, populations, and compositions are administered to a subject or patient having the particular disease or condition to be treated, e.g., via adoptive cell therapy, such as adoptive T cell therapy. In some embodiments, cells and compositions prepared by the provided methods, such as engineered compositions and end-of-production compositions following incubation and/or other processing steps, are administered to a subject, such as a subject having or at risk for the disease or condition. In some aspects, the methods thereby treat, e.g., ameliorate one or more symptom of, the disease or condition, such as by lessening tumor burden in a cancer expressing an antigen recognized by an engineered T cell.

Methods for administration of cells for adoptive cell therapy are known and may be used in connection with the provided methods and compositions. For example, adoptive T cell therapy methods are described, e.g., in US Patent Application Publication No. 2003/0170238 to Gruenberg et al; U.S. Pat. No. 4,690,915 to Rosenberg; Rosenberg (2011) Nat Rev Clin Oncol. 8(10):577-85). See, e.g., Themeli et al. (2013) *Nat Biotechnol.* 31(10): 928-933; Tsukahara et al. (2013) *Biochem Biophys Res Commun* 438(1): 84-9; Davila et al. (2013) *PLoS ONE* 8(4): e61338.

As used herein, a "subject" is a mammal, such as a human or other animal, and typically is human. In some embodiments, the subject, e.g., patient, to whom the cells, cell populations, or compositions are administered is a mammal, typically a primate, such as a human. In some embodiments, the primate is a monkey or an ape. The subject can be male or female and can be any suitable age, including infant, juvenile, adolescent, adult, and geriatric subjects. In some embodiments, the subject is a non-primate mammal, such as a rodent.

As used herein, "treatment" (and grammatical variations thereof such as "treat" or "treating") refers to complete or partial amelioration or reduction of a disease or condition or disorder, or a symptom, adverse effect or outcome, or phenotype associated therewith. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. The terms do not imply complete curing of a disease or complete elimination of any symptom or effect(s) on all symptoms or outcomes.

As used herein, "delaying development of a disease" means to defer, hinder, slow, retard, stabilize, suppress and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

"Preventing," as used herein, includes providing prophylaxis with respect to the occurrence or recurrence of a disease in a subject that may be predisposed to the disease but has not yet been diagnosed with the disease. In some embodiments, the provided cells and compositions are used to delay development of a disease or to slow the progression of a disease.

As used herein, to "suppress" a function or activity is to reduce the function or activity when compared to otherwise same conditions except for a condition or parameter of interest, or alternatively, as compared to another condition. For example, cells that suppress tumor growth reduce the rate of growth of the tumor compared to the rate of growth of the tumor in the absence of the cells.

An "effective amount" of an agent, e.g., a pharmaceutical formulation, cells, or composition, in the context of administration, refers to an amount effective, at dosages/amounts and for periods of time necessary, to achieve a desired result, such as a therapeutic or prophylactic result.

A "therapeutically effective amount" of an agent, e.g., a pharmaceutical formulation or cells, refers to an amount effective, at dosages and for periods of time necessary, to achieve a desired therapeutic result, such as for treatment of a disease, condition, or disorder, and/or pharmacokinetic or pharmacodynamic effect of the treatment. The therapeutically effective amount may vary according to factors such as the disease state, age, sex, and weight of the subject, and the populations of cells administered. In some embodiments, the provided methods involve administering the cells and/or compositions at effective amounts, e.g., therapeutically effective amounts.

A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

The disease or condition that is treated can be any in which expression of an antigen is associated with and/or involved in the etiology of a disease condition or disorder, e.g. causes, exacerbates or otherwise is involved in such disease, condition, or disorder. Exemplary diseases and conditions can include diseases or conditions associated with malignancy or transformation of cells (e.g. cancer), autoimmune or inflammatory disease, or an infectious disease, e.g. caused by a bacterial, viral or other pathogen. Exemplary antigens, which include antigens associated with various diseases and conditions that can be treated, are described above. In particular embodiments, the chimeric antigen receptor or transgenic TCR specifically binds to an antigen associated with the disease or condition.

Thus, the provided methods and uses include methods and uses for adoptive cell therapy. In some embodiments, the methods include administration of the cells or a composition containing the cells to a subject, tissue, or cell, such as one having, at risk for, or suspected of having the disease, condition or disorder. In some embodiments, the cells, populations, and compositions are administered to a subject having the particular disease or condition to be treated, e.g., via adoptive cell therapy, such as adoptive T cell therapy. In some embodiments, the cells or compositions are administered to the subject, such as a subject having or at risk for the disease or condition, ameliorate one or more symptom of the disease or condition.

In some embodiments, the cell therapy, e.g., adoptive T cell therapy, is carried out by autologous transfer, in which the cells are isolated and/or otherwise prepared from the subject who is to receive the cell therapy, or from a sample derived from such a subject. Thus, in some aspects, the cells are derived from a subject, e.g., patient, in need of a treatment and the cells, following isolation and processing are administered to the same subject.

In some embodiments, the cell therapy, e.g., adoptive T cell therapy, is carried out by allogeneic transfer, in which the cells are isolated and/or otherwise prepared from a subject other than a subject who is to receive or who ultimately receives the cell therapy, e.g., a first subject. In such embodiments, the cells then are administered to a different subject, e.g., a second subject, of the same species. In some embodiments, the first and second subjects are genetically identical. In some embodiments, the first and second subjects are genetically similar. In some embodiments, the second subject expresses the same HLA class or supertype as the first subject. The cells can be administered by any suitable means. Dosing and administration may depend in part on whether the administration is brief or chronic. Various dosing schedules include but are not limited to single or multiple administrations over various timepoints, bolus administration, and pulse infusion.

In certain embodiments, the cells, or individual populations of sub-types of cells, are administered to the subject at a range of about one million to about 100 billion cells and/or that amount of cells per kilogram of body weight, such as, e.g., 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges and/or per kilogram of body weight. Again, dosages may vary depending on attributes particular to the disease or disorder and/or patient and/or other treatments. In some embodiments, the cells are administered as part of a combination treatment, such as simultaneously with or sequentially with, in any order, another therapeutic intervention, such as an antibody or engineered cell or receptor or agent, such as a cytotoxic or therapeutic agent. The cells in some embodiments are co-administered with one or more additional therapeutic agents or in connection with another therapeutic intervention, either simultaneously or sequentially in any order. In some contexts, the cells are co-administered with another therapy sufficiently close in time such that the cell populations enhance the effect of one or more additional therapeutic agents, or vice versa. In some embodiments, the cells are administered prior to the one or more additional therapeutic agents. In some embodiments, the cells are administered after the one or more additional therapeutic agents. In some embodiments, the one or more additional agents includes a cytokine, such as IL-2, for example, to enhance persistence. In some embodiments, the methods comprise administration of a chemotherapeutic agent.

Following administration of the cells, the biological activity of the engineered cell populations in some embodiments is measured, e.g., by any of a number of known methods. Parameters to assess include specific binding of an engineered or natural T cell or other immune cell to antigen, in vivo, e.g., by imaging, or ex vivo, e.g., by ELISA or flow cytometry. In certain embodiments, the ability of the engineered cells to destroy target cells can be measured using any suitable method known in the art, such as cytotoxicity assays described in, for example, Kochenderfer et al., J. Immunotherapy, 32(7): 689-702 (2009), and Herman et al. J. Immunological Methods, 285(1): 25-40 (2004). In certain embodiments, the biological activity of the cells is measured by assaying expression and/or secretion of one or more cytokines, such as CD 107a, IFN-γ, IL-2, and TNF. In some aspects the biological activity is measured by assessing clinical outcome, such as reduction in tumor burden or load.

In certain embodiments, the engineered cells are further modified in any number of ways, such that their therapeutic or prophylactic efficacy is increased. For example, the engineered CAR or TCR expressed by the population can be conjugated either directly or indirectly through a linker to a targeting moiety. The practice of conjugating compounds, e.g., the CAR or TCR, to targeting moieties is known in the art. See, for instance, Wadwa et al., J. Drug Targeting 3: 1 1 1 (1995), and U.S. Pat. No. 5,087,616.

VI. ARTICLES OF MANUFACTURE AND KITS

In some embodiments, also provided are systems, apparatuses, and kits useful in performing the provided methods. In some embodiments, provided are articles of manufacture, such as kits or devices, containing viral particles and an oligomeric protein (e.g. mutein streptavidin) reagent, and optionally instructions for use. In some embodiments, the kits can be used in methods for transducing cells, such as in accord with preparing genetically engineered cells for adoptive cell therapy.

In some embodiments, the articles of manufacture include one or more containers, typically a plurality of containers, packaging material, and a label or package insert on or associated with the container or containers and/or packaging, generally including instructions for transduction of cells, such as transduction of cells from a subject.

The articles of manufacture provided herein contain packaging materials. Packaging materials for use in packaging the provided materials are well known to those of skill in the art. See, for example, U.S. Pat. Nos. 5,323,907, 5,052,558 and 5,033,252, each of which is incorporated herein in its entirety. Examples of packaging materials include, but are not limited to, blister packs, bottles, tubes, inhalers, pumps, bags, vials, containers, syringes, or bottles. The articles of manufacture can include a needle or other injection device so as to facilitate dispensing of the materials. Typically, the packaging is non-reactive with the compositions contained therein.

In some embodiments, the viral particles and oligomeric protein (e.g. streptavidin) reagent are packaged separately. In some embodiments, each container can have a single compartment. In some embodiments, a container containing the viral particles is one that is amenable to addition of the oligomeric reagent by the user, for example through an opening in the compartment, or vice versa. Any container or other article of manufacture that is amenable to having a defining space for containment of the viral particles and/or oligomeric protein reagent and that is amenable to simple manipulation to permit addition of the final components necessary for mixture to produce a composition containing viral particles associated with the oligomeric protein reagent is contemplated. In some embodiments, the oligomeric protein (e.g. streptavidin reagent) is added to the viral particles prior to contacting with cells, such as up to 1 hour prior to contacting with cells.

In some embodiments, such materials are packaged separately in the same container, for example, such that the components can be mixed or combined in the container. In some aspects, examples of such containers include those that have an enclosed, defined space that contains the viral particles, and a separate enclosed, defined space containing the oligomeric protein reagent such that the two spaces are separated by a readily removable membrane which, upon removal, permits the components to mix. Any container or other article of manufacture is contemplated in which the components can be kept separate. In some embodiments, an article of manufacture can contain each component in adjacent compartment separated by a dividing member, such as a membrane, that, upon compression of the article or manufacture ruptures permitting separated components to mix. For suitable embodiments see e.g., containers described in U.S. Pat. Nos. 3,539,794 and 5,171,081.

In some embodiments, also provided is a system or apparatus that can be used for transduction so cells. In some embodiments, the systems or apparatuses can be used for selecting and/or activating cells and transducing cells. In some aspects, the system is used to carry out each of these steps in a closed or sterile environment, for example, to minimize error, user handling and/or contamination.

In some embodiments, the system is or comprises a stationary phase for chromatography, i.e. is or comprises a chromatography matrix. In some embodiments, the stationary phase is suitable for one or more of activating, transducing and/or stimulating cells. In some embodiments, the first stationary phase is a gel filtration matrix and/or affinity chromatography matrix, wherein the gel filtration and/or affinity chromatography matrix comprises a protein (e.g. streptavidin mutein) reagent, such as an oligomeric protein (e.g. streptavidin mutein) reagent. In some embodiments, the protein (e.g. streptavidin mutein) reagent, such as an oligomeric protein (e.g. streptavidin mutein) reagent, comprises a binding site Z1 capable of specifically binding to a binding partner C1 comprised in a binding agent, which can be a first binding agent (e.g. a selection agent and/or stimulatory agent). In some embodiments, the protein (e.g. streptavidin mutein) reagent, such as an oligomeric protein (e.g. streptavidin mutein) reagent, also comprises a binding site Z2 capable of specifically binding to a binding partner C2 comprised in a second binding agent (e.g. a selection agent and/or stimulatory agent). In some embodiments, the stationary phase is capable of associating with viral vector particles, and, if containing a binding agent specific for cells also is capable of reversibly binding to one or more molecules present on the surface of a cell. In this arrangement the stationary phase is either comprised in a chromatography column or is a planar stationary phase.

In some embodiments, the stationary phase is a first stationary phase that is operably connected to a second or third stationary phase, such as configured similarly to described above. In some embodiments, one or more of, such as each of, the stationary phases are operably connected to a removal chamber that contains a removal agent that is able to bind with high affinity to an elution reagent used to reversibly dissociate the oligomeric protein reagent from the one or more cells bound thereto via binding partner C1 or C2 of the binding agent. In some embodiments, the apparatus, such as the stationary phase, may comprise a sample inlet suitable for applying viral particles and/or cells to the stationary phase.

In some embodiments, the stationary phase is provided as a system in arrangement with or operably connected to a bioreactor. In some embodiments, the bioreactor is suitable for the expansion of cells, and the stationary phase is suitable for cell selection, cell activation or stimulation and/or cell transduction. In some embodiments, the bioreactor and the stationary phase are fluidly connected. This arrangement can be used in the serial expansion as explained above and can be integrated into known cell expansion systems such as the Quantum® cell expansion system) or the Xuri Cell Expansion System W25.

In some embodiments, the closed system is automated. In some embodiments, components associated with the system can include an integrated microcomputer, peristaltic pump, and various valves, such as pinch valves or stop cocks, to control flow of fluid between the various parts of the system. The integrated computer in some aspects controls all components of the instrument and directs the system to perform repeated procedures in a standardized sequence. In some embodiments, the peristaltic pump controls the flow rate throughout the tubing set and, together with the pinch valves, ensures the controlled flow of buffer through the system. In some embodiments, the apparatus may be designed as a functionally closed system.

VII. DEFINITIONS

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

As used herein, the singular forms "a," "an," and "the" include plural referents unless the context clearly dictates otherwise. For example, "a" or "an" means "at least one" or "one or more." It is understood that aspects and variations described herein include "consisting" and/or "consisting essentially of" aspects and variations.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

The term "about" as used herein refers to the usual error range for the respective value readily known to the skilled person in this technical field. Reference to "about" a value or parameter herein includes (and describes) embodiments that are directed to that value or parameter per se. For example, description referring to "about X" includes description of "X".

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors." Among the vectors are viral vector particles, such as retroviral, e.g., gammaretroviral and lentiviral vectors.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

As used herein, a composition refers to any mixture of two or more products, substances, or compounds, including cells. It may be a solution, a suspension, liquid, powder, a paste, aqueous, non-aqueous or any combination thereof.

As used herein, "enriching" when referring to one or more particular cell type or cell population, refers to increasing the number or percentage of the cell type or population, e.g., compared to the total number of cells in or volume of the composition, or relative to other cell types, such as by positive selection based on markers expressed by the population or cell, or by negative selection based on a marker not present on the cell population or cell to be depleted. The term does not require complete removal of other cells, cell type, or populations from the composition and does not require that the cells so enriched be present at or even near 100% in the enriched composition.

As used herein, a statement that a cell or population of cells is "positive" for a particular marker refers to the detectable presence on or in the cell of a particular marker, typically a surface marker. When referring to a surface marker, the term refers to the presence of surface expression as detected by flow cytometry, for example, by staining with an antibody that specifically binds to the marker and detecting said antibody, wherein the staining is detectable by flow cytometry at a level substantially above the staining detected carrying out the same procedure with an isotype-matched control under otherwise identical conditions and/or at a level substantially similar to that for cell known to be positive for the marker, and/or at a level substantially higher than that for a cell known to be negative for the marker.

As used herein, a statement that a cell or population of cells is "negative" for a particular marker refers to the absence of substantial detectable presence on or in the cell of a particular marker, typically a surface marker. When referring to a surface marker, the term refers to the absence of surface expression as detected by flow cytometry, for example, by staining with an antibody that specifically binds to the marker and detecting said antibody, wherein the staining is not detected by flow cytometry at a level substantially above the staining detected carrying out the same procedure with an isotype-matched control under otherwise identical conditions, and/or at a level substantially lower than that for cell known to be positive for the marker, and/or at a level substantially similar as compared to that for a cell known to be negative for the marker.

The term "expression", as used herein, refers to the process by which a polypeptide is produced based on the encoding sequence of a nucleic acid molecule, such as a gene. The process may include transcription, post-transcriptional control, post-transcriptional modification, translation, post-translational control, post-translational modification, or any combination thereof.

As used herein, a control refers to a sample that is substantially identical to the test sample, except that it is not treated with a test parameter, or, if it is a plasma sample, it can be from a normal volunteer not affected with the condition of interest. A control also can be an internal control.

VIII. EXEMPLARY EMBODIMENTS

Among the embodiments provided herein are:

1. A method for transducing cells, comprising contacting an input composition comprising a plurality of cells with (1) an oligomeric reagent; and (2) a viral particle,
optionally wherein the method produces an output composition comprising one or more transduced cells.

2. The method of embodiment 1, wherein:
the oligomeric reagent is an oligomeric protein reagent; and/or
the oligomeric reagent comprises a plurality of polypeptide monomeric units, wherein each unit optionally comprises at least at or about 10, 20, 30, or 40 amino acids in length, optionally at least at or about 50, 60, 65, 70, 80, 90, 100, 125, or 150 amino acids in length and/or comprises a weight of at least at or about 20, 30, 40, or 50 kDa, optionally wherein the reagent comprises an oligomer comprised of a plurality of multimeric subunits, which are optionally tetrameric, units and individually comprise the monomeric unit; and/or
the oligomeric reagents comprises a molecular weight of at least at or about 100, and/or between at or about 150 kDa to about 2000 kDa, about 150 kDa to about 1.500 kDa, about 150 kDa to about 1250 kDa, about 150 kDa to about 1000 kDa, about 150 kDa to about 500 kDa or about 150 kDa to about 300 kDa, about 300 kDa to about 2000 kDa, about 300 kDa to about 1500 kDa, about 300 kDa to about 1250 kDa, about 300 kDa to about 1000 kDa, about 300 kDa to about 500 kDa, about 500 kDa to about 2000 kDa, about 500 kDa to about 1500 kDa, about 500 kDa to about 1250 kDa, about 500 kDa to about 1000 kDa, about 1000 kDa to about 2000 kDa, about 1000 kDa to about 1500 kDa, about 1000 kDa to about 1250 kDa, about 1250 kDa to about 2000 kDa or about 1500 kDa to about 2000 kDa.

3. The method of embodiment 1 or embodiment 2, wherein the oligomeric protein reagent comprises, and optionally comprises multiple units of, a streptavidin, an avidin, a streptavidin analog or mutein or an avidin analog or mutein or a biologically active fragment of any of the foregoing, and/or a multimer of any of the foregoing.

4. A method for transducing cells, comprising contacting a plurality of cells with (1) a protein reagent comprising, and optionally comprising multiple units of, a streptavidin, an avidin, a streptavidin analog or mutein, an avidin analog or mutein or a biologically active fragment of any of the foregoing, and/or a multimer of any of the foregoing; and (2) a viral particle, optionally wherein the method produces an output composition comprising one or more transduced cells.

5. The method of embodiment 4, wherein the reagent is or comprises an oligomer.

6. The method of any of embodiments 1-5, wherein the contacting comprises admixing the cell with the reagent and with the viral particle, simultaneously or sequentially, in either order.

7. The method of any of embodiments 1-6, wherein during at least a portion of the contacting, the reagent and viral particle are in the presence of or contacted with the cell simultaneously.

8. The method of any of embodiments 1-7, wherein the one or more transduced cells in the output composition express a recombinant protein encoded by a heterologous nucleic acid comprised by the viral particles.

9. The method of any of embodiments 1-8, further comprising subsequently incubating the cells contacted with the viral particle, thereby producing the output composition comprising one or more transduced cells.

10. A method for transducing cells, the method comprising:
(a) contacting a viral particle with an oligomeric reagent, thereby generating a mixture comprising viral particles associated with the reagent; and
(b) contacting the mixture with an input composition comprising a plurality of cells,
optionally wherein the method produces an output composition comprising one or more transduced cells.

11. The method of embodiment 10, wherein:
the oligomeric reagent is an oligomeric protein reagent; and/or
the oligomeric reagent comprises a plurality of polypeptide monomeric units, wherein each unit optionally comprises at least at or about 10, 20, 30, or 40 amino acids in length, optionally at least at or about 50, 60, 65, 70, 80, 90, 100, 125, or 150 amino acids in length and/or comprises a weight of at least at or about 20, 30, 40, or 50 kDa, optionally wherein the reagent comprises an oligomer comprised of a plurality of multimeric subunits, which are optionally tetrameric, units and individually comprise the monomeric unit; and/or
the oligomeric reagents comprises a molecular weight of at least at or about 100, and/or between at or about 150 kDa to about 2000 kDa, about 150 kDa to about 1500 kDa, about 150 kDa to about 1250 kDa, about 150 kDa to about 1000 kDa, about 150 kDa to about 500 kDa or about 150 kDa to about 300 kDa, about 300 kDa to about 2000 kDa, about 300 kDa to about 1500 kDa, about 300 kDa to about 1250 kDa, about 300 kDa to 1000 kDa, about 300 kDa to about 500 kDa, about 500 kDa to about 2000 kDa, about 500 kDa to about 1500 kDa, about 500 kDa to about 1250 kDa, about 500 kDa to 1000 kDa, about 1000 kDa to about 2000 kDa, about 1000 kDa to about 1500 kDa, about 1000 kDa to about 1250 kDa, about 1250 kDa to about 2000 kDa or about 1500 kDa to about 2000 kDa.

12. The method of embodiment 10 or embodiment 11, wherein the oligomeric protein reagent comprises and optionally comprises multiple units of, a streptavidin, an avidin, a streptavidin analog or mutein or an avidin analog or mutein or a biologically active fragment of any of the foregoing and/or a multimer of any of the foregoing.

13. A method for transducing cells, the method comprising:
(a) contacting a viral particle with a protein reagent comprising, and optionally comprising multiple units of, a streptavidin, an avidin, a streptavidin analog or mutein, an avidin analog or mutein or a biologically active fragment of any of the foregoing and/or a multimer of any of the foregoing, thereby generating a mixture comprising viral particles associated with the reagent; and
(b) contacting the mixture with an input composition comprising a plurality of cells,
optionally wherein the method produces an output composition comprising one or more transduced cells.

14. The method of embodiment 13, wherein the reagent is or comprises an oligomer.

15. The method of any of embodiments 10-14, further comprising subsequently incubating the cells contacted with the mixture, thereby producing the output composition comprising one or more transduced cells.

16. The method of any of embodiments 9 or 15, wherein the incubation is carried out and wherein the reagent is not removed from the composition prior to the incubation, is not removed from the composition during the incubation, or is not removed from the composition during at least half of the incubation.

17. The method of any of embodiments 1-16, wherein:
the reagent is naked;
the reagent does not comprise and/or is not conjugated or reversibly bound to a binding agent;
the reagent does not comprise and or is not conjugated or bound to a molecule with a binding domain specific for a cell surface marker, optionally selected from among adhesion molecules, integrins, chemokines, cytokines, growth factors, extracellular matrix-binding molecules, viral proteins, viral entry-promoting cell surface receptors, heparin, heparan, glycans a T-cell surface marker, a CD3, a CD28 a CD4 and/or a CD8;
the reagent does not comprise and or is not conjugated or bound to a mammalian cell surface marker, an extracellular matrix component, adhesion molecule, an integrin, a lectin, an integrin-binding protein, a chemokines, a cytokine, a growth factor, an extracellular matrix-binding molecule, an ECM component, a viral protein, a viral entry-promoting cell surface receptor, heparin, heparan, glycans; and/or
the reagent does not comprise a heparin-binding domain and/or does not comprise an integrin-binding domain and/or does not comprise a VLA4-binding domain and/or does not comprise a VLA5-binding domain; and/or
the reagent does not comprise and/or is not conjugated or coupled or bound to a viral binding agent or a cell selection agent.

18. The method of any of embodiments 1-17, wherein prior to or during the contacting with the reagent, and optionally the further incubation, activating the cells in the presence of a stimulatory agent and/or wherein the contacting or incubating or portion thereof is carried out under conditions whereby the cells are stimulated or activated by the stimulatory agent, which optionally is a binding agent reversibly bound to the reagent.

19. The method of any of embodiments 1-18, wherein the reagent further comprises and/or is reversibly bound to a plurality of one or more binding agents that each is capable of specifically binding to a molecule on the surface of the viral particle and/or the surface of a target cell, which optionally is a mammalian cell, optionally a human cell.

20. A method for transducing cells, comprising incubating an input composition comprising a plurality of cells with:
1) an oligomeric protein reagent comprising a plurality of binding sites capable of reversibly binding to a binding agent, wherein one or more binding sites are reversibly bound to the binding agent; and
2) a viral particle,
wherein at least a portion of the incubation in (1) occurs simultaneously with (2) and optionally wherein the method produces an output composition comprising one or more transduced cells.

21. The method of any of embodiments 9, 15, 16 and 20, wherein:

the incubation and/or further incubation is carried out at or about 37° C.±2° C.; and/or the incubation and/or further incubation is carried out in the presence of a further agent that is capable of delivering a signal to T cells during at least a portion of the incubation and/or further incubation.

22. The method embodiment 21, wherein the further agent is capable of enhancing or inducing proliferation of CD3+ T cells, CD4+ T cells and/or CD8+ T cells.

23. The method of embodiment 21, wherein the further agent is a cytokine selected from among IL-2, IL-15, IL-7 and IL-21.

24. The method of any of embodiments 21-23, wherein the incubation or further incubation is carried out for a time that is no more than 14 days, no more than 12 days, no more than 10 days, no more than 8 days or no more than 6 days.

25. The method of any of embodiments 10-24, wherein the binding agent is a stimulatory agent and/or is capable of delivering a stimulatory signal through a TCR/CD3 complex in a T cell, a CD3-containing complex in a T cell, and/or an ITAM-containing molecule in a T cell.

26. The method any of embodiments 19-25, wherein:

the reagent comprises a plurality of binding sites capable of reversibly binding to each of the binding agents, the plurality of binding sites comprising one or more binding site, Z, which is capable of binding to a binding partner, C; and the binding agent further comprises on or more of the binding partner, C.

27. The method of any of embodiments 19-26, wherein the binding agent is or comprises a receptor-binding agent.

28. The method of embodiment 27, wherein the receptor-binding agent comprises:

a stimulatory agent capable of delivering a stimulatory signal through a TCR/CD3 complex in a T cell, a CD3-containing complex in a T cell, and/or an ITAM-containing molecule in a T cell; or specifically binds to a members or a TCR/CD3 complex or specifically binds to CD3.

29. The method of embodiment 28, wherein the receptor binding agent is a first receptor binding agent and the reagent comprises a plurality of binding sites capable of reversibly binding a second receptor binding agent, said second receptor binding agent being an accessory binding agent capable of specifically binding to a second molecule on the surface of one or more of the cells, which second molecule is optionally capable of inducing or enhancing, dampening, or modifying a signal delivered through the first receptor binding agent.

30. The method of embodiment 29, wherein:

the first receptor binding agent comprises a binding partner C1, which is capable of reversibly binding to binding site Z1 on the reagent; and the second receptor binding agent comprises a binding partner C2, which is capable of reversibly binding to binding site Z2 on the reagent.

31. The method of embodiment 30, wherein:

C1 and C2 are the same or substantially the same, or contain the same or substantially the same moiety; and/or Z1 and Z2 are the same or substantially the same or contain the same or substantially the same moiety.

32. The method of any of embodiment 19-31, wherein the binding agent is a selection agent capable of specifically binding to a molecule expressed on the surface of a target cell.

33. The method of any of embodiments 29-32, wherein the reagent comprises a further binding agent that is a selection agent capable of specifically binding to a molecule expressed on the surface of a target cell.

34. The method of embodiment 33, wherein:

the first receptor binding agent comprises a binding partner C1, which is capable of reversibly binding to binding site Z1 on the reagent;

the second receptor binding agent comprises a binding partner C2, which is capable of reversibly binding to binding site Z2 on the reagent;

the selection agent comprises a binding partner C3, which is capable of reversibly binding to binding site Z3 on the reagent.

35. The method of embodiment 34, wherein:

C1, C2 and C3 are the same or substantially the same, or contain the same or substantially the same moiety; and/or Z1, Z2 and Z3 are the same or substantially the same or contain the same or substantially the same moiety.

36. The method of any of embodiments 31-35, wherein the molecule is or comprises CD25, CD28, CD62L, CCR7, CD27, CD127, CD3, CD4, CD8, CD45RA, CD45RO and/or CD56.

37. The method of any of embodiments 31-36, wherein, during at least a portion of the method, the contacting, and/or the incubation, the binding agent binds to the molecule expressed on the surface of the target cell, thereby facilitating association between the reagent and the target cell.

38. The method of embodiment 37, wherein the association between the reagent and the target cell is capable of enhancing the transduction of the target cell, compared to transduction of a non-target cell that does not express the molecule or is not specifically bound by a binding agent on or bound to the reagent.

39. The method of any of embodiments 18-38, wherein the binding agent is or comprises an antibody, an antibody fragment, a monovalent antibody fragment, a proteinaceous binding molecule with antibody-like binding properties, a molecule containing Ig domains, a cytokine, a chemokine, an aptamer, and MHC molecule or binding fragments thereof.

40. The method of embodiment 39, wherein the antibody fragment comprises a fragment selected from the group consisting of a Fab fragment, an Fv fragment, a (Fab')$_2$-fragment, and a divalent single-chain Fv (scFv) fragment.

41. The method of any of embodiments 19-40, wherein the plurality of binding agents comprise at least 2, 4, 8, 12, 16, 20, 24, 28, 32, 36, 40, 44, 48, 52, 56, 60, 64, 72 or more.

42. The method of any of embodiments 18-41, wherein the binding agent, optionally stimulatory agent, binds to a molecule expressed on the surface of the cell that is or comprises CD3 and/or CD28.

43. The method of embodiment 42, wherein the binding agent, optionally stimulatory agent, comprises an anti-CD3 and/or anti-CD28 antibody or fragment.

44. The method of any of embodiments 1-43, wherein the input composition comprises T cells.

45. The method of embodiment 44, wherein the T cells comprise CD4+ and/or CD8+ T cells and/or a subpopulation or subset thereof and/or are enriched for a population of any of the foregoing.

46. The method of any of embodiments 1-45, wherein the input composition comprises resting or naïve cells and/or a subpopulation or subset thereof and/or are enriched for a population of any of the foregoing.

47. The method of embodiment 1-46, wherein no more than 10% of the T cells in the input composition comprise a T cell activation marker selected from the group consisting of HLA-DR, CD25, CD69, CD71, CD40L and 4-1BB; and/or lack intracellular expression of a cytokine selected from the group consisting of IL-2, IFNgamma, TNF-alpha; and/or are capable of proliferating.

48. The method of any of embodiments 1-47, wherein, prior to said contacting, the method does not comprise stimulating cells of the population under conditions that promote T cell activation.

49. The method of any of embodiments 1-48, wherein the cells in the input composition have not, prior to said contacting, been subjected to: (a) an ex vivo stimulation comprising incubation at about 37° C. and/or (b) incubation in the presence of an agent or agents selected from the group consisting of agents capable of activating, inducing a signal through a TCR complex in T cells, CD4+ T cells, and/or CD8+ T cells; agents capable of inducing proliferation of T cells, CD4+ T cells, and/or CD8+ T cells; CD3-binding molecules; CD28-binding molecules.

50. The method of any of embodiments 1-45, wherein the input composition comprises activated cells.

51. The method of any of embodiments 1-50, wherein the viral particle associates with the reagent.

52. The method of any of embodiments 1-51, wherein the reagent is not toxic to the cells or at least or at least about 75%, 85%, 90%, 95% or more of the cells are viable after the contacting, or optionally further incubating.

53. The method of any of embodiments 1-52, wherein:
the toxicity of the cells subsequent to the contacting, and/or further incubating, is reduced by greater than or greater than about 1.2-fold, 1.5-fold, 2.0-fold, 3.0-fold, 4.0-fold, 5.0-fold or 10-fold compared to the toxicity of the cells when contacted or incubated with a polycation transduction adjuvant, optionally protamine sulfate, or a fibronectin-derived transduction adjuvant, optionally RetroNectin under the same conditions; and/or
the viability of the cells subsequent to the contacting, and/or further incubating, is reduced by greater than or greater than about 1.2-fold, 1.5-fold, 2.0-fold, 3.0-fold, 4.0-fold, 5.0-fold or 10-fold compared to the toxicity of the cells when contacted or incubated with a polycation transduction adjuvant, optionally protamine sulfate, or a fibronectin-derived transduction adjuvant, optionally RetroNectin under the same conditions.

54. The method of any of embodiments 1-53, wherein individual molecules of the oligomer are crosslinked by a polysaccharide or a bifunctional linker.

55. The method of any of embodiments 1-54, wherein the reagent comprises SEQ ID NO:1 or SEQ ID NO:2 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO:1 or SEQ ID NO:2.

56. The method of any of embodiments 1-55, wherein:
the reagent comprises a streptavidin analog or mutein comprising the amino acid sequence $Val^{44}$-$Thr^{45}$-$Ala^{46}$ or $Ile^{44}$-$Gly^{45}$-$Ala^{46}$-$Arg^{47}$ at sequence positions corresponding to positions 44 to 47 with reference to positions in streptavidin in the sequence of amino acids set forth in SEQ ID NO:1; or
the streptavidin analog or mutein comprises the amino acid sequence $Val^{44}$-$Thr^{45}$-$Ala^{46}$-$Arg^{47}$ at sequence positions corresponding to positions 44 to 47 with reference to positions in streptavidin in the sequence of amino acids set forth in SEQ ID NO:1.

57. The method of any of embodiments 1-56, wherein the reagent comprises a streptavidin analog or mutein, which comprises:
a) the sequence of amino acids set forth in any of SEQ ID NOS: 3-6, 27 and 28;
b) a sequence of amino acids that exhibits at least 85%, 86%, 87%, 88%, 89%, 89%, 90%, 91%, 92%, 93%, 94%, 95%, 96%, 97%, 98%, 99% or more sequence identity to any of SEQ ID NOS:3-6, 27 and 28 and contains the amino acid sequence corresponding to $Val^{44}$-$Thr^{45}$-$Ala^{46}$-$Arg^{47}$ or $Ile^{44}$-$Gly^{45}$-$Ala^{46}$-$Arg^{47}$ and that reversibly binds to biotin or a biologically active form thereof, a biotin analog or mutein or a biologically active fragment thereof or a streptavidin-binding peptide; or
c) a functional fragment of a) or b) that reversibly binds to biotin or a biologically active form thereof, a biotin analog or mutein or a biologically active fragment thereof or a streptavidin-binding peptide.

58. The method of embodiment 56 or embodiment 57, wherein the streptavidin analog or mutein further comprises an amino acid replacement or replacements at a position corresponding to 117, 120 and/or 121 with reference to positions in streptavidin in the sequence of amino acids set forth in SEQ ID NO:1.

59. The method of embodiment 58, wherein:
the amino acid replacement or replacements are selected from among Glu117, Asp117, Arg117, Ser120, Ala120, Gly120, Trp121, Tyr121 or Phe121; or the amino acid replacement or replacements are selected from one or more of Glu117, Gly120 or Tyr121; or
the amino acid replacements are selected from Glu117, Gly120 or Tyr121.

60. The method of any of embodiments 1-59, wherein the reagent comprises a streptavidin analog or mutein, which comprises:
a) the sequence of amino acids set forth in SEQ ID NO: 27 or 28;
b) a sequence of amino acids that exhibits at least 85%, 86%, 87%, 88%, 89%, 89%, 90%, 91%, 92%, 93%, 94%, 95%, 96%, 97%, 98%, 99% or more sequence identity to SEQ ID NOS:28 and contains the amino acid sequence corresponding to $Val^{44}$, $Thr^{45}$, $Ala^{46}$, $Arg^{47}$, $Glu^{117}$, $Gly^{120}$ and $Tyr^{121}$ and reversibly binds to biotin or a biologically active fragment, a biotin analog or mutein or a biologically active fragment thereof or a streptavidin-binding peptide; or
c) a functional fragment of a) or b) that reversibly binds to biotin or a biologically active fragment, a biotin analog or mutein or a biologically active fragment thereof or a streptavidin-binding peptide.

61. The method of any of embodiments 19-60, wherein the binding agent comprises a streptavidin-binding peptide.

62. The method of any embodiment 61, wherein the streptavidin-binding peptide is selected from the group consisting of Trp-Ser-His-Pro-Gln-Phe-Glu-Lys (SEQ ID NO: 8), Trp-Ser-His-Pro-Gln-Phe-Glu-Lys-(GlyGlyGlySer)$_3$-Trp-Ser-His-Pro-Gln-Phe-Glu-Lys (SEQ ID NO: 17), Trp-Ser-His-Pro-Gln-Phe-Glu-Lys-(GlyGlyGlySer)$_2$-Trp-Ser-His-Pro-Gln-Phe-Glu-Lys (SEQ ID NO: 18) and Trp-Ser-His-Pro-Gln-Phe-Glu-Lys-(GlyGlyGlySer)$_2$Gly-Gly-Ser-Ala-Trp-Ser-His-Pro-Gln-Phe-Glu-Lys (SEQ ID NO: 19).

63. The method of any of embodiments 19-61, comprising disrupting the reversible binding between the binding agent and the reagent.

64. The method of embodiment 63, wherein said disruption comprises introducing to the cells a composition comprising a substance capable of reversing the bond between the second receptor-binding agent and the reagent, which can be the second reagent.

65. The method of any of embodiments 1-64, wherein transduction of the cells is increased by greater than or greater than or about 1.2-fold, 1.5-fold, 2-fold, 3-fold, 4-fold, 5-fold, 10-fold or more compared to the transduction with the viral particle in the absence of the reagent.

66. The method of any of embodiments 1-65, wherein the genome of the viral vector comprises a nucleic acid molecule encoding a recombinant protein.

67. The method of embodiment 66, wherein the recombinant protein is an antigen receptor.

68. The method of any of embodiments 1-67, wherein the viral particle is a retrovirus.

69. The method of embodiment 68, wherein the retrovirus is a lentivirus.

70. The method of embodiment 68, wherein the retrovirus is a gammaretrovirus.

71. The method of any of embodiments 1-70, wherein the viral particle is replication defective.

72. The method of any of embodiments 1-71, wherein the cells comprise blood cells, leukocytes, lymphocytes, B cells, T cells or NK cells.

73. The method of any of embodiments 1-72, wherein the cells comprise antigen-specific T cells or a population thereof, a T helper cell or population thereof, a cytotoxic T cell or population thereof, a memory T cell or population thereof, a regulatory T cell or population thereof, an NK cell or population thereof, antigen-specific B cells or a population thereof, a memory B cell or population thereof, or a regulatory B cell or population thereof.

74. The method of any of embodiments 1-73, wherein the cells are primary cells.

75. The method of any of embodiments 1-74, wherein the cells comprise T cells.

76. The method of any of embodiments 1-75, wherein the T cells are unfractionated T cells, are enriched or isolated CD3+ T cells, are enriched or isolated CD4+ T cells or are enriched or isolated CD8+ T cells.

77. The method of any of embodiments 1-76, wherein the reagent is soluble.

78. The method of any of embodiments 1-77, wherein the reagent is bound to a support during at least a portion of the contacting or further incubation.

79. The method of embodiment 78, wherein the support is a solid support or a stationary phase.

80. A composition comprising an oligomeric reagent associated with a viral particle.

81. A kit, comprising an oligomeric reagent capable of associating with a viral vector particle, a viral vector particle, and, optionally, instructions for use.

82. The composition of embodiment 80 or kit of embodiment 81, wherein:
the oligomeric reagent is an oligomeric protein reagent; and/or
the oligomeric reagent comprises a plurality of polypeptide monomeric units, wherein each unit optionally comprises at least at or about 10, 20, 30, or 40 amino acids in length, optionally at least at or about 50, 60, 65, 70, 80, 90, 100, 125, or 150 amino acids in length and/or comprises a weight of at least at or about 20, 30, 40, or 50 kDa, optionally wherein the reagent comprises an oligomer comprised of a plurality of multimeric subunits, which are optionally tetrameric, units and individually comprise the monomeric unit; and/or
the oligomeric reagents comprises a molecular weight of at least at or about 100, and/or between at or about 150 kDa to about 2000 kDa, about 150 kDa to about 1500 kDa, about 150 kDa to about 1250 kDa, about 150 kDa to 1000 kDa, about 150 kDa to about 500 kDa or about 150 kDa to about 300 kDa, about 300 kDa to about 2000 kDa, about 300 kDa to about 1500 kDa, about 300 kDa to about 1250 kDa, about 300 kDa to 1000 kDa, about 300 kDa to about 500 kDa, about 500 kDa to about 2000 kDa, about 500 kDa to about 1500 kDa, about 500 kDa to about 1250 kDa, about 500 kDa to 1000 kDa, about 1000 kDa to about 2000 kDa, about 1000 kDa to about 1500 kDa, about 1000 kDa to about 1250 kDa, about 1250 kDa to about 2000 kDa or about 1500 kDa to about 2000 kDa.

83. The composition of any of embodiments 80-92, wherein the oligomeric protein reagent comprises, and optionally comprises multiple units of, a streptavidin, an avidin, a streptavidin analog or mutein or an avidin analog or mutein or a biologically active fragment of any of the foregoing, and/or a multimer of any of the foregoing.

84. A composition, comprising a reagent associated with a viral vector particle, wherein the reagent is or comprises, and optionally comprises multiple units of, a streptavidin, avidin, a streptavidin analog or mutein or and an avidin analog or mutein or biologically active fragments thereof and/or a multimer of any of the foregoing.

85. A kit, comprising a reagent capable of associating with a viral vector particle, a viral vector particle, and, optionally, instructions for use, wherein the reagent is or comprises, and optionally comprises multiple units of, a streptavidin, avidin, a streptavidin analog or mutein or and an avidin analog or mutein or biologically active fragments thereof and/or a multimer of any of the foregoing 86. The composition or kit of any of embodiment 80-85, wherein the viral particles comprise a sequence of nucleotides encoding a heterologous nucleic acid.

87. The composition or kit of any of embodiments 80-86, 17. The method of any of embodiments 1-16, wherein:
the reagent is naked;
the reagent does not comprise and/or is not conjugated or reversibly bound to a binding agent;
the reagent does not comprise and or is not conjugated or bound to a molecule with a binding domain specific for a cell surface marker, optionally selected from among adhesion molecules, integrins, chemokines, cytokines, growth factors, extracellular matrix-binding molecules, viral proteins, viral entry-promoting cell surface receptors, heparin, heparan, glycans a T-cell surface marker, a CD3, a CD28 a CD4 and/or a CD8;
the reagent does not comprise and or is not conjugated or bound to a mammalian cell surface marker, an extracellular matrix component, adhesion molecule, an integrin, a lectin, an integrin-binding protein, a chemokines, a cytokine, a growth factor, an extracellular matrix-binding molecule, an ECM component, a viral protein, a viral entry-promoting cell surface receptor, heparin, heparan, glycans; and/or
the reagent does not comprise a heparin-binding domain and/or does not comprise an integrin-binding domain and/or does not comprise a VLA4-binding domain and/or does not comprise a VLA5-binding domain; and/or
the reagent does not comprise and/or is not conjugated or coupled or bound to a viral binding agent or a cell selection agent.

88. The composition or kit of any of embodiments 80-87, wherein the reagent further comprises and/or is reversibly bound to a plurality of one or more binding agents that each is capable of specifically binding to a molecule on the surface of the viral particle and/or the surface of a target cell, which optionally is a mammalian cell, optionally a human cell.

89. The composition or kit of embodiment 88, wherein:
the reagent comprises a plurality of binding sites capable of reversibly binding to each of the binding agents, the plurality of binding sites comprising one or more binding site, Z, which is capable of binding to a binding partner, C; and
the binding agent further comprises on or more of the binding partner, C.

90. The composition or kit of embodiment 88 or embodiment 89, wherein the binding agent is or comprises a receptor-binding agent.

91. The composition or kit of embodiment 90, wherein the receptor-binding agent comprises:
a stimulatory agent capable of delivering a stimulatory signal through a TCR/CD3 complex in a T cell, a CD3-containing complex in a T cell, and/or an ITAM-containing molecule in a T cell; or
specifically binds to a members or a TCR/CD3 complex or specifically binds to CD3.

92. The composition or kit of embodiment 91, wherein the receptor binding agent is a first receptor binding agent and the reagent comprises a plurality of binding sites capable of reversibly binding a second receptor binding agent, said second receptor binding agent being an accessory binding agent capable of specifically binding to a second molecule on the surface of one or more of the cells, which second molecule is optionally capable of inducing or enhancing, dampening, or modifying a signal delivered through the first receptor binding agent.

93. The composition or kit of embodiment 92, wherein:
the first receptor binding agent comprises a binding partner C1, which is capable of reversibly binding to binding site Z1 on the reagent; and
the second receptor binding agent comprises a binding partner C2, which is capable of reversibly binding to binding site Z2 on the reagent.

94. The composition or kit of embodiment 93, wherein:
C1 and C2 are the same or substantially the same, or contain the same or substantially the same moiety; and/or
Z1 and Z2 are the same or substantially the same or contain the same or substantially the same moiety.

95. The composition or kit of embodiment 88 or embodiment 89, wherein the binding agent is a selection agent capable of specifically binding to a molecule expressed on the surface of a target cell.

96. The composition or kit of any of embodiments 90-95, wherein the reagent comprises a further binding agent that is a selection agent capable of specifically binding to a molecule expressed on the surface of a target cell.

97. The composition or kit of embodiment 96, wherein:
the first receptor binding agent comprises a binding partner C1, which is capable of reversibly binding to binding site Z1 on the reagent;
the second receptor binding agent comprises a binding partner C2, which is capable of reversibly binding to binding site Z2 on the reagent;
the selection agent comprises a binding partner C3, which is capable of reversibly binding to binding site Z3 on the reagent.

98. The composition or kit of embodiment 97, wherein:
C1, C2 and C3 are the same or substantially the same, or contain the same or substantially the same moiety; and/or
Z1, Z2 and Z3 are the same or substantially the same or contain the same or substantially the same moiety.

99. The composition or kit of any of embodiments 95-98, wherein the molecule is or comprises CD25, CD28, CD62L, CCR7, CD27, CD127, CD3, CD4, CD8, CD45RA, CD45RO and/or CD56.

100. The composition or kit of any of embodiments 88-99, wherein the binding agent is or comprises an antibody, an antibody fragment, a monovalent antibody fragment, a proteinaceous binding molecule with antibody-like binding properties, a molecule containing Ig domains, a cytokine, a chemokine, an aptamer, and MHC molecule or binding fragments thereof.

101. The composition or kit of embodiment 100, wherein the antibody fragment comprises a fragment selected from the group consisting of a Fab fragment, an Fv fragment, a (Fab')$_2$-fragment, and a divalent single-chain Fv (scFv) fragment.

102. The composition or kit of any of embodiments 88-10, wherein the plurality of binding agents comprises at least 2, 4, 8, 12, 16, 20, 24, 28, 32, 36, 40, 44, 48, 52, 56, 60, 64, 72 or more.

103. The method of any of embodiments 88-102, wherein the binding agent, optionally stimulatory agent, binds to a molecule expressed on the surface of the cell that is or comprises CD3 and/or CD28.

104. The composition or kit of embodiment 103, wherein the binding agent, optionally stimulatory agent, comprises an anti-CD3 and/or anti-CD28 antibody or fragment.

105. The composition or kit of any of embodiments 80-104, wherein individual molecules of the oligomer are crosslinked by a polysaccharide or a bifunctional linker.

106. The composition or kit of any of embodiments 80-105, wherein the reagent comprises SEQ ID NO:1 or SEQ ID NO:2 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO:1 or SEQ ID NO:2.

107. The composition or kit of any of embodiments 80-106, wherein:
the reagent comprises a streptavidin analog or mutein comprising the amino acid sequence $Val^{44}$-$Thr^{45}$-$Ala^{46}$-$Arg^{47}$ or $Ile^{44}$-$Gly^{45}$-$Ala^{46}$-$Arg^{47}$ at sequence positions corresponding to positions 44 to 47 with reference to positions in streptavidin in the sequence of amino acids set forth in SEQ ID NO:1; or
the streptavidin analog or mutein comprises the amino acid sequence $Val^{44}$-$Thr^{45}$-$Ala^{46}$-$Arg^{47}$ at sequence positions corresponding to positions 44 to 47 with reference to positions in streptavidin in the sequence of amino acids set forth in SEQ ID NO:1.

108. The composition or kit of any of embodiments 80-107, wherein the reagent comprises a streptavidin analog or mutein, which comprises:
a) the sequence of amino acids set forth in any of SEQ ID NOS: 3-6, 27 and 28;
b) a sequence of amino acids that exhibits at least 85%, 86%, 87%, 88%, 89%, 89%, 90%, 91%, 92%, 93%, 94%, 95%, 96%, 97%, 98%, 99% or more sequence identity to any of SEQ ID NOS:3-6, 27 and 28 and contains the amino acid sequence corresponding to $Val^{44}$-$Thr^{45}$-$Ala^{46}$-$Arg^{47}$ or $Ile^{44}$-$Gly^{45}$-$Ala^{46}$-$Arg^{47}$ and that reversibly binds to biotin or a biologically active form thereof, a biotin analog or mutein or a biologically active fragment thereof or a streptavidin-binding peptide; or c) a functional fragment of a) or b) that reversibly binds to biotin or a biologically active form thereof, a biotin analog or mutein or a biologically active fragment thereof or a streptavidin-binding peptide.

109. The composition or kit of any of embodiments 80-108, wherein the streptavidin analog or mutein further comprises an amino acid replacement or replacements at a position corresponding to 117, 120 and/or 121 with reference to positions in streptavidin in the sequence of amino acids set forth in SEQ ID NO:1.

110. The composition or kit of embodiment 109, wherein:
the amino acid replacement or replacements are selected from among Glu117, Asp117, Arg117, Ser120, Ala120, Gly120, Trp121, Tyr121 or Phe121; or
the amino acid replacement or replacements are selected from one or more of Glu117, Gly120 or Tyr121; or
the amino acid replacements are selected from Glu117, Gly120 or Tyr121.

111. The composition or kit of any of embodiments 80-110, wherein the reagent comprises a streptavidin analog or mutein, which comprises:
a) the sequence of amino acids set forth in SEQ ID NO: 27 or 28;
b) a sequence of amino acids that exhibits at least 85%, 86%, 87%, 88%, 89%, 89%, 90%, 91%, 92%, 93%, 94%, 95%, 96%, 97%, 98%, 99% or more sequence identity to SEQ ID NOS:28 and contains the amino acid sequence corresponding to $Val^{44}$, $Thr^{45}$, $Ala^{46}$, $Arg^{47}$, $Glu^{117}$, $Gly^{120}$ and $Tyr^{121}$ and reversibly binds to biotin or a biologically active fragment, a biotin analog or mutein or a biologically active fragment thereof or a streptavidin-binding peptide; or
c) a functional fragment of a) or b) that reversibly binds to biotin or a biologically active fragment, a biotin analog or mutein or a biologically active fragment thereof or a streptavidin-binding peptide.

112. The composition or kit of any of embodiments 88-111, wherein the binding agent comprises a streptavidin-binding peptide.

113. The composition or kit of embodiment 112, wherein the streptavidin-binding peptide is selected from the group consisting of Trp-Ser-His-Pro-Gln-Phe-Glu-Lys (SEQ ID NO: 8), Trp-Ser-His-Pro-Gln-Phe-Glu-Lys-(GlyGlyGly Ser)₃-Trp-Ser-His-Pro-Gln-Phe-Glu-Lys (SEQ ID NO: 17), Trp-Ser-His-Pro-Gln-Phe-Glu-Lys-(GlyGlyGlySer)₂-Trp-Ser-His-Pro-Gln-Phe-Glu-Lys (SEQ ID NO: 18) and Trp-Ser-His-Pro-Gln-Phe-Glu-Lys-(GlyGlyGlySer)₂Gly-Gly-Ser-Ala-Trp-Ser-His-Pro-Gln-Phe-Glu-Lys (SEQ ID NO: 19).

114. The composition or kit of any of embodiments 80-113, wherein the genome of the viral vector comprises a nucleic acid molecule encoding a recombinant protein.

115. The composition or kit of embodiment 114, wherein the recombinant protein is an antigen receptor.

116. The composition or kit of any of embodiments 80-115, wherein the viral particle is a retrovirus.

117. The composition or kit of embodiment 116, wherein the retrovirus is a lentivirus.

118. The composition or kit of embodiment 116, wherein the retrovirus is a gammaretrovirus.

119. The composition or kit of any of embodiments 80-118, wherein the viral particle is replication defective.

120. The composition or kit of any of embodiments 80-119, wherein the reagent is soluble.

121. The composition or kit of any of embodiments 80-120, wherein the reagent is bound to a support during at least a portion of the contacting or further incubation.

122. The composition or kit of embodiment 121, wherein the support is a solid support or a stationary phase.

123. A method for transducing cells, the method comprising:
(1) combining (a) a composition comprising a plurality of target cells and (b) a selection agent that (i) is capable of specifically binding to a selection marker expressed by one or more of the at least a plurality of the target cells and ii) is reversibly bound to a reagent comprising a plurality of binding sites capable of reversibly binding to the selection agent; and
(2) incubating at least a plurality of the target cells in the presence of a composition comprising viral particles comprising a genome containing a nucleic acid molecule encoding a recombinant antigen receptor, wherein the contacting in (1) and the incubating in (2) are carried out simultaneously or sequentially, in either order, wherein the method generates an incubated composition comprising a plurality of the target cells transduced with the viral vector.

124. The method of embodiment 123, wherein the viral vector particles are reversibly bound to the reagent, said reagent comprising a plurality of binding sites capable of reversibly binding, directly or indirectly, to a molecule on the surface of the viral particle.

125. The method of embodiment 123 or embodiment 124, wherein:
the reagent is not, and is not bound to or associated with, a solid support, stationary phase, a bead, a microparticle, a magnetic particle, and/or a matrix during said incubation; and/or
the reagent is flexible, does not contain a metal or magnetic core, is comprised entirely or primarily of organic multimer, is not spherical, is not substantially spherical or uniform in shape and/or is not rigid.

126. The method of any of embodiments 123-125, wherein:
the reagent is immobilized, or is capable of being immobilized, on a support, directly or indirectly, whereby the selection agent is immobilized, or is capable of being immobilized on the support; and
in (1) further combining (c) the support, whereby one or more target cells of the at least a plurality are immobilized on the support via the selection agent during at least a portion of the incubation.

127. The method of embodiment 126, wherein one or more viral vector particles are immobilized on the support via the direct or indirect binding to the molecule during at least a portion of the incubation.

128. The method of any of embodiments 123-127, wherein the reagent comprises a plurality of binding sites, Z1, capable of reversibly binding to the selection agent and/or the reagent comprise a plurality of binding sites, Z2, capable of reversibly binding to the one or more viral particles.

129. A method for transducing cells, the method comprising:
(1) combining (a) a composition comprising a plurality of target cells, (b) a selection agent that (i) is capable of specifically binding to a selection marker expressed by one or more of the at least a plurality of the target cells and ii) is immobilized, or is capable of being immobilized, on a support, directly or indirectly; and (c) the support, whereby one or more target cells of the at least a plurality are immobilized on the support via the selection agent; and
(2) incubating at least a plurality of the target cells in the presence of a composition comprising a plurality of viral particles comprising a genome containing a nucleic acid molecule encoding a recombinant receptor, wherein one or more of the plurality of viral particles are capable of being immobilized on the support, directly or indirectly, wherein:

the contacting in (1) and the incubating in (2) are carried out simultaneously or sequentially, in either order;

the one or more target cells and the one or more viral vector particles are immobilized on the support during at least a portion of the incubation; and the method generates an incubated composition comprising a plurality of the target cells transduced with the viral vector.

130. The method of any of embodiments 126-129, wherein:

the support is or comprises a stationary phase; and/or
the support is or comprises a solid support.

131. The method of embodiment 128 or embodiment 130, wherein a reagent is immobilized, or is capable of being immobilized, on the support, said reagent comprising a plurality of binding sites, Z1, capable of reversibly binding to the selection agent and a plurality of binding sites, Z2, capable of reversibly binding to the one or more viral particles.

132. The method of embodiment 131, comprising in (1) further combining (d) the reagent, wherein the reagent is immobilized on the support.

133. The method of embodiment 132, wherein the reagent and the support are combined prior to combining thereto the selection agent and/or the composition comprising a plurality of cells.

134. The method of any of embodiments 128 and 131-133, wherein:

the selection agent comprises a binding partner C1; and
the plurality of binding sites comprises two or more binding sites, Z1, which each are capable of binding to the binding partner C1 to form the reversible bond between the selection agent and the reagent.

135. The method of any of embodiments 124-6 and 131-134, wherein the viral vector particles are reversibly bound to the reagent via a viral particle-binding agent.

136. The method of embodiment 135, wherein:

the viral particle-binding agent comprises a binding partner C2; and the plurality of binding sites comprises two or more binding sites, Z2, which each are capable of binding to the binding partner C2 to form the reversible bond between the viral particle-binding agent and the reagent.

137. The method of embodiment 128 and any of embodiments 131-136, wherein:

C1 and C2 are the same or substantially the same, or contain the same or substantially the same moiety; and/or Z1 and Z2 are the same or substantially the same or contain the same or substantially the same moiety.

138. The method of any of embodiments 123-137, wherein the selection agent further comprises a binding site B1, wherein the specific binding between the selection agent and the selection marker on the target cells comprises interaction between B1 and the marker.

139. The method of any of embodiments 123-138, wherein the selection marker is a first selection marker and the selection agent is further capable of binding to a second selection marker, which is expressed on the surface of at least a plurality of the target cells.

140. The method of any of embodiments 123-139, wherein the selection agent is a first selection agent, the selection marker is a first selection marker and the incubation is further carried out in the presence of a second selection agent, which is capable of specifically binding to a second selection marker which is expressed on the surface of at least a plurality of the target cells.

141. The method of embodiment 140, wherein the reagent comprises a plurality of binding sites capable of reversibly binding to the second selection agent, whereby the second selection agent is reversibly bound to the reagent.

142. The method of embodiment 141, wherein the plurality of binding sites capable of reversibly binding to the first selection agent and the plurality of binding sites capable of reversibly binding to the second selection agent can be the same or different.

143. The method of embodiment 142, wherein:

the second selection agent comprises one or more of the binding partner, C1; and/or the second selection agent comprises one or more of a binding partner, C2, which is capable of binding to the binding site, Z1; and/or the second selection agent comprises one or more of a binding partner, C2, which is capable of binding to a binding site, Z2, and the reagent further comprises one or more of the binding site Z2.

144. The method of any of embodiments 139-143, wherein the second selection agent comprises one or more of a binding site, B3, which facilitates the specific binding between the second selection agent and the second selection marker.

145. The method of any of embodiments 123-138, wherein:

the selection marker, which can be a first selection marker, and/or the second selection marker expressed on the surface of the target cells is a protein or polypeptide; and/or the selection marker, which can be a first selection marker, and/or the second selection marker is a protein or polypeptide.

146. The method of any of embodiments 123-145, wherein:

the target cells comprise blood cells;
the target cells comprise leukocytes;
the target cells comprise lymphocytes;
the target cells comprise B cells;
the target cells comprise a B cell population
the target cells comprise T cells;
the target cells comprise a T cell population; and/or
the target cells comprise natural killer (NK) cells;
the target cells comprise dendritic cells;
the target cells comprise macrophages.

147. The method of embodiment 146, wherein the target cells comprise antigen-specific T cells or a population thereof, a T helper cell or population thereof, a cytotoxic T cell or population thereof, a memory T cell or population thereof, a regulatory T cell or population thereof, or a NK cell or population thereof, antigen-specific B cells or a population thereof, a memory B cell or population thereof, or a regulatory B cell or population thereof.

148. The method of any of embodiments 123-147, wherein the target cells comprise T cells.

149. The method of embodiment 148, wherein at least 40%, at least 50%, at least 60%, at least 70%, at least 80%, or at least 90% of the T cells are surface negative for a T cell activation marker selected from the group consisting of HLA-DR, CD25, CD69, CD71, CD40L and 4-1BB; and/or lack intracellular expression of a cytokine selected from the group consisting of IL-2, IFNgamma, TNF-alpha; and/or are capable of proliferating.

150. The method of any of embodiments 123-149, comprising stimulating one or more of the plurality targets cells, optionally one or more of the plurality of T cells, prior to and/or during said incubation, said stimulating comprising exposing said cells to stimulating conditions, thereby inducing one or more targets cells or T cells to proliferate.

151. The method of embodiment 150, wherein said stimulating conditions comprise the presence of an agent capable of activating one or more intracellular signaling domains of one or more components of a TCR complex.

152. The method of embodiment 151, wherein said agent comprises a primary agent that specifically binds to a member of a TCR complex and a secondary agent that specifically binds to a T cell costimulatory molecule.

153. The method of embodiment 152, wherein the primary agent specifically binds to CD3; and/or
the costimulatory molecule is selected from the group consisting of CD28, CD137 (4-1BB), OX40, CD27 or ICOS.

154. The method of embodiment 152 or embodiment 153, wherein said primary and secondary agents comprise antibodies and/or are present on the surface of a solid support.

155. The method of any of embodiments 123-154, further comprising:
(3) culturing at least a plurality of cells in the presence of a stimulatory agent reversibly bound to a reagent, which optionally is a second reagent, the (second) reagent comprising a plurality of binding sites each capable of reversibly binding to the stimulatory agent, under conditions whereby the stimulatory agent specifically binds to a molecule expressed on the surface of the cells, thereby inducing or modulating a signal in the cells.

156. The method of embodiment 155, wherein said culturing is carried out and/or is initiated prior to said incubating.

157. The method of embodiment 155 or embodiment 156, wherein:
the second reagent is not, and is not bound to or associated with, a solid support, stationary phase, a bead, a microparticle, a magnetic particle, and/or a matrix during said incubation, and/or
the second reagent is flexible, does not contain a metal or magnetic core, is comprised entirely or primarily of organic multimer, is not spherical, is not substantially spherical or uniform in shape, and/or is not rigid.

158. The method of embodiment 155 or embodiment 156, wherein the second reagent is immobilized on a support, which optionally is a solid support or a stationary phase.

159. The method of any of embodiments 155-158, wherein the stimulatory agent comprises a comprises an MHC I:peptide complex or functional portion thereof, an MHCII:peptide complex or functional portion thereof, and/or is capable of delivering a stimulatory signal through a TCR/CD3 complex in a T cell, a CD3-containing complex in a T cell, and/or an ITAM-containing molecule in a T cell.

160. The method of any of embodiments 155-159, wherein the stimulatory agent is a first stimulatory agent and the culturing is further carried out in the presence of a second stimulatory agent, which is capable of specifically binding to a second molecule which is expressed on the surface of at least a plurality of the target cells, thereby inducing a second signal in the cells to enhance, dampen or modify a signal delivered through the first molecule.

161. The method of embodiment 160, wherein the reagent (second) reagent comprises a plurality of binding sites capable of reversibly binding to the second stimulatory agent, whereby the second stimulatory agent is reversibly bound to the reagent.

162. The method of embodiment 160 or embodiment 161, wherein the second molecule is a costimulatory molecule, accessory molecule, cytokine receptor, chemokine receptor, immune checkpoint molecule or is a member of the TNF family or the TNF receptor family.

163. The method of any of embodiments 155-162, wherein the incubating and culturing are performed in separate vessels, which are operably connected, optionally by tubing.

164. The method of any of embodiments 123-163, wherein the incubating and culturing are performed in a closed system.

165. The method of any of embodiments 155-164, comprising recovering cells reversibly bound to and stimulated by the stimulatory agent, which can be the first stimulatory agent, and/or the second stimulatory agent, thereby producing cultured cells, wherein the cultured cells are or comprise the plurality of target cells.

166. The method of any of embodiments 123-148, wherein at least 40%, at least 50%, at least 60%, at least 70%, at least 80%, or at least 90% of the T cells in the population so-cultured:
are surface negative for a T cell activation marker selected from the group consisting of HLA-DR, CD25, CD69, CD71, CD40L and 4-1BB; and/or
lack intracellular expression of a cytokine selected from the group consisting of IL-2, IFNgamma, TNF-alpha; and/or
are in the G0 or $G_0G_{1a}$ stage of the cell cycle.

167. The method of any of embodiments 123-166, wherein:
the selection marker is a B cell or T cell coreceptor;
the selection marker is or comprises a member of a T cell or B cell antigen receptor complex;
the selection marker is or comprises a CD3 chain;
the selection marker is or comprises a CD3 zeta chain;
the selection marker is or comprises a CD8;
the selection marker is or comprises a CD4 and/or
the specific binding between the selection agent and the selection marker does not induce a signal, or does not induce a stimulatory or activating or proliferative signal, to the target cells.

168. The method of any of embodiments 123-167, wherein after said combining, further comprising separating and/or removing, from the immobilized target cells, other cells of the composition.

169. The method of embodiment 167 or 168, further comprising performing a wash step.

170. The method of embodiment 168 or embodiment 169, wherein said separating and/or said wash step is carried out prior to initiation of said incubation.

171. The method of any of embodiments 123-170, wherein:
said incubating is carried out and/or is initiated prior to said combining; or
said incubating is carried out and/or is initiated subsequently to said combining.

172. The method of any of embodiments 123-171, wherein said combining is carried out during at least a portion of said incubation.

173. The method of any of embodiments 123-172, wherein the immobilization of the selection agent on the support is reversible.

174. The method of any of embodiments 135-173, wherein the viral particle binding agent further comprises a binding site V1, wherein the binding between the molecule on the surface of the virus and the viral particle-binding agent comprises interaction between B1 and the molecule.

175. The method of embodiment 174, wherein the molecule on the surface of the viral particle is selected from among an envelope glycoprotein, a variant of an envelope glycoprotein, a chimeric envelope glycoprotein, a viral capsid protein, a variant of a viral capsid protein, a viral matrix protein, a variant of a viral matrix protein, a synthetic moiety, a peptide and a tag.

176. The method of embodiment 175, wherein the envelope glycoprotein is selected from among a VSV glycoprotein (VSV-G), Sindbis glycoprotein, optionally SIN, a MMLV glycoprotein, an HSV glycoprotein, an MMTV glycoprotein, Measles virus glycoprotein, HTLV glycoprotein, SIV glycoprotein, an GALV glycoproteins, a HIV glycoprotein, optionally gp160, gp120 or gp41, and an RSV glycoprotein, optionally gp85 or gp37, or are variant, portion sufficient to be bound by the viral particle-binding agent or chimeric molecule thereof.

177. The method of embodiment 175, wherein the synthetic moiety, peptide or tag is selected from among glutathione-S-transferase (GST), chitin binding protein (CBP), calmodulin binding peptide (CBP), FLAG-peptide, themagglutinin peptide, VSV-G-tag, HSV-tag, T7 epitope, maltose binding protein (MBP), HSV epitope, myc epitope, V5-tag, and a streptavidin-binding peptide.

178. The method of embodiment 175 or embodiment 177, wherein the molecule is a synthetic moiety, peptide or tag and the viral particle is engineered to express the synthetic moiety, peptide or tag on its surface.

179. The method of embodiment 177 or embodiment 178, wherein the streptavidin-binding peptide comprises the sequence of amino acids set forth in any of SEQ ID NO: 7, 8, 13, 14, and 15-19.

180. The method of embodiments 135-174, wherein the viral particle-binding agent is selected from among protamine, POLYBRENE® and RETRONECTIN®.

181. The method of any of embodiments 123-134 and 136-173, wherein:
the viral particle comprises a binding partner C1 or C2; and
the reagent comprises a plurality of binding sites, Z1 or Z2, capable of binding to the binding partner, C1 or C2, to form the reversible bond between the viral particle and the reagent.

182. The method of embodiment 181, wherein the viral particle is engineered to express a synthetic moiety, peptide or tag on its surface, wherein the synthetic moiety, peptide or tag is or comprises the binding partner C1 or C2.

183. The method of embodiment 182, wherein the peptide is a streptavidin-binding peptide.

184. The method of embodiment 183, wherein the streptavidin-binding peptide comprises the sequence of amino acids set forth in any of SEQ ID NO: 7, 8, 13, 14, and 15-19.

185. The method of any of embodiments 123-184, wherein the viral particle is a retroviral vector particle.

186. The method of any of embodiments 123-185, wherein the viral particle is a lentiviral vector particle.

187. The method of embodiment 186, wherein the lentiviral vector particle comprises a genome that is derived from HIV-1.

188. The method of any of embodiments 123-185, wherein the retroviral vector particle is a gammaretrovirus particle.

189. The method of embodiment 188, wherein the gammaretrovirus particle is a murine leukemia virus (MLV) particle.

190. The method of any of embodiments 123-189, wherein the viral vector particle is pseudotyped with a viral envelope glycoprotein.

191. The method of embodiment 190, wherein the viral envelope glycoprotein is VSV-G.192. The method of any of embodiments 123-191, wherein the recombinant antigen receptor is a chimeric antigen receptor (CAR), which comprises an extracellular antigen-recognition domain that specifically binds to a target antigen and an intracellular signaling domain comprising an ITAM.

193. The method of embodiment 192, wherein the intracellular signaling domain comprises an intracellular domain of a CD3-zeta (CD3ζ) chain.

194. The method of embodiment 192 or embodiment 193, further comprising a transmembrane domain linking the extracellular domain and the intracellular signaling domain.

195. The method of embodiment 194, wherein the transmembrane domain comprises a transmembrane portion of CD28.

196. The method of any of embodiments 192-195, wherein the intracellular signaling domain further comprises an intracellular signaling domain of a T cell costimulatory molecule.

197. The method of embodiment 196, wherein the T cell costimulatory molecule is selected from the group consisting of CD28 and 41BB.

198. The method of any of embodiments 123-197, wherein the nucleic acid further comprises a promoter operably linked to the nucleic acid encoding the recombinant antigen receptor.

199. The method of any of embodiments 123-198, wherein:
the reversible binding between the selection agent and the reagent, which can be a first reagent, is capable of being disrupted by the addition of a substance; and/or
the reversible binding between the second selection agent and the reagent, which can be a first reagent, and/or second reagent is capable of being disrupted by the addition of a substance; and/or
the reversible binding between the molecule on the surface of the virus and the reagent, which can be a first reagent, is capable of being disrupted by the addition of a substance; and/or
the reversible binding between the viral particle-binding agent and the reagent, which can be a first reagent, is capable of being disrupted by the addition of a substance; and/or
the reversible binding between the stimulatory agent, which can be a first stimulatory agent, and the second reagent, is capable of being disrupted by the addition of a substance; and/or
the reversible binding between the second stimulatory agent and the second agent, is capable of being disrupted by the addition of a substance.

200. The method of embodiment 199, wherein said disruption comprises introducing to the cells a composition comprising the substance.

201. The method of embodiment 199 or embodiment 200, wherein the substance is a free binding partner and/or is a competition agent.

202. The method of any of embodiments 199-201, wherein the substance in the composition is not detrimental to the T cells or to the target cells and/or wherein the addition of said substance does not reduce the percentage of surviving T cells or target cells to less than 90%, 80%, 70%, 60%, or 50%, as compared to incubation of the T cells or target cells, respectively, under comparable or the same conditions, without the substance.

203. The method of any of embodiments 123-202, wherein:

the reagent is or comprises a streptavidin, avidin, a streptavidin analog or mutein or and an avidin analog or mutein or biologically active fragments thereof; and the substance comprises a streptavidin-binding peptide, biotin or a biologically active fragment, optionally a D-biotin, or a biotin analog or biologically active fragment.

204. The method of embodiment 203, wherein:

the substance is a streptavidin-binding peptide is selected from the group consisting of Trp-Ser-His-Pro-Gln-Phe-Glu-Lys (SEQ ID NO: 8), Trp-Ser-His-Pro-Gln-Phe-Glu-Lys-(GlyGlyGlySer)$_3$-Trp-Ser-His-Pro-Gln-Phe-Glu-Lys (SEQ ID NO: 17), Trp-Ser-His-Pro-Gln-Phe-Glu-Lys-(GlyGlyGlySer)$_2$-Trp-Ser-His-Pro-Gln-Phe-Glu-Lys (SEQ ID NO: 18) and Trp-Ser-His-Pro-Gln-Phe-Glu-Lys-(GlyGlyGlySer)$_2$Gly-Gly-Ser-Ala-Trp-Ser-His-Pro-Gln-Phe-Glu-Lys (SEQ ID NO: 19); and/or the substance is C1 or an analog thereof or is C2 or an analog thereof.

205. The method of any of embodiments 123-204, wherein:

the selection agent, which can be a first selection agent, and/or the second selection agent each individually are selected from among an antibody fragment, a monovalent antibody fragment, a proteinaceous binding molecule with antibody-like binding properties, a molecule containing Ig domains, a cytokine, a chemokine, an aptamer, and MHC molecule and binding fragments thereof; and/or the stimulatory agent, which can be a first stimulatory agent, and/or the second stimulatory agent each individually are selected from among an antibody fragment, a monovalent antibody fragment, a proteinaceous binding molecule with antibody-like binding properties, a molecule containing Ig domains, a cytokine, a chemokine, an aptamer, and MHC molecule and binding fragments thereof; and/or the viral particle-binding agent is selected from among an antibody fragment, a monovalent antibody fragment, a proteinaceous binding molecule with antibody-like binding properties, a molecule containing Ig domains, a cytokine, a chemokine, an aptamer, and MHC molecule and binding fragments thereof.

206. The method of any of embodiments 123-205, wherein:

the selection agent, stimulatory agent, and/or viral particle-binding agent comprise an antibody fragment;

the selection agent, stimulatory agent, and/or viral particle-binding agent comprise a Fab fragment;

the selection agent, stimulatory agent, and/or viral particle-binding agent are is a divalent antibody fragment selected from among a (Fab')$_2$-fragment and a divalent single-chain Fv (scFv) fragment;

the selection agent, stimulatory agent, and/or viral particle-binding agent is a monovalent antibody fragment selected from among a Fab fragment, an Fv fragment and an scFv fragment; and/or the selection agent, stimulatory agent, and/or viral particle-binding agent is a proteinaceous binding molecule with antibody-like binding properties selected from among aptamers, muteins based on a polypeptide of the lipocalin family, glubodies, proteins based on the ankyrin scaffold, proteins based on the crystalline scaffold, adnectins and avimers.

207. The method of any of embodiments 123-206, wherein the reagent is or comprises streptavidin, avidin, an analog or mutein of streptavidin that reversibly binds biotin, a biotin analog or a biologically active fragment thereof; an analog or mutein of avidin or streptavidin that reversibly binds a streptavidin-binding peptide; a reagent that comprises at least two chelating groups K, wherein the at least two chelating groups are capable of binding to a transition metal ion; an agent capable of binding to an oligohistidine affinity tag; an agent capable of binding to a glutathione-S-transferase; calmodulin or an analog thereof; an agent capable of binding to calmodulin binding peptide (CBP); an agent capable of binding to a FLAG-peptide; an agent capable of binding to an HA-tag; an agent capable of binding to maltose binding protein (MBP); an agent capable of binding to an HSV epitope; an agent capable of binding to a myc epitope; or an agent capable of binding to a biotinylated carrier protein.

208. The method of any of embodiments 123-207, wherein:

the reagent is or comprises a streptavidin analog or mutein or an avidin analog or mutein that reversibly binds to biotin or a biologically active fragment;

the reagent is or comprises a streptavidin analog or mutein or an avidin analog or mutein that reversibly binds to a biotin analog or a biologically active fragment; and/or the reagent is or comprises a streptavidin analog or mutein or an avidin analog or mutein that reversibly binds to a streptavidin-binding peptide.

209. The method of any of embodiments 123-208, wherein the reagent is an oligomer or polymer of streptavidin, avidin, an analog or mutein of streptavidin that reversibly binds biotin or a biologically active fragment; a streptavidin or avidin analog or mutein that reversibly binds a streptavidin-binding peptide; a reagent that comprises at least two chelating groups K, wherein the at least two chelating groups are capable of binding to a transition metal ion; an agent capable of binding to an oligohistidine affinity tag; an agent capable of binding to a glutathione-S-transferase; calmodulin or an analog thereof; an agent capable of binding to calmodulin binding peptide (CBP); an agent capable of binding to a FLAG-peptide; an agent capable of binding to an HA-tag; an agent capable of binding to maltose binding protein (MBP); an agent capable of binding to an HSV epitope; an agent capable of binding to a myc epitope; or an agent capable of binding to a biotinylated carrier protein.

210. The method of any of embodiments 123-209, wherein the reagent comprises an oligomer or polymer of streptavidin, avidin, a streptavidin analog or mutein or and an avidin analog or mutein.

211. The method of embodiment 209 or embodiment 210, wherein individual molecules of the oligomer or polymer are crosslinked by a polysaccharide or a bifunctional linker.

212. The method of any of embodiments 123-211, wherein the plurality of binding sites comprises at least 2, 4, 8, 12, 16, 20, 24, 28, 32, 36, 40, 44, 48, 52, 56, 60, 64, 72 or more binding sites.

213. The method of any of embodiments 207-212, wherein the streptavidin-binding peptide is selected from the group consisting of Trp-Ser-His-Pro-Gln-Phe-Glu-Lys (SEQ ID NO: 8), Trp-Ser-His-Pro-Gln-Phe-Glu-Lys-(GlyGlyGlySer)$_3$-Trp-Ser-His-Pro-Gln-Phe-Glu-Lys (SEQ ID NO: 17), Trp-Ser-His-Pro-Gln-Phe-Glu-Lys-(GlyGlyGlySer)$_2$-Trp-Ser-His-Pro-Gln-Phe-Glu-Lys (SEQ ID NO: 18) and Trp-Ser-His-Pro-Gln-Phe-Glu-Lys-(GlyGlyGlySer)$_2$Gly-Gly-Ser-Ala-Trp-Ser-His-Pro-Gln-Phe-Glu-Lys (SEQ ID NO: 19).

214. The method of any of embodiments 123-213, wherein:
the reagent comprises a streptavidin analog or mutein comprising the amino acid sequence Val$^{44}$-Thr$^{45}$-Ala$^{46}$-Arg$^{47}$ or Ile$^{44}$-Gly$^{45}$-Ala$^m$-Arg$^{47}$ at sequence positions corresponding to positions 44 to 47 with reference to positions in streptavidin in the sequence of amino acids set forth in SEQ ID NO:1; or
the streptavidin analog or mutein comprises the amino acid sequence Val$^{44}$-Thr$^{45}$-Ala$^{46}$-Arg$^{47}$ at sequence positions corresponding to positions 44 to 47 with reference to positions in streptavidin in the sequence of amino acids set forth in SEQ ID NO:1.

215. The method of any of embodiments 123-214, wherein the streptavidin analog or mutein comprises:
  a) the sequence of amino acids set forth in any of SEQ ID NOS: 3-6, 27 and 28;
  b) a sequence of amino acids that exhibits at least 85%, 86%, 87%, 88%, 89%, 89%, 90%, 91%, 92%, 93%, 94%, 95%, 96%, 97%, 98%, 99% or more sequence identity to any of SEQ ID NOS:3-6, 27 and 28 and contains the amino acid sequence corresponding to Val$^{44}$-Thr$^{45}$-Ala$^{46}$-Arg$^{47}$ or Ile$^{44}$-Gly$^{45}$-Ala$^{46}$-Arg$^{47}$ and that reversibly binds to biotin or a biologically active form thereof, a biotin analog or mutein or a biologically active fragment thereof or a streptavidin-binding peptide; or
  c) a functional fragment of a) or b) that reversibly binds to biotin or a biologically active form thereof, a biotin analog or mutein or a biologically active fragment thereof or a streptavidin-binding peptide.

216. The method of embodiment 214 or embodiment 215, wherein the streptavidin analog or mutein further comprises an amino acid replacement or replacements at a position corresponding to 117, 120 and/or 121 with reference to positions in streptavidin in the sequence of amino acids set forth in SEQ ID NO:1.

217. The method of embodiment 216, wherein:
the amino acid replacement or replacements are selected from among Glu117, Asp117, Arg117, Ser120, Ala120, Gly120, Trp121, Tyr121 or Phe121; or the amino acid replacement or replacements are selected from one or more of Glu117, Gly120 or Tyr121; or
the amino acid replacements are selected from Glu117, Gly120 or Tyr121.

218. The method of any of embodiments 123-217, wherein the streptavidin analog or mutein comprises:
  a) the sequence of amino acids set forth in SEQ ID NO: 27 or 28;
  b) a sequence of amino acids that exhibits at least 85%, 86%, 87%, 88%, 89%, 89%, 90%, 91%, 92%, 93%, 94%, 95%, 96%, 97%, 98%, 99% or more sequence identity to SEQ ID NOS:28 and contains the amino acid sequence corresponding to Val$^{44}$, Thr$^{45}$, Ala$^{46}$, Arg$^{47}$, Glu$^{117}$, Gly$^{120}$ and Tyr$^{121}$ and reversibly binds to biotin or a biologically active fragment, a biotin analog or mutein or a biologically active fragment thereof or a streptavidin-binding peptide; or
  c) a functional fragment of a) or b) that reversibly binds to biotin or a biologically active fragment, a biotin analog or mutein or a biologically active fragment thereof or a streptavidin-binding peptide.

219. The method of any of embodiments 123-218, wherein the binding partner C1 and/or the binding partner C2, independently, comprises a streptavidin-binding peptide selected from the group consisting of Trp-Ser-His-Pro-Gln-Phe-Glu-Lys (SEQ ID NO: 8), Trp-Ser-His-Pro-Gln-Phe-Glu-Lys-(GlyGlyGlySer)$_3$-Trp-Ser-His-Pro-Gln-Phe-Glu-Lys (SEQ ID NO: 17), Trp-Ser-His-Pro-Gln-Phe-Glu-Lys-(GlyGlyGlySer)$_2$-Trp-Ser-His-Pro-Gln-Phe-Glu-Lys (SEQ ID NO: 18) and Trp-Ser-His-Pro-Gln-Phe-Glu-Lys-(GlyGlyGlySer)$_2$Gly-Gly-Ser-Ala-Trp-Ser-His-Pro-Gln-Phe-Glu-Lys (SEQ ID NO: 19).

220. The method of any of embodiments 123-219, comprising, after said disruption, recovering the cells and further incubating the composition comprising the incubated cells, thereby generating a further incubated composition.

221. The method of embodiment 220, wherein:
the incubation and further incubation are carried out in the same vessel; and/or
the further incubation is carried out in the presence of the substance; and/or
the method does not comprise removing the substance, selection agent, stimulatory agent, viral particle-binding agent and/or reagent from the incubated composition prior to the further incubation.

222. The method of embodiment 220 or embodiment 221, wherein the further incubation is performed under conditions to expand the cells.

223. The method of any of embodiments 124-222, wherein:
the support comprises a resin or matrix;
the support comprises a gel filtration matrix;
the support comprises a chromatography matrix; and/or
the support comprises a cellulose-based or organic polymer-based membrane.

224. The method of embodiment 222, wherein the chromatography matrix is present within a column and/or wherein the chromatography is column chromatography or planar chromatography.

225. The method of any of embodiments 124-222, wherein the support comprises a microparticle, rigid particle, magnetic particle, or bead.

226. The method of any of embodiments 124-222, wherein the support is a stationary phase, present within a container during all or part of said incubation and/or said contacting.

227. The method of embodiment 226, wherein the container comprises a container selected from the group consisting of: columns, containers suitable for bidirectional flow, pipette tips, tubes, and columns suitable for flow-through of a liquid sample.

228. The method of any of embodiments 123-227, wherein the method results in selective transduction of cells expressing the selection marker, which can be the first selection marker, and/or the second selection marker.

229. The method of embodiment 228, wherein transduction is at least 2-fold, 3-fold, 4-fold, 5-fold, 6-fold, 7-fold, 8-fold, 9-fold, 10-fold or greater in cells that express the selection marker (first and/or second selection marker) than in cells present in the composition that do not express the selection marker (first and/or second selection marker).

230. The method of any of embodiments 123-229, wherein:
at least 2.5%, at least 5%, at least 6%, at least 8%, at least 10%, at least 20%, at least 25%, at least 30%, at least 40%, at least 50%, or at least 75% of said cells in said incubated composition are transduced with said viral vector by the method; and/or
at least 2.5%, at least 5%, at least 6%, at least 8%, at least 10%, at least 20%, at least 25%, at least 30%, at least 40%, at least 50%, or at least 75% of said cells in said further incubated composition are transduced with said viral vector; and/or
at least 2.5%, at least 5%, at least 6%, at least 8%, at least 10%, at least 20%, at least 25%, at least 30%, at least 40%, at least 50%, or at least 75% of said cells in said incubated composition and/or further incubated composition express a product of a heterologous nucleic acid comprised within said viral vector.

231. The method of any of embodiments 123-230 that is performed ex vivo.

232. The method of any of embodiments 123-231, further comprising recovering or isolating the transduced cells produced by the method.

233. A transduced cell produced by the method of any of embodiments 123-232.

234. A composition, comprising the transduced cell of embodiment 233.

235. A composition, comprising:
a viral vector particle-binding agent reversibly bound to a reagent, wherein the viral particle-binding agent is capable of specifically binding to a molecule on the surface of a viral particle; or
a viral vector particle reversibly bound to a reagent.

236. The composition of embodiment 235, wherein the reagent comprises a plurality of binding sites, each capable of reversibly binding to the viral particle-binding agent.

237. The composition of embodiment 235 or embodiment 236, further comprising a selection agent that is capable of reversibly binding to the reagent and is capable of specifically binding to a selection marker on a target cell.

238. The composition of embodiment 237, wherein the selection agent is reversibly bound to the reagent.

239. The composition of any of embodiments 235-238, wherein the composition further comprises a support and the reagent is immobilized on the support.

240. The composition of embodiment 239, wherein the support is or comprises a stationary phase and/or a solid support.

241. The composition of any of embodiments 235-240, further comprising:
the viral particle; and/or
the target cell, wherein the target cell optionally comprises a recombinant molecule or nucleic acid expressing a recombinant molecule, which optionally is a chimeric receptor.

242. The composition of any of embodiments 235-241, further comprising a substance capable of disrupting the reversible binding between the reagent and the viral particle-binding agent agent and/or capable of disrupting between the reagent and the selection agent.

243. An article of manufacture for the transduction of target cells, the article of manufacture comprising:
(a) a viral particle-binding agent capable of specifically binding to a molecule on the surface of a viral particle;
(b) a reagent, which comprises a plurality of binding sites, each capable of reversibly binding to the viral particle-binding agent.

244. The article of manufacture of embodiment 243, further comprising a selection agent that is capable of reversibly binding to the reagent and is capable of specifically binding to a selection marker on a target cell.

245. The article of manufacture of embodiment 244, wherein the selection agent is reversibly bound to the reagent.

246. The article of manufacture of any of embodiments 243-245, wherein the composition further comprises a support and the reagent is immobilized on the support.

247. The article of manufacture of embodiment 246, wherein the support is or comprises a stationary phase and/or a solid support.

248. The article of manufacture of embodiment 247, wherein the support is a stationary phase which is or comprises a chromatography matrix, wherein the article of manufacture further comprises a container, which is optionally a first container, in which all or part of the chromatography matrix is contained, which (first) container is optionally a column.

249. An apparatus comprising the composition of any of embodiments 235-242 or the article of manufacture of any of embodiments 243-248, and optionally further comprising a fluid inlet, being fluidly connected to the composition or to one or more component of the apparatus, and/or a fluid outlet, being fluidly connected to the composition and/or to one or more component of the apparatus.

250. An apparatus comprising:
(a) a viral particle-binding agent capable of specifically binding to a molecule on the surface of a viral particle, and which is capable of reversibly binding to a reagent;
(b) a selection agent that is capable of reversibly binding to the reagent and is capable of specifically binding to a selection marker on a target cell;
(c) a reagent, which is capable of reversibly binding to the viral particle-binding agent and selection agent; and
(d) a support.

251. The apparatus of embodiment 250, wherein the components in (a)-(d) are present in a plurality of containers, at least some of which are in fluid connection, optionally in a closed or sterile system, whereby one or more of the components pass from one container to another within the apparatus.

252. The article of manufacture or apparatus of any of embodiments 243-251, further comprising a sample outlet fluidly connected to one of the at least one stationary phase for chromatography.

253. The article of manufacture or apparatus of any of embodiments 243-252, wherein the apparatus is a functionally closed system.

254. The article of manufacture or apparatus of any of embodiments 243-253, further comprising one or more controls, capable of regulating or adjusting pH, $pO_2$, $pCO_2$, and/or thermostatic control of one or more containers or components thereof, and optionally of at least one of the at least one stationary phase for chromatography.

255. The article of manufacture or apparatus of any of embodiments 243-254, further comprising a fluid connection to a container comprising medium and/or one or more nutrients and/or one or more carbon sources, whereby the connection is capable of delivering such medium, nutrients, and/or carbon sources to cells within the apparatus, optionally when said cells are immobilized on the stationary phase for chromatography.

256. The article of manufacture or apparatus of any of embodiments 243-255, wherein at least one of the recited components and/or a container comprising the same is detachable from the apparatus in a sterile or aseptic fashion.

257. A viral vector particle, comprising a streptavidin-binding peptide.

258. The viral vector particle of embodiment 257, wherein the streptavidin-binding peptide is a fusion protein with an envelope glycoprotein.

259. The viral vector particle of embodiment 258, wherein the envelope glycoprotein is VSV-G.

260. The viral vector particle of any of embodiments 257-259, wherein the viral vector is a retroviral vector, optionally a lentiviral vector.

261. The viral vector particle of any of embodiments 257-260, wherein the streptavidin-binding peptide selected from the group consisting of Trp-Ser-His-Pro-Gln-Phe-Glu-Lys (SEQ ID NO: 8), Trp-Ser-His-Pro-Gln-Phe-Glu-Lys-(GlyGlyGlySer)$_3$-Trp-Ser-His-Pro-Gln-Phe-Glu-Lys (SEQ ID NO: 17), Trp-Ser-His-Pro-Gln-Phe-Glu-Lys-(GlyGlyGlySer)$_2$-Trp-Ser-His-Pro-Gln-Phe-Glu-Lys (SEQ ID NO: 18) and Trp-Ser-His-Pro-Gln-Phe-Glu-Lys-(GlyGlyGlySer)$_2$Gly-Gly-Ser-Ala-Trp-Ser-His-Pro-Gln-Phe-Glu-Lys (SEQ ID NO: 19).

262. A kit, comprising:
the viral vector particle of any of embodiments 257-261; and
a reagent comprising one or a plurality of binding sites capable or reversibly binding the viral vector particle.

263. The kit of embodiment 262, further comprising a selection agent capable of binding a selection marker on the surface of a target cells, wherein the reagent comprise one or a plurality of binding sites capable of reversibly binding the selection agent.

264. The viral vector particle or kit of any of embodiments 257-263, wherein the viral vector particle comprises a genome encoding a recombinant antigen receptor, optionally a chimeric antigen receptor.

IX. EXAMPLES

The following examples are included for illustrative purposes only and are not intended to limit the scope of the invention.

Example 1—Generation of a Soluble Stimulatory Reagent, Containing Multimerized Anti-CD3 and Anti-CD28 Fab Fragments Reversibly Bound to an Oligomeric Streptavidin Mutein Reagent Stimulatory agents (anti-CD3 and anti-CD28 Fab fragments) were multimerized by reversibly binding to a multimerization reagent, which was an oligomeric streptavidin mutein. The reagent contained multiple binding sites for peptide tags, which were present on the Fab fragments. The oligomeric streptavidin mutein was prepared by polymerizing the streptavidin mutein designated Strep-tactin® m1 (a streptavidin homo-tetramer containing the mutein sequence of amino acids set forth in SEQ ID NO:6, see e.g. U.S. Pat. No. 6,103,493 and Voss and Skerra (1997) Protein Eng., 1:975-982) with sulfo-SMCC (sulfosuccinimidyl 4-(N-maleimidomethyl)cyclohexane-1-carboxylate, product #22122 Thermo Scientific) and iminothiolan (product #26101 Thermo Scientific) according to the manufacturer's instructions (Thermo Scientific). The oligomeric streptavidin mutein molecules were separated from monomeric (unreacted) and dimeric streptavidin mutein by size exclusion chromatography.

Anti-CD3 and anti-CD28 Fab fragments were reversibly bound to the oligomeric streptavidin mutein via a streptavidin peptide-binding partner fused to each Fab fragment. The anti-CD3 Fab fragment was derived from the CD3 binding monoclonal antibody produced by the hybridoma cell line OKT3 (ATCC® CRL-8001™; see also U.S. Pat. No. 4,361,549), and contained the heavy chain variable domain and light chain variable domain of the anti-CD3 antibody OKT3 described in Arakawa et al J. Biochem. 120, 657-662 (1996). These sequences are set forth in SEQ ID NOs:31 and 32, respectively. The anti-CD28 Fab fragment was derived from antibody CD28.3 (deposited as a synthetic single chain Fv construct under GenBank Accession No. AF451974.1; see also Vanhove et al, BLOOD, 15 Jul. 2003, Vol. 102, No. 2, pages 564-570) and contained the heavy and light chain variable domains of the anti-CD28 antibody CD28.3 set forth in SEQ ID NOS: 33 and 34, respectively. The Fab fragments were individually fused at the carboxy-terminus of their heavy chain to a streptavidin peptide-binding sequence containing a sequential arrangement of two streptavidin binding modules having the sequence of amino acids SAWSHPQFEK(GGGS)$_2$GGSAWSHPQFEK (SEQ ID NO: 16). The peptide-tagged Fab fragments were recombinantly produced (see International patent applications, publication numbers WO 2013/011011 and WO 2013/124474).

To effect reversible binding, peptide-tagged anti-CD3 and anti-CD28 Fab fragments were mixed with the multimerizing reagent, at approximately room temperature, thereby reversibly binding them to the reagent via interaction between twin-strep-tags on the Fab fragments, which were binding partners capable of reversibly binding to binding sites on the reagent, Specifically, in this study, approximately 0.5 μg of the anti-CD3 peptide tagged Fab fragment and approximately 0.5 μg of the anti-CD28 peptide-tagged Fab fragment were added to approximately 3 μg of soluble oligomeric Strep-tactin® at room temperature. In some cases, the peptide-tagged Fab fragments were pre-mixed prior to immobilization onto the soluble oligomeric mutein streptavidin backbone, which, in some instances, can result in a more uniform distribution of the different Fab molecules. The resulting soluble anti-CD3/anti-CD28 multimerized agent was used to stimulate T cells. In some cases, the resulting soluble anti-CD3/anti-CD28 multimerized agent was stored on ice prior to stimulation of cells.

Example 2: Stimulation/Expansion of CD3+T Responder Cells with αCD3/αCD28 Fab Fragments that were Reversibly Immobilized on Beads Coated with the Streptavidin Mutein Strep-Tactin®

300,000 CD3+CD62L-responder T cells (Tresp, isolated by serial magnetic enrichment from a non-mobilized donor apheresis product) were labeled with 3 μM CFSE and stimulated with 5 μl of a 15 μl preparation of Streptactin® beads (10 mg magnetic particles/ml, loaded with 35 μg Streptactin®/mg beads) either loaded with 0.5 μg αCD3 Fab fragment alone, 0.5 μg αCD28 Fab fragment alone, or a mixture of 0.5 μg αCD3 Fab fragment and 0.5 μg αCD28 Fab.

The αCD3 Fab fragment used was derived from the CD3 binding monoclonal antibody produced by the hybridoma cell line OKT3. The hybridoma cell line OKT3 and the OKT3 antibody are described in U.S. Pat. No. 4,361,549, the cell line has been deposited under accession number ATCC® CRL-8001™). The CD28 Fab used was derived from the monoclonal anti-human CD28 antibody CD28.3 (Vanhove et al, BLOOD, 15 Jul. 2003, Vol. 102, No. 2, pages 564-570). The nucleotide sequence of the variable domains of this antibody CD28.3 has been deposited in GenBank in the form of a synthetic single chain Fv construct anti-human CD28 antibody scFv28.3 under GenBank accession number AF451974.1).

Both Fab fragments were recombinantly produced in *E. coli* as described in International patent applications WO2013/011011 and WO 2013/124474 carrying as constant domains (CH1 and Ckappa) an IgG1 consensus sequence. The heavy chain of both Fab fragments was carboxy-terminally fused with a sequential arrangement of two streptavidin binding modules (SAWSHPQFEK(GGGS) 2GGSAWSHPQFEK)(SEQ ID NO: 16), that is commercially available as "Twin-Strep-tag® from IBA GmbH, Göttingen, Germany). The αCD3 Fab fragment was used as first agent with the streptavidin binding peptide serving as binding partner C1 and the αCD28 Fab fragment was used as second agent with the streptavidin binding peptide serving as binding partner C2. The (tetrameric) streptavidin mutein "Strep-tactin®" serves as the reagent on which both Fab fragments were reversibly immobilized.

Figure 7C:
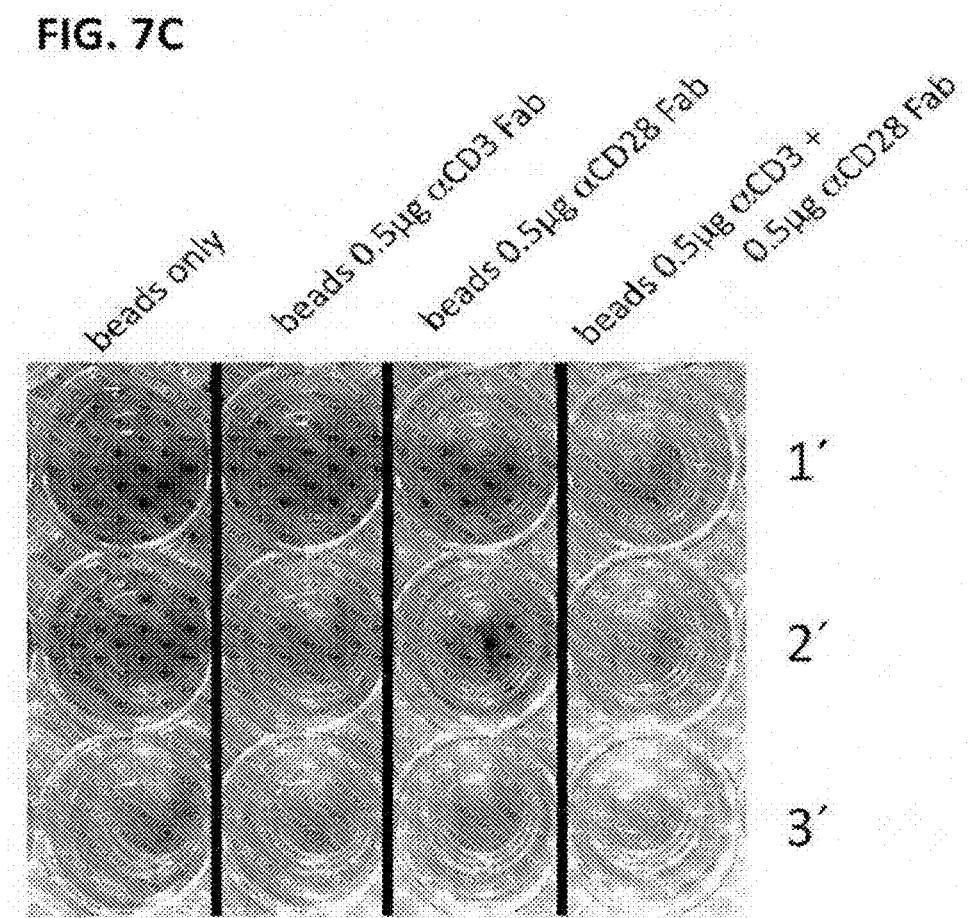

In the expansion experiment, Tresp cells stimulated with blank beads (no Fab) served as negative control. Tresp cells were seeded in triplets in 48-well plates along with 300,000 CD3 cells autologous feeder cells (irradiated with 30 Gy) in 3 ml complete cell culture medium (RPMI (Gibco) supplemented with 10% (v/v) fetal calf serum, L-glutamine, b-mercapto ethanol, HEPES, penicillin, streptomycine and gentamycine) supplemented with 10 U/ml interleukin 2 (IL-2). The cells were incubated at 37° C. without media exchange and analyzed after 4 days by FACS analysis. FACS staining and analysis was done after 10 min incubation with 100 µM D-biotin. One representative plot for each condition is shown in FIG. 7A. Plots show live CD3+ cells that were stained with propidium iodide (PI) for live/dead discrimination. FIG. 7A is a histogram showing size-distribution (forward scatter) of stimulated cells. FIG. 7A shows that a specific cell population of Tresp cells was stimulated and expanded (increase in size/number compared to the unstimulated "beads only" control) when incubated in the presence of beads on which a mixture of 0.5 µg αCD3 Fab fragment and 0.5 µg αCD28 Fab was immobilized, after being stimulated in vitro with αCD3/αCD28 Fab fragments that were reversibly immobilized on beads coated with the streptavidin mutein Strep-tactin®. FIG. 7B depicts histograms of the dilution of the proliferation dye CFSE representing the degree of proliferation according to the number of cells per cell division (indicated on top of FIG. 7B, 0 represents undivided cells; 5 represents cells that have gone through at least 5 divisions). It can be seen from FIG. 7B that the population of T cells stimulated with the beads on which a mixture of 0.5 µg αCD3 Fab fragment and 0.5 µg αCD28 Fab was immobilized have mostly gone through three cell divisions and represent a more uniform proliferation pattern than with a single stimulus alone (small number of cells within the undivided peak "0"). The increased absolute amount of proliferation (more cells have proliferated uniformly after 4d stimulation with αCD3 and αCD28 functionalized beads) is also represented by a more intense consumption of media as depicted by an indicator color change to yellow (depicted as lighter liquid in wells in FIG. 7C).

Example 3: Stimulation/Expansion of CD3+T Responder Cells with αCD3/αCD28 Fab Fragments that were Reversibly Immobilized on Soluble Strep-Tactin In this example CD3+T responder cells (isolated by magnetic selection from a sample of fresh PBMCs obtained from a Ficoll gradient) were expanded after in vitro stimulation with αCD3/αCD28 Fab fragments that were reversibly immobilized on soluble oligomeric Strep-tactin® acting as a soluble reagent. The oligomeric streptavidin mutein was obtained substantially as described in Example 1 by polymerizing Strep-tactin® with sulfo SMCC (sulfosuccinimidyl 4-(N-maleimidomethyl)cyclohexane-1-carboxylate, product #22122 Thermo Scientific) and iminothiolan (product #26101 Thermo Scientific) according to the protocol of the manufacturer (Thermo Scientific). The oligomeric streptavidin muteins were separated from monomeric (unreacted) and dimeric streptavidin muteins by size exclusion chromatography and the so obtained fraction of the oligomeric streptavidin mutein (n≥3) was used as soluble reagent.

Figure 8D:
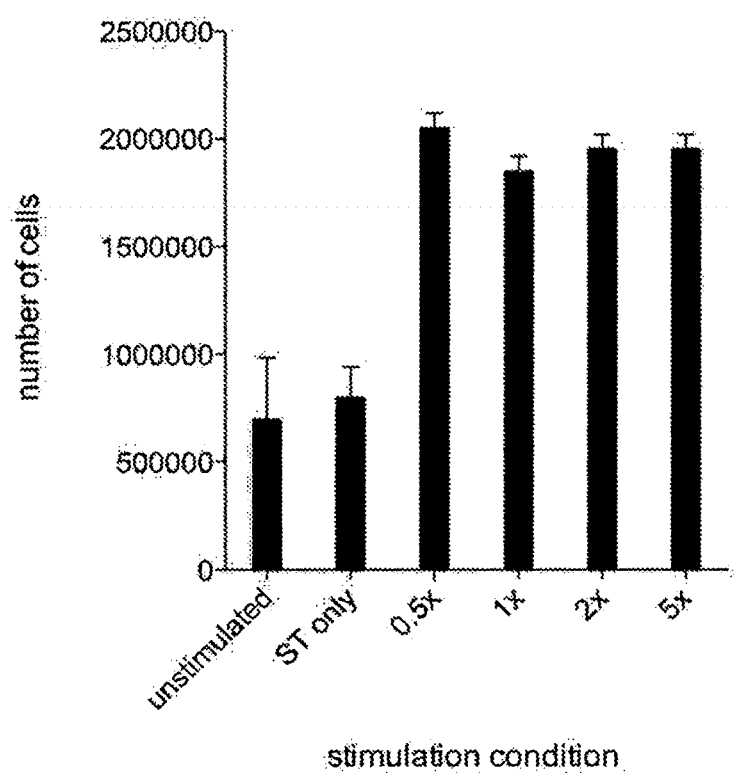
Figure 8E:
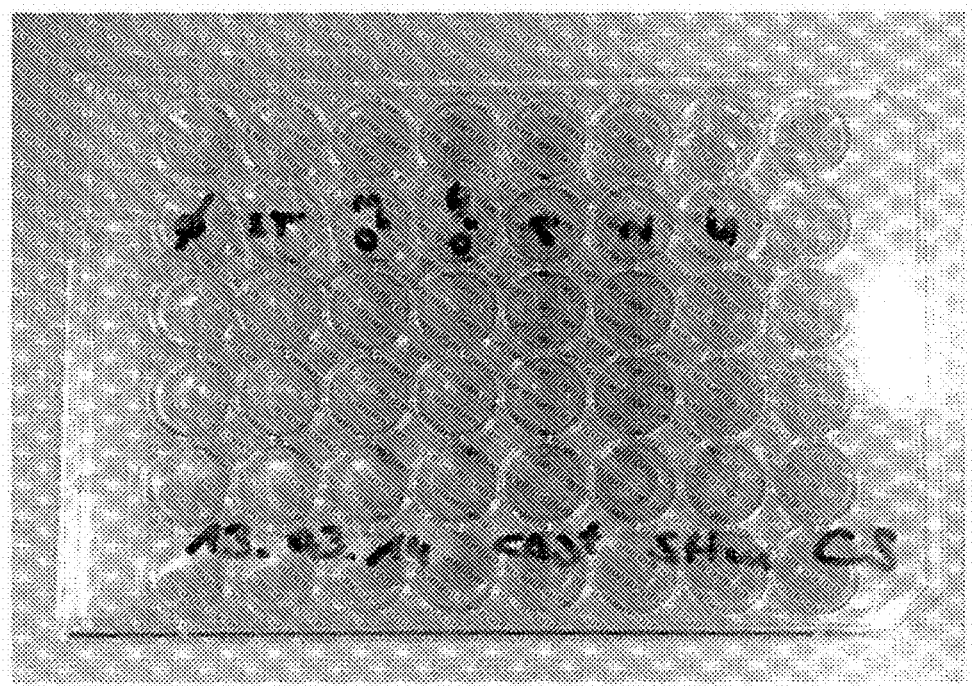

For the in vitro expansion, 300,000 CD3+ responder T cells (Tresp) were labeled with 2 µM Carboxyfluorescein succinimidyl ester (CFSE) and stimulated with varying amounts of a preparation of soluble oligomeric streptavidin mutein on which a combination of the above described αCD3 OKT3 Fab fragment and the αCD28 Fab fragment of the antibody 28.3 (both carrying the above-mentioned Twin-Strep-tag® as streptavidin binding peptide at the heavy chain) were immobilized. ("1×" corresponds to 3 µg oligomeric streptavidin mutein functionalized with 0.5 µg of the αCD3- and 0.5 µg αCD28 monomeric Fab fragment, the numbers "0.5×", "2×" and "5×" indicate the respective n-fold amount of "1×"). Tresp cells either left unstimulated or were stimulated with blank oligomeric streptavidin mutein (no Fab) served as negative controls. Tresp cells were seeded in duplicates in 48-well plates along with 300,000 CD3 negative autologous feeder cells (irradiated with 30 Gy) in 1 ml cell culture medium supplemented with 20 U/ml IL-2. Cells were incubated at 37° C. without media exchange and proliferation was analyzed according to CFSE dilution after 5 days by FACS analysis. FIG. 8A shows the increase in the size distribution of proliferating cells after 5 days in culture compared to the negative controls. FIG. 8B shows that CD3+ Tresp cells were properly stimulated and proliferated vigorously when incubated with soluble oligomeric streptavidin mutein (as compared to solid Streptactin magnetic particles in FIGS. 7A-7C) on which a mixture of αCD3 Fab and αCD28 Fab fragments were immobilized. The results in FIGS. 8A and 8B indicate that under these in vitro conditions most of the CD3+T responder cells divided (2 to 5 cell divisions) after engagement of the surface CD28 and TCR/CD3 complex with the αCD3 and αCD28 Fab fragments that were reversibly immobilized on soluble oligomeric streptavidin mutein. After in vitro expansion the soluble multimerized agents were dissociated and removed after D-biotin treatment. The dissociation and removal of monomeric Fab fragments was flow-cytometrically analyzed by restaining cells with phycoerythrine label Strep-Tactin®) (ST-PE). A representative histogram (dark grey histogram) is shown compared to the appropriate ST-PE only negative control (light gray histogram). It can be seen from FIG. 8C that both Fab fragments had completely dissociated and were entirely removed from the expanded cells. FIG. 8D shows the absolute number of live (trypan blue negative) cells after 5 days. The number was counted using a Neubauer counting chamber and plotted against the respective stimulation condition. Median cell numbers are shown in FIG. 8D; error bars indicate standard deviation (SD). FIG. 8D shows that all which mixtures of αCD3 Fab fragments and αCD28 Fab fragments that were immobilized on a soluble oligomeric streptavidin mutein reagent were equally effective in expanding the CD3+ cells and resulted in an approx. 4-fold increase of absolute cell numbers.

Example 4: Kinetics of Proliferation of Purified CD4+ and CD8+T Responder Cells Stimulated In Vitro with Reversible αCD3/αCD28 Fab-Streptamer Multimers without Medium Exchange In this example the expansion kinetics of proliferation of purified CD4+ and CD8+T responder cells (Tresp) that were stimulated in vitro with αCD3/αCD28 Fab fragments that were reversibly immobilized soluble oligomeric streptavidin muteins were examined. For this purpose, soluble oligomeric Strep-tactin® mutein of two different sizes served as soluble reagent. The first kind of oligomeric Strep-tactin® was the fraction of the oligomeric streptavidin mutein (n≥3) obtained in Example 3 (also referred herein as "conventional oligomeric streptavidin mutein backbone", illustrated by the triangle symbol with the tip on top in FIGS. 9A and 9B). The second kind of this oligomeric streptavidin mutein used as soluble reagent was an oligomeric streptavidin mutein (n≥3) that was reacted with biotinylated human serum albumin (also referred herein as "large oligomeric streptavidin mutein backbone).

Figure 9A:
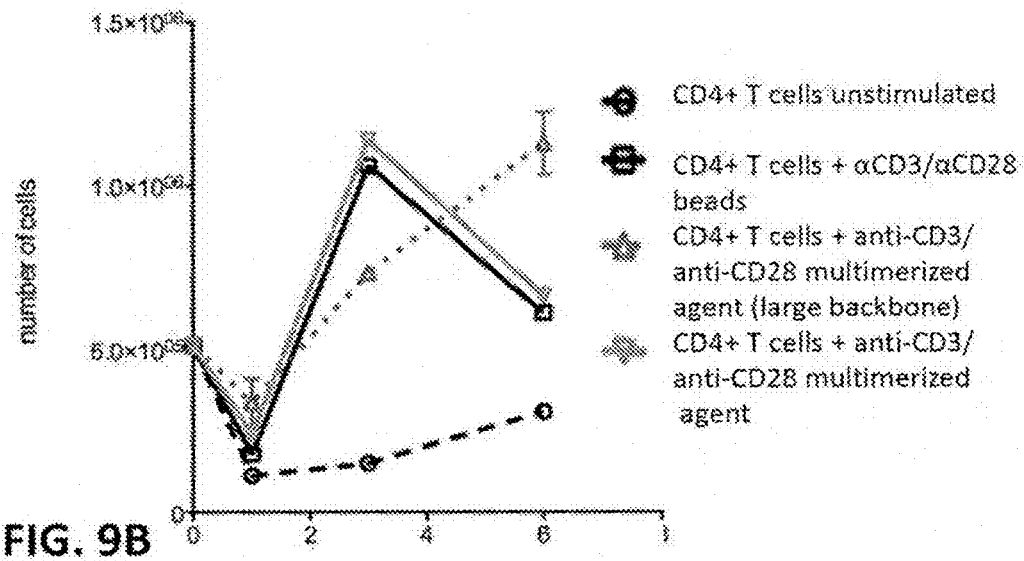
FIGS. 9A and 9B show the expansion kinetics of proliferation of purified CD4+ and CD8+T responder cells (Tresp) that were stimulated in vitro either with αCD3/αCD28 Fab fragments or with αCD3/αCD28/αCD8 that were reversibly immobilized on two kinds of a soluble oligomeric streptavidin mutein acting as soluble reagent. The first kind of oligomeric streptavidin mutein was the fraction of the oligomeric streptavidin mutein (n≥3) obtained in Example 3 (also referred herein as "conventional" or "smaller" oligomeric streptavidin mutein backbone, illustrated by the triangle symbol with the tip down in FIGS. 9A and 9B), the second kind of this oligomeric streptavidin mutein used as soluble reagent was an oligomer that was obtained by reacting the soluble oligomeric streptavidin mutein with biotinylated human serum albumin (HSA). This HSA based soluble reagent is also referred herein as "larger" oligomeric streptavidin mutein backbone). In the experiments of FIGS. 9A and 9B the expansion was carried out without medium exchange. The results for the CD4+T responder cells are shown in FIG. 9A, the results for the CD8+T responder cells are shown in FIG. 9B. In this context, it is noted that the experimentally used soluble reagents that were functionalized by reversibly binding first agents, and optionally second and third agents are referred to as "Streptamer® multimers."
Figure 9B:
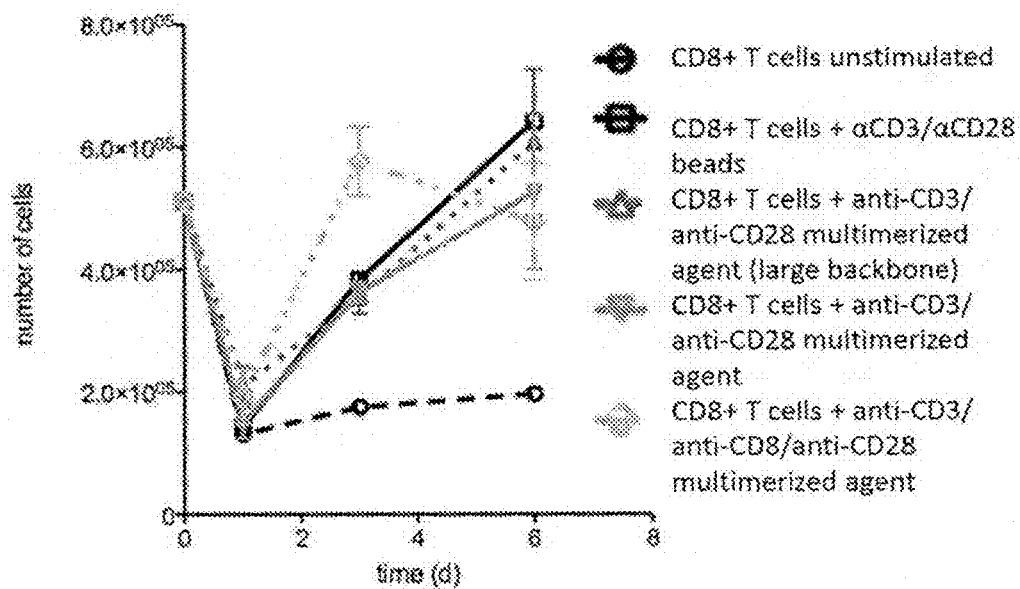

In this example 500,000 purified CD4+ or CD8+ responder T cells (Tresp) were separately stimulated with these two different Streptamer multimers as explained above, i.e. with either the oligomeric streptavidin mutein backbone of Example 3 (using a solution with a concentration of 1 mg oligomeric streptavidin mutein/ml)) or with the large oligomeric streptavidin mutein backbones (0.1 mg/ml). 3 µl of the both different backbones were either loaded with a combination of 0.5 µg of the αCD3 and 0.5 µg αCD28 Fab used in the earlier Examples that carried a streptavidin binding peptide SAWSHPQFEK(GGGS)2GG-SAWSHPQFEK (SEQ ID NO: 16) at the C-terminus of the heavy chain of the Fab fragment. In addition, 4.5 µl of the conventional oligomeric streptavidin mutein backbone was loaded with 0.5 µg αCD3 Fab fragment, 0.5 µg αCD8 Fab fragment (IBA GmbH Göttingen, that also carries at the C-terminus of the Fab fragment the streptavidin binding peptide SAWSHPQFEK(GGGS)2GGSAWSHPQFEK (SEQ ID NO: 16) and 0.5 µg αCD28 Fab fragment. Untreated (unstimulated) Tresp cells served as negative control and Tresp cells stimulated with commercially available anti-CD3/anti-CD28 beads (beads on which αCD3 and αCD28 monoclonal antibodies are irreversible immobilized) as positive control. Tresp cells were seeded in duplicates in 48-well plates in 1 ml cell culture medium (RPMI 1640 (Gibco) supplemented with 10% (v/v fetal calf serum, 0.025% (w/v) L-glutamine, 0.025% (w/v) L-arginine, 0.1% (w/v) HEPES, 0.001% (w/v) gentamycine, 0.002% (w/v) streptomycine, 0.002% (w/v) peniciline) supplemented with 30 U/ml IL-2. Cells were incubated at 37° C. without media exchange and cell count was analyzed after 1, 3 and 6 days. In the experiments of FIGS. 9A and 9B the expansion was carried out without medium exchange. The results for the CD4+T responder cells are shown in FIG. 9A, the results for the CD8+T responder cells are shown in FIG. 9B, with the graphs representing degree of proliferation according to the number of cells harvested per time point for CD4+ Tresp (FIG. 9A) and for CD8+ Tresp in FIG. 9B.

As can be seen from FIG. 9A the "smaller" soluble reagent on which αCD3 and αCD28 Fab fragments were reversibly immobilized provided for the same amount of expansion of CD4+ T cells as anti-CD3/anti-CD28 beads (which are so far the standard reagent for the expansion of T cells), while the "larger" soluble multimerized agent provided for even better expansion compared to Dynabead. This improvement might be caused by the soluble "larger" multimerized being able to bind to more T cells at the same time than the "smaller" multimerized agent, thereby being able to stimulate more CD4+ T cells than the "smaller" multimerized agent.

As evident from FIG. 9B, using the soluble multimerized agents disclosed herein, CD8+ T cells could be expanded within the first 3 days at least as efficiently as with anti-CD3/anti-CD28 beads. Notably, in this time period, the expansion experiment that used a soluble reagent that in addition to αCD3 and αCD28 Fab fragments (as first and second agent) carried reversibly immobilized thereon αCD8 Fab fragment, showed the best degree of expansion under these culturing conditions. This indicates that it is possible by using a stimulus that is specific for a particular subpopulation of cells (here the αCD8 Fab fragment) to increase or modulate the selectivity of the expansion, thereby being able to obtain larger amounts of a desired cell (sub)-population.

Thus, summarizing the above, Example 4 shows that the functionality of the soluble multimerized agent in terms of triggering expansion of T cells is comparable to the current standard methodology of using anti-CD3/anti-CD28 beads for this purpose. However, since the stimulation can be controlled (and terminated, if wanted) by adding a competitor such as biotin in the case of a streptavidin based reversible interaction between the first and second agent and the reagent, the compositions and methods described herein provide a significant advantage over the anti-CD3/anti-CD28 beads technology since the expansion conditions can be optimized (it would for example be possible to stop the stimulation in the experiment of FIG. 9B after 3 days). In addition, since the soluble reagent can be easily removed from the reaction (for example, by immobilizing the reagent on a biotinylated column after the expansion reaction), the expansion methods disclosed herein can be carried out and automated in closed systems that are, for example, needed for GMP production of cells for therapeutic purposes, without having to deal with the removal of beads such as anti-CD3/anti-CD28 beads.

Example 5: Kinetics of Proliferation of Purified CD4+ and CD8+T Responder Cells Stimulated In Vitro with Reversible αCD3/αCD28 Fab-Streptamer Multimers with Medium Exchange In this example the expansion kinetics of proliferation of purified CD4+ and CD8+T responder cells (Tresp) that were stimulated in vitro with αCD3/αCD28 Fab fragments that were reversibly immobilized on soluble oligomeric streptavidin muteins were examined. For this purpose, soluble oligomeric Strep-tactin® mutein of two different sizes served as soluble reagent. The first kind of oligomeric Strep-tactin® was the fraction of the oligomeric streptavidin mutein (n≥3) obtained in Example 3 (also referred herein as "conventional oligomeric streptavidin mutein backbone", illustrated by the triangle symbol with the tip down in FIGS. 10A and 10B). The second kind of this oligomeric streptavidin mutein used as soluble reagent was obtained by reacting the oligomeric Strep-tactin (n≥3) obtained in Example 3 with biotinylated human serum albumin. This soluble oligomeric reagent is also referred herein as "large oligomeric streptavidin mutein backbone.

In this example, 400,000 purified CD4+ or CD8+ responder T cells (Tresp) were separately stimulated with these two different oligomeric streptavidin muteins as explained above, i.e. with either the oligomeric streptavidin mutein backbone of Example 3 (1.0 mg/ml) or with the large oligomeric streptavidin mutein backbones (0.1 mg/ml). 3 µl of both the different backbones were either loaded with a combination of 0.5 µg αCD3 and 0.5 µg αCD28 Fab fragments described above. In addition, 4.5 µl of the oligomeric streptavidin mutein backbone of Example 3 was loaded with 0.5 µg αCD3, 0.5 µg αCD8 Fab and 0.5 µg αCD28 Fab fragment as described above. Untreated (unstimulated) Tresp cells served as negative control and Tresp cells stimulated with anti-CD3/anti-CD28 beads (on which αCD3 and αCD28 monoclonal antibodies are irreversible immobilized) as positive control. Tresp cells were seeded in duplicates in 48-well plates in 1 ml cell culture medium supplemented with 30 U/ml IL-2. Cells were incubated at 37° C. with media exchange on day 3 and cell count was analyzed after 1, 3 and 6 days. The results for the CD4+T responder cells are shown in FIG. 10A, the results for the CD8+T responder cells are shown in FIG. 10B, with the graphs representing degree of proliferation according to the number of cells harvested per time point for CD4+ Tresp (FIG. 10A) and for CD8+ Tresp in FIG. 10B.

Figure 1:
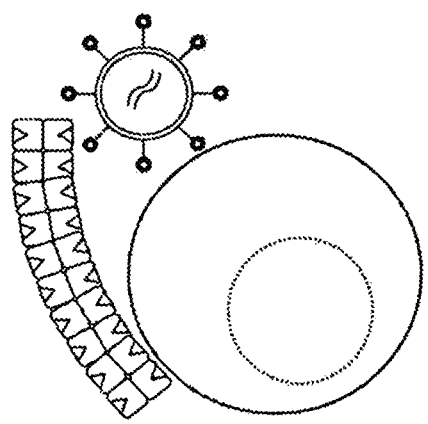
FIG. 1 provides a schematic of the provided method of transduction involving incubating or contacting a plurality of cells comprising a target cell with an oligomeric protein (e.g. an oligomer of a streptavidin mutein) reagent and a viral particle.
Figure 2A:
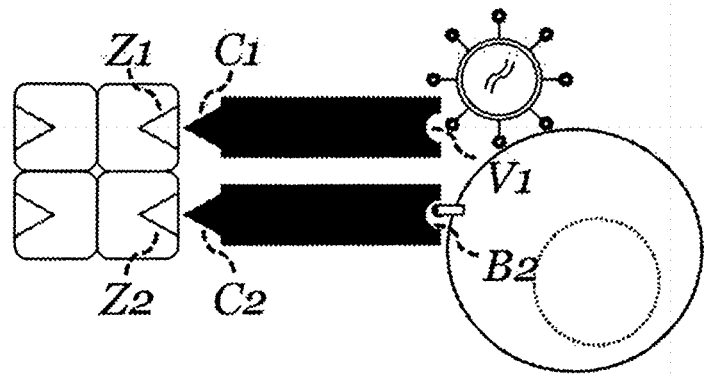
FIG. 2A shows a reagent reversibly bound to a first and second agent. The first agent is capable of specifically binding to a molecule on a viral particle. The second agent is capable of specifically binding to a molecule on a cell. The reagent has a plurality of binding sites Z1 and Z2, which can be the same or different, each capable of reversibly binding to an agent. The first agent contains at least one binding partner C1 that can hind to at least one binding site Z1 of the reagent and the second agent contains at least one binding partner C2 that can specifically bind to at least one binding site Z2 of the reagent. In some cases, C1 and C2 are different. In some cases, C1 and C2 are the same or substantially the same. The first agent contains at least one binding site V1, which can specifically bind to a molecule on the surface of a viral particle. The second agent contains at least one binding site B2, which can specifically bind to a molecule on the surface of a cell. In some embodiments, the first and/or second agent can be selection agents. Here, the first agent is bound to a molecule on the surface of a viral particle and the second agent is bound to a molecule on the surface of a cell.
Figure 2B:
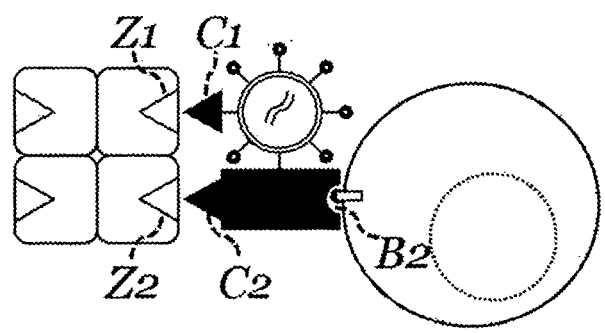
FIG. 2B shows a reagent reversibly bound to a viral particle and an agent. The agent is capable of specifically binding to a molecule on a cell. The reagent has a plurality of binding sites Z1 and Z2, which can be the same or different, each capable of reversible binding. The viral particle contains at least one binding partner C1 that can specifically bind to at least one binding site Z1 of the reagent. The agent contains at least one binding partner C2 that can specifically bind to at least one binding site Z2 of the reagent. In some cases, C1 and C2 are different. In some cases, C1 and C2 are the same or substantially the same. The agent contains at least one binding site B2, which can specifically bind to a molecule on the surface of a cell. In some embodiments, the agent can be a selection agent.
Figure 2C:
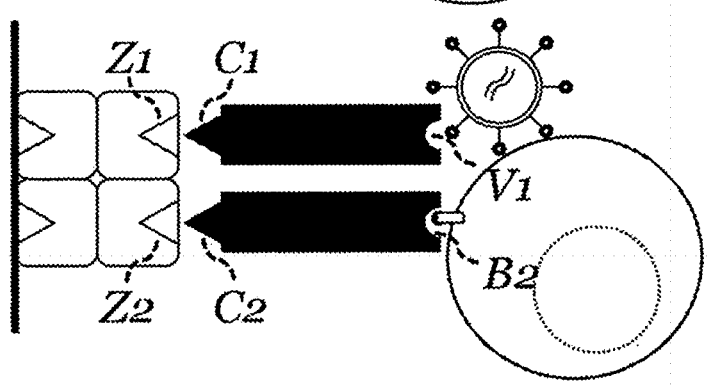
FIG. 2C shows a reagent bound to a support, e.g. solid support and/or stationary phase, and reversibly bound to a first and second agent. The first agent is capable of specifically binding to a molecule on a viral particle. The second agent is capable of specifically binding to a molecule on a cell. The reagent has a plurality of binding sites Z1 and Z2, which can be the same or different, each capable of reversibly binding to an agent. The first agent contains at least one binding partner C1 that can bind to at least one binding site Z1 of the reagent and the second agent contains at least one binding partner C2 that can specifically bind to at least one binding site Z2 of the reagent. In some cases, C1 and C2 are different. In some cases, C1 and C2 are the same or substantially the same. The first agent contains at least one binding site V1, which can specifically bind to a molecule on the surface of a viral particle. The second agent contains at least one binding site B2, which can specifically bind to a molecule on the surface of a cell. In some embodiments, the first and/or second agent can be selection agents. Here, the first agent is hound to a molecule on the surface of a viral particle and the second agent is bound to a molecule on the surface of a cell.
Figure 2D:
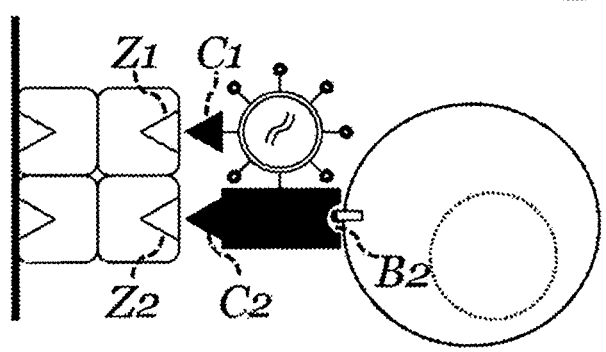
FIG. 2D shows a reagent bound to a support, e.g. solid support and/or stationary phase, and reversibly bound to a viral particle and an agent. The agent is capable of specifically binding to a molecule on a cell. The reagent has a plurality of binding sites Z1 and Z2, which can be the same or different, each capable of reversible binding. The viral particle contains at least one binding partner C1 that can specifically bind to at least one binding site Z1 of the reagent. The agent contains at least one binding partner C2 that can specifically bind to at least one binding site Z2 of the reagent. In some cases, C1 and C2 are different. In some cases, C1 and C2 are the same or substantially the same. The agent contains at least one binding site B2, which can specifically bind to a molecule on the surface of a cell. In some embodiments, the agent can be a selection agent.
Figure 3A:
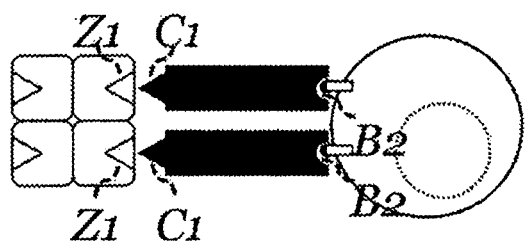
FIG. 3A shows a schematic representation of a reagent (or representative portion thereof) with a plurality of binding sites for reversible binding to agents. In this case, the reagent is shown as capable of reversibly binding to two agents, each of which is capable of specifically binding to a molecule on a cell. The reagent has a plurality of binding sites, including a plurality of the binding site, Z1, each capable of reversibly binding to the agents. The first and second agents, which, in some cases, can be the same, in the schematic representation shown each contain at least one binding partner C1. Binding partner C1 reversibly binds to binding site Z1. The first and second agents each also contain a binding site, B2, which can specifically bind to a molecule on the surface of a cell, which, in some cases, can be on the same cell. Here, the first and second agents are shown specifically binding to molecules on the same cell.
Figure 3B:
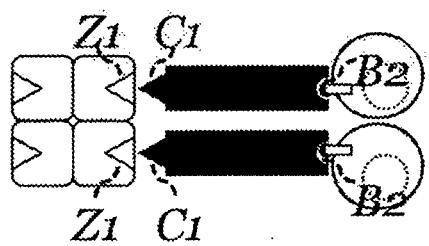
FIG. 3B shows a schematic representation of a reagent with a plurality of binding sites, capable of reversibly binding to a first and second agent, which agents are each capable of specifically binding to a molecule on a first and second cell, respectively. The reagent has a plurality of binding sites Z1, each capable of reversibly binding to an agent. The first and second agents, which, in some cases, can be the same, each contain a binding partner C1, which reversibly binds to binding site Z1. The first and second agents each contain a binding site B2, which can specifically bind to a molecule on the surface of a cell, which, in some cases, can be on the same cell or a different cell. Here, the first agent is bound to a molecule on the surface of a first cell and the second agent is bound to a molecule on the surface of a second cell.
Figure 3C:
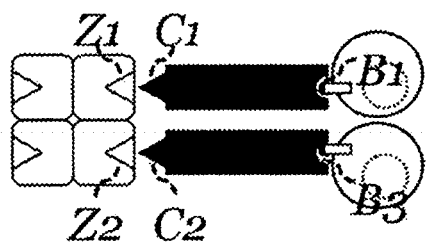
FIG. 3C shows a reagent capable of reversibly binding to a first and second agents, which agents are each capable of specifically binding to a molecule on a first and second cell, respectively. The reagent has a plurality of binding sites Z1 and Z2, which can be the same or different, each capable of reversibly binding to one or both of the agents. The first agent contains a binding partner C1, which reversibly binds to Z1; the second agent contains a binding partner C2, which can reversibly bind to Z2. In some cases, C1 and C2 are different. In some cases, C1 and C2 are the same or substantially the same. The first agent contains a binding site B1, which can specifically bind to a molecule on the surface of a cell and the second agent contains at least one binding site B3, which can specifically bind to a molecule on the surface of a cell. Binding sites B1 and B3 in some cases bind to two different cell surface molecules, or different epitopes on a single molecule, or the same or different molecules on the surface of different cells. Here, the first agent is shown as being bound, via B1, to a molecule on the surface of a first cell, and the second agent is bound to a molecule on the surface of a second cell.
Figure 3D:
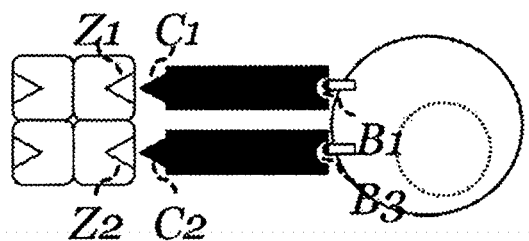
FIG. 3D shows a reagent capable of reversibly binding to a first and second agent, such as selection agents, which are each capable of specifically binding to a molecule on a cell. The reagent has a plurality of binding sites, including Z1 and Z2, which can be the same or different, each capable of reversibly binding to an agent. The first agent contains a binding partner C1 that can specifically bind to binding site Z1 and the second agent contains at least one binding partner C2 that can specifically bind to binding site Z2. In some cases, C1 and C2 are different. In some cases, C1 and C2 are the same or substantially the same. The first agent contains a binding site B1, which can specifically bind to a molecule on the surface of a cell and the second agent contains a binding site B3, which can specifically bind to a molecule on the surface of a cell. In some embodiments, the first agent and second agent can be a selection agent. Binding sites B1and B3 can bind the same or different molecules (e.g. receptor) on the surface of a cell, the same or different epitopes on a molecule, or the same or different molecules on the surface of different cells. Here, the first agent is bound to a first molecule on the surface of a cell and the second agent is bound to a second molecule on the surface of the same cell.
Figure 3E:
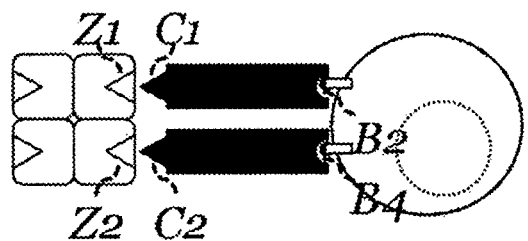
FIG. 3E shows a reagent reversibly bound to a first and second agent, which agents are each capable of specifically binding to a molecule on a cell. The reagent has a plurality of binding sites, including Z1 and Z2, which can be the same or different, each capable of reversibly binding to an agent. The first agent contains a binding partner C1 that can reversibly hind to Z1 of the reagent and the second agent contains a binding partner C2 that can reversibly bind to Z2. In some cases, C1 and C2 are different. In some cases, C1 and C2 are the same or substantially the same. The first agent contains at least one binding site B2, which can specifically bind to a molecule on the surface of a cell and the second agent contains at least one binding site B4, which can specifically bind to a molecule on the surface of a cell. In some embodiments, the first agent and second agent can be stimulatory agents. Binding sites B2 and B4 can bind the same or different molecules on the surface of a cell, the same or different epitopes on a molecule, or the same or different molecules on the surface of different cells. Here, the first agent is hound to a first molecule on the surface of a cell and the second agent is bound to a second molecule on the surface of the same cell.
Figure 4A:
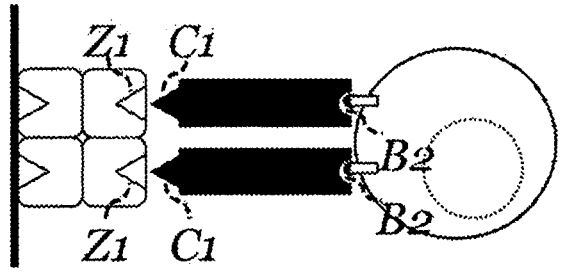
FIG. 4, which includes FIGS. 4A-4E, provide schematic representations of exemplary embodiments as shown in FIGS. 3A-3E, respectively, except that the depicted reagents are shown as being immobilized on a support, such as a stationary phase.
Figure 4B:
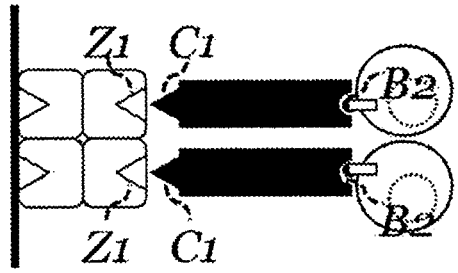
Figure 4C:
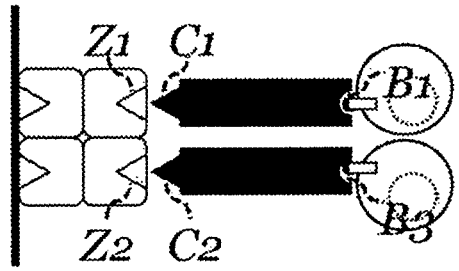
Figure 4D:
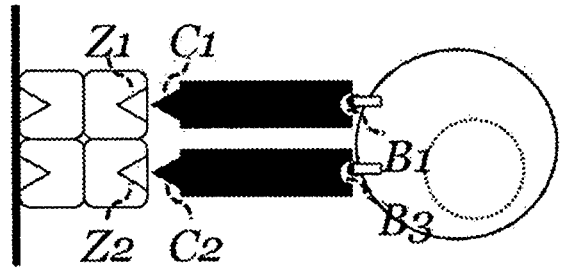
Figure 4E:
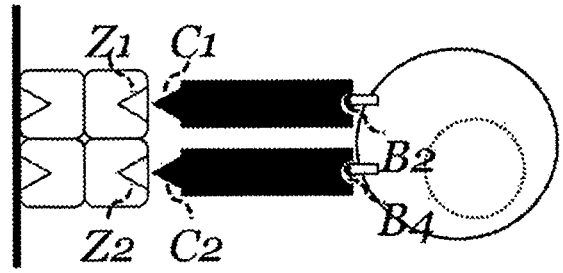
Figure 6:
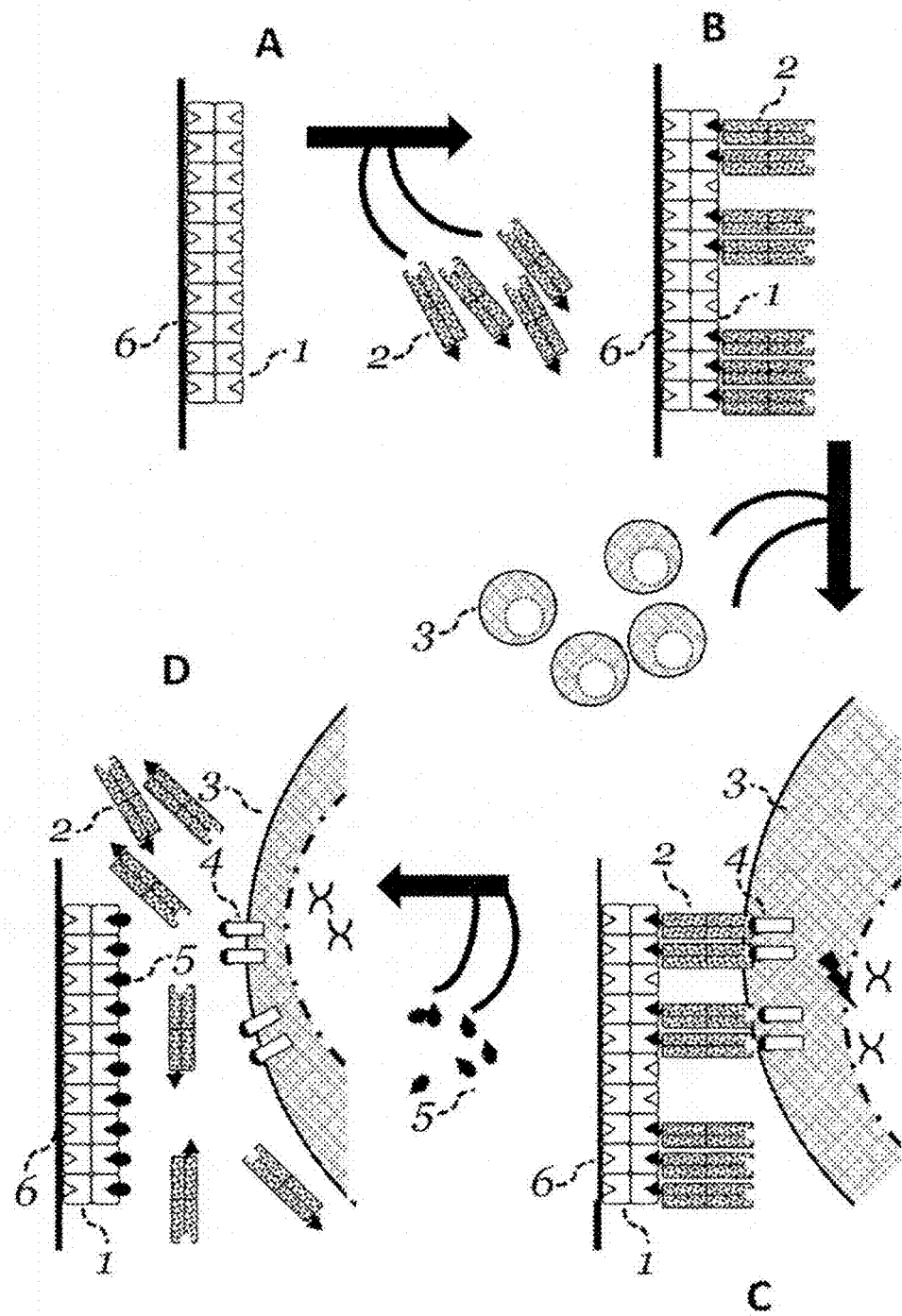
FIG. 6 provides a schematic representation of exemplary embodiments of a reversible system attached to a support, such as a solid support or a surface, including a stationary phase. Panel A shows a support 6 containing the reagent 1. Agents 2, such as Fab fragments, that are capable of specifically binding to a molecule on the surface of a cell are added to the system. The agents 2, such as Fab fragments, comprise a binding partner (e.g. binding partner C) that is capable of reversibly binding to a binding site (e.g. binding site Z) on the reagent. Panel B depicts the binding partner reversibly binding to a binding site on the reagent. Cells 3 are added to the system. Panel C depicts the agents 2, e.g. Fab fragments, binding to the molecules 4 on the surface of a cell 3. In some embodiments, the scFvs comprise a receptor-binding agent or a selection agent. In some embodiments, the agents, e.g. Fab fragments, can be a receptor-binding agent or a selection agent. Panel C depicts an exemplary receptor-binding agent or agents (e.g. a first receptor-binding agent and/or a second receptor-binding agent), which can induce or modulate a signal in a cell upon binding of the agent, e.g. Fab fragment, to the molecule on the cell. A substance 5, such as a competitive reagent (e.g. biotin), is added, which can be a substance that exhibits a higher binding affinity for the binding site on the reagent than for the binding partner on the agent, e.g. Fab fragment, thereby disrupting binding between the reagent and the agent. Panel D depicts disruption of the binding between the agent 2, e.g. Fab fragment, and the reagent, thereby resulting in dissociation of the reagent from the agent, and thereby the cell. In some cases, the agent, e.g. Fab fragment, also can dissociate from its interaction with the molecule 4 on the cell 3. In some cases, this can disrupt, lessen and/or terminate the signaling, in the cell.

As can be seen from FIG. 1 OA the soluble reagents on which αCD3 and αCD28 Fab fragments were reversibly immobilized (the multimerized agents) provided for better expansion of CD4+ T cells than anti-CD3/anti-CD28 beads.

As evident from FIG. 10B, using the multimerized agents, CD8+ T cells could be expanded within the first 6 days at least as efficiently as with anti-CD3/anti-CD28 beads. Notably, in this time period, the expansion experiment that used the larger soluble reagent that carried αCD3 and αCD28 Fab fragments (as first and second agent) showed the best degree of expansion under these culturing conditions. This might again be caused by the soluble "larger" multimerized agent being able to bind to more T cells at the same time than the "smaller" multimerized agent, thereby being able to stimulate more CD4+ T cells than the "smaller" multimerized agent.

Figure 11A:
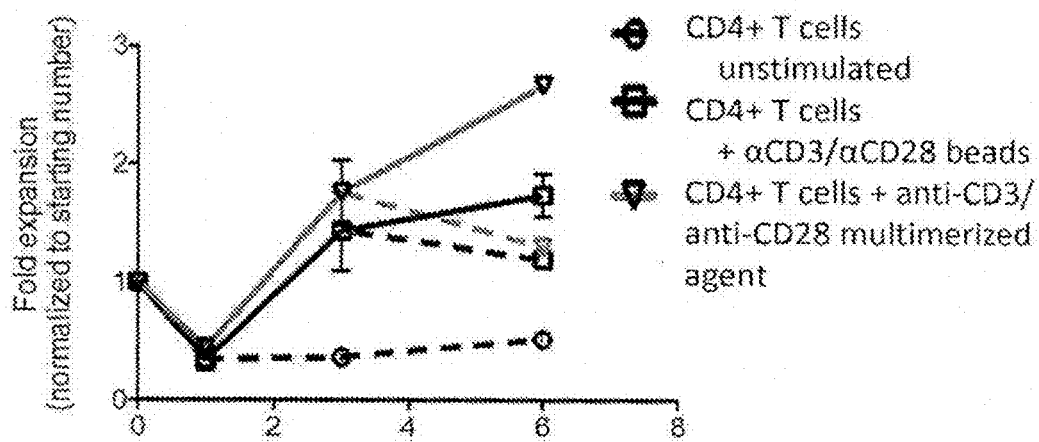
FIGS. 11A and 11B show the combined data from the results obtained in FIGS. 9A-B and 10A-B for the expansion kinetics of proliferation of purified CD4+ and CD8+T responder cells, with FIG. 11A depicting the results for CD4+ T cells and FIG. 11B depicting the results for the CD8+ T cells. Straight lines are used for the culturing with medium exchange on day 3, while dashed lines depict the values obtained for the degree of expansion without media exchange on day 3. The data shown in FIGS. 11A and 11B are normalized on the input cell number. Only data for the Tresp stimulated with the oligomeric streptavidin mutein (n≥3), the Tresp stimulated with the commercially available anti-CD3/anti-CD28 beads (positive control) and the unstimulated T cells (negative control) are shown but no data on the reagent with the "large backbone".
Figure 11B:
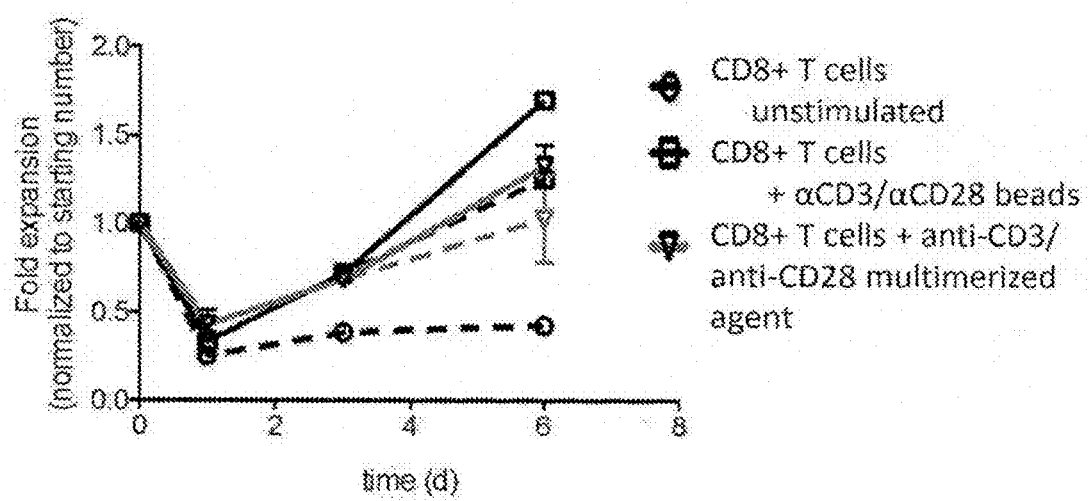

Example 6: Expansion Kinetics of Purified CD4+ and CD8+ T Cell Cultures with or without Medium Exchange In this Example the combined data from Examples 4 and 5 were normalized on input cell number for the "smaller" multimerized agent and positive and negative control. No normalization data was obtained on the "larger" multimerized agent. As explained in Examples 4 and 5, 400,000 to 500,000 CD4+ or CD8+ responder T cells (Tresp) were stimulated with 3 µl of a preparation of multimerized agent (1 mg/ml; on which 0.5 µg αCD3 Fab fragment and 0.5 µg αCD28 Fab fragment were immobilized). Untreated (unstimulated) Tresp cells served as negative control and Tresp cells stimulated with anti-CD3/anti-CD28 beads as positive control. Tresp cells were seeded in duplicates in 48-well plates in 1 ml cell culture medium supplemented with 30 U/ml IL-2. Cells were incubated at 37° C. with media exchange (straight lines in FIGS. 11A and 11B) or without media exchange (dashed lines in FIGS. 11A and 11B) on day 3 and cell count was analyzed after 1, 3 and 6 days. As evident from the normalized data of FIG. 11A, the "smaller" soluble reagent on which αCD3 and αCD28 Fab fragments were reversibly immobilized yielded an about 2.5 fold expansion of CD4+ T cells, while the expansion using anti-CD3/anti-CD28 beads yielded an about 1.8 fold expansion rate. Thus, the use of a multimerized agent even provides for an improvement in the expansion of CD4+ T cells over anti-CD3/anti-CD28 beads. Similarly, FIG. 11B, confirms that CD8+ T cells could be expanded using the multimerized agents within the first 3 days at least as efficiently as with anti-CD3/anti-CD28 beads.

Example 7: Expansion Kinetics & Phenotype of Polyclonal Activated/Expanded Bulk CD3+ Central Memory T Cells (Tcm)

Figure 12A:
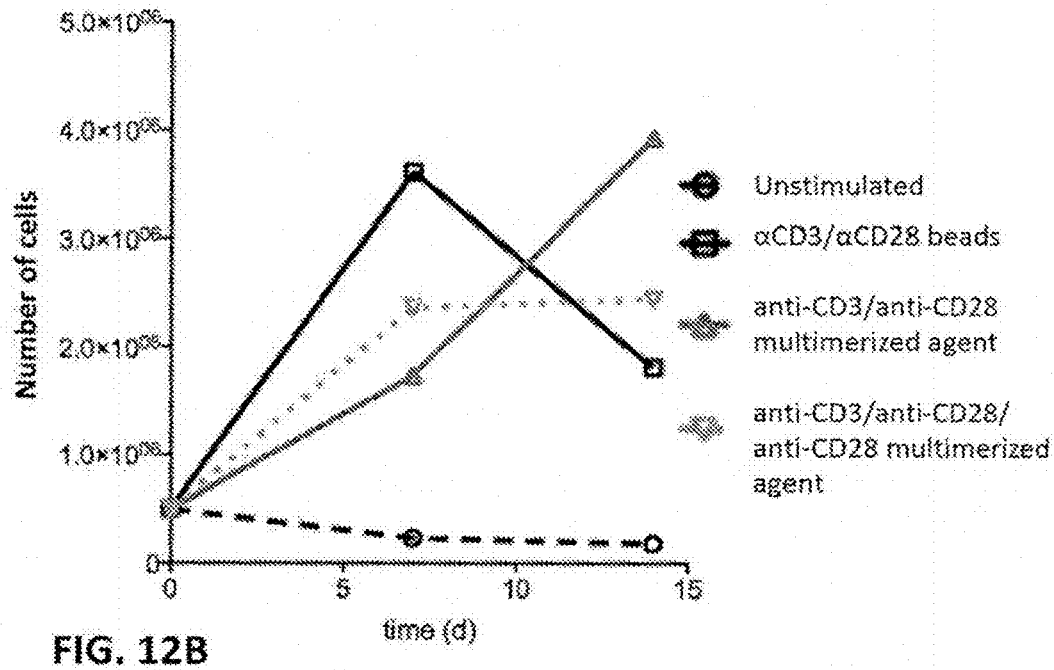
Figure 12B:
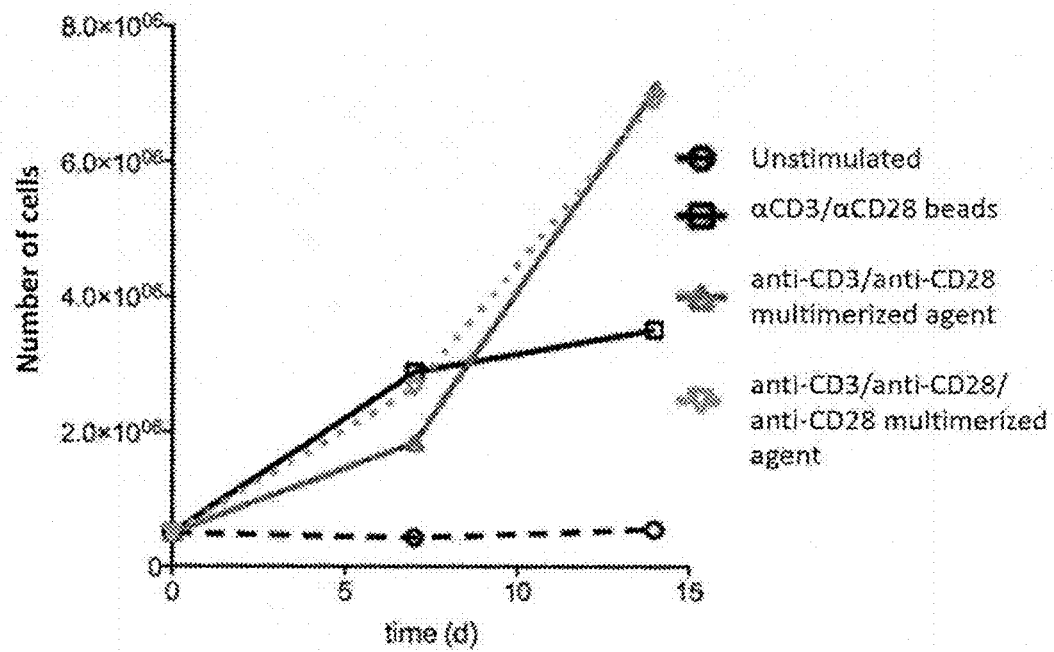

In this Example, 500,000 CD3+CD62L+CD45RA− responder Tcm cells (Tresp) were stimulated with 3 µl of a preparation of the soluble oligomeric streptavidin mutein of Example 3 (1 mg/ml) that was either loaded with a combination of 0.5 µg αCD3 and 0.5 µg αCD28 Fab. Furthermore, 4.5 µl of a preparation of oligomeric streptavidin mutein loaded with 0.5 mg αCD3, 0.5 µg αCD8 Fab and 0.5 µg αCD28 Fab was used as an additional stimulation condition. Untreated (unstimulated) Tresp cells served as negative control and Tresp cells stimulated with anti-CD3/anti-CD28 beads (on which αCD3 and αCD28 monoclonal antibodies are irreversible immobilized) as positive control. Tresp cells were seeded in 48-well plates in 1 ml cell culture medium supplemented with 30 U/ml IL-2 only or 30 U/ml IL-2 and 5 ng/ml IL-15. Cells were incubated at 37° C. with media exchange every 3 days and cell count was analyzed after 7 and 14 days. Graphs represent degree of proliferation according to the number of cells harvested per time point, in FIG. 12A only IL-2 supplemented media and in FIG. 12B IL-2 and IL-15 supplemented media. As can be seen from both FIG. 12A and FIG. 12B, the soluble reagent that has reversibly bound thereon CD3 Fab fragment and αCD28 Fab fragment yields better cell expansion than the anti-CD3/anti-CD28 beads. As further shown by the flow-cytometric analysis of CD62L and CD127 surface expression after 14 days of culture in variable cytokine milieus of FIG. 12C, the experimental approaches using multimerized agents retain, under both conditions chosen here, a higher content of CD127-expressing long-lived memory T cells than expansion with anti-CD3/anti-CD28 beads. This illustrates a further advantage of the methods of the present compositions and methods described herein.

Example 8: Yield and Phenotype of Expanded CD8+ T Cells—Size Variation of Soluble Reagent and Addition of αCD8-Fab Addition for Stimulation In this Example, the expansion of purified CD8+T responder cells stimulated in vitro with αCD3/αCD28 Fab fragments that were reversibly immobilized soluble oligomeric streptavidin muteins were examined. In addition, the effect of adding αCD8-Fab to the reagent for increasing the specificity of the expansion for CD8+ T cells was examined.

Figure 13A:
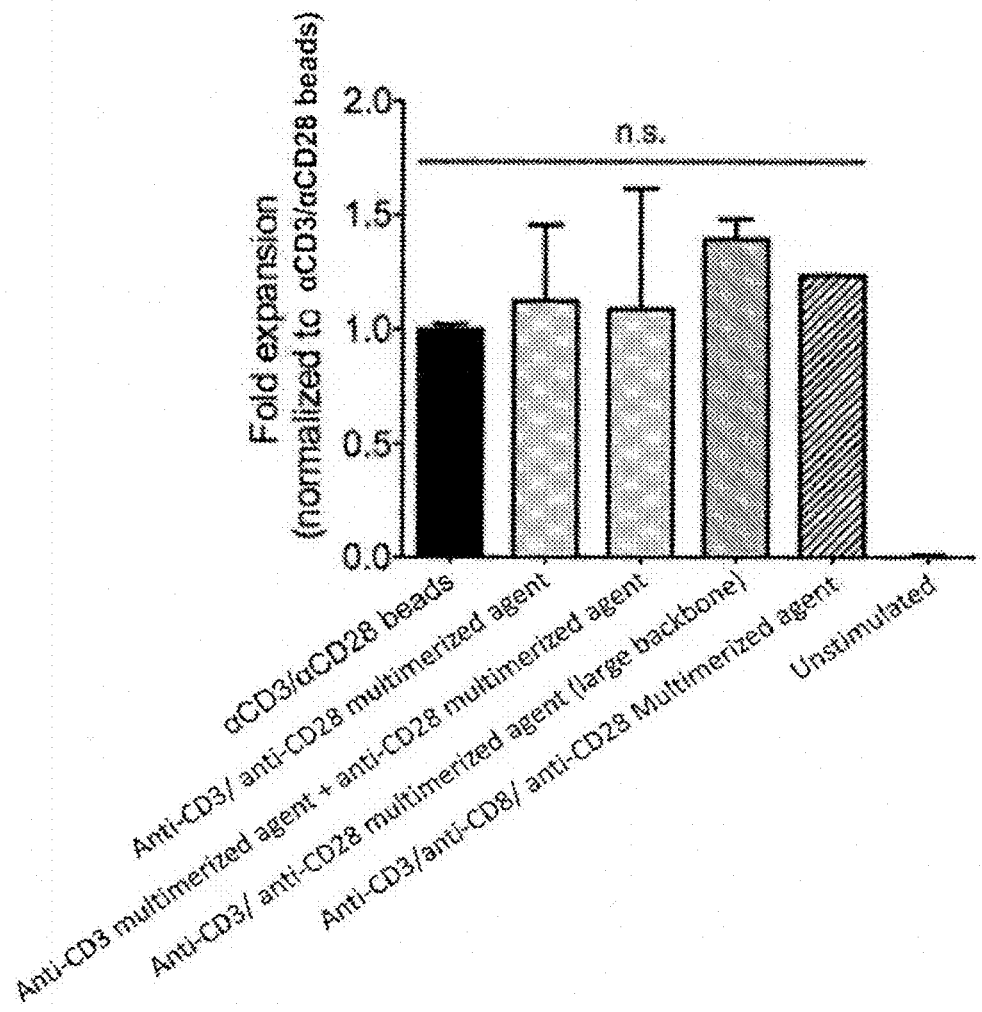
FIGS. 13A and 13B show the yield and phenotype of expansion of purified CD8+T responder cells stimulated in vitro with αCD3/αCD28 Fab fragments that were reversibly immobilized on two kinds of soluble oligomeric streptavidin muteins acting a soluble reagent. The first kind of oligomeric streptavidin mutein was the fraction of the oligomeric streptavidin mutein (obtained in Example 3 (conventional backbone), the second kind of this oligomeric streptavidin mutein used as soluble reagent was the soluble oligomer described above and referred herein as "large" backbone. In these experiments, the fraction of the oligomeric conventional streptavidin mutein (n≥3) was also used as a reagent that were either functionalized with single Fab fragments (third bar in FIG. 13A and FIG. 13B) or with a combination of αCD3 and αCD28 Fab-fragments. Furthermore to the combined stimulation with αCD3/αCD28 Fab fragments, also an additional αCD8 Fab fragment (commercially available from IBA GmbH, Göttingen, Germany) was immobilized in order to test whether it is possible to preferentially stimulate a specific T cell subpopulation.
Figure 13B:
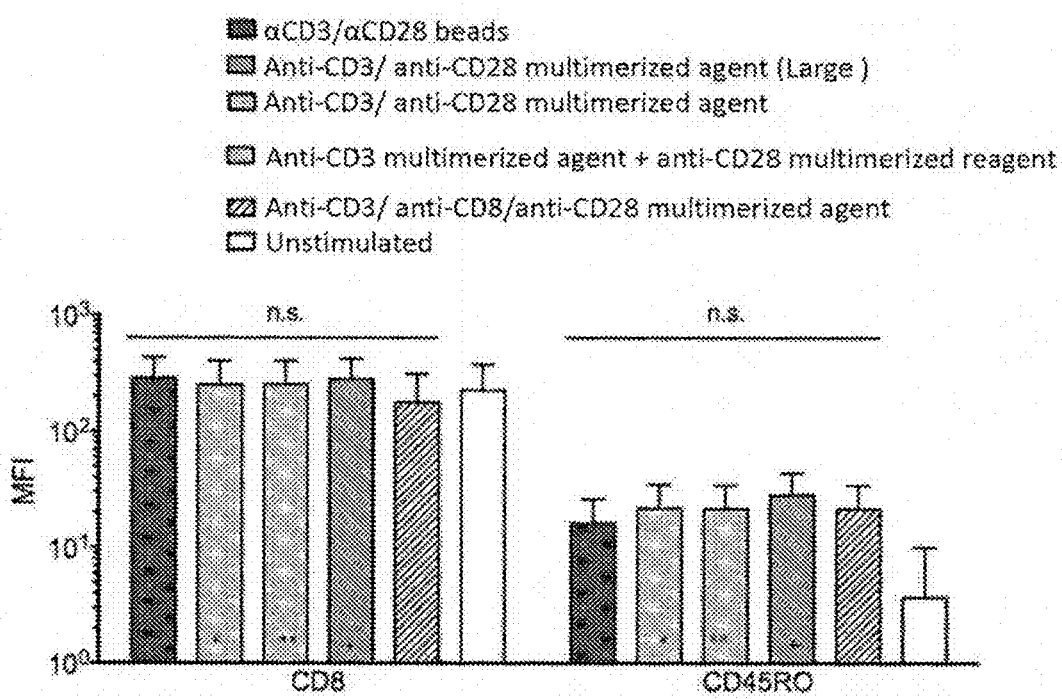

For this purpose, 300,000 purified CD8+ responder T cells (Tresp) were separately stimulated with two different Streptactin based reagents, namely either the small multimerized agent of Example 3 (1 mg/ml) or the larger multimerized agent described above (0.1 mg/ml). 3 µl of both oligomeric streptavidin mutein reagent backbones were either loaded with a combination of the 0.5 µg αCD3 and 0.5 mg αCD28 Fab fragments described above to form the multimerized agents. In addition, 4.5 µl of the smaller oligomeric streptavidin mutein backbone was loaded with 0.5 µg αCD3, 0.5 µg αCD8 Fab and 0.5 µg αCD28 Fab fragments described above. Furthermore 3 µl of the "smaller" oligomeric streptavidin mutein backbone only functionalized with 0.5 µg αCD3 Fab fragment alone or 0.5 µg αCD28 Fab fragment alone was used. Unstimulated Tresp cells served as negative control and Tresp stimulated with anti-CD3/anti-CD28 beads served as positive control. Tresp cells were seeded in duplicates in 48-well plates in 1 ml cell culture medium supplemented with 30 U/ml IL-2. Cells were incubated at 37° C. with media exchange after 3 days and analyzed after 6 days. FIG. 13A depicts the degree of proliferation according to the number of cells harvested at day 6 compared to the negative controls and normalized to the positive control. FIG. 13A shows that the expansion of the CD8+ T cells using the multimerized agents result in higher yields of the CD8+ T cells than expansion using anti-CD3/anti-CD28 beads. The FACS analysis of CD8 surface expression and CD45RO surface expression (FIG. 13B) after cell culture shows that the same phenotype of CD8+ T cells were expanded by either the multimerized agents or anti-CD3/anti-CD28 beads (the various stimulating conditions were compared using one-way ANOVA and no significant difference (n.s.) was detected). The improved yield of the CD8+ cells using the expansion methods disclosed herein compared to the anti-CD3/anti-CD28 beads might be due to the fact that the soluble multimerized agents can access their target receptors on the cell surface better than the antibodies that are immobilized on the anti-CD3/anti-CD28 beads. This improved yield might become very advantageous when expanding rare population of cells from an initial sample.

In addition, comparing the yield of expansion achieved with the reagent on which both the 0.5 μg αCD3 and 0.5 μg αCD28 Fab fragments were jointly immobilized (second column from the left in FIG. 13B) to the yield using two reagents which were functionalized only with the αCD3 Fab fragment alone or the αCD28 Fab fragment alone (third column from the left in FIG. 13B), it can be seen that both experiments had the same expansion efficiency. Thus, these experiments show that using one reagent on which both the first agent and the second agent are jointly immobilized is functionally equivalent to using for the expansion two separate reagents which are loaded with only the first agent and the second agent, respectively.

Example 9: Yield & Phenotype of Expanded CD8+ T Cells—Titration of Separate Soluble Reagents with Different Ratios of αCD3- and αCD28 Fab Fragment Immobilized Thereon In this Example, the yield and the phenotype of expanded CD8+T responder cells (Tresp) that were stimulated in vitro with αCD3/αCD28 Fab fragments that were reversibly immobilized in different amounts on soluble oligomeric streptavidin muteins were examined.

For this purpose 300,000 CD8+ responder T cells (Tresp) were stimulated with varying amounts of a mixture of preparations of the "small" oligomeric streptavidin muteins (1 mg/ml) functionalized with αCD3 Fab alone and αCD28 Fab alone ("1×" corresponds to 1.5 μg oligomeric streptavidin mutein functionalized with 0.5 μg αCD3 alone and 1.5 μg oligomeric streptavidin mutein functionalized with 0.5 μg αCD28 Fab fragment alone), or 3 μl of a preparation of the oligomeric streptavidin mutein loaded with 0.5 μg αCD3 and α0.5 μg CD28 Fab, or 4.5 μl of a preparation of the oligomeric streptavidin mutein loaded with 0.5 μg αCD3, 0.5 μg strep-tagged αCD8 and 0.5 μg αCD28 Fab. Untreated Tresp cells served as negative control and Tresp stimulated with anti-CD3/anti-CD28 beads as positive control. Tresp cells were seeded in 48-well plates in 1 ml cell culture medium supplemented with 30 U/ml IL-2. Cells were incubated at 37° C. without media exchange and analyzed after 5 days. FIG. 14A depicts the degree of proliferation according to the number of cells harvested at day 5 compared to the negative controls and normalized to the positive control. FIG. 14A shows that the expansion of the CD8+ T cells using the various multimerized agents result in higher yields of the CD8+ T cells than expansion using anti-CD3/anti-CD28 beads (especially the cumulative total reagent amount of the 5× condition resulted in an optimal expansion of cells especially over time/increase in total cells by beginning cell division). The FACS analysis of CD8 surface expression and CD45RO (FIG. 14B) surface expression after cell culture shows that the same phenotype of CD8+ T cells were expanded by either the multimerized agents or by the commercially available anti-CD3/anti-CD28 beads.

Figure 15A:
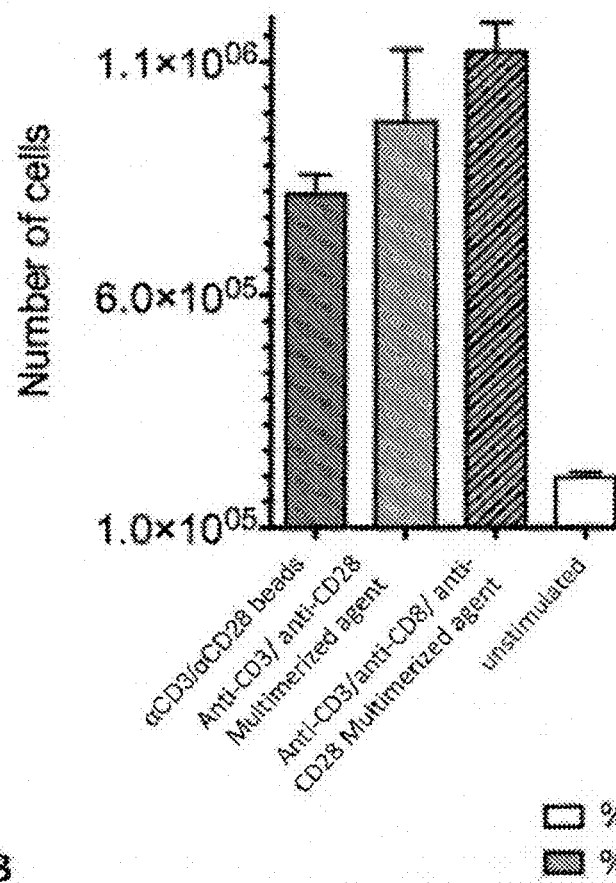
FIGS. 15A and 15B show the expansion of purified CD3+T responder cells stimulated in vitro with αCD3/αCD28 Fab fragments that were reversibly immobilized on the soluble oligomeric streptavidin mutein of Example 3 that served as a soluble reagent. In one experiment, in addition to αCD3/αCD28 Fab fragments, also an αCD8 Fab fragment commercially available from IBA GmbH, Göttingen, Germany (catalogue number 6-8000-203) was immobilized on the soluble oligomer of the streptavidin mutein in order to test whether it is possible to preferentially stimulate in vitro the CD8+ T cell subpopulation within the bulk CD3+ culture with a reagent having reversibly immobilized thereon also an αCD8 Fab fragment. In more detail, 500,000 purified CD3+ responder T cells (Tresp) were stimulated with 3 µl of a preparation of oligomeric streptavidin mutein (1 mg/ml) loaded with a combination of 0.5 µg of the αCD3 and 0.5 µg of the αCD28 Fab. As an alternative approach, 4.5 µl of the oligomeric streptavidin mutein were loaded with 0.5 µg αCD3, 0.5 µg αCD8 Fab and 0.5 µg αCD28 Fab described above. Unstimulated Tresp cells served as negative control and Tresp stimulated with anti-CD3/anti-CD28 beads (beads on which αCD3 and αCD28 monoclonal antibodies are irreversible immobilized) served as positive control.
Figure 15B:
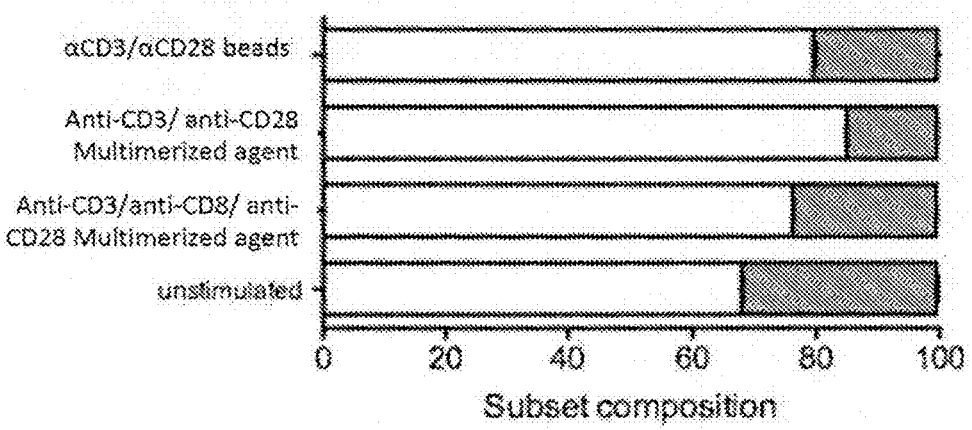

Example 10: Yield and Subset Composition of Expanded CD3+ T Cells with Addition of αCD8-Fab for Stimulation The experiment shows the expansion of purified CD3+T responder cells stimulated in vitro with αCD3/αCD28 Fab fragments that were reversibly immobilized on the soluble oligomeric streptavidin muteins of Example 3 that served as a soluble reagent. In one experiment, in addition to αCD3/αCD28 Fab fragments, a αCD8 Fab fragment commercially available from IBA GmbH, Göttingen, Germany (catalogue number 6-8000-203) was immobilized on the soluble oligomeric streptavidin mutein in order to test whether it is possible to preferentially stimulate a specific T cell subpopulation in vitro with the reversible αCD3/αCD28 multimerized agents. In more detail, 500,000 purified CD3+ responder T cells (Tresp) were stimulated with 3 μl of a preparation of oligomeric streptavidin muteins (1 mg/ml) loaded with a combination of 0.5 μg of the αCD3 and 0.5 μg of the αCD28 Fab. As an alternative approach, 4.5 μl of the oligomeric streptavidin muteins were loaded with 0.5 μg αCD3, 0.5 μg strep-tagged αCD8 Fab and 0.5 μg strep-tagged αCD28 Fab. Unstimulated Tresp cells served as negative control and Tresp stimulated with anti-CD3/anti-CD28 beads (beads on which αCD3 and αCD28 monoclonal antibodies are irreversible immobilized) served as positive control. As can be seen from FIG. 15A, the reagent that is reversibly loaded with the αCD3 Fab fragment, the αCD28 Fab fragment and also the αCD8 Fab fragment provided the highest number of expanded CD3+ T cells. With 1×, 1×10$^6$ the number of expanded cells the yield was about 30% higher than for expansion of these T cells using commercially available anti-CD3/anti-CD28 beads. In addition and more important, as shown in FIG. 15B with this reagent that carries the αCD3 Fab fragment, the αCD28 Fab fragment and the αCD8 Fab fragment, the amount of CD8+T cells were the highest, compared to both the expansion with anti-CD3/anti-CD28 beads or a soluble reagent that caries only the αCD3 Fab fragment and the αCD28 Fab fragment as first and second agent as described herein. Thus, also this experiment shows the advantage of the compositions and methods described herein that in addition to a first agent that provides a primary activation signal to the desired cell population and optionally a second agent that provides a co-stimulatory signal, a further agent that is specific for the activation of the desired cell population can be immobilized on the reagent. Thus, by so doing, the compositions and methods described herein provide for the possibility of preferentially expanding or selectively enriching any desired cell population or subpopulation from a sample that, for example, comprises a variety of different subpopulations.

Example 11: Analysis of the Differential Intracellular Calcium Mobilization in Jurkat Cells Real-time low-cytometric analysis of the differential intracellular calcium mobilization induced in Jurkat cells that are either labeled with the αCD3 antibody clone OKT3 or with Fab fragments of OKT3 being multimerized with Strep-tactin® was examined here.

For this purpose, Jurkat cells were loaded with the calcium-sensitive dye Indo-1-AM and calcium release was triggered by injection of either αCD3 monoclonal antibody OKT3 (produced by the hybridoma cell line OKT3, see above, black squares) or αCD3 Fab fragments (derived from the parental cell line OKT3) that were multimerized by reversible binding of its streptavidin binding peptide to soluble Strep-Tactin fluorescently conjugated with phycoerythrin. In the case of the intact multimeric OKT3 Fab-Strep-Tactin complexes, the calcium release was triggered over an identical time period as with the parental antibody clone (dark grey triangles). Activation of cells could be completely avoided by injection of D-biotin treated, pre-dissociated Fab-Strep-Tactin complexes (light grey circles) identical to injection of the PBS negative control (inverted white triangles). Application of ionomycine served as positive control for calcium influx. Time-resolved changes in intracellular $Ca^{2+}$ concentration were monitored by flow-cytometry based on the change in FL6/FL7 ratio. It can be seen from FIG. 16A that both the parental antibody OKT3 as well as the multimerized monovalent Fab fragment of OKT3 effected calcium release, meaning that the multimerized monovalent Fab fragment of OKT3 is essentially as functional as the parental antibody. Notably, the multimeric OKT3 Fab fragment was not able to trigger calcium release if biotin was added to Strep-tactin on which the OKT3 Fab fragment was immobilized prior to the addition of the Streptactin-OKT3 Fab fragment. In this case, the biotin disrupted the reversible bond formed between Strep-tactin as multimerization agent and the OKT3 Fab fragment. The monovalent Fab fragment was therefore displaced from the multimerization agent and after dissociation was not able to trigger calcium release by binding to CD3 of the Jurkat cells.

Figure 16A:
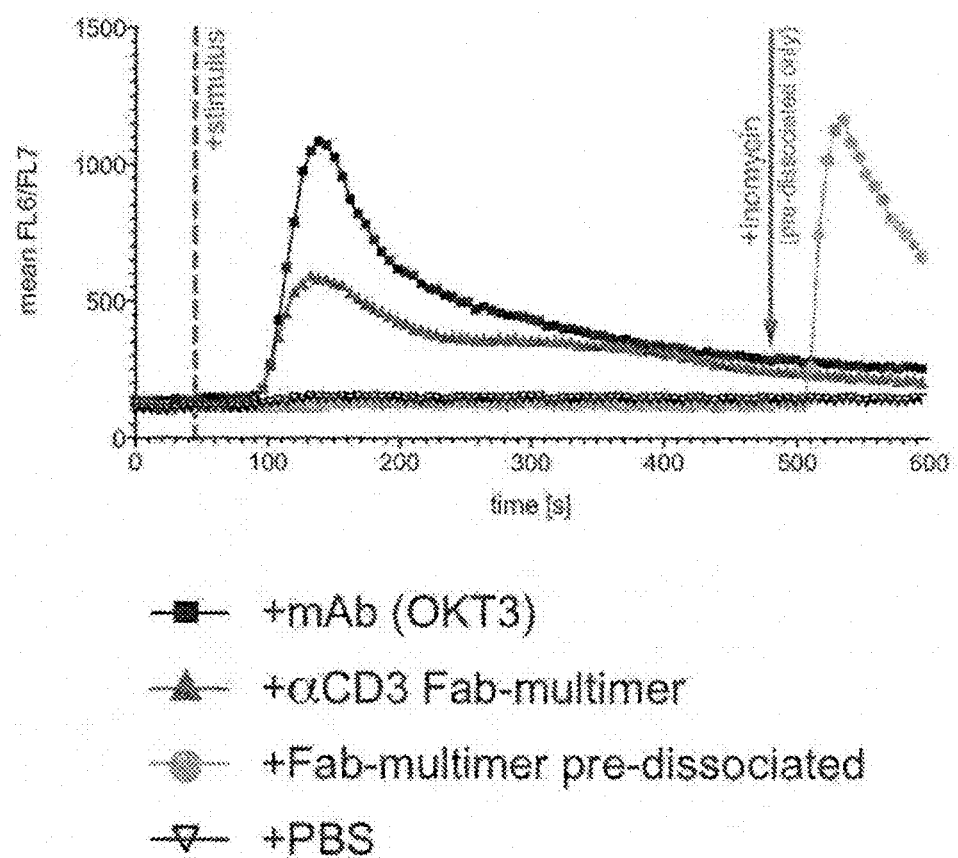
FIGS. 16A and 16B shows the results of the differential intracellular calcium mobilization in Jurkat cells that are either labelled with the αCD3 antibody OKT3 or with Fab fragments of OKT3 being multimerized with Strep-tactin® (also referred to as Fab multimers herein).
Figure 16B:
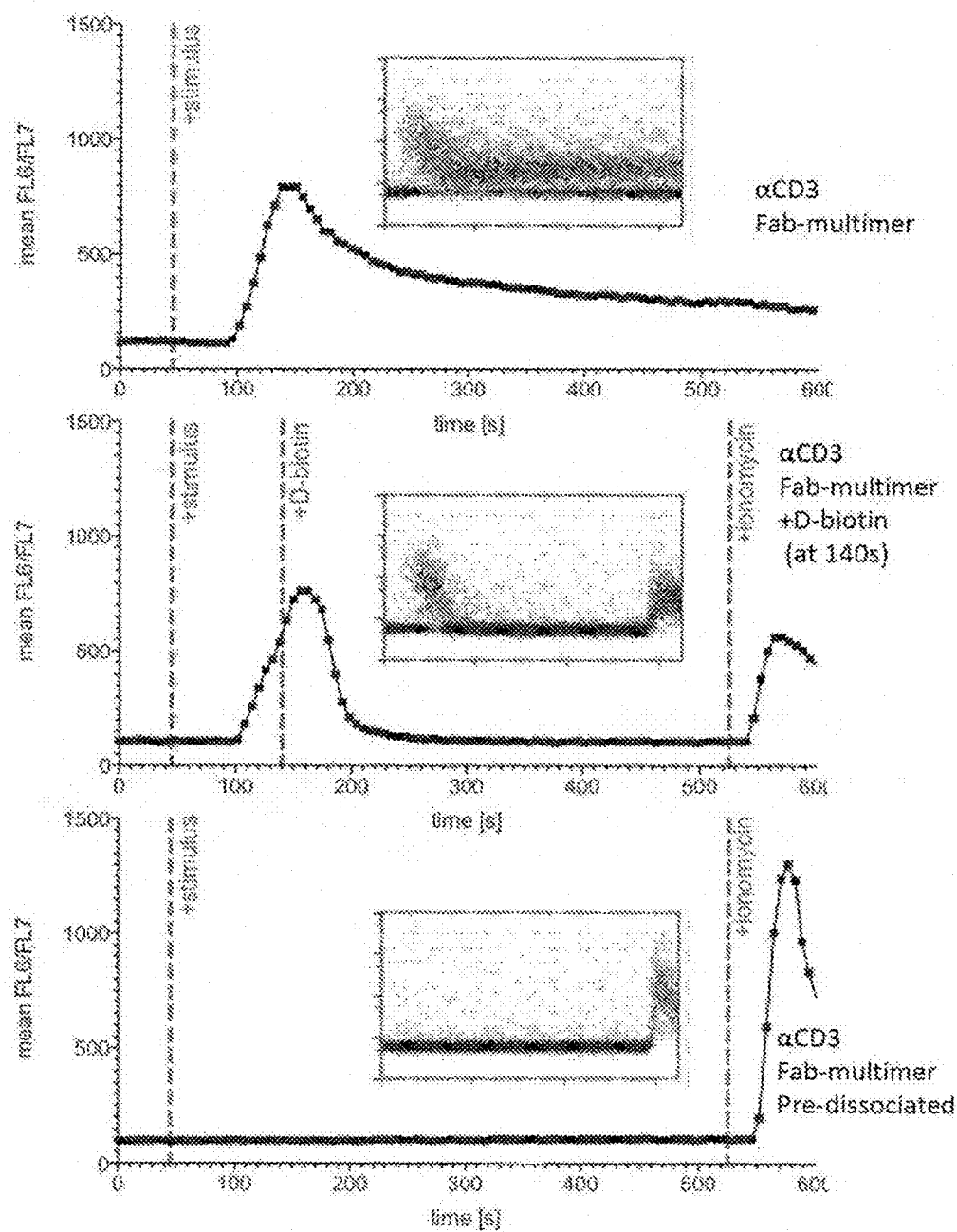

In the experiments shown in FIG. 16B indo-1-AM-labeled Jurkat cells were activated by OKT3 derived αCD3 Fab-Strep-Tactin-complexes as described in FIG. 16A. Injection of intact (upper graph) or pre-dissociated complexes (lower graph) served as positive or negative controls respectively. In addition, stimulation of cells with intact Fab-Strep Tactin-complexes followed by subsequent injection of D-biotin (near the peak activation at t=140 s) resulted in abrupt disruption of αCD3 Fab-multimer signaling (middle graph). Injection of ionomycine into the pre-dissociated Fab complex group served as positive control. Data are representative of three different experiments. Importantly, FIG. 16B shows that the addition of D-biotin to the sample rapidly displaces the Fab fragment from the Streptactin multimerization agent, thereby effectively terminating the calcium release even under ongoing calcium stimulation and demonstrating that the dissociated OKT3 Fab fragment is not any longer biologically active. Likewise, the multimeric OKT3 Fab fragment was also not able to trigger calcium release when biotin was added to the Strep-tactin-OKT3 Fab fragment multimer prior to the addition of the Streptactin-OKT3 Fab sample to the Jurkat cells.

Example 12: Reversible Staining of Cells by CD3 Fab-Multimers

Figure 17:
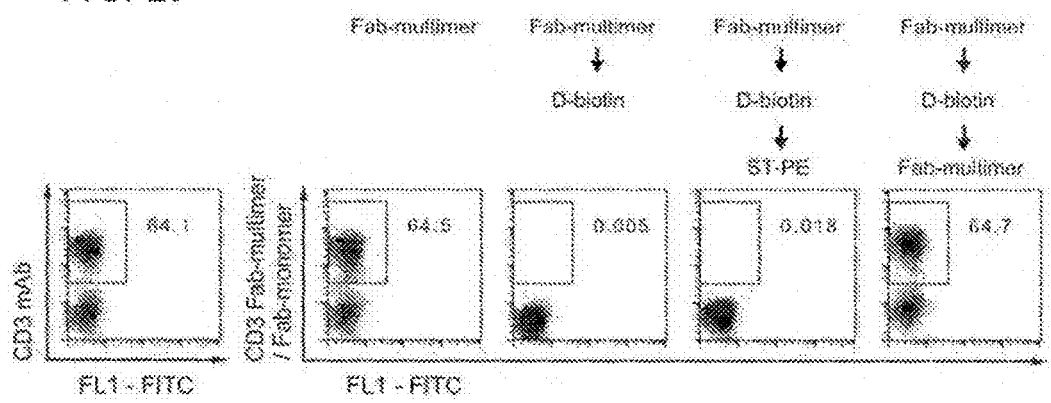
FIG. 17 shows the result of the reversible staining of cells by anti CD3 OKT3 Fab-multimers. Freshly isolated PBMCs were stained with either a monoclonal antibody (left dot plot, parental clone for the Fab-multimers) or cognate PE-labeled Fab-multimers and analyzed either before (second left column) or after treatment with D-biotin (middle column). Remaining Fab monomers were then detected after subsequent washing steps using fresh PE-labeled Strep-Tactin® (second right column). Secondary Fab-multimer staining of reversibly stained cells served as control (right column). Only live (PInegative) cells are shown. Numbers in dot plots indicate the percentage of cells within gates.

This Example examines the reversible staining of cells by CD3 Fab-multimers. Freshly isolated PBMCs were stained with either the αCD3 monoclonal antibody clone OKT3 (left dot plot, parental clone for the Fab-multimers) or cognate phycoerythrine (PE)-labeled OKT3 Fab-multimers and analyzed either before (second left column) or after treatment with D-biotin (middle column). Remaining Fab monomers were then detected after subsequent washing steps using fresh PE-labeled Strep-Tactin® (second right column). Secondary Fab-multimer staining of reversibly stained cells served as control (right column). Only live CD3 cells which are negative in staining with propidium iodide (PI) for live/dead discrimination are shown in FIG. 17. Numbers in dot plots indicate the percentage of cells within gates. This experiment shows that the staining of CD3+ PBMCs with an anti-CD3 Fab fragment multimerized with Streptactin as multimerization reagent is fully reversible by addition of D-biotin and that the monovalent Fab fragment alone does not bind to the CD3 molecule present on PBMCs.

Example 13: Reversible Isolation of Cells by CD28 Fab-Multimers

Figure 18:
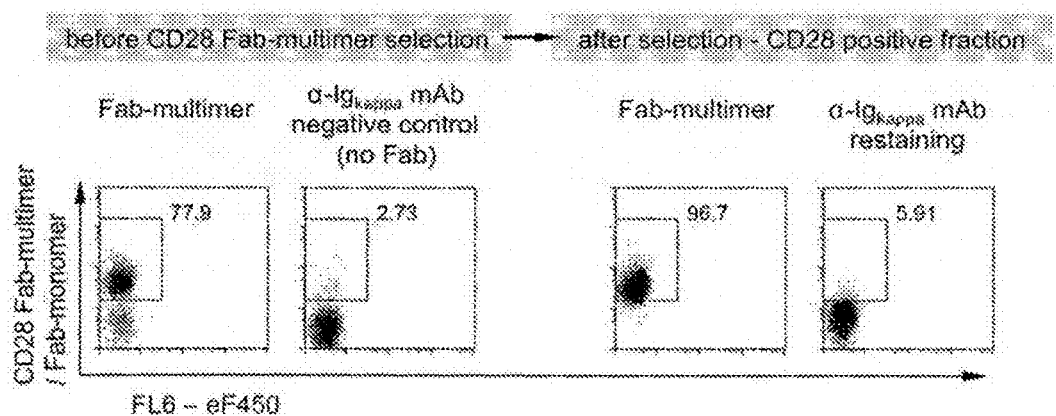
FIG. 18 shows the isolation of cells by reversible binding of anti-CD28 Fab fragments multimerized with Strep-Tactin® labeled with phycoerythrine as a fluorescent label. CD28+ cells were selected/isolation by Fab-multimer magnetic cell selection from freshly isolated PMBCs as described in International Patent Application WO2013/011011. Before selection cells were control stained with either the cognate fluorescent αCD28-multimers (left dot plot) or with an antibody directed against the immunoglobulin kappa light chain (second left dot plot, α-Ig kappa mAb).

This Example shows the isolation of cells by reversible binding of anti-CD28 Fab fragments multimerized with Strep-Tactin® magnetic particles (the magnetic particles are available from IBA GmbH Göttingen, Germany). The Fab fragments derived from the antibody CD28.3 described in Example 2 above were used for this purpose. CD28+ cells were selected/isolation by Fab-multimer magnetic cell selection from freshly isolated PMBCs as essentially described in International Patent Application WO2013/011011. Before selection cells were control stained with either the cognate fluorescent αCD28-multimers (left dot plot) or with an antibody directed against the immunoglobulin kappa light chain (second left dot plot, α-Ig kappa mAb) as a control staining. After selection, CD28+ cells were treated with D-biotin and subsequently washed to remove magnetic beads and Fab-monomers. Liberated CD28+ cells were subsequently (re-) stained either with CD28 Fab-multimers (second right dot plot) or with the α-Igkappa mAb (right dot plot) to detect potentially remaining Fab-monomers. Only live ($PI^{negative}$) CD3+ cells are shown. Numbers in dot plots indicate the percentage of cells within gates. FIG. 18 shows that CD28+ cells can be isolated from PMBC using such multimerized anti-CD28 Fab fragment and that all isolation reagents including the anti CD28 Fab-monomers can be removed after selection.

Example 14: Early Cluster Formation after Activation of Purified CD4+ and CD8+T Responder Cells Stimulated In Vitro with Reversible aCD3/aCD28 Fab-Streptamer Multimers In this Example, 400,000 CD4+ or CD8+ responder T cells (Tresp) were stimulated with 3 μl of a preparation of oligomeric Streptactin multimerization reagent (1 mg/ml) loaded with a combination of 0.5 μg αCD3- and 0.5 μg αCD28 Fab. Untreated (unstimulated) Tresp cells served as negative control and Tresp cells stimulated with anti-CD3/anti-CD28 beads as positive control. Tresp cells were seeded in duplicates in 48-well plates in 1 ml cell culture medium supplemented with 30 U/ml IL-2. Cells were incubated at 37° C. and microscopically analyzed after 1 and 2 days. Stimulation of CD4+ Tresp (FIG. 19A) and CD8+ Tresp (FIG. 19B) are shown for anti-CD3/anti-CD28 beads (middle row) and Streptamer multimers (lower row) respectively. The photographs represent degree of cluster formation: For better visibility exemplary clusters are indicated by circles for the stimulation with soluble streptavidin mutein oligomers in FIG. 19A and FIG. 19B. Clusters within the Dynabead stimulation are readily visibly by accumulation of dark stimulatory particles. As evident, both for CD4+ and CD8+ T cells early clusters formed when using the expansion method of the invention that employs a soluble oligomeric multimerization reagent.

Example 15: Selective Antigen-Specific Expansion of Tcm Responder Cells Out of Bulk CD3+ Central Memory T Cells (Kinetics & Phenotype)

In this Example, the kinetics and the phenotype of selective Antigen specific (Ag-specific) expansion out of purified CD3+CD62L+CD45RA− Tcm responder cells was examined.

In more detail, CD3+CD62L+CD45RA− Tcm responder cells were stimulated in vitro with both a peptide:MHC molecule complex (that acts as first agent that provides a primary activation signal to the cells) and an αCD28 Fab fragment (that acts as second reagent that stimulates an accessory molecule on the surface of the cells). Both the complex of antigen specific peptide with the MHC molecule and the αCD28 Fab fragment were reversibly immobilized on the soluble oligomeric streptavidin mutein (with n≥3) described in Example 3. The peptide that was used for the antigen specific expansion was the peptide CRVLCCYVL (SEQ ID NO: 38), amino acids 309-317 of the immediate-early 1 protein (described in Ameres et al, PLOS Pathogens, May 2013, vol. 9, issue 5, e1003383) representing an HLA-C7/IE-1 epitope that is specific for cytomegalovirus (CMV). The MHC I molecule that presents the peptide carries at the C-terminus of the α chain (heavy chain) the streptavidin binding peptide (SAWSHPQFEK(GGGS)$_2$GG-SAWSHPQFEK, (SEQ ID NO: 16) that is commercially available as "Twin-Strep-tag®" from IBA GmbH, Göttingen, Germany).

For this purpose, 500,000 CD3+CD62L+CD45RA− responder Tcm cells (Tresp) were stimulated Ag-specifically using 3 μl of a preparation of soluble oligomeric Streptactin multimerization reagent functionalized with 0.5 μg of the peptide:MHC class I complexes equipped with the streptavidin binding peptide and with 0.5 μg of the αCD28 Fab described above. As an alternative, 4.5 μl of a of preparation of the Streptactin multimerization reagent were loaded with 0.5 μg of these peptide:MHC class I complexes, 0.5 μg CD8 αFab and 0.5 μg αCD28 Fab. For comparison, polyclonal stimulation was performed, using 3 μl of a preparation of Streptactin multimerization reagent (1 mg/ml) either loaded with a combination of 0.5 μg αCD3 Fab and 0.5 μg αCD28 Fab. Again as the alternative stimulation condition described above, 4.5 μl of a preparation of Streptactin multimerization reagent reversibly loaded with 0.5 μg αCD3 Fab, 0.5 μg αCD8 Fab and 0.5 μg αCD28 Fab was used. Untreated (unstimulated) Tresp cells served as negative control and Tresp cells stimulated polyclonal with anti-CD3/anti-CD28 beads (beads on which αCD3 and αCD28 monoclonal antibodies are irreversible immobilized) as positive control. Tresp cells were seeded in 48-well plates in 1 ml cell culture medium supplemented with 30 U/ml IL-2 and 5 ng/ml IL-15. Cells were incubated at 37° C. with media exchange every 3 days and cell count was analyzed after 7 and 14 days. The exemplary flow-cytometric analysis for the fraction of Ag-specific cells that was stimulated/expanded via the soluble strept-tactin oligomer on which the peptide:MHC-I complex for an HLA-C7/IE-1 epitope (for CMV) was immobilized (FIG. 20A) show that these antigen-specific T cells were specifically expanded. The graphs of FIG. 20B to FIG. 20E (that represent the degree of expansion of distinct Ag-specificities according to the number of peptide:MHCI multimer-positive cells harvested per time point in analogy to the expansion experiment shown in FIG. 20A) show that, the multimerization reagent that uses the respective complex of the Ag-specific peptide and MHC 1 molecule provided for the highest number of expanded cells (ranging from an twentyfold increase in the number of cells for the Ag-specific cells that recognize the pp65 epitope of CMV (amino acids 341-350 (QYDPVAALF, (SEQ ID NO: 39)) restricted by HLA-A2402) (see FIG. 20B) to an 98 fold increase in the number of Ag-specific cells that recognize the HLA-B7/IE-1$_{309-317}$ epitope (CRVLCCYVL (SEQ ID NO: 38)) of CMV (see FIG. 20E), thereby showing that the expansion method of the present invention is fully applicable to the expansion of Ag-specific cells. Finally, the exemplary flow-cytometric analysis of CD62L and CD127 surface expression after 14 days of culture for HLA-B7/Hexon5 epitope (for adenovirus) shown in FIG. 20F further confirms that experimental approaches using the soluble multimerization reagents of the present invention retain a higher content of CD127-expressing long-lived memory T cells in polyclonal and Ag-specific stimulatory conditions.

Example 16: Selective Ag-Specific Expansion Kinetics & Phenotype of Bulk Central Memory T Cells This Example examines the kinetics of selective Ag-specific expansion out of purified CD3+CD62L+CD45RA-Tcm responder cells that were stimulated in vitro with a) antigen specific peptide MHC I complexes and b) αCD28 Fab fragments that were reversibly immobilized as first and second agent on soluble oligomeric streptavidin muteins.

For this purpose 500,000 CD3+CD62L+CD45RA− responder Tcm cells (Tresp) were stimulated Ag-specifically using 3 μl of a preparation of Streptactin multimerization reagent functionalized with 0.5 μg peptide:MHC class I complexes equipped with a streptavidin binding peptide (the specific peptide represents amino acids 114-124 (CPYSGTAYNSL, SEQ ID NO: 41) of the Hexon 5 protein of adenovirus) restricted by HLA-B07) and 0.5 μg αCD28 Fab. As an alternative, 4.5 μl of a preparation of Streptactin multimerization reagent loaded with 0.5p g this peptide:MHC class I complex, 0.5 μg αCD8 Fab and 0.5 μg αCD28 Fab. For comparison, polyclonal stimulation was performed, using 3 μl of a preparation of Streptactin multimerization reagent (1 mg/ml) either loaded with a combination of 0.5 μg αCD3 Fab and 0.5 μg αCD28 Fab. Again as the alternative stimulation condition described above, 4.5 μl of a preparation of Streptactin multimers loaded with 0.5 μg αCD3 Fab, 0.5 μg αCD8 Fab and 0.5 μg αCD28 Fab was used. Untreated (unstimulated) Tresp cells served as negative control and Tresp cells stimulated polyclonal with anti-CD3/anti-CD28 beads as positive control. Tresp cells were seeded in 48-well plates in 1 ml cell culture medium supplemented with 30 U/ml IL-2 and 5 ng/ml IL-15. Cells were incubated at 37° C. with media exchange every 3 days and cell count was analyzed after 7 and 14 days. The pictures shown in FIG. 21 represent degree of cluster formation on day 5, exemplary Ag-specific stimulation is illustrated for the HLA-B7/Hexon 5 epitope of adenovirus. As can be seen from FIG. 21, such adenovirus antigen specific cells could be specifically expanded from the original CD3+CD62L+CD45RA-Tcm responder population.

Example 17: Activation of Intracellular Signaling Cascades after Streptamer Multimers Stimulation of αCD19-CAR Transduced Jurkat Cells In this Example the activation of intracellular signaling cascades of transduced Jurkat cells that have been modified to express a tumor-specific chimeric antigen receptor (CAR), namely here CD19 and that were stimulated using the oligomeric Strep-tactin® of Example 3 as soluble multimerization reagent was examined.

For this purpose, 300,000 Jurkat responder cells (Jresp) were stimulated with (A) varying amounts of a mixture of preparations of Streptactin multimerization reagent (1 mg/ml) functionalized with αCD3 Fab and αCD28 Fab fragments described here ("×1" corresponds to 3 µg Streptactin multimerization reagent functionalized with 0.5 µg αCD3- and 0.5 µg αCD28 Fab—this provides a "polyclonal Streptactin based multi merization reagent"), or (B) 3 µl of a preparation of Streptactin multimerization reagent functionalized with 0.5 µg (×1) or 1 µg (×2) of the extracellular domain (ECD) of CD19 (the natural ligand for the αCD19-CAR—this provides a "CAR-specific Streptactin based multimerization reagent"), or 3 µl of a preparation of Streptactin multimerization reagent loaded with 0.5 µg (×1) or 1 µg (×2) αIgG recognizing the IgG4 spacer within the αCD19-CAR—this also provides a "CAR-specific Streptavidin mutein based multimerization reagent). ECD of CD19 equipped with a hexahistidine tag was obtained from Sino Biological/Life technologies (SEQ ID NO: 49) and was functionalized for binding to the streptavidin based multimerization reagent by mixing the ECD of CD19 with the adapter molecule His-STREPPER (IBA GmbH, Germany, Order number 2-0920-005) at a molecular ratio of 1:1 and incubating for 15 min at room temperature. The His-STREPPER adapter molecule contains a chelating portion that binds to the hexahistidine tag and a streptavidin binding peptide, thereby temporarily providing the target molecule, here the ECD of CD19 with a streptavidin binding peptide that can reversibly bind to a streptavidin mutein based multimerization reagent. Jresp stimulated with anti-CD3/anti-CD28 heads (beads having irreversibly immobilized thereon αCD3- and αCD28- monoclonal antibodies) or PMA and Ionomycin served as positive controls. Jresp cells were seeded in 1.5 ml Eppendorf tubes in 200 µl cell culture medium supplemented with 30 U/ml IL-2. Cells were incubated at 37° C. and put on ice and lysed after 0 min to 20 min of stimulation. Detection of phosphorylated ERK indicates active MAPK signaling, staining of the housekeeper β-Actin indicates loading of equal amounts of total protein per condition and time point. As can be seen from the comparison of FIG. 22A showing activation of the Jurkat cells via the "polyclonal Streptactin multimerization reagent" and FIG. 22B showing activation of the Jurkat cells via the two "CAR-specific Streptactin based multimerization reagents", the Jurkat cells can be activated/expanded via the binding of the CD19 extracellular domain to the CD19 specific chimeric antigen receptor. Since genetic down-stream processing of T cells is almost exclusively performed on pre-selected cell populations, a generic activation via cross-linking of introduced CARs via the IgG4 spacer domain (this is conserved within various CARs with different specificities) broadens the applicability for reversible cell stimulation/expansion in these in vitro cell-processing situations.

Thus, this experiment shows that in principle any cell population that is activated by binding of an agent (ligand) that provides a primary activation signal to the cell population can be expanded using a first agent reversibly immobilized on a multimerization reagent as described here.

Example 18: Parallel Antigen-Specific Expansion of Tcm Responder Cells Out of a Single Pool In this Example, the kinetics of parallel Antigen specific (Ag-specific) expansion out of a single pool of T responder cells stimulated in vitro with multiple reversible peptide: MHC/αCH28 Fab-Streptamer multimers is examined.

500,000 CD3+CD62L+CD45RA− responder Tcm cells (Tresp) are simultaneously stimulated for multiple Ag-specificities using for each specificity, 3 µl of Streptactin multimers functionalized with 0.5 µg of the respective peptide: MHC class I complexes that carries a streptavidin binding peptide and 0.5 µg αCD28 Fab that also carries a streptavidin binding peptide. As an alternative approach, of Streptactin based multimerization reagent functionalized with 0.5 µg peptide:MHC class I complexes carrying a streptavidin binding peptide, 0.5 µg αCD8 Fab and 0.5 µg αCD28 Fab as described here are used for each specificity. For comparison, polyclonal stimulation is performed, using 3 µl of a preparation of Streptactin based multimerization reagent (1 mg/ml) either reversibly loaded with a combination of 0.5 µg αCD3 Fab and 0.5 mg αCD28 Fab. Again as the alternative stimulation condition described above, 4.5 µl of a preparation of the Streptactin based multimerization reagent reversibly loaded with 0.5 µg αCD3 Fab, 0.5 µg αCD8 Fab and 0.5 µg αCD28 Fab (each of them carrying a streptavidin binding peptide can be used. Untreated (unstimulated) Tresp cells serve as negative control and Tresp cells stimulated polyclonal with anti-CD3/anti-CD28 beads (αCD3- and αCD28- mAb coated beads) as positive control. Tresp cells are seeded in 48-well plates in 1 ml cell culture medium supplemented with 30 U/ml IL-2 and 5 ng/ml IL-15. Cells are incubated at 37° C. with media exchange every 3 days and cell count are analyzed after 7 and 14 days.

Example 19: Preferential Proliferation of CD8+ T Cells Among CD3+T Responder Cells Stimulated In Vitro with Streptavidin Based Multimerization Reagents Reversibly Functionalized with αCD3/αCD8/αCD28 Fab Fragments 300,000 CD3+ responder T cells (Tresp) are stimulated with 3 µl of a preparation of Streptactin multimerization (1 mg/ml) or a preparation of a multimerization reagent using the large Streptactin backbone (0.1 mg/ml) either loaded with a combination of 0.5 µg αCD3 and 0.5 µg αCD28 Fab, or 4.5 µl of a preparation of Streptactin based multimerization reagent loaded with 0.5 µg αCD3, 0.5 µg αCD8 Fab and 0.5 µg αCD28 Fab, or 3 µl of a mixture of preparations of Streptactin based multimerization reagent with 0.5 µg αCD3 Fab alone and 0.5 µg αCD28 Fab alone (each Fab fragment again carries a streptavidin binding peptide). Untreated Tresp cells serve as negative control and Tresp stimulated with anti-CD3/anti-CD28 beads (αCD3- and αCD28- mAb coated beads) as positive control. Tresp cells are seeded in duplicates in 48-well plates in 1 ml cell culture medium supplemented with 30 U/ml IL-2. Cells are incubated at 37° C. with media exchange after 3 days and analyzed after 6 days.

Example 20: Preferential Proliferation of CD8+ T Cells Among CD3+T Responder Cells Stimulated In Vitro with Streptavidin Based Multimerization Reagents Reversibly Functionalized with αCD3 and αCD28 Fab Fragments 300,000 CD3+ responder T cells (Tresp) are stimulated with varying amounts of a mixture of preparations of Streptactin based multimerization reagent (1 mg/ml) functionalized with αCD3 Fab fragment alone and αCD28 Fab fragment alone (1.5 µg Streptactin based multimerization reagent functionalized with 0.5 µg αCD3 Fab fragment alone and 1.5 μg Streptactin based multimerization reagent functionalized with 0.5 μg αCD28 Fab fragment alone), or varying amounts of a mixture of preparations of Streptactin based multimerization reagent functionalized with αCD3 Fab fragment and αCD28 Fab fragment with or without αCD8 Fab fragment (each Fab fragment again carries a streptavidin binding peptide) (3 μg Streptactin based multimerization reagent functionalized with 0.5 μg αCD3- and 0.5 μg αCD28 Fab fragment—without αCD8 Fab fragment, or 4.5 μl of a preparation of Streptactin multimerization reagent loaded with 0.5 μg αCD3 Fab fragment, 0.5 μg αCD8 Fab fragment and 0.5 μg αCD28 Fab fragment, wherein Fab fragment again carries a streptavidin binding peptide). Untreated Tresp cells serve as negative control and Tresp stimulated with anti-CD3/anti-CD28 beads (αCD3- and αCD28- mAb coated beads) as positive control. Tresp cells are seeded in 48-well plates in 1 ml cell culture medium supplemented with 30 U/ml IL-2. Cells are incubated at 37° C. with media exchange after 3 days and analyzed after 6 days.

Example 21: Use of Oligomeric Streptavidin Mutein Reagent as a Transduction Adjuvant Oligomeric streptavidin mutein reagents were generated and demonstrated to exhibit transduction adjuvant activity, in studies showing enhanced transduction of T cells in the presence of these reagents, as compared to the presence of available transduction-enhancing adjuvants.

Production of Oligomeric Streptavidin Mutein Reagents

An oligomeric form of streptavidin mutein was prepared substantially as described in Example 1 by polymerizing the streptavidin mutein designated Strep-tactin® ml (a streptavidin homo-tetramer containing the mutein sequence of amino acids set forth in SEQ ID NO:6, see e.g. U.S. Pat. No. 6,103,493 and Voss and Skerra (1997) Protein Eng., 1:975-982) with sulfo-SMCC (sulfosuccinimidyl 4-(N-maleimidomethyl)cyclohexane-1-carboxylate, product #22122 Thermo Scientific) and iminothiolan (product #26101 Thermo Scientific) according to the manufacturer's instructions (Thermo Scientific). The oligomeric streptavidin mutein molecules were separated from monomeric (unreacted) and dimeric streptavidin mutein by size exclusion chromatography.

In this study, the oligomeric streptavidin mutein reagents were reversibly bound to one or more Fab fragments, which included binding domains specific for T cell surface-expressed molecule(s) and contained streptavidin-binding peptide tags at their heavy chain carboxy termini. In this study, two different oligomeric streptavidin mutein reagents were used, having reversibly bound thereto: (1) anti-CD3 and anti-CD28 Fab fragments and (2) anti-CD8 Fab fragments, respectively. In this study, the tags had a sequential arrangement of two streptavidin binding modules having the sequence of amino acids SAWSHPQFEK(GGGS)2GG-SAWSHPQFEK (SEQ ID NO: 16), which permitted reversible binding of the Fab fragments to individual streptavidin mutein portions of the oligomeric streptavidin mutein reagent. To effect reversible binding, the peptide-tagged Fab fragments were mixed with the oligomeric streptavidin mutein, at approximately room temperature, reversibly binding them to the reagent via interaction between tags and binding sites on the oligomeric reagent.

T Cell Selection and Stimulation with Antibody-Conjugated Magnetic Particles

T cells were isolated via immunoaffinity-based selection, from a human peripheral blood mononuclear cell (PBMC) sample. The selected cells were stimulated by culturing with magnetic beads coated with anti-CD3 and anti-CD28 antibody fragments, at 37° C. for approximately 72 hours, prior to transduction.

Transduction and Expansion

Cells of the resulting stimulated population were subjected to transduction under various conditions, as follows.

Approximately $2.1 \times 10^6$ of the stimulated T cells were added to individual wells of a 24-well plate in a 200 uL volume. Gammaretroviral vector particles containing a nucleic acid encoding a heterologous molecule (in this case an exemplary chimeric antigen receptor (CAR)) were mixed with a polycation transduction adjuvant (in this case, protamine sulfate) (1), and a fibronectin-derived transduction adjuvant, in this case RetroNectin® (a recombinant fibronectin fragment-based transduction adjuvant) (2), or one of the two oligomeric streptavidin mutein-based reagents, reversibly bound, respectively, to anti-CD3/CD28 Fab fragments (3) or anti-CD8 Fab fragments (4). Each of the respective mixtures then was added to cells of the stimulated T cell population, at a concentration of 3.6 infectious units (IU) viral vector particle per cell, with the same or approximately the same cells/liquid volume across the different conditions. The final volume per well was adjusted to 1.1 mL. Each resulting composition was subjected to centrifugation for approximately 1 hour and then incubated for 24 hours at 37° C. Cells then were expanded at 37° C. in the presence of media and IL-2. Media was exchanged at 24 and 72 hours post-transduction and cells were passaged to target $1 \times 10^6$ cells per mL by volume addition.

At day 8 post-activation (after approximately 5.7 population doublings), the total number of nucleated cells in each composition was determined. As a measure of transduction efficiency, a flow cytometry-based assay was used to determine the percentage of the viable CD3+ cells in the composition were also positive for surface expression of the CAR (in this case, detected using a labeled goat anti-mouse antibody that specifically bound to the murine variable region portions within the extracellular domain (ECD) of the CAR).

The results for conditions (1)-(4), shown in Table 1, indicated that the presence of oligomeric streptavidin mutein reagent during transduction resulted in an increased transduction efficiency as compared to the presence of either a polycation or fibronectin-based adjuvant, consistent with the utility of such reagents as non-toxic transduction adjuvants. Similar transduction efficiencies were observed using the oligomeric reagent reversibly bound to the anti-CD3/anti-CD28 Fabs (3) as compared to the oligomeric reagent reversibly bound to the anti-CD8 Fab fragments (4). This observation indicated that the increased percentage of live T cells at day 8 expressing the heterologous CAR resulted from enhancement of transduction and/or reduced toxic effects compared to the other transduction adjuvants, rather than from activating or stimulatory effects mediated by the CD3 and CD28 Fabs reversibly bound to the reagent in (3).

TABLE 1

| | Condition | | | |
|---|---|---|---|---|
| | 1 | 2 | 3 | 4 |
| Activation Reagent | Anti-CD3/Anti-CD28 magnetic beads | Anti-CD3/Anti-CD28 magnetic beads | Anti-CD3/Anti-CD28 magnetic beads | Anti-CD3/Anti-CD28 magnetic beads |
| Transduction Adjuvant | polycation | RetroNectin ® | Anti-CD3/Anti-CD28 streptavidin mutein oligomeric reagent | Anti-CD8 Streptavidin mutein oligomeric reagent |
| Vector (IU/cell) | 3.6 | 3.6 | 3.6 | 3.6 |
| Total nucleated cells at day 8 (×10$^6$) | 52.4 | 51.5 | 54.3 | 51.5 |
| Doublings | 5.7 | 5.7 | 5.7 | 5.7 |
| % CAR+ (of CD3+/live cells)- | 67.4% | 55.6% | 84.3% | 82.3% |

Example 22: Use of a Single Oligomeric Streptavidin Mutein Reagent for T Cell Activation and to Enhance Viral Transduction In another set of conditions (5), selected T cells were stimulated for 24-48 hours essentially as described for (1)-(4) in Example 21, with the exception that the stimulation was performed in the presence of the oligomeric streptavidin mutein reagent having reversibly bound to it the anti-CD3/anti-CD28 Fab fragments, rather than the anti-CD3/anti-CD28-coated magnetic particles. For this condition, transduction with the gamma retroviral particles was carried out as described in Example 21, except using a ratio of at 1.0 IU virus/cell, and without adding further transduction adjuvant (beyond the oligomeric reagent used during stimulation).

Transduction efficiency at d.8 was measured by assessing percentage of live T cells that were surface positive for the CAR, assayed as described in Example 21. The results (as compared to those for (1) and (2) in Table 1 are shown in Table 2. The results showed effective transduction of T cells following stimulation of the cells in the presence of the oligomeric anti-CD3/anti-CD28-bound streptavidin mutein reagent, without removal of the reagent and without the addition of a separate or further transduction adjuvant. Moreover, despite the approximately 70% reduction in amount of virus (number of infectious units per cell) used in this condition (5), comparable transduction efficiency was observed, as compared to conditions (1 and 2) involving stimulation using anti-CD3/anti-CD28-coated magnetic beads and addition of other transduction-enhancing adjuvants at initiation of transduction. Thus, even when the oligomeric reagent was added day(s) prior to initiation of transduction (and without adding any additional or further adjuvant prior to or during transduction), use of the streptavidin mutein oligomeric reagent enhanced transduction efficiency to a comparable degree as other transduction-enhancing adjuvants.

In other studies, activation of T cells using various stimulatory reagents, followed by transduction in the presence of various transduction adjuvants, indicated that when anti-CD3/anti-CD28-bound oligomeric streptavidin mutein reagents were used for T cell activation prior to transduction, enhanced transduction efficiency (measured as percentage of live cells expressing a viral vector-encoded heterologous protein) in the output composition was observed, consistent with the conclusion that the oligomeric reagent could enhance transduction even when included from hours or days prior to transduction initiation, and that the effect could be additive to enhancement by other transduction-enhancing adjuvants such as fibronectin fragment-based or polycation transduction-enhancing agents. The results demonstrated that a single oligomeric reagents could be used for activation and to enhance or promote viral transduction of T cells, in this study when added at a single time-point prior to transduction.

TABLE 2

| | Condition | | |
|---|---|---|---|
| | 1 | 2 | 5 |
| Activation Reagent | Anti-CD3/Anti-CD28 magnetic beads | Anti-CD3/Anti-CD28 magnetic beads | Anti-CD3/Anti-CD28 streptavidin mutein oligomeric reagent |
| Transduction Adjuvant added during transduction | polycation | RetroNectin | None |
| Vector (IU/cell) | 3.6 | 3.6 | 1.0 |
| Total nucleated cells at day 8 (×10$^6$) | 52.4 | 51.5 | 51.5 |
| Doublings | 5.7 | 5.7 | 5.7 |
| % CAR+ of CD3+/Casp- | 67.4% | 55.6% | 51.2% |

Example 23: Assessment of Enhanced Transduction of a Targeted Subset of Cells Using an Oligomeric Streptavidin Mutein Reagent Streptavidin mutein oligomeric reagents as described in Example 21, reversibly bound to a Fab fragment specific for CD8, a cell surface marker expressed on a T cell subset of T cells, were included during transduction of bulk T cell compositions. A composition including bulk (CD4+ and CD8+) T cells that had been isolated by immunoaffinity-based selection from human blood-derived samples was stimulated as described in Example 21 in the presence of anti-CD3/anti-CD28 magnetic beads, for 24-48 hours.

Following stimulation, transduction was initiated. Gammaretroviral vector particles encoding a CAR were mixed with the anti-CD8-bound oligomeric streptavidin mutein reagent or the polycation-based transduction adjuvant. The virus/adjuvant mixtures were added to the stimulated T cell samples to promote transduction, followed by expansion, substantially as described in Example 21. Flow cytometry was used to assess surface markers and CAR surface expression as in Example 21. For each condition, the percentage of live T cells with surface expression of the CAR was compared to the percentage of live CD4+ T cells surface positive for the CAR.

The results are set forth in FIG. 23, showing levels of surface expression of CD4 (y axis) versus CAR (x axis) of live T (CD3+ gated cells. The results showed preferentially increased transduction efficiency (as measured by percentage of live cells expressing the heterologous product (CAR)) in CD8+ T cells (compared to CD4+ T cells), as compared to the efficiency observed when transduction was carried out in the presence of the polycation transduction adjuvant.

For cells of a mock transduction control, no detectable CAR-expression was observed in this study, indicating the specificity of the assay for assessing transduction with the heterologous nucleic acid.

The results demonstrated that, in addition to the ability of the oligomeric streptavidin mutein reagents to increase transduction efficiency, the specificity of these reagents conferred through the Fab reversibly immobilized to the oligomeric streptavidin mutein reagent, could be used to selectively enhance transduction of CD8+ cells within a mixed cell population. The results are consistent with the utility of oligomeric reagents containing reversibly bound antibodies specific for target molecules, for preferentially enhancing or promoting the transduction of target cells, e.g., in mixed cell populations in which one or more other cell populations are present that do not contain or express the target molecule.

The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure.

SEQUENCE TABLE

| No. | Sequence | Description |
|---|---|---|
| 1 | DPSKDSKAQVSAAEAGITGTWYNQLGSTFIVTAGADGALTGTYESAVGNAESRYVLTGRYDSA PATDGSGTALGWTVAWKNNYRNAHSATTWSGQYVGGAEARINTQWLLTSGTTEANAWKSTLVG HDTFTKVKPSAASIDAAKKAGVNNGNPLDAVQQ | Streptavidin Species: *Streptomyces avidinii* UniProt No. P22629 |
| 2 | EAGITGTWYNQLGSTFIVTAGADGALTGTYESAVGNAESRYVLTGRYDSAPATDGSGTALGWT VAWKNNYRNAHSATTWSGQYVGGAEARINTQWLLTSGTTEANAWKSTLVGHDTFTKVKPSAAS | Minimal streptavidin Species: *Streptomyces avidinn* |
| 3 | DPSKDSKAQVSAAEAGITGTWYNQLGSTFIVTAGADGALTGTYVTARGNAESRYVLTGRYDSA PATDGSGTALGWTVAWKNNYRNAHSATTWSGQYVGGAEARINTQWLLTSGTTEANAWKSTLVG HDTFTKVKPSAASIDAAKKAGVNNGNPLDAVQQ | Mutein Streptavidin Val44-Thr45-Ala46-Arg47 Species: *Streptomyces avidinii* |
| 4 | EAGTTGTWYNQLGSTFIVTAGADGALTGTYVTARGNAESRYVLTGRYDSAPATDGSGTALGWT VAWKNNYRNAHSATTWSGQYVGGAEARINTQWLLTSGTTEANAWKSTLVGHDTFTKVKPSAAS | Mutein Streptavidin Val44-Thr45-Ala46-Arg47 Species: *Streptomyces avidinii* |
| 5 | DPSKDSKAQVSAAEAGITGTWYNQLGSTFIVTAGADGALTGTYIGARGNAESRYVLTGRYDSA PATDGSGTALGWTVAWKNNYRNAHSATTWSGQYVGGAEARINTQWLLTSGTTEANAWKSTLVG HDTFTKVKPSAASIDAAKKAGVNNGNPLDAVQQ | Mutein Streptavidin Ile44-Gly45-Ala-46-Arg47 Species: *Streptomyces avidinii* |
| 6 | EAGITGTWYNQLGSTFIVTAGADGALTGTYIGARGNAESRYVLTGRYDSAPATDGSGTALGWT VAWKNNYRNAHSATTWSGQYVGGAEARINTQWLLTSGTTEANAWKSTLVGHDTFTKVKPSAAS | Mutein Streptavidin Ile44-Gly45-Ala-46-Arg47 Species: *Streptomyces avidinii* |
| 7 | Trp-Arg-His-Pro-Gln-Phe-Gly-Gly | Streptavidin binding peptide, Strep-tag ® |
| 8 | WSHPQFEK | Strep-tag ® II |
| 9 | His-Pro-Xaa | Streptavidin Binding peptide Xaa is selected from glutamine, asparagine and methionine |
| 10 | His-Pro-Gln-Phe | Streptavidin-binding peptide |
| 11 | $Xaa_1$-$Xaa_2$-His-Pro-Gln-Phe-$Xaa_3$-$Xaa_4$ | Streptavidin-binding peptide $Xaa_1$ is Trp, Lys or Arg; $Xaa_2$ is any amino acid; $Xaa_3$ is Gly or Glu $Xaa_4$ is Gly, Lys or Arg |

| No. | Sequence | Description |
|---|---|---|
| 12 | -Trp-Xaa$_1$-His-Pro-Gln-Phe-Xaa$_2$-Xaa$_3$- | Streptavidin-binding peptide<br>Xaa$_1$ is any amino acid;<br>Xaa$_2$ is Gly or Glu<br>Xaa$_3$ is Gly, Lys or Arg |
| 13 | Trp-Ser-His-Pro-Gln-Phe-Glu-Lys-(Xaa)n-Trp-Ser-His-Pro-Gln-Phe-Glu-Lys- | Sequential modules of streptavidin-binding peptide<br>Xaa is any amino acid;<br>n is either 8 or 12 |
| 14 | Trp-Ser-His-Pro-Gln-Phe-Glu-Lys-(GlyGlyGlySer)n-Trp-Ser-His-Pro-Gln-Phe-Glu-Lys | Sequential modules of streptavidin-binding peptide<br>n is 2 or 3 |
| 15 | SAWSHPQFEKGGGSGGGSGGGSWSHPQFEK | Twin-Strep-tag |
| 16 | SAWSHPQFEKGGGSGGGSGGSAWSHPQFEK | Twin-Strep-tag |
| 17 | WSHPQFEKGGGSGGGSGGGSWSHPQFEK | Twin-Strep-tag |
| 18 | WSHPQFEKGGGSGGGSWSHPQFEK | Twin-Strep-tag |
| 19 | WSHPQFEKGGGSGGGSGGSAWSHPQFEK | Twin-Strep-tag |
| 20 | Tyr-Pro-Tyr-Asp-Val-Pro-Asp-Tyr-Ala | HA-tag |
| 21 | Tyr-Thr-Asp-Ile-Glu-Met-Asn-Arg-Leu-Gly-Lys | VSV-G-tag |
| 22 | Gln-Pro-Glu-Leu-Ala-Pro-Glu-Asp-Pro-Glu-Asp | HSV-tag |
| 23 | Ala-Ser-Met-Thr-Gly-Gly-Gln-Gln-Met-Gly | T7 epitope |
| 24 | Gln-Pro-Glu-Leu-Ala-Pro-Glu-Asp-Pro-Glu-Asp | HSV cpitopc |
| 25 | Glu-Gln-Lys-Leu-Ile-Ser-Glu-Glu-Asp-Leu | Myc epitope |
| 26 | Gly-Lys-Pro-Ile-Pro-Asn-Pro-Leu-Leu-Gly-Leu-Asp-Ser-Thr | V5-tag |
| 27 | EAGITGTWYNQLGSTFIVTAGADGALTGTYVTARGNAESRYVLTGRYDSAPATDGSGTALGWTVAWKNNYRNAHSATTWSGQYVGGAEARINTQWLLTSGTTEENAGYSTLVGHDTFTKVKPSAAS | Mutein Streptavidin Val44-Thr45-Ala46-Arg47 and Glu117, Gly120, Try121 (mutein m1-9)<br>Species: *Streptomyces avidinii* |
| 28 | DPSKDSKAQVSAAEAGITGTWYNQLGSTFIVTAGADGALTGTYVTARGNAESRYVLTGRYDSAPATDGSGTALGWTVAWKNNYRNAHSATTWSGQYVGGAEARINTQWLLTSGTTEENAGYSTLVGHDTFTKVKPSAAS | Mutein Streptavidin Val44-Thr45-Ala46-Arg47 and Glu117, Gly120, Try121 (mutein m1-9)<br>Species: *Streptomyces avidinii* |
| 29 | AMQVQLKQSG PGLVQPSQSL SITCTVSGFS LTTFGVHWVR FFKLNSLQPD QSPGKGLEWLGVIWASGITD YNVPFMSRLS ITKDNSKSQV DTAIYYCAKNDPGTGFAYWG QGTLVTVSAG STKGPSVFPL APSSKSTSGG TAALGCLVKDYFPEPVTVSW NSGALTSGVH TFPAVLQSSG LYSLSSVVTV PSSSLGTQTY ICNVNHKPSN TKVDKKVEPK SCGSAWSHPQ FEKGGGSGGG SGGSAWSHPQFEK | Variable Heavy chain of Fab fragment m13B8.2 |
| 30 | AMDIQMTQSP ASLSASVGET VTFTCRASEM IYSYLAWYQQ KQGKSPQLLVHDAKTLAEGV PSRFSGGGSG TQFSLKINTL QPEDFGTYYC QAHYGNPPTFGGGTKLEIKR GIAAPSVFIF PPSDEQLKSG TASVVCLLNN FYPREAKVQWKVDNALQSGN SQESVTEQDS KDSTYSLSST LTLSKADYEK HKVYACEVTH QGLSSPVTKS FNRGECGS | Variable Light chain of Fab Fragment m13B8.2 |
| 31 | Gln Val Gln Leu Gln Gln Ser Gly Ala Glu Leu Ala Arg Pro Gly Ala Ser Val Lys Met Ser Cys Lys Ala Ser Gly Tyr Thr Phe Thr Arg Tyr Thr Met His Trp Val Lys Gln Arg Pro Gly Gln Gly Leu Glu Trp Ile Gly Tyr Ile Asn Pro Ser Arg Gly Tyr Thr Asn Tyr Asn Gln Lys Phe Lys Asp Lys Ala Thr Leu Thr Thr Asp Lys Ser Ser Ser Thr Ala Tyr Met Gln Leu Ser Ser Leu Thr Ser Glu Asp Ser Ala Val Tyr Tyr Cys Ala Arg Tyr Tyr Asp Asp His Tyr Cys Leu Asp Tyr Trp Gly Gln Gly Thr Thr Leu Thr Val Ser Ser | Variable Heavy chain of anti-CD3 antibody OKT3 |

SEQUENCE TABLE

| No. | Sequence | Description |
|---|---|---|
| 32 | Gln Ile Val Leu Thr Gln Ser Pro Ala Ile Met Ser Ala Ser Pro Gly<br>Glu Lys Val Thr Met Thr Cys Ser Ala Ser Ser Ser Val Ser Tyr Met<br>Asn Trp Tyr Gln Gln Lys Ser Gly Thr Ser Pro Lys Arg Trp Ile Tyr<br>Asp Thr Ser Lys Leu Ala Ser Gly Val Pro Ala His Phe Arg Gly Ser<br>Gly Ser Gly Thr Ser Tyr Ser Leu Thr Ile Ser Gly Met Glu Ala Glu<br>Asp Ala Ala Thr Tyr Tyr Cys Gln Gln Trp Ser Ser Asn Pro Phe Thr<br>Phe Gly Ser Gly Thr Lys Leu Glu Ile Asn | Variable Light chain of anti-CD3 antibody OKT3 |
| 33 | Leu Gln Gln Ser Gly Ala Glu Leu Val Lys Pro Gly Ala Ser Val Arg<br>Leu Ser Cys Lys Ala Ser Gly Tyr Thr Phe Thr Glu Tyr Ile Ile His<br>Trp Ile Lys Leu Arg Ser Gly Gln Gly Leu Glu Trp Ile Gly Trp Phe<br>Tyr Pro Gly Ser Asn Asp Ile Gln Tyr Asn Ala Lys Phe Lys Gly Lys<br>Ala Thr Leu Thr Ala Asp Lys Ser Ser Ser Thr Val Tyr Met Glu Leu<br>Thr Gly Leu Thr Ser Glu Asp Ser Ala Val Tyr Phe Cys Ala Arg Arg<br>Asp Asp Phe Ser Gly Tyr Asp Ala Leu Pro Tyr Trp Gly Gln Gly<br>Thr Met Val Thr Val | Variable Heavy chain of anti-CD28 antibody CD28.3 |
| 34 | Asp Ile Gln Met Thr Gln Ser Pro Ala Ser Leu Ser Val Ser Val Gly<br>Glu Thr Val Thr Ile Thr Cys Arg Thr Asn Glu Asn Ile Tyr Ser Asn<br>Leu Ala Trp Tyr Gln Gln Lys Gln Gly Lys Ser Pro Gln Leu Leu Ile<br>Tyr Ala Ala Thr His Leu Val Glu Gly Val Pro Ser Arg Phe Ser Gly<br>Ser Gly Ser Gly Thr Gln Tyr Ser Leu Lys Ile Thr Ser Leu Gln Ser<br>Glu Asp Phe Gly Asn Tyr Tyr Cys Gln His Phe Trp Gly Thr Pro<br>Cys Thr Phe Gly Gly Gly Thr Lys Leu Glu Ile Lys Arg | Variable Light chain of anti-CD28 antibody CD28.3 |
| 35 | His-Asn-His-Arg-His-Lys-His-Gly-Gly-Gly-Cys | MAT tag |
| 36 | Gln Val Thr Leu Lys Glu Ser Gly Pro Gly Ile Leu Gln Pro Ser Gln<br>Thr Leu Ser Leu Thr Cys Ser Phe Ser Gly Phe Ser Leu Arg Thr Ser<br>Gly Met Gly Val Gly Trp Ile Arg Gln Pro Ser Gly Lys Gly Leu Glu<br>Trp Leu Ala His Ile Trp Trp Asp Asp Asp Lys Arg Tyr Asn Pro Ala<br>Leu Lys Ser Arg Leu Thr Ile Ser Lys Asp Thr Ser Ser Asn Gln Val<br>Phe Leu Lys Ile Ala Ser Val Asp Thr Ala Asp Thr Ala Thr Tyr Tyr<br>Cys Ala Gln Ile Asn Pro Ala Trp Phe Ala Tyr Trp Gly Gln Gly Thr<br>Leu Val Thr Val Ser Ser | αCD+ 6 antibody 3G8 VI-1 |
| 37 | Asp Ile Val Leu Thr Gln Ser Pro Ala Ser Leu Ala Val Ser Leu Gly<br>Gln Arg Ala Thr Ile Ser Cys Lys Ala Ser Gln Ser Val Asp Phe Asp<br>Gly Asp Ser Phe Met Asn Trp Tyr Gln Gln Lys Pro Gly Gln Pro Pro<br>Lys Leu Leu Ile Tyr Thr Thr Ser Asn Leu Glu Ser Gly Ile Pro Ala<br>Arg Phe Ser Ala Ser Gly Ser Gly Thr Asp Phe Thr Leu Asn Ile His<br>Pro Val Glu Glu Glu Asp Thr Ala Thr Tyr Tyr Cys Gln Gln Ser Asn<br>Glu Asp Pro Tyr Thr Phe Gly Gly Gly Thr Lys Leu Glu Ile Lys | αCD16 antibody 3G8 VL |
| 38 | CRVLCCYVL | antigen-specific peptide |
| 39 | QYDPVAALF | pp65 epitope of CMV (amino acids 341-350) |
| 40 | RPHERNGFTV | pp65 epitope of CMV (amino acids 265-274) |
| 41 | CPYSGTAYNSL | hexon 5 epitope of adenovirus (amino acids 114-124) |
| 42 | Met Gly Ser His Ser Met Arg Tyr Phe Ser Thr Ser Val Ser Arg Pro<br>Gly Arg Gly Glu Pro Arg Phe Ile Ala Val Gly Tyr Val Asp Asp Thr<br>Gln Phe Val Arg Phe Asp Ser Asp Ala Ala Ser Gln Arg Met Glu Pro<br>Arg Ala Pro Trp Ile Glu Gln Glu Gly Pro Glu Tyr Trp Asp Glu Glu<br>Thr Gly Lys Val Lys Ala His Ser Gln Thr Asp Arg Glu Asn Leu Arg<br>Ile Ala Leu Arg Tyr Tyr Asn Gln Ser Glu Ala Gly Ser His Thr Leu<br>Gln Met Met Phe Gly Cys Asp Val Gly Ser Asp Gly Arg Phe Leu Arg<br>Gly Tyr His Gln Tyr Ala Tyr Asp Gly Lys Asp Tyr Ile Ala Leu Lys<br>Glu Asp Leu Arg Ser Trp Thr Ala Ala Asp Met Ala Ala Gln Ile Thr<br>Lys Arg Lys Trp Glu Ala Ala His Val Ala Glu Gln Gln Arg Ala Tyr<br>Leu Glu Gly Thr Cys Val Asp Gly Leu Arg Arg Tyr Leu Glu Asn Gly<br>Lys Glu Thr Leu Gln Arg Thr Asp Pro Pro Lys Thr His Met Thr His<br>His Pro Ile Ser Asp His Glu Ala Thr Leu Arg Cys Trp Ala Leu Gly<br>Phe Tyr Pro Ala Glu Ile Thr Leu Thr Trp Gln Arg Asp Gly Glu Asp<br>Gln Thr Gln Asp Thr Glu Leu Val Glu Thr Arg Pro Ala Gly Asp Gly<br>Thr Phe Gln Lys Trp Ala Ala Val Val Val Pro Ser Gly Glu Glu Gln<br>Arg Tyr Thr Cys His Val Gln His Glu Gly Leu Pro Lys Pro Leu Thr<br>Leu Arg Trp Glu Pro Pro Pro Ser Gly Ser Ser Ala Trp Ser His Pro | HLA-A*2402 |

SEQUENCE TABLE

| No. | Sequence | Description |
|---|---|---|
| | Gln Phe Glu Lys Gly Gly Gly Ser Gly Gly Gly Ser Gly Gly Gly Ser<br>Ser Ala Trp Ser His Pro Gln Phe Glu Lys | |
| 43 | Met Gly Ser His Ser Met Arg Tyr Phe Tyr Thr Ser Val Ser Arg Pro<br>Gly Arg Gly Glu Pro Arg Phe Ile Ser Val Gly Tyr Val Asp Asp Thr<br>Gln Phe Val Arg Phe Asp Ser Asp Ala Ala Ser Pro Arg Glu Glu Pro<br>Arg Ala Pro Trp Ile Glu Gln Glu Gly Pro Glu Tyr Trp Asp Arg Asn<br>Thr Gln Ile Tyr Lys Ala Gln Ala Gln Thr Asp Arg Glu Ser Leu Arg<br>Asn Leu Arg Gly Tyr Tyr Asn Gln Ser Glu Ala Gly Ser His Thr Leu<br>Gln Ser Met Tyr Gly Cys Asp Val Gly Pro Asp Gly Arg Leu Leu Arg<br>Gly His Asp Gln Tyr Ala Tyr Asp Gly Lys Asp Tyr Ile Ala Leu Asn<br>Glu Asp Leu Arg Ser Trp Thr Ala Ala Asp Thr Ala Ala Gln Ile Thr<br>Gln Arg Lys Trp Glu Ala Ala Arg Glu Ala Glu Gln Arg Arg Ala Tyr<br>Leu Glu Gly Glu Cys Val Glu Trp Leu Arg Arg Tyr Leu Glu Asn Gly<br>Lys Asp Lys Leu Glu Arg Ala Asp Pro Pro Lys Thr His Val Thr His<br>His Pro Ile Ser Asp His Glu Ala Thr Leu Arg Cys Trp Ala Leu Gly<br>Phe Tyr Pro Ala Glu Ile Thr Leu Thr Trp Gln Arg Asp Gly Glu Asp<br>Gln Thr Gln Asp Thr Glu Leu Val Glu Thr Arg Pro Ala Gly Asp Arg<br>Thr Phe Gln Lys Trp Ala Ala Val Val Pro Ser Gly Glu Glu Gln<br>Arg Tyr Thr Cys His Val Gln His Glu Gly Leu Pro Lys Pro Leu Thr<br>Leu Arg Trp Glu Pro Pro Pro Ser Gly Ser Ser Ala Trp Ser His Pro<br>Gln Phe Glu Lys Gly Gly Gly Ser Gly Gly Gly Ser Gly Gly Gly Ser<br>Ser Ala Trp Ser His Pro Gln Phe Glu Lys | HLA-B*0702 |
| 44 | Met Ala Leu Thr Glu Thr Trp Ala Cys Ser His Ser Met Arg Tyr Phe<br>Asp Thr Ala Val Ser Arg Pro Gly Arg Gly Glu Pro Arg Phe Ile Ser<br>Val Gly Tyr Val Asp Asp Thr Gln Phe Val Arg Phe Asp Ser Asp Ala<br>Ala Ser Pro Arg Gly Glu Pro Arg Ala Pro Trp Val Glu Gln Glu Gly<br>Pro Glu Tyr Trp Asp Arg Glu Thr Gln Lys Tyr Lys Arg Gln Ala Gln<br>Ala Asp Arg Val Ser Leu Arg Asn Leu Arg Gly Tyr Tyr Asn Gln Ser<br>Glu Asp Gly Ser His Thr Leu Gln Arg Met Ser Gly Cys Asp Leu Gly<br>Pro Asp Gly Arg Leu Leu Arg Gly Tyr Asp Gln Ser Ala Tyr Asp Gly<br>Lys Asp Tyr Ile Ala Leu Asn Glu Asp Leu Arg Ser Trp Thr Ala Ala<br>Asp Thr Ala Ala Gln Ile Thr Gln Arg Lys Leu Glu Ala Ala Arg Ala<br>Ala Glu Gln Leu Arg Ala Tyr Leu Glu Gly Thr Cys Val Glu Trp Leu<br>Arg Arg Tyr Leu Glu Asn Gly Lys Glu Thr Leu Gln Arg Ala Glu Pro<br>Pro Lys Thr His Val Thr His His Pro Leu Ser Asp His Glu Ala Thr<br>Leu Arg Cys Trp Ala Leu Gly Phe Tyr Pro Ala Glu Ile Thr Leu Thr<br>Trp Gln Arg Asp Gly Glu Asp Gln Thr Gln Asp Thr Glu Leu Val Glu<br>Thr Arg Pro Ala Gly Asp Gly Thr Phe Gln Lys Trp Ala Ala Val Val<br>Val Pro Ser Gly Gln Glu Gln Arg Tyr Thr Cys His Met Gln His Glu<br>Gly Leu Gln Glu Pro Leu Thr Leu Ser Trp Glu Pro Ser Ser Gln Pro<br>Thr Ile Gly Ser Ala Trp Ser His Pro Gln Phe Glu Lys Gly Gly Gly<br>Ser Gly Gly Gly Ser Gly Gly Ser Ala Trp Ser His Pro Gln Phe Glu<br>Lys | HLA-C*0702 |
| 45 | Met Ile Gln Arg Thr Pro Lys Ile Gln Val Tyr Ser Arg His Pro Ala<br>Glu Asn Gly Lys Ser Asn Phe Leu Asn Cys Tyr Val Ser Gly Phe His<br>Pro Ser Asp Ile Glu Val Asp Leu Leu Lys Asn Gly Glu Arg Ile Glu<br>Lys Val Glu His Ser Asp Leu Ser Phe Ser Lys Asp Trp Ser Phe Tyr<br>Leu Leu Tyr Tyr Thr Glu Phe Thr Pro Thr Glu Lys Asp Glu Tyr Ala<br>Cys Arg Val Asn His Val Thr Leu Ser Gln Pro Lys Ile Val Lys Trp<br>Asp Arg Asp Met | β₂ microglobulin |
| 46 | YTDIEMNRLGK | VSV-G tag |
| 47 | WREPGRMELN | 10 amino acid tag from the collagen-binding domain of von Willebrand factor |
| 48 | GGGS | Linker peptide |
| 49 | PEEPLVVKVEEGDNAVLQCLKGTSDGPTQQLTWSRESPLKPFLKLSLGLPGLGIHMRPLAIWL<br>FIFNVSQQMGGFYLCQPGPPSEKAWQPGWTVNVEGSGELFRWNVSDLGGLGCGLKNRSSEGPS<br>SPSGKLMSPKLYVWAKDRPEIWEGEPPCLPPRDSLNQSLSQDLTMAPGSTLWLSCGVPPDSVS<br>RGPLSWTHVHPKGPKSLLSLELKDDRPARDMWVMETGLLLPRATAQDAGKYYCHRGNLTMSFH<br>LEITARPVLWHWURTGGWKAHHHHHHHHHH | human CD19 extracellular domain with His-Tag |

What is claimed:

1. A method for transducing T cells, comprising incubating a plurality of T cells with (1) a soluble oligomeric protein reagent that (i) is reversibly bound to a selection agent and (ii) comprises an oligomer of at least three crosslinked streptavidin mutein tetramers; and (2) a viral particle, wherein the selection agent comprises (i) a monovalent antibody fragment that is a Fab that specifically binds to a molecule expressed on the surface of the T cells and (ii) a streptavidin-binding peptide that reversibly binds a binding site of a streptavidin mutein of the oligomeric protein reagent, and wherein the method produces an output composition comprising one or more T cells transduced with the viral particle.

2. The method of claim 1, wherein the incubating comprises:
   (a) contacting the viral particle with the oligomeric protein reagent, thereby generating a composition comprising viral particles and the oligomeric protein reagent; and
   (b) incubating the composition in (a) with the plurality of T cells.

3. The method of claim 1, wherein the oligomeric protein reagent further comprises a viral-binding agent that specifically binds to a molecule on the surface of the viral particle.

4. The method of claim 3, wherein the oligomeric protein reagent is reversibly bound to the viral-binding agent.

5. The method of claim 1, wherein at least a portion of the incubation with the oligomeric protein reagent in (1) occurs simultaneously with the incubation with the viral particle in (2).

6. The method of claim 4, wherein:
   the viral-binding agent comprises a streptavidin binding peptide that reversibly binds a binding site of a streptavidin mutein of the oligomeric protein reagent.

7. The method of claim 1, wherein the selection agent specifically binds to a molecule selected from the group consisting of CD25, CD28, CD62L, CCR7, CD27, CD127, CD3, CD4, CD8, CD45RA, and CD45RO.

8. The method of claim 1, wherein prior to or during the incubating with the oligomeric protein reagent, the method comprises activating the T cells in the presence of a stimulatory agent under stimulating conditions whereby the T cells are stimulated or activated by the stimulatory agent.

9. The method of claim 8, wherein the stimulatory agent activates one or more intracellular signaling domains of one or more components of a TCR complex.

10. The method of claim 9, wherein said stimulatory agent comprises a primary agent that specifically binds to a member of a TCR complex and a secondary agent that specifically binds to a T cell costimulatory molecule.

11. The method of claim 10, wherein:
    the primary agent specifically binds to CD3; and
    the costimulatory molecule is selected from the group consisting of CD28, CD137 (4-1BB), CD27, OX40, and ICOS.

12. The method of claim 1, further comprising:
    culturing the plurality of T cells in the presence of a receptor-binding agent that (i) specifically binds a receptor expressed on the surface of the T cells to deliver a stimulatory signal and (ii) is reversibly bound to the oligomeric protein reagent or a second reagent, the oligomeric protein reagent or the second reagent comprising a plurality of binding sites each capable of reversibly binding to the receptor-binding agent, thereby stimulating a signal in the T cells.

13. The method of claim 12, wherein said culturing is initiated prior to said incubating.

14. The method of claim 12, wherein the receptor binding agent is a first receptor binding agent, the receptor is a first receptor, and the culturing is further carried out in the presence of a second receptor binding agent that is reversibly bound to the oligomeric protein reagent or to the second reagent, said second receptor binding agent being an accessory binding agent that specifically binds to a second receptor on the surface of the T cells, thereby providing an accessory signal to the T cells.

15. The method of claim 14, wherein the second receptor is a costimulatory molecule, accessory molecule, cytokine receptor, chemokine receptor, immune checkpoint molecule or a member of the TNF family or the TNF receptor family.

16. The method of claim 14, wherein the first receptor binding agent binds to CD3, and the second receptor binding agent binds to CD28.

17. The method of claim 1, wherein the genome of the viral particle comprises a heterologous nucleic acid molecule encoding a recombinant protein.

18. The method of claim 17, wherein the recombinant protein is a chimeric antigen receptor.

19. The method of claim 1, wherein the viral particle is a retroviral vector particle.

20. The method of claim 1, wherein individual molecules of the oligomeric protein reagent are crosslinked by a polysaccharide or a bifunctional linker.

21. The method of claim 1, wherein the streptavidin mutein comprises the amino acid sequence $Val^{44}$-$Thr^{45}$-$Ala^{46}$-$Arg^{47}$ or $Ile^{44}$-$Gly^{45}$-$Ala^{46}$-$Arg^{47}$ at sequence positions corresponding to positions 44 to 47 with reference to positions in streptavidin in the sequence of amino acids set forth in SEQ ID NO:1.

22. The method of claim 1, wherein the streptavidin mutein comprises:
    a) the sequence of amino acids set forth in any of SEQ ID NOS: 3-6, 27 and 28; or
    b) a sequence of amino acids that exhibits at least 85%, 86%, 87%, 88%, 89%, 90%, 91%, 92%, 93%, 94%, 95%, 96%, 97%, 98%, 99% or more sequence identity to any of SEQ ID NOS:3-6, 27 and 28, which contains the amino acid sequence corresponding to $Val^{44}$-Thr45-$Ala^{46}$-$Arg^{47}$ or $Ile^{44}$-$Gly^{45}$-$Ala^{46}$-$Arg^{47}$ that reversibly binds to biotin or a biologically active form thereof, a biotin analog- or a biologically active fragment thereof, or a streptavidin-binding peptide; wherein the amino acid positions of the peptide $Val^{44}$-$Thr^{45}$-$Ala^{46}$-$Arg^{47}$ or $Ile^{44}$-$Gly^{45}$-$Ala^{46}$-$Arg^{47}$ correspond to positions 44 to 47 of the amino acid sequence set forth in SEQ ID NO: 1.

23. The method of claim 1, wherein the streptavidin-binding peptide is SAWSHPQFEK(GGGS)₂GG-SAWSHPQFEK (SEQ ID NO:16).

24. The method of claim 1, wherein the streptavidin-binding peptide is selected from the group consisting of Trp-Ser-His-Pro-Gln-Phe-Glu-Lys (SEQ ID NO: 8), Trp-Ser-His-Pro-Gln-Phe-Glu-Lys-(GlyGlyGlySer)₃-Trp-Ser-His-Pro-Gln-Phe-Glu-Lys (SEQ ID NO: 17), Trp-Ser-His-Pro-Gln-Phe-Glu-Lys-(GlyGlyGlySer)₂-Trp-Ser-His-Pro-Gln-Phe-Glu-Lys (SEQ ID NO: 18), Trp-Ser-His-Pro-Gln-Phe-Glu-Lys-(GlyGlyGlySer)₂Gly-Gly-Ser-Ala-Trp-Ser-His-Pro-Gln-Phe-Glu-Lys (SEQ ID NO: 19), and SAWSHPQFEK(GGGS)₂GGSAWSHPQFEK (SEQ ID NO:16).

25. The method of claim 1, wherein the method comprises disrupting the reversible binding between the selection agent and the oligomeric protein reagent.

26. The method of claim 25, wherein said disruption comprises introducing to the T cells a substance capable of reversing the bond between the selection agent and the oligomeric protein reagent.

27. The method of claim 26, wherein:
    the substance comprises a streptavidin-binding peptide, biotin or a biologically active fragment thereof, or a biotin analog or biologically active fragment thereof.

28. The method of claim 25, comprising, after said disruption, recovering the T cells.

29. The method of claim 28, comprising further incubating the T cells.

30. The method of claim 26, wherein the substance is D-biotin.

31. The method of claim 1, wherein the streptavidin mutein is the sequence of amino acids set forth in SEQ ID NO:6.

32. The method of claim 19, wherein the genome of the retroviral vector particle comprises a heterologous nucleic acid molecule encoding a recombinant protein.

33. The method of claim 32, wherein the recombinant protein is a chimeric antigen receptor.

34. The method of claim 1, wherein the viral particle is a lentiviral vector particle.

35. The method of claim 34, wherein the genome of the lentiviral vector particle comprises a heterologous nucleic acid molecule encoding a recombinant protein.

36. The method of claim 35, wherein the recombinant protein is a chimeric antigen receptor.

37. The method of claim 7, wherein the streptavidin mutein comprises:
  a) the sequence of amino acids set forth in any of SEQ ID NOS: 3-6, 27 and 28; or
  b) a sequence of amino acids that exhibits at least 85%, 86%, 87%, 88%, 89%, 90%, 91%, 92%, 93%, 94%, 95%, 96%, 97%, 98%, 99% or more sequence identity to any of SEQ ID NOS:3-6, 27 and 28, which contains the amino acid sequence corresponding to $Val^{44}$-$Thr^{45}$-$Ala^{46}$-$Arg^{47}$ or $Ile^{44}$-$Gly^{45}$-$Ala^{46}$-$Arg^{47}$ that reversibly binds to biotin or a biologically active form thereof, a biotin analog or a biologically active fragment thereof, or a streptavidin-binding peptide; wherein the amino acid positions of the peptide $Val^{44}$-$Thr^{45}$-$Ala^{46}$-$Arg^{47}$ or $Ile^{44}$-$Gly^{45}$-$Ala^{46}$-$Arg^{47}$ correspond to positions 44 to 47 to the amino acid sequence set forth in SEQ ID NO: 1.

38. The method of claim 1, wherein:
  (i) the selection agent specifically binds to a molecule selected from the group consisting of CD25, CD28, CD62L, CCR7, CD27, CD127, CD3, CD4, CD8, CD45RA, and CD45RO;
  (ii) the streptavidin mutein comprises the amino acid sequence $Val^{44}$-$Thr^{45}$-$Ala^{46}$-$Arg^{47}$ or $Ile^{44}$-$Gly^{45}$-$Ala^{46}$-$Arg^{47}$ at sequence positions corresponding to positions 44 to 47 with reference to positions in streptavidin in the sequence of amino acids set forth in SEQ ID NO:1; and
  (iii) the viral particle is a lentiviral vector particle, wherein the genome of the lentiviral vector particle comprises a heterologous nucleic acid molecule encoding a recombinant protein.

39. The method of claim 38, wherein the streptavidin-binding peptide is selected from the group consisting of Trp-Ser-His-Pro-Gln-Phe-Glu-Lys (SEQ ID NO: 8), Trp-Ser-His-Pro-Gln-Phe-Glu-Lys-(GlyGlyGlySer)$_3$-Trp-Ser-His-Pro-Gln-Phe-Glu-Lys (SEQ ID NO: 17), Trp-Ser-His-Pro-Gln-Phe-Glu-Lys-(GlyGlyGlySer)$_2$-Trp-Ser-His-Pro-Gln-Phe-Glu-Lys (SEQ ID NO: 18), Trp-Ser-His-Pro-Gln-Phe-Glu-Lys-(GlyGlyGlySer)$_2$-Gly-Gly-Ser-Ala-Trp-Ser-His-Pro-Gln-Phe-Glu-Lys (SEQ ID NO: 19) and SAWSHPQFEK(GGGS)$_2$GGSAWSHPQFEK (SEQ ID NO:16).

40. The method of claim 38, wherein the streptavidin-binding peptide is SAWSHPQFEK(GGGS)$_2$GGSAWSHPQFEK (SEQ ID NO:16).

41. The method of claim 38, wherein the recombinant protein is a chimeric antigen receptor.

42. The method of claim 7, wherein the method comprises disrupting the reversible binding between the selection agent and the oligomeric protein reagent, wherein said disruption comprises introducing biotin to the T cells.

43. The method of claim 38, wherein the method comprises disrupting the reversible binding between the selection agent and the oligomeric protein reagent, wherein said disruption comprises introducing biotin to the T cells.

44. The method of claim 40, wherein the recombinant protein is a chimeric antigen receptor.

45. The method of claim 40, wherein the method comprises disrupting the reversible binding between the selection agent and the oligomeric protein reagent, wherein said disruption comprises introducing biotin to the T cells.

46. The method of claim 44, wherein the method comprises disrupting the reversible binding between the selection agent and the oligomeric protein reagent, wherein said disruption comprises introducing biotin to the T cells.

47. The method of claim 21, wherein the streptavidin-binding peptide is SAWSHPQFEK(GGGS)$_2$GGSAWSHPQFEK (SEQ ID NO:16).

48. The method of claim 47, wherein the viral particle is a lentiviral vector particle, wherein the genome of the lentiviral vector particle comprises a heterologous nucleic acid molecule encoding a recombinant protein.

49. The method of claim 48, wherein the recombinant protein is a chimeric antigen receptor.

* * * * *

UNITED STATES PATENT AND TRADEMARK OFFICE
CERTIFICATE OF CORRECTION

PATENT NO. : 11,248,238 B2
APPLICATION NO. : 15/770177
DATED : February 15, 2022
INVENTOR(S) : Keenan Bashour et al.

It is certified that error appears in the above-identified patent and that said Letters Patent is hereby corrected as shown below:

In the Claims

At Column 212, Claim number 15, Line number 3, please replace "molecule" with --molecule,--.

At Column 212, Claim number 22, Line number 27, please replace "27" with --27,--.

At Column 212, Claim number 22, Line number 31, please replace "27" with --27,--.

At Column 212, Claim number 22, Line number 32, please replace "Thr45-" with --Thr45--.

At Column 212, Claim number 22, Line number 35, please replace "analog-" with --analog--.

At Column 212, Claim number 22, Line number 36, please replace "peptide;" with --peptide,--.

At Column 213, Claim number 37, Line number 23, please replace "27" with --27,--.

At Column 213, Claim number 37, Line number 27, please replace "27" with --27,--.

At Column 213, Claim number 37, Line number 32, please replace "peptide;" with --peptide,--.

At Column 213, Claim number 37, Line number 35, please replace "to the" with --of the--.

At Column 214, Claim number 39, Line number 13, please replace "19)" with --19),--.

Signed and Sealed this
Twentieth Day of August, 2024

Katherine Kelly Vidal
*Director of the United States Patent and Trademark Office*